US012612664B2

(12) United States Patent
Allawi et al.

(10) Patent No.: US 12,612,664 B2
(45) **Date of Patent: *Apr. 28, 2026**

(54) DETECTION AND ANALYSIS OF METHYLATED DNA

(71) Applicants: Exact Sciences Corporation, Madison, WI (US); Mayo Foundation for Medical Education and Research, Rochester, MN (US)

(72) Inventors: Hatim Allawi, Middleton, WI (US); Graham P. Lidgard, Middleton, WI (US); Maria Giakoumopoulos, Middleton, WI (US); David A. Ahlquist, Rochester, MN (US); William R. Taylor, Lake City, MN (US); Douglas Mahoney, Rochester, MN (US)

(73) Assignees: Exact Sciences Corporation, Madison, WI (US); Mayo Foundation for Medical Education and Research, Rochester, MN (US)

( * ) Notice: Subject to any disclaimer, the term of this patent is extended or adjusted under 35 U.S.C. 154(b) by 42 days.

This patent is subject to a terminal disclaimer.

(21) Appl. No.: 17/314,099

(22) Filed: May 7, 2021

(65) Prior Publication Data

US 2021/0262042 A1 Aug. 26, 2021

Related U.S. Application Data

(60) Division of application No. 16/460,647, filed on Jul. 2, 2019, now Pat. No. 11,028,447, which is a continuation of application No. 15/471,337, filed on Mar. 28, 2017, now Pat. No. 10,385,406.

(60) Provisional application No. 62/462,677, filed on Feb. 23, 2017, provisional application No. 62/332,295, filed on May 5, 2016.

(51) Int. Cl.
C12Q 1/6886 (2018.01)
C12Q 1/6806 (2018.01)

(52) U.S. Cl.
CPC ......... *C12Q 1/6886* (2013.01); *C12Q 1/6806* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. |
| 4,486,530 A | 12/1984 | David et al. |
| 4,683,195 A | 7/1987 | Mullis et al. |
| 4,683,202 A | 7/1987 | Mullis |
| 4,735,214 A | 4/1988 | Berman |
| 4,965,188 A | 10/1990 | Mullis et al. |
| 5,011,769 A | 4/1991 | Duck et al. |
| 5,124,246 A | 6/1992 | Urdea et al. |
| 5,288,609 A | 2/1994 | Engelhardt et al. |
| 5,338,671 A | 8/1994 | Scalice et al. |
| 5,403,711 A | 4/1995 | Walder et al. |
| 5,409,818 A | 4/1995 | Davey et al. |
| 5,475,610 A | 12/1995 | Atwood et al. |
| 5,494,810 A | 2/1996 | Barany et al. |
| 5,508,169 A | 4/1996 | Deugau et al. |
| 5,538,871 A | 7/1996 | Nuovo et al. |
| 5,602,756 A | 2/1997 | Atwood et al. |
| 5,612,473 A | 3/1997 | Wu et al. |
| 5,624,802 A | 4/1997 | Urdea et al. |
| 5,639,611 A | 6/1997 | Wallace et al. |
| 5,660,988 A | 8/1997 | Duck et al. |
| 5,710,264 A | 1/1998 | Urdea et al. |
| 5,773,258 A | 6/1998 | Birch et al. |
| 5,786,146 A | 7/1998 | Herman et al. |
| 5,792,614 A | 8/1998 | Western et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,958,692 A | 9/1999 | Cotton et al. |
| 5,965,408 A | 10/1999 | Short |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |

(Continued)

FOREIGN PATENT DOCUMENTS

| | | |
|---|---|---|
| CA | 2743473 A1 | 5/2010 |
| CN | 103415625 A | 11/2013 |

(Continued)

OTHER PUBLICATIONS

MagMAX™ Cell-Free DNA Isolation Kit User Guide: Isolation of cfDNA from plasma and serum samples, Applied Biosystems, Catalog No. A29319; Publication No. MAN0014327 (Year: 2015).*

(Continued)

*Primary Examiner* — Aaron A Priest
*Assistant Examiner* — Tian Yu
(74) *Attorney, Agent, or Firm* — Casimir Jones, S.C.; Mary Ann D. Brow

(57) ABSTRACT

Provided herein is technology for lung neoplasia screening and particularly, but not exclusively, to methods, compositions, and related uses for detecting the presence of lung cancer.

15 Claims, 155 Drawing Sheets

Specification includes a Sequence Listing.

(56)                 References Cited

U.S. PATENT DOCUMENTS

| | | | |
|---|---|---|---|
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,251,594 B1 | 6/2001 | Gonzalgo et al. |
| 6,329,178 B1 | 12/2001 | Patel et al. |
| 6,335,167 B1 | 1/2002 | Pinkel et al. |
| 6,395,524 B2 | 5/2002 | Loeb et al. |
| 6,602,695 B2 | 8/2003 | Patel et al. |
| 6,605,451 B1 | 8/2003 | Marmaro et al. |
| 6,872,816 B1 | 3/2005 | Hall et al. |
| 7,037,650 B2 | 5/2006 | Gonzalgo et al. |
| 7,087,414 B2 | 8/2006 | Gerdes et al. |
| 7,122,364 B1 | 10/2006 | Lyamichev et al. |
| 7,256,020 B2 | 8/2007 | Lyamichev et al. |
| 7,662,594 B2 | 2/2010 | Kong et al. |
| 7,790,393 B2 | 9/2010 | Lyamichev et al. |
| 8,304,214 B2 | 11/2012 | Gerdes et al. |
| 8,361,720 B2 | 1/2013 | Oldham-Haltom et al. |
| RE44,596 E | 11/2013 | Stroun et al. |
| 8,715,937 B2 | 5/2014 | Zou et al. |
| 8,808,990 B2 | 8/2014 | Lidgard et al. |
| 8,916,344 B2 | 12/2014 | Zou et al. |
| 8,962,250 B2 | 2/2015 | Stanley |
| 9,000,146 B2 | 4/2015 | Bruinsma et al. |
| 9,096,893 B2 | 8/2015 | Allawi et al. |
| 9,127,318 B2 | 9/2015 | Oldham-Haltom et al. |
| 9,163,278 B2 | 10/2015 | Bruinsma et al. |
| 9,169,511 B2 | 10/2015 | Lidgard et al. |
| 9,212,392 B2 | 12/2015 | Allawi et al. |
| 9,315,853 B2 | 4/2016 | Domanico et al. |
| 9,422,592 B2 | 8/2016 | Morris et al. |
| 9,428,746 B2 | 8/2016 | Holmberg et al. |
| 9,546,403 B1 | 1/2017 | Warren et al. |
| 9,637,792 B2 | 5/2017 | Ahlquist et al. |
| 9,657,330 B2 | 5/2017 | Lidgard et al. |
| 9,657,511 B2 | 5/2017 | Lidgard et al. |
| 9,726,670 B2 | 8/2017 | Ataman-Onal et al. |
| 9,809,612 B2 | 11/2017 | Ritt et al. |
| 10,011,878 B2 | 7/2018 | Ahlquist et al. |
| 10,030,272 B2 | 7/2018 | Ahlquist et al. |
| 10,292,687 B2 | 5/2019 | Maguire et al. |
| 10,327,742 B2 | 6/2019 | Fitzgerald et al. |
| 10,370,726 B2 | 8/2019 | Ahlquist et al. |
| 10,385,406 B2 | 8/2019 | Allawi et al. |
| 10,435,755 B2 | 10/2019 | Ahlquist et al. |
| 10,465,248 B2 | 11/2019 | Allawi et al. |
| 10,519,510 B2 | 12/2019 | Ahlquist et al. |
| 10,648,025 B2 | 5/2020 | Allawi et al. |
| 10,648,035 B2 | 5/2020 | Agarwal et al. |
| 10,704,081 B2 | 7/2020 | Lidgard et al. |
| 10,738,069 B2 | 8/2020 | Ritt et al. |
| 10,822,638 B2 | 11/2020 | Allawi et al. |
| 11,118,228 B2 | 9/2021 | Allawi et al. |
| 11,345,949 B2 | 5/2022 | Allawi et al. |
| 11,479,823 B2 | 10/2022 | Allawi et al. |
| 2003/0224040 A1 | 12/2003 | Baylin et al. |
| 2003/0224437 A1 | 12/2003 | Gerdes et al. |
| 2004/0072182 A1 | 4/2004 | Lyamichev et al. |
| 2004/0175733 A1 | 9/2004 | Andersen et al. |
| 2004/0234960 A1 | 11/2004 | Olek et al. |
| 2005/0048527 A1 | 3/2005 | Allawi et al. |
| 2005/0214926 A1 | 9/2005 | Zielenski et al. |
| 2005/0239101 A1 | 10/2005 | Sukumar et al. |
| 2006/0134663 A1 | 6/2006 | Harkin et al. |
| 2006/0147955 A1 | 7/2006 | Allawi et al. |
| 2006/0171952 A1 | 8/2006 | Mather et al. |
| 2007/0048748 A1 | 3/2007 | Williams et al. |
| 2007/0161062 A1 | 7/2007 | Tacke et al. |

| | | | |
|---|---|---|---|
| 2007/0190540 A1 | 8/2007 | Stanley |
| 2007/0202525 A1 | 8/2007 | Quake et al. |
| 2007/0264659 A1 | 11/2007 | An et al. |
| 2008/0003571 A1 | 1/2008 | McKernan et al. |
| 2008/0221056 A1 | 9/2008 | Baylin et al. |
| 2009/0203011 A1 | 8/2009 | Liebenberg et al. |
| 2009/0253142 A1 | 10/2009 | Allawi et al. |
| 2010/0075334 A1 | 3/2010 | Kim et al. |
| 2011/0009277 A1 | 1/2011 | Devos et al. |
| 2011/0123990 A1 | 5/2011 | Baker et al. |
| 2011/0160446 A1 | 6/2011 | Ritt et al. |
| 2011/0217717 A1 | 9/2011 | Brody et al. |
| 2011/0287424 A1 | 11/2011 | Chen |
| 2011/0318738 A1 | 12/2011 | Jones et al. |
| 2012/0122088 A1 | 5/2012 | Zou et al. |
| 2012/0122105 A1 | 5/2012 | Oldham-Haltom et al. |
| 2012/0122106 A1 | 5/2012 | Zou et al. |
| 2012/0264618 A1 | 10/2012 | Nygren |
| 2012/0288868 A1 | 11/2012 | Bruinsma et al. |
| 2013/0022974 A1* | 1/2013 | Chinnaiyan .......... C12Q 1/6886 |
| | | | 435/6.11 |
| 2013/0084287 A1 | 4/2013 | Shames et al. |
| 2013/0164819 A1 | 6/2013 | Sjoeblom et al. |
| 2013/0196332 A1 | 8/2013 | Morris et al. |
| 2013/0231256 A1 | 9/2013 | Oldham-Haltom et al. |
| 2013/0296738 A1 | 11/2013 | Swain et al. |
| 2014/0017672 A1 | 1/2014 | Holmberg et al. |
| 2014/0087382 A1 | 3/2014 | Allawi et al. |
| 2015/0037802 A1 | 2/2015 | Wang et al. |
| 2015/0105276 A1 | 4/2015 | Hofmann et al. |
| 2015/0292029 A1 | 10/2015 | Agarwal et al. |
| 2015/0368694 A1 | 12/2015 | Pan et al. |
| 2015/0376608 A1 | 12/2015 | Kaper et al. |
| 2016/0010081 A1 | 1/2016 | Allawi et al. |
| 2016/0017435 A1 | 1/2016 | Myers et al. |
| 2016/0081671 A1 | 3/2016 | Lubinski et al. |
| 2016/0090634 A1 | 3/2016 | Kisiel et al. |
| 2016/0168643 A1 | 6/2016 | Ahlquist et al. |
| 2016/0194721 A1 | 7/2016 | Allawi et al. |
| 2016/0251727 A1 | 9/2016 | Ahlquist et al. |
| 2016/0312299 A1 | 10/2016 | Tyler et al. |
| 2016/0333424 A1 | 11/2016 | Morris et al. |
| 2016/0340740 A1 | 11/2016 | Zhang |
| 2017/0029808 A1 | 2/2017 | Tsukamoto |
| 2017/0121704 A1 | 5/2017 | Allawi et al. |
| 2017/0121757 A1 | 5/2017 | Lidgard et al. |
| 2017/0321286 A1 | 11/2017 | Allawi et al. |
| 2017/0335401 A1 | 11/2017 | Allawi et al. |
| 2018/0030547 A1 | 2/2018 | Hofmann et al. |
| 2018/0143198 A1 | 5/2018 | Wen et al. |
| 2018/0245157 A1 | 8/2018 | Allawi et al. |
| 2019/0085406 A1 | 3/2019 | Mortimer et al. |
| 2019/0177769 A1 | 6/2019 | Allawi et al. |
| 2019/0218601 A1 | 7/2019 | Allawi et al. |
| 2019/0330702 A1 | 10/2019 | Allawi et al. |
| 2020/0248233 A1 | 8/2020 | Allawi et al. |
| 2020/0291458 A1 | 9/2020 | Lidgard et al. |
| 2022/0071605 A1 | 3/2022 | Eisele et al. |
| 2022/0349009 A1 | 11/2022 | Taylor et al. |
| 2023/0046033 A1 | 2/2023 | Zubin et al. |

FOREIGN PATENT DOCUMENTS

| | | |
|---|---|---|
| CN | 104781421 | 7/2015 |
| JP | 2008-502890 | 1/2008 |
| JP | 2010-533853 | 10/2010 |
| JP | 2017086043 A | 5/2017 |
| KR | 10-2016-0128136 | 11/2016 |
| WO | WO 1992/02258 | 2/1992 |
| WO | WO 1993/10820 | 6/1993 |
| WO | WO 1994/22892 | 10/1994 |
| WO | WO 1994/24144 | 10/1994 |
| WO | WO 1995/000669 | 1/1995 |
| WO | WO 1995/015373 | 6/1995 |
| WO | WO 1997/046705 | 12/1997 |
| WO | WO 1999/028498 | 6/1998 |
| WO | WO 2001/94634 | 12/2001 |
| WO | WO 2002/070755 | 9/2002 |
| WO | WO 2005/023091 | 3/2005 |

(56)          References Cited

FOREIGN PATENT DOCUMENTS

| WO | WO 2005/038041 | 4/2005 |
| WO | WO 2005/038051 | 4/2005 |
| WO | WO 2005/098050 | 10/2005 |
| WO | WO 2005/124356 | 12/2005 |
| WO | WO-2005124356 A2 | 12/2005 |
| WO | WO 2006/084132 | 8/2006 |
| WO | WO 2006/113770 | 10/2006 |
| WO | WO 2007/121489 | 10/2007 |
| WO | WO 2008/084219 | 7/2008 |
| WO | WO 2008/100913 | 8/2008 |
| WO | WO 2008/103763 | 8/2008 |
| WO | WO 2009/035447 | 3/2009 |
| WO | WO 2009/102788 | 8/2009 |
| WO | WO-2009146776 A2 | 12/2009 |
| WO | WO-2010064702 A1 | 6/2010 |
| WO | WO 2010/074924 | 7/2010 |
| WO | WO 2010/086389 | 8/2010 |
| WO | WO 2010/089538 | 8/2010 |
| WO | WO 2011/058316 | 5/2011 |
| WO | WO 2011/119934 | 9/2011 |
| WO | WO 2012/067831 | 5/2012 |
| WO | WO 2012/106525 | 8/2012 |
| WO | WO 2012/155072 | 11/2012 |
| WO | WO-2012150276 A1 | 11/2012 |
| WO | WO 2013/058868 | 4/2013 |
| WO | WO-2013058569 A2 | 4/2013 |
| WO | WO 2013/070950 | 5/2013 |
| WO | WO 2013/116375 | 8/2013 |
| WO | WO 2013/142545 | 9/2013 |
| WO | WO 2014/039556 | 3/2014 |
| WO | WO 2014/062218 | 4/2014 |
| WO | WO 2014/159650 | 10/2014 |
| WO | WO 2014/159652 | 10/2014 |
| WO | WO 2014/160117 | 10/2014 |
| WO | WO-2014198727 A2 | 12/2014 |
| WO | WO 2015/066695 | 5/2015 |
| WO | WO 2015/095689 | 6/2015 |
| WO | WO 2015/153283 | 10/2015 |
| WO | WO 2015/153284 | 10/2015 |
| WO | WO 2016/094813 | 6/2016 |
| WO | WO 2016/094839 | 6/2016 |
| WO | WO 2017/040627 | 3/2017 |
| WO | WO 2017/075061 | 5/2017 |
| WO | WO 2017/129716 | 8/2017 |
| WO | WO 2017/180886 | 10/2017 |
| WO | WO 2017/192221 | 11/2017 |
| WO | WO 2017/201164 | 11/2017 |
| WO | WO 2017/223216 | 12/2017 |
| WO | WO 2018/017740 | 1/2018 |
| WO | WO 2018/045322 | 3/2018 |
| WO | WO 2018/160576 | 9/2018 |
| WO | WO 2019/108626 | 6/2019 |
| WO | WO 2020/112869 | 7/2020 |
| WO | WO 2020/154665 | 7/2020 |
| WO | WO 2020/206256 | 10/2020 |
| WO | WO 2021/041726 | 3/2021 |
| WO | WO 2021/055508 | 3/2021 |
| WO | WO 2021/076969 | 4/2021 |
| WO | WO 2021/087275 | 5/2021 |
| WO | WO 2021/212031 | 10/2021 |
| WO | WO 2021/226071 | 11/2021 |
| WO | WO 2021/226074 | 11/2021 |
| WO | WO 2022/039904 | 2/2022 |
| WO | WO 2022/040306 | 2/2022 |
| WO | WO 2022/165247 | 8/2022 |
| WO | WO 2022/187695 | 9/2022 |
| WO | WO 2023/081796 | 5/2023 |

OTHER PUBLICATIONS

Snellenberg et al. Development of a multiplex methylation-specific PCR as candidate triage test for women with an HPV-positive cervical scrape. BMC Cancer 12, 551 (2012). doi.org/10.1186/1471-2407-12-551 (Year: 2012).*

Zhou et al. Quantification of Methylated Markers with a Multiplex Methylation-Specific Technology, Clinical Chemistry, vol. 58, Issue 2, Feb. 1, 2012, pp. 375-383, (Year: 2012).*

Taskesen et al. ; Pan-cancer subtyping in a 2D-map shows substructures that are driven by specific combinations of molecular characteristics. Sci Rep 6, 24949 (Apr. 2016) (Year: 2016).*

Zhou et al.; Quantification of Methylated Markers with a Multiplex Methylation-Specific Technology, Clinical Chemistry, vol. 58, Issue 2, Feb. 1, 2012, pp. 375-383, doi.org/10.1373/clinchem.2011. 171264; cited on IDS filed May 7, 2021 (Year: 2012).*

Nolan et al. Good practice guide for the application of quantitative PCR (qPCR), LGC (Year: 2013).*

Olkhov-Mitsel et al. Strategies for discovery and validation of methylated and hydroxymethylated DNA biomarkers. Cancer Med. Oct. 2012; 1(2):237-60. doi: 10.1002/cam4.22. Epub Sep. 14, 2012. PMID: 23342273; PMCID: PMC3544446. (Year: 2012).*

Sittampalam et al. Preface. May 1, 2012 [Updated Mar. 31, 2017]. In: Markossian S, Grossman A, Baskir H, et al., editors. Assay Guidance Manual [Internet]. Bethesda (MD): Eli Lilly & Company and the National Center for Advancing Translational Sciences (Year: 2012).*

Lu, TP., Chen, K., Tsai, MH. et al. Identification of Genes with Consistent Methylation Levels across Different Human Tissues. Sci Rep 4, 4351 (2014) doi.org/10.1038/srep04351 (Year: 2014).*

Aboelsoud et al.; Discovery of Novel DNA Methylation Markers for the Detection of Cholangiocarcinoma by Methylome-Wide Analysis: 1241. Hepatology 60():p. 798A-799A, Oct. 2014 (Year: 2014).*

Taskesen et al. ; Pan-cancer subtyping in a 2D-map shows substructures that are driven by specific combinations of molecular characteristics. Sci Rep 6, 24949 (2016) (Year: 2016).*

Carvalho et al. Genomewide DNA methylation analysis identifies novel methylated genes in non-small-cell lung carcinomas. J Thorac Oncol. May 2013;8(5):562-73. doi: 10. 1097/JTO.0b013e3182863ed2. PMID: 23524404 (Year: 2013).*

Feng et al. DNA methylation in tumor and matched normal tissues from non-small cell lung cancer patients. Cancer Epidemiol Biomarkers Prev. Mar. 2008; 17(3):645-54. doi: 10.1158/1055-9965. EPI-07-2518. PMID: 18349282; PMCID: PMC2798850 (Year: 2008).*

Shames et al. A genome-wide screen for promoter methylation in lung cancer identifies novel methylation markers for multiple malignancies. PLOS Med. Dec. 2006;3(12):e486. doi: 10.1371/journal. pmed.0030486. PMID: 17194187; PMCID: PMC1716188; cited as NPL #004 in IDS filed on Feb. 27, 2026 (Year: 2006).*

Nilsson et al., Altered DNA Methylation and Differential Expression of Genes Influencing Metabolism and Inflammation in Adipose Tissue From Subjects With Type 2 Diabetes. Diabetes. Sep. 2014;63:2962-76.

Dowdy et al., Statistics for Research, John Wiley & Sons, New York, 1983. TOC only. 6 pages.

Finger et al., The wonders of flap endonucleases: structure, function, mechanism and regulation. Subcell Biochem. 2012;62:301-26.

Gardiner-Garden et al., CpG Islands in Vertebrate Genomes. J. Mol. Biol. 1987;196: 261-281.

Iyer et al., Accurate nonendoscopic detection of Barrett's esophagus by methylated DNA Markers: A multisite case control study. Am J Gastroenterol 2020;115:1201-1209.

Iyer et al., Accurate non-endoscopic detection of Barrett's esophagus in a multicenter prospective validation cohort: the sos 2 trial. AGA Abstracts. 2018:878. S-175-S-176.

Iyer et al., Independent validation of an accurate methylated DNA marker panel for the non-endoscopic detection of Barrett's esophagus: a multisite case control study. AGA Abstracts. 2020; 1084: S-211.

Kawai et al., Comparison of DNA methylation patterns among mouse cell lines by restriction landmark genomic scanning. Mol Cell Biol. Nov. 1994;14(11):7421-7.

Moon et al., Identification of novel hypermethylated genes and demethylating effect of vincristine in colorectal cancer. J Exp Clin Cancer Res. 2014;33:4. 10 pages.

Shen et al., Multiple but dissectible functions of FEN-1 nucleases in nucleic acid processing, genome stability and diseases. Bioessays. Jul. 2005;27(7):717-29.

(56)            References Cited

OTHER PUBLICATIONS

He et al., Development of a multiplex MethyLight assay for the detection of multigene methylation in human colorectal cancer. Cancer Genet Cytogenet. Oct. 1, 2010;202(1):1-10.

Iqbal et al., Safety and efficacy of a minimally invasive cell sampling device ('Cytosponge') in the diagnosis of esophageal pathology: a systematic review. Eur J Gastroenterol Hepatol. Nov. 2018;30(11):1261-1269.

Toth et al., Detection of methylated Sep. 9 in plasma is a reliable screening method for both left- and right-sided colon cancers. PLoS One. 2012;7(9):e46000.

Zheng et al., Detection of Single Nucleotide Polymorphism Genotyping by Real-time Polymerase Chain Reaction Coupled with High Specific Invader Assay in Single Tube. Chin J Anal Chem. 2015;43(7):1001-8.

Bentley et al., Accurate Whole Human Genome Sequencing using Reversible Terminator Chemistry. Nature. Nov. 6, 2008; 456(7218):53-59.

Berezikov et al., Approaches to microRNA discovery. Nat Genet. Jun. 2006;38 Suppl:S2-7.

Chapman et al., Autoantibodies in lung cancer: possibilities for early detection and subsequent cure. Thorax. Mar. 2008;63(3):228-33.

Dassonville et al., Expression of epidermal growth factor receptor and survival in upper aerodigestive tract cancer. J Clin Oncol. Oct. 1993;11(10):1873-8.

Egeblad et al., New functions for the matrix metalloproteinases in cancer progression. Nat Rev Cancer. Mar. 2002;2(3):161-74.

Elbashir et al., RNA interference is mediated by 21- and 22-nucleotide RNAs. Genes Dev. Jan. 15, 2001;15(2):188-200.

Extended European Search Report for EP 19890483.1, mailed Sep. 29, 2022, 10 pages.

Fedurco et al., BTA, a novel reagent for DNA attachment on glass and efficient generation of solid-phase amplified DNA colonies. Nucleic Acids Res. Feb. 9, 2006;34(3):e22.

Gatlin et al., Automated identification of amino acid sequence variations in proteins by HPLC/microspray tandem mass spectrometry. Anal Chem. Feb. 15, 2000;72(4):757-63.

Gemperle et al., Regulation of the formyl peptide receptor 1 (FPR1) gene in primary human macrophages. PLoS One. 2012;7(11):e50195. 6 pages.

GenBank Accession No. NM005621. National Library of Medicine. Retrieved from the internet Sep. 29, 2022. 4 pages.

GenPept Accession No. NP05612. Sep. 11, 2022. 3 pages.

Grandis et al., TGF-alpha and EGFR in Head and Neck Cancer. Journal of Cellular Biochemistry, 1993; Supplement 17f:188-191.

Harris et al., Single-molecule DNA sequencing of a viral genome. Science. Apr. 4, 2008;320(5872):106-9.

Heid et al., Real time quantitative PCR . Genome Res. Oct. 1996;6(10):986-94.

Hua et al., Quantitative methylation analysis of multiple genes using methylation-sensitive restriction enzyme-based quantitative PCR for the detection of hepatocellular carcinoma. Exp Mol Pathol. Aug. 2011;91(1):455-60.

Huang et al., Transactivation of the epidermal growth factor receptor by formylpeptide receptor exacerbates the malignant behavior of human glioblastoma cells. Cancer Res. Jun. 15, 2007;67(12):5906-13.

International Preliminary Report on Patentability for PCT/US2020/048270. Mailed Mar. 10, 2022. 11 pages.

International Search Report and Written Opinion for PCT/US2020/048270. Mailed Dec. 7, 2020. 12 pages.

Jongeneel et al., An atlas of human gene expression from massively parallel signature sequencing (MPSS) Genome Res. Jul. 2005;15(7):1007-14.

Kling. Ultrafast DNA sequencing. Nat Biotechnol. Dec. 2003;21(12):1425-7.

Mandal et al., Lipopolysaccharide induces formyl peptide receptor 1 gene expression in macrophages and neutrophils via transcriptional and posttranscriptional mechanisms. J Immunol. Nov. 1, 2005;175(9):6085-91.

Mandal et al., Signaling in lipopolysaccharide-induced stabilization of formyl peptide receptor 1 mRNA in mouse peritoneal macrophages. J Immunol. Feb. 15, 2007;178(4):2542-8.

Marabella et al., Serum ribonuclease in patients with lung carcinoma. J Surg Oncol. 1976;8(6):501-5.

Margulies et al., Genome sequencing in microfabricated high-density picolitre reactors. Nature. Sep. 15, 2005;437(7057):376-80.

Melnikov et al., MSRE-PCR for analysis of gene-specific DNA methylation. Nucleic Acids Res. Jun. 8, 2005;33(10):e93.

Monte et al., Cloning, chromosome mapping and functional characterization of a human homologue of murine gtse-1 (B99) gene. Gene. Aug. 22, 2000;254(1-2):229-36.

Monte et al., hGTSE-1 expression stimulates cytoplasmic localization of p53. J Biol Chem. Mar. 19, 2004;279(12):11744-52.

Morris et al., Whole blood FPR1 mRNA expression predicts both non-small cell and small cell lung cancer. Int J Cancer. Jun. 1, 2018;142(11):2355-2362.

NCBI Ref. Seq. NM_001193306.1. Apr. 9, 2019. Retrieved from NIH Sep. 29, 2022. 5 pages.

Neuwelt et al., Possible sites of origin of human plasma ribonucleases as evidenced by isolation and partial characterization of ribonucleases from several human tissues. Cancer Res. Jan. 1978;38(1):88-93.

O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.

Osman et al., Expression of matrix metalloproteinases and tissue inhibitors of metalloproteinases define the migratory characteristics of human monocyte-derived dendritic cells. Immunology. Jan. 2002;105(1):73-82.

Reddi et al., Elevated serum ribonuclease in patients with pancreatic cancer. Proc Natl Acad Sci U S A. Jul. 1976; 73(7):2308-10.

Reinartz et al., Massively parallel signature sequencing (MPSS) as a tool for in-depth quantitative gene expression profiling in all organisms. Brief Funct Genomic Proteomic. Feb. 2002;1(1):95-104.

Ronaghi et al., A sequencing method based on real-time pyrophosphate. Science. Jul. 17, 1998;281(5375):363, 365.

Ronaghi et al., Real-time DNA sequencing using detection of pyrophosphate release. Anal Biochem. Nov. 1, 1996;242(1):84-9.

Rothberg et al., An integrated semiconductor device enabling non-optical genome sequencing. Nature. Jul. 20, 2011;475(7356):348-52.

Santani et al., Characterization, quantification, and potential clinical value of the epidermal growth factor receptor in head and neck squamous cell carcinomas. Head & Neck, 1991; 13(2): 132-139.

Schuuring et al., Characterization of the EMS1 gene and its product, human Cortactin. Cell Adhes Commun. 1998;6(2-3):185-209.

Schuuring et al., Identification and cloning of two overexpressed genes, U21B31/PRAD1 and EMS1, within the amplified chromosome 11q13 region in human carcinomas. Oncogene. Feb. 1992;7(2):355-61.

Shao et al., Formyl peptide receptor ligands promote wound closure in lung epithelial cells. Am J Respir Cell Mol Biol. Mar. 2011;44(3):264-9.

Shendure et al., Accurate multiplex polony sequencing of an evolved bacterial genome. Science. Sep. 9, 2005;309(5741):1728-32.

Shendure et al., Next-generation DNA sequencing. Nat Biotechnol. Oct. 2008;26(10):1135-45.

Turcatti et al., A new class of cleavable fluorescent nucleotides: synthesis and optimization as reversible terminators for DNA sequencing by synthesis. Nucleic Acids Res. Mar. 2008;36(4):e25. 13 pages.

Türeci et al., Humoral immune responses of lung cancer patients against tumor antigen NY-ESO-1. Cancer Lett. May 8, 2006;236(1):64-71.

Turner et al., Role of matrix metalloproteinase 9 in pituitary tumor behavior. J Clin Endocrinol Metab. Aug. 2000;85(8): 2931-5.

Umu et al., A comprehensive profile of circulating RNAs in human serum. RNA Biol. Feb. 1, 2018;15(2):242-250.

(56)        References Cited

OTHER PUBLICATIONS

Vancompernolle et al., Expression and function of formyl peptide receptors on human fibroblast cells. J Immunol. Aug. 15, 2003;171(4):2050-6.

Wang et al., Crosstalk to stromal fibroblasts induces resistance of lung cancer to epidermal growth factor receptor tyrosine kinase inhibitors. Clin Cancer Res. Nov. 1, 2009;15(21):6630-8.

Wang et al., DNA methylation study of fetus genome through a genome-wide analysis. BMC Med Genomics. Apr. 15, 2014;7:18.

Williams et al., Amplification of complex gene libraries by emulsion PCR. Nat Methods. Jul. 2006;3(7):545-50.

Yu et al., Significance of combined detection of LunX mRNA and tumor markers in diagnosis of lung carcinoma. Chin J Cancer Res. Feb. 2014;26(1):89-94.

Zhou et al., Massively parallel signature sequencing. Methods Mol Biol. 2006;331:285-311.

Ahlquist et al., Colorectal cancer screening by detection of altered human DNA in stool: Feasibility of a multitarget assay panel. Gastroenterology, 2000;119:1219-27.

Ahlquist et al., Next-Generation Stool DNA Test Accurately Detects Colorectal Cancer and Large Adenomas. Gastroenterology, 2012;142:248-56.

Ahlquist et al., Novel Use of Hypermethylated DNA Markers in Stool for Detection of Colorectal Cancer: A Feasibility Study. Gastroenterology 2002;122:Suppl A40.

Ahlquist et al., Stool DNA and Occult Blood Testing for Screen Detection of Colorectal Neoplasia. Ann Intern Med, 2008;149(7):441-50.

Allawi et al., Abstract 712: Detection of lung cancer by assay of novel methylated DNA markers in plasma. Proceedings: AACR Annual Meeting Apr. 1-5, 2017, Washington, DC. 3 pages.

Andersson et al., Properties of targeted preamplification in DNA and cDNA quantification. Expert Rev Mol Diagn. 2015;15(8):1085-100.

Antequera et al., High levels of de novo methylation and altered chromatin structure at CpG islands in cell lines. Cell. Aug. 10, 1990;62(3):503-14.

Arneson et al., GenomePlex Whole-Genome Amplification. Cold Spring Harb. Protoc. 2008; doi:10.1101/pdb.prot4920, 7 pages.

Aronchick CA, et al., A novel tableted purgative for colonoscopic preparation: Efficacy and safety comparisons with Colyte and Fleet Phospho-Soda. Gastrointestinal endoscopy, 2000;52:346-52.

Ballabio, et al., Screening for steroid sulfatase (STS) gene deletions by multiplex DNA amplification, Human Genetics, 1990, 84(6): 571-573.

Barany, Genetic disease detection and DNA amplification using cloned thermostable ligase, Proc. Natl. Acad. Sci USA, 1991, 88:189-93.

Bardan E, et al., Colonoscopic resection of large colonic polyps—a prospective study. Israel journal of medical sciences, 1997;33(12):777-80.

Barnay, Genetic disease detection and DNA amplification using cloned thermostable ligase, Proc. Natl. Acad. Sci USA, 1991, 88:189-93.

Belinsky SA, et al., Promoter Hypermethylation of Multiple Genes in Sputum Precedes Lung Cancer Incidence in a High-Risk Cohort. Cancer Res, 2006;66(6):3338-44.

Berger BM, et al., Stool DNA screening for colorectal neoplasia: biological and technical basis for high detection rates. Pathology 2012;44(2):80-8.

Bibikova, GoldenGate? Assay for Methyltion of BeadArrayTM Technology. Jan. 1, 2009; retrieved from http://agtc.wayne.edu/pdfs/goldengate_methylation_brochure.pdf, retrieved Aug. 29, 2016, 7 pages.

Boynton KA, et al., DNA Integrity as a Potential Marker for Stool-based Detection of Colorectal Cancer. Clin Chem 2003;49(7):1058-65.

Budd et al., Circulating tumor cells versus imaging—predicting overall survival in metastatic breast cancer. Clin Cancer Res. Nov. 1, 2006;12(21):6403-9.

Bustin, Absolute quantification of mRNA using real-time reverse transcription polymerase chain reaction assays, J. Molecular Endocrinology, 2000, 25:169-193.

Carvalho et al., Genome-wide DNA methylation profiling of non-small cell lung carcinomas. Epigenetics Chromatin. Jun. 22, 2012;5(1):9.

Ceska et al., Structure-specific DNA cleavage by 5' nucleases. Trends Biochem Sci. Sep. 1998;23(9):331-6.

Chamberlain et al., Deletion screening of the Duchenne muscular dystrophy locus via multiplex DNA amplification, Nucleic Acids Research, 1988, 16(23):11141-11156.

Chen et al., Detection in Fecal DNA of Colon Cancer-Specific Methylation of the Nonexpressed Vimentin Gene. J Natl Cancer Inst, 2005;97:1124-32.

Chen et al., HOPX is methylated and exerts tumour-suppressive function through Ras-induced senescence in human lung cancer. J Pathol. Feb. 2015;235(3):397-407.

Cohen et al., Relationship of circulating tumor cells to tumor response, progression-free survival, and overall survival in patients with metastatic colorectal cancer. J Clin Oncol. Jul. 1, 2008;26(19):3213-21.

Cristofanilli et al., Circulating tumor cells, disease progression, and survival in metastatic breast cancer. N Engl J Med. Aug. 19, 2004;351(8): 781-91.

Dammann et al., The CpG island of the novel tumor suppressor gene RASSF1A is intensely methylated in primary small cell lung carcinomas. Oncogene. Jun. 14, 2001;20(27):3563-7.

Devos et al., Circulating methylated Sep. 9 DNA in plasma is a biomarker for colorectal cancer. Clin Chem. Jul. 2009;55(7):1337-46.

Don et al., 'Touchdown' PCR to circumvent spurious priming during gene amplification, Nucleic Acids Research, 1991, 19(14):4008.

Eads et al., CpG island hypermethylation in human colorectal tumors is not associated with DNA methyltransferase overexpression. Cancer Res. May 15, 1999;59(10):2302-6.

Ebert, MP, et al., Aristaless-like Homeobox-4 Gene Methylation is a Potential Marker for Colorectal Adenocarcinomas. Gastroenterology, 2006;131:1418-30.

Fasman, "Practical Handbook of Biochemistry and Molecular Biology", pp. 385-394, 1989, CRC Press, Boca Raton, FL.

Feil et al., Methylation analysis on individual chromosomes: improved protocol for bisulphite genomic sequencing. Nucleic Acids Res. Feb. 25, 1994;22(4):695-6.

Frommer et al., A genomic sequencing protocol that yields a positive display of 5-methylcytosine residues in individual DNA strands. Proc Natl Acad Sci U S A. Mar. 1, 1992;89(5):1827-31.

Gonzalgo et al., Identification and characterization of differentially methylated regions of genomic DNA by methylation-sensitive arbitrarily primed PCR. Cancer Res. Feb. 15, 1997;57(4):594-9.

Gonzalgo et al., Rapid quantitation of methylation differences at specific sites using methylation-sensitive single nucleotide primer extension (Ms-SNuPE). Nucleic Acids Res. Jun. 15, 1997;25(12):2529-31.

Grady WM, et al., Detection of Aberrantly Methylated hMLH1 Promoter DNA in the Serum of Patients with Microsatellite Unstable Colon Cancer. Cancer Res 2001;61:900-2.

Grafstrom et al., The characteristics of DNA methylation in an in vitro DNA synthesizing system from mouse fibroblasts. Nucleic Acids Res. Apr. 25, 1985;13(8):2827-42.

Grafstrom RH, et al., The characteristics of DNA methylation in an in vitro DNA synthesizing system from mouse fibroblasts. Nucleic Acids Res. 1985;13(8): 2827-2842.

Grigg et al., Sequencing 5-methylcytosine residues in genomic DNA. Bioessays. Jun. 1994;16(6):431-6.

Grigg, Sequencing 5-methylcytosine residues by the bisulphite method. DNA Seq. 1996;6(4):189-98.

Grunau et al., Bisulfite genomic sequencing: systematic investigation of critical experimental parameters. Nucleic Acids Res. Jul. 1, 2001;29(13):E65-5.

Gu et al., Genome-scale DNA methylation mapping of clinical samples at single-nucleotide resolution. Nat Methods. Feb. 2010;7(2):133-6.

(56) References Cited

OTHER PUBLICATIONS

Guilfoyle et al., Ligation-mediated PCR amplification of specific fragments from a class-II restriction endonuclease total digest, Nucleic Acids Research, 1997, 25:1854-1858.

Hall et al., Sensitive detection of DNA polymorphisms by the serial invasive signal amplification reaction, PNAS, 2000, 97:8272.

Hardcastle, JD, et al., Randomised controlled trial of faecal-occult-blood screening for colorectal cancer. Lancet. 1996, 348:1472-7.

Hayden et al., Multiplex-Ready PCR: A new method for multiplexed SSR and SNP genotyping, BMC Genomics, 2008, 9:80.

Hayes et al., Circulating tumor cells at each follow-up time point during therapy of metastatic breast cancer patients predict progression-free and overall survival. Clin Cancer Res. Jul. 15, 2006;12(14 Pt 1):4218-24.

Hecker et al., High and low annealing temperatures increase both specificity and yield in touchdown and stepdown PCR, Biotechniques, 1996, 20(3):478-485.

Heitman, SJ, et al., Colorectal Cancer Screening for Average-Risk North Americans: An Economic Evaluation. PLoS Med, 2010;7(11):e1000370.

Heller et al., Lung cancer: from single-gene methylation to methylome profiling. Cancer Metastasis Rev. Mar. 2010;29(1):95-107.

Henegariu et al., Multiplex PCR: critical parameters and step-by-step protocol. Biotechniques. Sep. 1997;23(3):504-11.

Heresbach, D., et al., Review in depth and meta-analysis of controlled trials on colorectal cancer screening by faecal occult blood test. Eur J Gastroenterol Hepatol. 2006, 18(4):427-33.

Herman et al., Methylation-specific PCR: a novel PCR assay for methylation status of CpG islands. Proc Natl Acad Sci USA 1996; 93: 9821-9826.

Higuchi et al., A general method of in vitro preparation and specific mutagenesis of DNA fragments: study of protein and DNA interactions, Nucleic Acids Research, 1988, 16(15):7351-7367.

Higuchi et al., Simultaneous amplification and detection of specific DNA sequences, Biotechnology, 1992, 10:413-417.

Higuchi et al.,Kinetic PCR analysis: real-time monitoring of DNA amplification reactions, Biotechnology, 1993, 11:1026-1030.

Hoque et al., Genome-Wide Promoter Analysis Uncovers Portions of the Cancer Methylome. J Clin Oncol. 2005;23:6569-75.

Imperiale et al., Fecal DNA versus Fecal Occult Blood for Colorectal-Cancer Screening in an Average-Risk Population. N Engl J Med, 2004;351:2704-14.

Itzkowitz, SH, et al., Improved Fecal DNA Test for Colorectal Cancer Screening. Clin Gastroenterol Hepatol 2007;5(1):111-7.

Jiang et al., Lengthening and shortening of plasma DNA in hepatocellular carcinoma patients. Proc Natl Acad Sci U S A. Mar. 17, 2015;112(11):E1317-25.

Kaiser et al., A comparison of eubacterial and archaeal structure-specific 5'-exonucleases. J Biol Chem. Jul. 23, 1999;274(30):21387-94.

Kalinina et al., Nanoliter scale PCR with TaqMan detection, Nucleic Acids Research, 1997, 25:1999-2004.

Kann et al., Improved Marker Combination for Detection of De Novo Genetic Variation and Aberrant DNA in Colorectal Neoplasia. Clin Chem 2006;52:2299-302.

Karl et al., Improved Diagnosis of Colorectal Cancer Using a Combination of Fecal Occult Blood and Novel Fecal Protein Markers. Clin Gastroenterol Hepatol, 2008;6(10):1122-8.

Kneip et al., SHOX2 DNA methylation is a biomarker for the diagnosis of lung cancer in plasma. J Thorac Oncol. Oct. 2011;6(10):1632-8.

Kober et al., Methyl-CpG binding column based identification of nine genes hypermethylated in colorectal cancer. Mol Carcinog. Nov. 2011;50(11):846-56.

Korbie et al., Multiplex bisulfite PCR resequencing of clinical FFPE DNA. Clin Epigenetics. Mar. 17, 2015;7:28.

Kronborg et al., Randomized Study of Biennial Screening with a Faecal Occult Blood Test: Results After Nine Screening Rounds. Scand J Gastroenterol, 2004; 39:846-51.

Kuppuswamy et al., Single nucleotide primer extension to detect genetic diseases: experimental application to hemophilia B (factor IX) and cystic fibrosis genes. Proc Natl Acad Sci U S A. Feb. 15, 1991;88(4):1143-7.

Leontiou et al., Bisulfite Conversion of DNA: Performance Comparison of Different Kits and Methylation Quantitation of Epigenetic Biomarkers that Have the Potential to Be Used in Non-Invasive Prenatal Testing. PLoS One. Aug. 6, 2015;10(8):e0135058.

Leung et al., Detection of Epigenetic Changes in Fecal DNA as a Molecular Screening Test for Colorectal Cancer: A Feasibility Study. Clin Chem, 2004;50(11):2179-82.

Levin et al., Screening and Surveillance for the Early Detection of Colorectal Cancer and Adenomatous Polyps, 2008: A Joint Guideline From the American Cancer Society, the US Multi-Society Task Force on Colorectal Cancer, and the American College of Radiology. Gastroenterology, 2008;134(5):1570-95.

Liu et al., Flap endonuclease 1: a central component of DNA metabolism. Annu Rev Biochem. 2004;73:589-615.

Lokk et al., Methylation markers of early-stage non-small cell lung cancer. PLoS One. 2012;7(6):e39813.

Lyamichev et al., Polymorphism identification and quantitative detection of genomic DNA by invasive cleavage of oligonucleotide probes, Nat. Biotech., 1999, 17:292-296.

Mandel et al., Reducing Mortality from Colorectal Cancer by Screening for Fecal Occult Blood. N Engl J Med. 1993, 328:1365-71.

Martin et al., Genomic sequencing indicates a correlation between DNA hypomethylation in the 5' region of the pS2 gene and its expression in human breast cancer cell lines. Gene. May 19, 1995;157(1-2):261-4.

Maxwell® RSC ccfDNA Plasma Kit, Technical Manual, Instructions for Use of Product AS1480, Promega Corporation, Feb. 2016.

Meissner et al., Patterns of Colorectal Cancer Screening Uptake among Men and Women in the United States. Cancer Epidemiol Biomarkers Prev., 2006; 15:389-94.

Meissner et al., Reduced representation bisulfite sequencing for comparative high-resolution DNA methylation analysis. Nucleic Acids Res. Oct. 13, 2005;33(18):5868-77.

Moreno et al., Circulating tumor cells predict survival in patients with metastatic prostate cancer. Urology. Apr. 2005;65(4):713-8.

Muller et al., Methylation changes in faecal DNA: a marker for colorectal cancer screening? Lancet, 2004;363:1283-5.

Munson et al., Recovery of bisulfite-converted genomic sequences in the methylation-sensitive QPCR. Nucleic Acids Res. 2007;35(9):2893-903.

Noutsias et al., Preamplification techniques for real-time RT-PCR analyses of endomyocardial biopsies. BMC Molecular Biology Jan. 14, 2008;9:3.

Nyce et al. Variable effects of DNA-synthesis inhibitors upon DNA methylation in mammalian cells. Nucleic Acids Res. 1986;14:4353-4367.

Nyce et al., Variable effects of DNA-synthesis inhibitors upon DNA methylation in mammalian cells. Nucleic Acids Res. May 27, 1986;14(10):4353-67.

Olek et al., A modified and improved method for bisulphite based cytosine methylation analysis. Nucleic Acids Res. Dec. 15, 1996;24(24):5064-6.

Olek et al., The pre-implantation ontogeny of the H19 methylation imprint. Nat Genet. Nov. 1997;17(3):275-6.

Olivier, The Invader assay for SNP genotyping, Mutat Res. Jun. 3, 2005;573(1-2):103-10.

Ooki et al., Potential utility of HOP homeobox gene promoter methylation as a marker of tumor aggressiveness in gastric cancer. Oncogene. Jun. 3, 2010;29(22):3263-75.

Orpana, Fluorescence resonance energy transfer (FRET) using ssDNA binding fluorescent dye, Biomol Eng. Apr. 2004;21(2):45-50.

Osborn et al. Stool screening for colorectal cancer: Molecular approaches. Gastroenterology, 2005;128(1):192-206.

Pantel et al., Detection, clinical relevance and specific biological properties of disseminating tumour cells. Nat Rev Cancer. May 2008;8(5):329-40.

(56)                References Cited

OTHER PUBLICATIONS

Parekh et al., As tests evolve and costs of cancer care rise: reappraising stool-based screening for colorectal neoplasia. Aliment Pharmacol Ther 2008;27:697-712.

Petko et al., Aberrantly Methylated CDKN2A, Mgmt, and MLH1 in Colon Polyps and in Fecal DNA from Patients with Colorectal Polyps. Clin Cancer Res, 2005;11:1203-9.

Ponomaryova et al., Potentialities of aberrantly methylated circulating DNA for diagnostics and post-treatment follow-up of lung cancer patients. Lung Cancer. Sep. 2013;81(3):397-403.

Ramsahoye et al., Non-CpG methylation is prevalent in embryonic stem cells and may be mediated by DNA methyltransferase 3a. Proc Natl Acad Sci U S A. May 9, 2000;97(10):5237-42.

Ramsahoye et al., Non-CpG methylation is prevalent in embryonic stem cells and may be mediated by DNA methyltransferase 3a. Proc. Natl. Acad. Sci. USA, 2000; 97(10): 5237-5242.

Rein et al., Identifying 5-methylcytosine and related modifications in DNA genomes. Nucleic Acids Res. May 15, 1998;26(10):2255-64.

Rex et al., American College of Gastroenterology Guidelines for Colorectal Cancer Screening 2008. Am J Gastroenterol, 2009;104:739-50.

Roux, Using mismatched primer-template pairs in touchdown PCR, Biotechniques, 1994, 16(5):812-814.

Ruano et al., Biphasic amplification of very dilute DNA samples via 'booster' PCR. Nucleic Acids Res. Jul. 11, 1989;17(13):5407.

Sadri et al., Rapid analysis of DNA methylation using new restriction enzyme sites created by bisulfite modification. Nucleic Acids Res. Dec. 15, 1996;24(24):5058-9.

Salomon et al., Methylation of mouse DNA in vivo: di- and tripyrimidine sequences containing 5-methylcytosine. Biochim Biophys Acta. Apr. 15, 1970;204(2):340-51.

Salomon R. et al., Methylation of Mouse DNA In Vivo: DI- and Tripyrimidine Sequences Containing 5-Methylcytosine. Biochim. Biophys. Acta. 1970;204: 340-351.

Schmidt et al., SHOX2 DNA methylation is a biomarker for the diagnosis of lung cancer based on bronchial aspirates. Send to BMC Cancer. Nov. 3, 2010;10:600.

Schouten et al., Relative quantification of 40 nucleic acid sequences by multiplex ligation-dependent probe amplification, Nucleic Acids Research, 2002, 30(12): e57.

Selvin, Fluorescence resonance energy transfer, 1995, Methods Enzymol. 1995;246:300-34.

Sharaf et al., Comparative Effectiveness and Cost-Effectiveness of Screening Colonoscopy vs. Sigmoidoscopy and Alternative Strategies. Am J Gastroenterol. 2013;108:120-32.

Siegel et al., Cancer Statistics, 2013. CA Cancer J Clin. 2013;63:11-30.

Singer-Sam et al., A quantitative Hpall-PCR assay to measure methylation of DNA from a small Number of cells. Nucleic Acids Res. Feb. 11, 1990;18(3):687.

Singer-Sam et al., A sensitive, quantitative assay for measurement of allele-specific transcripts differing by a single nucleotide. PCR Methods Appl. Feb. 1992;1(3):160-3.

Singh, H, et al., Risk of Developing Colorectal Cancer Following a Negative Colonoscopy Examination Evidence for a 10-Year Interval Between Colonoscopies. JAMA. 2006, 295:2366-73.

Stryer, Fluorescence energy transfer as a spectroscopic ruler, Annu Rev Biochem. 1978;47:819-46.

Szabo et al., Allele-specific expression and total expression levels of imprinted genes during early mouse development: implications for imprinting mechanisms. Genes Dev. Dec. 15, 1995;9(24):3097-108.

Toyota et al., Identification of differentially methylated sequences in colorectal cancer by methylated CpG island amplification. Cancer Res. May 15, 1999;59(10):2307-12.

Triglia et al., A procedure for in vitro amplification of DNA segments that lie outside the boundaries of known sequences, Nucleic Acids Res., 1988, 16:8186.

Vogelstein et al. Digital PCR. Proc Natl Acad Sci USA. 1999;96; 9236-41.

Vogelstein et al., Cancer Genome Landscapes. Science, 2013;339:1546-58.

Vogelstein et al., Digital PCR, PNAS, 1999, 96: 9236-41.

Winawer et al., Screening for Colorectal Cancer With Fecal Occult Blood Testing and Sigmoidoscopy. J Natl Cancer Inst. 1993, 85(16):1311-8.

Woodcock et al. The majority of methylated deoxycytidines in human DNA are not in the CpG dinucleotide. Biochem. Biophys. Res. Commun. 1987; 145: 888-894.

Woodcock et al., The majority of methylated deoxycytidines in human DNA are not in the CpG dinucleotide. Biochem Biophys Res Commun. Jun. 15, 1987;145(2):888-94.

Wrangle et al., Functional identification of cancer-specific methylation of CDO1, HOXA9, and TAC1 for the diagnosis of lung cancer. Clin Cancer Res. Apr. 1, 2014;20(7):1856-64.

Xiong et al., COBRA: a sensitive and quantitative DNA methylation assay. Nucleic Acids Res. Jun. 15, 1997;25(12):2532-4.

Yamada et al., Fluorometric identification of 5-methylcytosine modification in DNA: combination of photosensitized oxidation and invasive cleavage. Bioconjug Chem. Jan. 2008;19(1):20-3.

Zeschnigk et al., Imprinted segments in the human genome: different DNA methylation patterns in the Prader-Willi/Angelman syndrome region as determined by the genomic sequencing method. Hum Mol Genet. Mar. 1997;6(3):387-95.

Zou et al., A Sensitive Method to Quantify Human Long DNA in Stool: Relevance to Colorectal Cancer Screening. Cancer Epidemiol Biomarkers Prev, 2006;15(6):1115-9.

Zou et al., Detection of Aberrant p16 Methylation in the Serum of Colorectal Cancer Patients. Clin Cancer Res 2002;8(1):188-91.

Zou et al., Quantification of methylated markers with a multiplex methylation-specific technology. Clin Chem 2012; 58: 375-383.

Zou et al., Quantification of methylated markers with a multiplex methylation-specific technology. Clin Chem. Feb. 2012;58(2):375-83.

Zou et al., Sensitive quantification of methylated markers with a novel methylation specific technology. Abstract D-144, Clin Chem 2010;56(6)Suppl:A199.

European Supplemental Search Report for EP17792973.4, mailed Jan. 3, 2020, 15 pages.

International Search Report and Written Opinion for PCT/US2016/058875, mailed Apr. 21, 2017, 17 pages.

International Search Report and Written Opinion for PCT/US2017/024468, mailed Sep. 1, 2017, 17 pages.

International Search Report and Written Opinion for PCT/US2018/015535, mailed Jun. 25, 2018, 20 pages.

International Search Report and Written Opinion for PCT/US2019/063401, mailed Feb. 20, 2020, 12 pages.

Certified Copy of U.S. Appl. No. 60/900,713, filed Feb. 12, 2007, in the name of Baylin et al., 188 pages.

Fackler et al., Quantitative multiplex methylation-specific PCR assay for the detection of promoter hypermethylation in multiple genes in breast cancer. Cancer Res. Jul. 1, 2004;64(13):4442-52.

Louwagie et al., Feasibility of a DNA methylation assay for noninvasive CRC screening. Clin Cancer Res. Oct. 2007;13(19 Suppl):B16.

Olkhov-Mitsel et al., Novel multiplex MethyLight protocol for detection of DNA methylation in patient tissues and bodily fluids. Sci Rep. Mar. 21, 2014;4:4432.

Schuebel et al., Comparing the DNA hypermethylome with gene mutations in human colorectal cancer. PLoS Genet. Sep. 2007;3(9):1709-23.

Straub et al., Base5, a versatile, highly integrated high-throughput methylation profiling for methylation specific PCR based marker identification applied to colorectal cancer. Clin Cancer Res. Oct. 2007; 13(19 Suppl):A61.

Swift-Scanlan et al., Two-color quantitative multiplex methylation-specific PCR. Biotechniques. Feb. 2006;40(2):210-9.

Yoo et al., Epigenetic therapy of cancer: past, present and future. Nat Rev Drug Discov. Jan. 2006;5(1):37-50.

Notice of Opposition and Statement filed in EP Pat 3434791, filed Mar. 5, 2021, 16 pages.

(56)        References Cited

OTHER PUBLICATIONS

Anderson et al., Methylated DNA Markers for Detection of Sporadic Colorectal Neoplasia: Comparison Between Age Groups Younger Than and Older Than 50. Abstract Su2013. Gastroenterology Apr. 1, 2016;150(4):S-611.

Ballester et al., Novel Methylated DNA Markers for the Detection of Colorectal Neoplasia in Lynch Syndrome. Abstract 307. Gastroenterology 2016;150(4):S-70.

Chen et al., DNA Methylation Identifies Loci Distinguishing Hereditary Nonpolyposis Colorectal Cancer Without Germ-Line MLH1/MSH2 Mutation from Sporadic Colorectal Cancer. Clin Transl Gastroenterol. Dec. 15, 2016;7(12):e208.

Gevaert et al., Pancancer analysis of DNA methylation-driven genes using MethylMix. Genome Biol. Jan. 29, 2015;16(1):17.

Kisiel et al., New DNA Methylation Markers for Pancreatic Cancer: Discovery, Tissue Validation, and Pilot Testing in Pancreatic Juice. Clin Cancer Res. Oct. 1, 2015;21(19):4473-81.

Kisiel et al., Novel Stool DNA Markers for Inflammatory Bowel Disease Associated Colorectal Cancer High Grade Dysplasia: High Specificity Across Three Independent International Populations. Abstract 185. Gastroenterology 2016;150(4):S-48.

Knute et al., MicroRNAs as Novel Targets for NSAID Chemoprevention of Color Carcinogenesis. Gastroenterology. May 2011; 140(5):S-41.

Lange et al., Genome-scale discovery of DNA-methylation biomarkers for blood-based detection of colorectal cancer. PLoS One. 2012;7(11):e50266.

Levin et al., Genetic Biomarker Prevalence Is Similar in Fecal Immunochemical Test Positive and Negative Colorectal Cancer Tissue. Dig Dis Sci. Mar. 2017;62(3):678-688.

Medina-Aguilar et al., Methylation Landscape of Human Breast Cancer Cells in Response to Dietary Compound Resveratrol. PLoS One. Jun. 29, 2016;11(6):e0157866.

Mitchell et al., A panel of genes methylated with high frequency in colorectal cancer. BMC Cancer. Jan. 31, 2014;14:54.

Mitchell et al., Evaluation of Methylation Biomarkers for Detection of Circulating Tumor DNA and Application to Colorectal Cancer. Genes (Basel). Dec. 15, 2016;7(12):125.

Taylor et al., Discovery of Novel DNA Methylation Markers for the Detection of Colorectal Neoplasia: Selection by Methylome-Wide Analysis. Abstract 109. Gastroenterology May 1, 2014;146(5)S-30.

Weisenberger et al., Comprehensive DNA Methylation Analysis on the Illumina® Infinium® Assay Platform. Jan. 1, 2010. https://emea.illumina.com/content/dam/illumina-marketing/documents/products/appnotes/appnote_dna_methylation_analysis_infinium.pdf. Retrieved Dec. 4, 2020. 4 pages.

Wu et al., Detection of Colorectal Cancer Using a Simplified SEPT9 Gene Methylation Assay Is a Reliable Method for Opportunistic Screening. J Mol Diagn. Jul. 2016;18(4):535-45.

European Supplemental Search Report for EP18744801.4, mailed Dec. 14, 2020, 23 pages.

Feng et al., Genome-wide analysis of DNA methylation and their associations with long noncoding RNA/mRNA expression in non-small-cell lung cancer. Epigenomics. Jan. 2017;9(2):137-153.

Hosono et al., Multiplex PCR-based real-time invader assay (mPCR-RETINA): a novel SNP-based method for detecting allelic asymmetries within copy number variation regions. Hum Mutat. Jan. 2008;29(1):182-9.

Kwiatkowski et al., Clinical, genetic, and pharmacogenetic applications of the Invader assay. Mol Diagn. Dec. 1999;4(4):353-64.

Tadokoro et al., Classification of hepatitis B virus genotypes by the PCR-Invader method with genotype-specific probes. J Virol Methods. Dec. 2006;138(1-2):30-9.

International Search Report and Written Opinion for PCT/US2021/027770. Mailed Aug. 5, 2021. 10 pages.

Koh et al., Prognostic Role of S100A8 and S100A9 Protein Expressions in Non-small Cell Carcinoma of the Lung. J Pathol Transl Med. Jan. 2019;53(1):13-22.

Lim et al., An extracellular matrix-related prognostic and predictive indicator for early-stage non-small cell lung cancer. Nat Commun. Nov. 23, 2017;8(1):1734.

Shi et al., Endogenous PAD4 in Breast Cancer Cells Mediates Cancer Extracellular Chromatin Network Formation and Promotes Lung Metastasis. Mol Cancer Res. May 2020; 18(5):735-747.

Extended European Search Report for 21195952.3. Mailed Apr. 12, 2022. 8 pages.

Partial EP Search Report for EP 20856304.9, mailed Oct. 26, 2023, 13 pages.

Extended EP Search Report for EP 20856304.9, mailed Apr. 18, 2024, 19 pages.

Ballester V., et al., "Novel Methylated DNA Markers for the Detection of Colorectal Neoplasia in Lynch Syndrome," Abstract 307, Gastroenterology, 2016, vol. 150, No. 4, p. S-70.

Campan M., et al., "Genome-Scale Screen for DNA Methylation-Based Detection Markers for Ovarian Cancer," PLoS One, Supporting Information, Dec. 2011, vol. 6, No. 12, e28141,23 Pages.

Carvalho R.H., et al., "Genomewide DNA Methylation Analysis Identifies Novel Methylated Genes in Non-Small-Cell Lung Carcinomas," Journal of Thoracic Oncology, May 2013, vol. 8, No. 5, pp. 562-573(12 Pages).

Extended European Search Report for European Application No. 18744801.4, mailed Dec. 14, 2020, 22 Pages.

Gevaert, et al., "Supplementary Figures for Pancancer Analysis of DNA Methylation-Driven Genes Using MethylMix," Jan. 1, 2015, pp. 1-17, figure 2, XP055756583 [Retrieved on Dec. 4, 2020] Retrieved from URL: https://static-content.springer.com/es m/art%3A10.1186%2Fs13059-014-0579-8/MediaObjects/13059_2014579_MOESMI_ESM.pdf.

Hoque M.O., et al., "Genome-Wide Promoter Analysis Uncovers Portions of the Cancer Methylome," Cancer Research, Apr. 15, 2008, vol. 68, No. 8, pp. 2661-2670 (11 Pages).

Hua D., et al., "Quantitative Methylation Analysis of Multiple Genes Using Methylation-Sensitive Restriction Enzyme-based Quantitative PCR for the Detection of Hepatocellular Carcinoma," Experimental and Molecular Pathology, Aug. 2011, vol. 91, No. 1, pp. 455-460.

Illumina: "Infinium HumanMethylation450K BeadChip, Product Files," CSV Format, May 23, 2013, 2 Pages, Retrieved from URL:support.illumina.com/array/array_kits/infinium_humanmethylation450_beadchip_ kit/downloads. html.

Ivetic A., et al., "L-selectin: A Major Regulator of Leukocyte Adhesion, Migration and Signaling", Frontiers in Immunology, vol. 10, 1068, May 14, 2019, pp. 1-22.

Maxwell RSC CCFDNA Plasma Kit: "Revised Feb. 2016 TM454 Revised Feb. 2016 TM454," Promega, Feb. 1, 2016, XP055653488, [Retrieved on Feb. 17, 2019] Retrieved from URL: https://www.nmas.no/files/nmas/Documents/Celle-%20og%20molekyl%C3%A6rbiologi/DNA%20og%20RNA%20systemer/maxwell-rsc-ccfdna- plasma-kit-protocol.pdf.

Nakamura K., et al., "Epigenetic Silencing of HOPX and its Potential Tumor Suppressive Role in Gastrointestinal Cancer," Journal of the Japan Society of Molecular Tumor Marker Research, 2014, vol. 29, pp. 22-23.

Osman M., et al., "Expression of Matrix Metalloproteinases and Tissue Inhibitors of Metalloproteinases Define the Migratory Characteristics of Human Monocyte-derived Dendritic Cells," Immunology, Jan. 2002, vol. 105, No. 1, pp. 73-82.

Partial Supplementary European Search Report for European Application No. 18744801.4, mailed Sep. 7, 2020, 15 Pages.

Sharan R.N., et al., "Consensus Reference Gene(s) for Gene Expression Studies in Human Cancers: End of the Tunnel Visible?", Cellular Oncology, vol. 38, Sep. 2015, pp. 419-431.

Waraya M., et al., "Clinical Relevance of Cancer-Specific Promoter DNA Methylation of Homeobox only Protein (HOPX) in Pancreatic Cancer," Journal of the Japan Society of Molecular Tumor Marker Research, 2012, vol. 27, pp. 65-66.

Zhou S., et al., "DNA Methylation of METTL7A Gene Body Regulates Its Transcriptional Level in Thyroid Cancer", Oncotarget, vol. 8, No. 21, Mar. 2017, pp. 34652-34660.

(56) References Cited

OTHER PUBLICATIONS

Morris S.M., et al., "Whole blood FPR1 mRNA expression identifies both non-small cell and small cell lung cancer", Journal of Thoracic Oncology, vol. 11 No. 2S, Apr. 2010, p. S34.

Rousseaux S., et al., "Ectopic Activation of Germline and Placental Genes Identifies Aggressive Metastasis-Prone Lung Cancers", Science Translational Medicine, vol. 5, No. 186, pp. 1-11, Supplementary Materials, pp. 1-211, May 22, 2013, 222 pages.

Sandoval-Pinto E., "Influence of Haplotypes, Gene Expression and Soluble Levels of L-selectin on the Risk of Acute Coronary Syndrome", Gene, vol. 625, 2017, pp. 31-41, https://doi.org/10.1016/j.gene.2017.05.005.

Shames D.S., et al., "A Genome-Wide Screen for Promoter Methylation in Lung Cancer Identifies Novel Methylation Markers for Multiple Malignancies", PLoS Medicine, vol. 3, No. 2, e486, Dec. 2006, pp. 2244-2263.

Smirnov D.A., et al., "Global Gene Expression Profiling of Circulating Endothelial Cells in Patients with Metastatic Carcinomas", Cancer Research, vol. 66, No. 6, Mar. 15, 2006, pp. 2918-2922.

Xu W., et al., "Genome-Wide Plasma Cell-Free DNA Methylation Profiling Identifies Potential Biomarkers for Lung Cancer", Disease Markers, vol. 2019, Feb. 2, 2019, doi: 10.1155/2019/4108474, pp. 1-7.

Yan-Jun S., et al., "Up-regulation of the expression of S100A8 and S100A9 in lung adenocarcinoma and its correlation with inflammation and other clinical features", Chinese Medical Journal, vol. 123, No. 16, pp. 2215-2220.

* cited by examiner

FIG. 1

AGRN Target DNA (SEQ ID NO:1)

5'GTTCCCGGAACGGCCTCTTGGGGGCGTTCCAGCCCCACGGACCCGCAGGGAGTCCCCGCGCCAATTTGCATGGGG
CTCATTTGCATGACCCCCGCCCCCGCGGGGAGTCGGGGGCGC3'

Bisulfite-converted Target DNA: (SEQ ID NO:2)

5'GTTTTCGGAACGGTTTTTTGGGGGCGTTTTTAGTTTTTACGGATTCCGTAGGGAGTTTTTCGTCGTAATTTGTATGGGG
TTTATTTGTATGATTTCGTTTCGTTTCGCGCGGGAGTCGGGGGCGT3'

PCR and Flap Assay Oligonucleotides:

AGRN Forward Primer:    5' GGCGTTTTTAGTTTTTACGGATTCG3' (SEQ ID NO:3)
AGRN Reverse Primer:    5' ACAAATAAACCCCATACAAATTACGAC3' (SEQ ID NO:4)
AGRN Flap oligo.:       5' CGCCGAGGCGAAAACTCCCT/3C6/ (SEQ ID NO:5)

FIG. 1 (cont'd)

ANGPT1 Target DNA: (SEQ ID NO:6)

5'CGGATTCAACATGGGCAATGTGCCTACACTTTCATTCTTCCAGAACACGATGGCAACTGTCGTGAGAGTACGACA
GACCAGTACAACACACAAACGCCTCTGCAGAGAGATGCTCCACACGTGGAACCG3'

Bisulfite-converted Target DNA: (SEQ ID NO:7)

5'CGGATTTAATATGGGTAATGTGTTTATATTTTTATTTTTTTAGAATACGATGGTAATTGTCGTGAGAGTACGATA
GATTAGTATAATATAAACGTTTTGTAGAGAGATGTTTTATACGTGGAATCG3'

PCR and Flap Assay Oligonucleotides:

ANGPT1 Forward Primer:    5'TTTTAGAATACGATGGTAATTGTCGT3'    (SEQ ID NO:8)
ANGPT1 Reverse Primer:    5'ACATCTCTCTACAAAACGTTTATATTATACTAATC3'(SEQ ID NO:9)
ANGPT1 Flap oligo.:       5'CGCCGAGGCTATCGTACTCT/3C6/ (SEQ ID NO:10)

FIG. 1 (cont'd)

ANKRD13B Target DNA: (SEQ ID NO:11)

5'GGAGCTACGACGAGCAGCTGCGGCTGGCGATGGAACTGTCGGGCGCAGGAGCAGGAGGAGGAGGCGGCGGCGCGC
GCCAGGAGGAGGAGGAGCTGGAGCGCATCCCTGAG3'

Bisulfite-converted Target DNA: (SEQ ID NO:12)

5'GGAGTTACGACGAGTAGTTGCGGTTGGCGATGGAATTGTCGGGCGTAGGAGTAGGAGGAGGAGGCGGCGGCGCGC
GTTAGGAGGAGGAGGAGTTGGAGCGTATTTTGAG3'

PCR and Flap Assay Oligonucleotides:

ANKRD13B Forward Primer:     5'AGTTACGACGAGTAGTTGCG3' (SEQ ID NO:13)
ANKRD13B Reverse Primer:     5'TCCTCCTACTCCTACGCC3' (SEQ ID NO:14)
ANKRD13B Flap oligo.:        5'CCACGACGACGACAATTCCAT/3C6/(SEQ ID NO:15)

FIG. 1 (cont'd)

ARHGEF4 Target DNA: (SEQ ID NO:16)

5'GGTGGCAACGGCTGGAGTGCCGTCGCCCGCCCACTCACCCCGCGCGGCGCCCTGCGCGGCGCTCAGCGGGAAG
GCCAGCAGGAAGATCAGTACGACGTTGATGAGAACCAGGAGCGCACGGGCGGAGACCACCACGCG3'

Bisulfite-converted Target DNA: (SEQ ID NO:17)

5'GGTGGTAACGGTTGGAGTGTCGTCGTTCGTTTATTTATTTCGGCGCGTTTTGCGCGGTCGTTTAGCGGGAAG
GTTAGTAGGAAGATTAGTACGACGTTGATGAGAATTAGGAGCGTTAGTACGGGCGGAGATTATTACGCG3'

PCR and Flap Assay Oligonucleotides:

ARHGEF4 Forward Primer: 5'CGTTCGCGTTATTTATTTCGGCG3' (SEQ ID NO:18)
ARHGEF4 Reverse Primer: 5'GCTCCTAATTCTCATCAACGTCGT3' (SEQ ID NO:19)
ARHGEF4 Flap oligo.: 5'CGCCGAGGGCGGCGGTTTTGC/3C6/ (SEQ ID NO:20)

FIG. 1 (cont'd)

B3GALT6 Target DNA: (SEQ ID NO:384)

5'GGCCACACAGGCCCACTCTGGCCCTCTGAGCCCCGGCGGACCCCAGGGCATTCAAGGAGGCCTCTGGGCTGCCA
GCGCAGGCCTCCGCGCAAACACAGCAGGCTGGAAGTGGCGCTCATCACCGGCACGTCTTCCCAG3'

Bisulfite-converted target DNA with primer and Flap oligo. sites: (SEQ ID
NO:385)

5'GGTTATATAGGTTTATTTTGGTTTTTTTGAGTTTTTCGGCGGGATTTAGGGTATTTAAGGAGGCGGTTTTGGGTTGTTA
GCGTAGGTTTTTCGCGTAAATATAGTAGGTTGGAAGTGGCGTTTATTATCGGTACGTTTTTTTAG3'

PCR and Flap Assay oligonucleotides:

B3GALT6 Forward Primer:   5'GGTTTATTTTGGTTTTTTTGAGTTTTCGG3' (SEQ ID NO:386)
B3GALT6 Reverse Primer:   5'TCCAACCTACTATATTTACGCGAA3' (SEQ ID NO:387)
B3GALT6 Flap oligo.:   5'CCACGGACGGGCGGATTTAGGG/3C6/ (SEQ ID NO:388)

FIG. 1 (cont'd)

BARX1 Target DNA: (SEQ ID NO:21)

5'GGCCCGGGGCCCGCTGGGCCCCTAGGGGCTGGACGTCAACCTGTTAGATAGAGGGGCGTGGGACCCCCCGCAGGCG
GCTGCTCGGACGACCGCATCCGGAG3'

Bisulfite-converted Target DNA: (SEQ ID NO:22)

5'GGTTCGGGGTCGTTTGGGTTTTTAGGGGTTGGACGTTAATTTGTTAGATAGAGGGGCGTGGGATTTTTCGTAGGCG
GTTGTTCGGACGATCGTATTCGGAG3'

PCR and Flap Assay Oligonucleotides:

BARX1 Forward Primer:        5'CGTTAATTTGTTAGATAGAGGGGCG3' (SEQ ID NO:23)
BARX1 Reverse Primer:        5'ACGATCGTCCGAACAACC3' (SEQ ID NO:24)
BARX1 Flap oligo.:           5'CCACGGACGCGCCTACGAAAA/3C6/ (SEQ ID NO:25)

BARX1 Forward Primer:        5'CGTTAATTTGTTAGATAGAGGGGCG3' SEQ ID NO:23)
BARX1 Reverse Primer Universal:    5' TCCGAACAACCGCCTAC3'(SEQ ID NO:26)
BARX1 Flap oligo. Universal:  5' CCACGGACGCGAAAAATCCCA/3C6/ (SEQ ID NO:27)

FIG. 1 (cont'd)

BCAT1 Target DNA: (SEQ ID NO:28)

5'GCTTCCAGCCGCGGCGCTCCGTGCCACTGCCGCTCTCTGCAGCCCCGCGTCCCGAGCCTCCCCATGGCCAGCCC
GCTTCGCTCCGCTGCGGGGCCCTTGCCCGCGCCAGGTACCTCGAACCC3'

Bisulfite-converted Target DNA: (SEQ ID NO:29)

5'GTTTTTAGTCGCGGCGTTTCGTGTTATTGTCGTTTTTTGTAGTTTCGCGTAGTTTTTTTATGGTTAGTTC
GTTTCGTTTCGTTGCGGTTTTTGCGGTTTTTGTGTTAGGTATTTCGAATTT3'

PCR and Flap Assay Oligonucleotides:

BCAT1 Forward Primer:    5'GTGTTATTGTCGTTTTTTGTAGTTTCG3' (SEQ ID NO:30)
BCAT1 Reverse Primer:    5'CGCAACGAAACGAAACGA3' (SEQ ID NO:31)
BCAT1 Flap oligo.:       5'CGCCGAGGGCGTTTTCGTAG/3C6/ (SEQ ID NO:32)

FIG. 1 (cont'd)

BCL2L11 Target DNA: (SEQ ID NO:33)

5′GCCCGGCCGCACGGCCGCAATGCTCCGCGCTCCCCGCGGGGGTCGGGCGACTCAGACAGGGACCGGAAAAGAACCACG
CAGAAGAAAGCCCTATTTCTTGTCGTCTGTTCCTGTGCTCGTTCCTGTTCCTGTGCAGCCTTGCAGCCTTCGCCGCCCCCGCGT3′

Bisulfite-converted Target DNA: (SEQ ID NO:34)

5′GTTCGTCGTACGTCGTAATGTTTCGCGGGGTCGGGCGTTTTTCGCGGGGGTCGGGCGATTTAGATAGGGATCGGAAAAGAATTACG
TAGAAGAAAGTTTATTTTTGTCGTTTTGTGTAGTTTTGTTAGTTTTCGTCGTTTTCGCGT3′

PCR and Flap Assay Oligonucleotides:

BCL2L11 Forward Primer:     5′CGTAATGTTTCGCGTTTTTCG3′ (SEQ ID NO:35)

BCL2L11 Reverse Primer:     5′ACTTTCTTCTACGTAATTCTTTTCCGA3′ (SEQ ID NO:36)

BCL2L11 Flap oligo.:        5′CGCCGAGGGCGGGGGTCGGGC/3C6/ (SEQ ID NO:37)

FIG. 1 (cont'd)

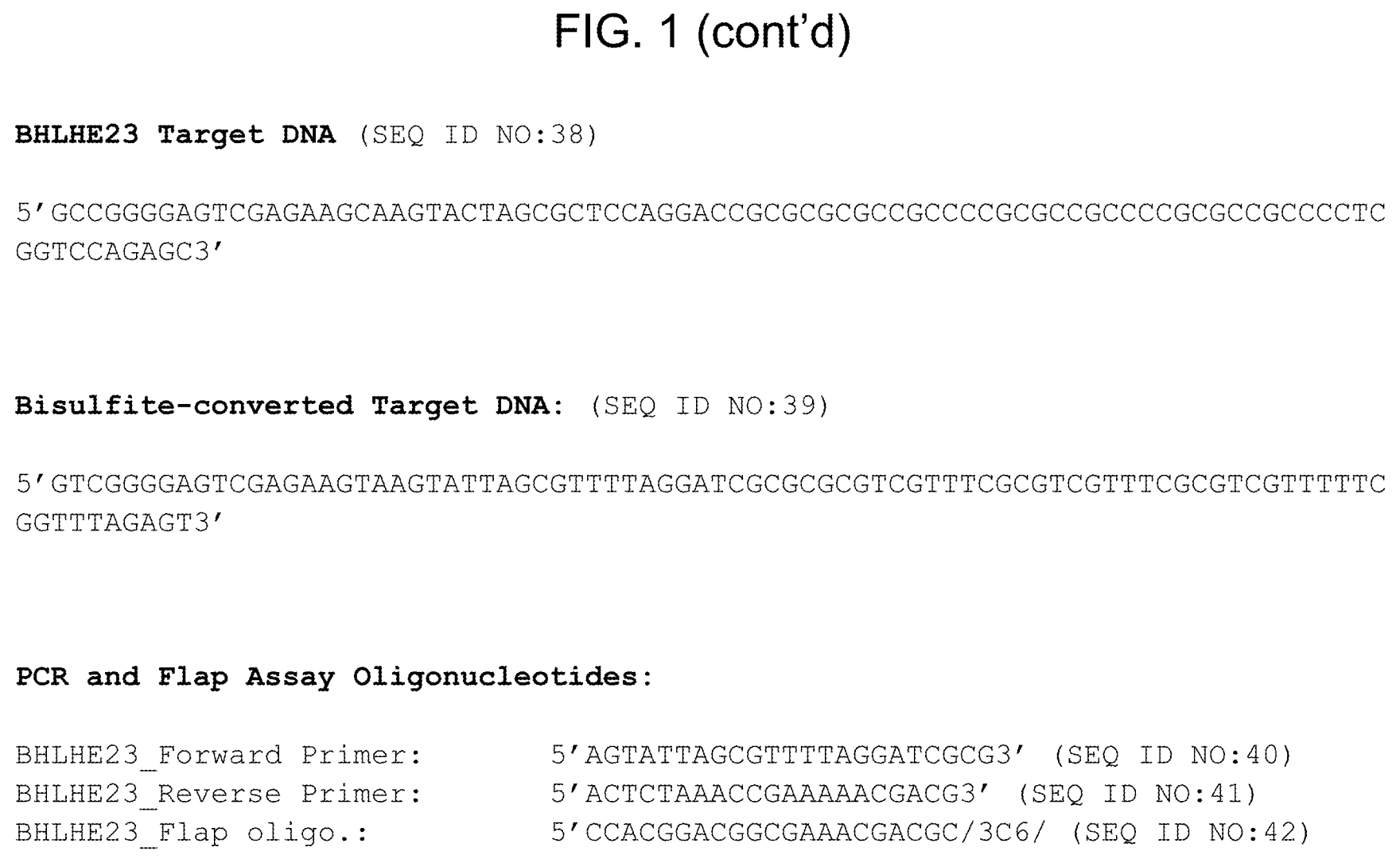

BHLHE23 Target DNA (SEQ ID NO:38)

5'GCCGGGGAGTCGAGAAGCAAGTACTAGCGCTCCAGGACCGCGCGGCGCCCGCGCGCCGCCCCTC
GGTCCAGAGC3'

Bisulfite-converted Target DNA: (SEQ ID NO:39)

5'GTCGGGGAGTCGAGAAGTAAGTATTAGCGTTTTAGGATCGCGCGGCGTTTCGCGGTCGTTTTTC
GGTTTAGAGT3'

PCR and Flap Assay Oligonucleotides:

BHLHE23_Forward Primer:    5'AGTATTAGCGTTTTAGGATCGGCG3'  (SEQ ID NO:40)
BHLHE23_Reverse Primer:    5'ACTCTAAACCGAAAAACGACACG3'  (SEQ ID NO:41)
BHLHE23_Flap oligo.:    5'CCACGGACGCGGCGAAACGACGACGC/3C6/ (SEQ ID NO:42)

FIG. 1 (cont'd)

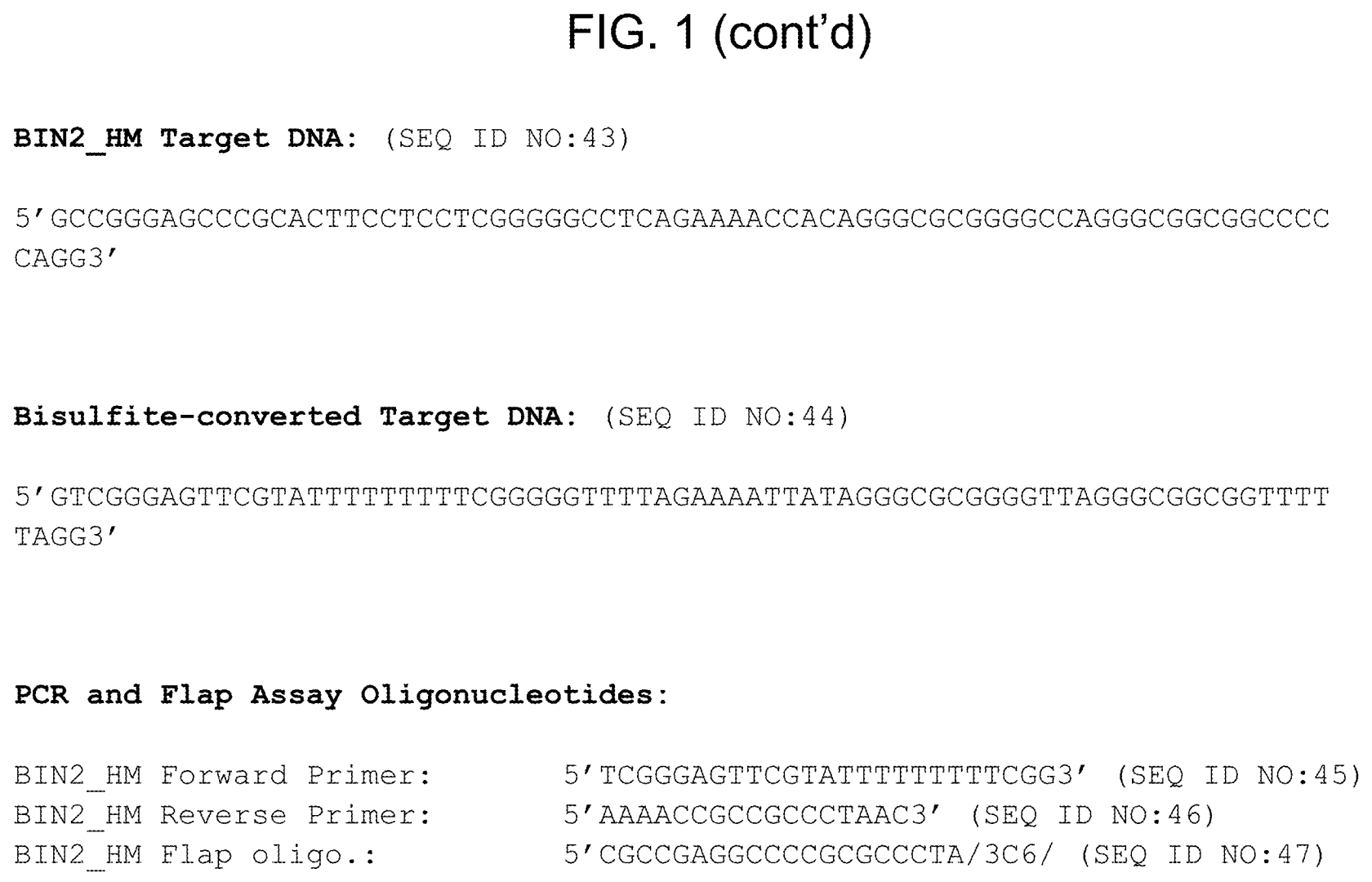

BIN2_HM Target DNA: (SEQ ID NO:43)

5'GCCGGGAGCCCGCACTTCCTCCTCGGGGGCCTCAGAAAACCACAGGGCGCGGGGCCAGGGCGCGGCCCC
CAGG3'

Bisulfite-converted Target DNA: (SEQ ID NO:44)

5'GTCGGGAGTTCGTATTTTTTTTTTCGGGGGTTTTAGAAAATTATAGGGCGCGGGGTTAGGGGCGCGGTTTT
TAGG3'

PCR and Flap Assay Oligonucleotides:

BIN2_HM Forward Primer:    5'TCGGGGAGTTCGTATTTTTTTTTCGG3'  (SEQ ID NO:45)
BIN2_HM Reverse Primer:    5'AAAACCGCCGCCCTAAC3'  (SEQ ID NO:46)
BIN2_HM Flap oligo.:    5'CGCCGAGGCCCGCCCCTA/3C6/  (SEQ ID NO:47)

FIG. 1 (cont'd)

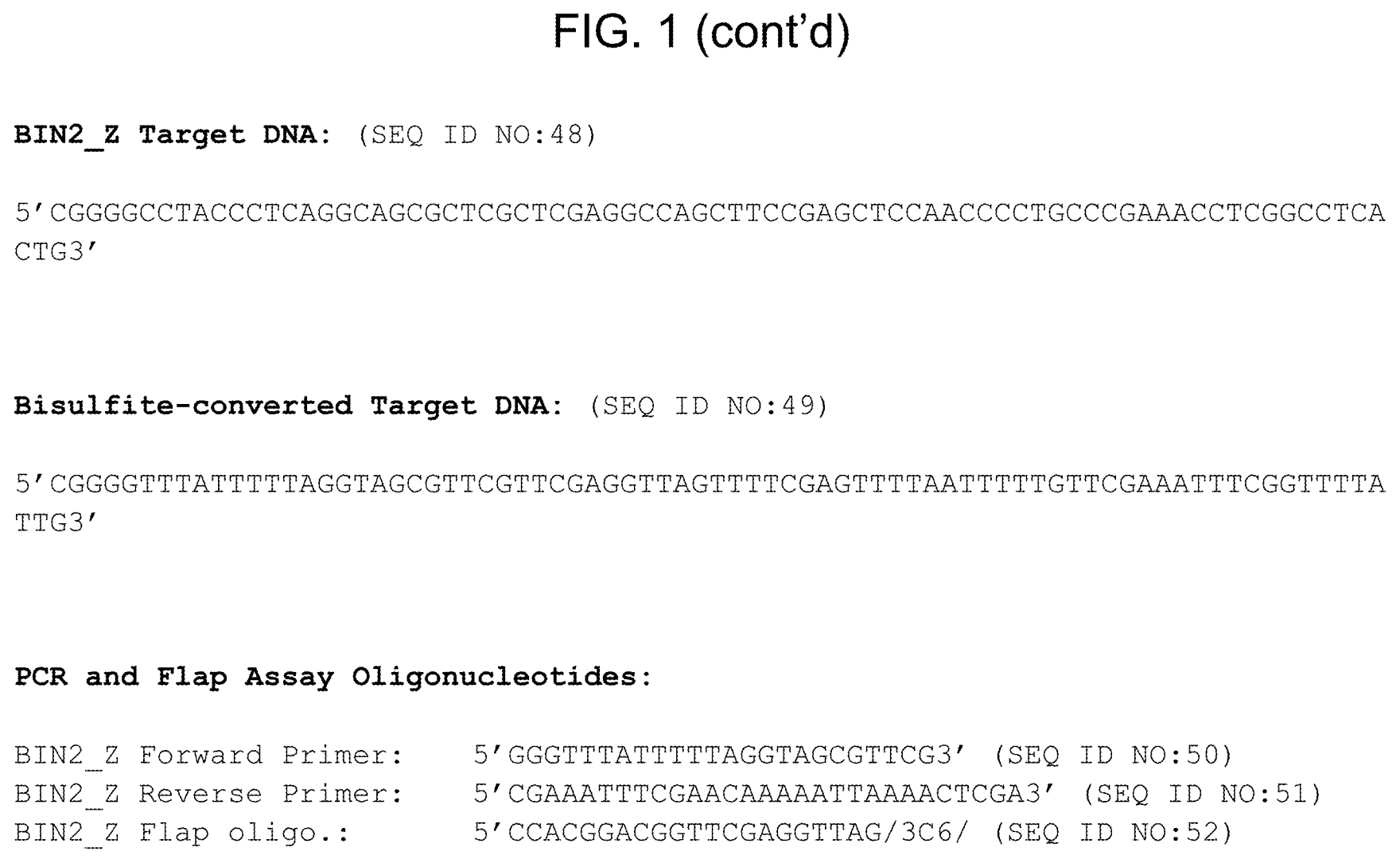

BIN2_Z Target DNA: (SEQ ID NO:48)

5'CGGGGCCTACCCCTCAGGCAGCGCTCGCTCGAGGCCAGCTTCCGAGCTCCAACCCCTGCCCGAAACCTCGGCCTCA CTG3'

Bisulfite-converted Target DNA: (SEQ ID NO:49)

5'CGGGGTTTATTTTTAGGTAGCGTTCGTTCGAGGTTAGTTTTTGTTCGAAATTTCGGTTTTA TTG3'

PCR and Flap Assay Oligonucleotides:

BIN2_Z Forward Primer:    5'GGGTTTATTTTTAGGTAGCGTTCG3' (SEQ ID NO:50)
BIN2_Z Reverse Primer:    5'CGAAATTTCGAACAAAAATTAAAACTCGA3' (SEQ ID NO:51)
BIN2_Z Flap oligo.:    5'CCACGGACGGTTCGAGGTTAG/3C6/ (SEQ ID NO:52)

FIG. 1 (cont'd)

CAPN2 Target DNA (SEQ ID NO:53)

5'TGTCCTGACACGATGGCCACAGGCACAGTTTGTGGTGATGCCCAGGGGCGCGCGGCCCCACGGTGGTCCAGTT
TACACTCGGGCCCCGCACTCCTGAAGTTCCGCGCGGGAGGAGAAGGGCGTCCCTTTCGCAGCTCGG3'

Bisulfite-converted Target DNA: (SEQ ID NO:54)

5'TGTTTTGATACGATGGTTATAGGTATAGTTTGTGGTGATGTTTAGGGGTTCGCGCGGTTTTACGGTGGTTTAGTT
TATATTCGGGTTTCGTATTTTTGAAGTTTCGCGCGGGAGGAGAAGGGCGTTTTTTCGTAGTTCGG3'

PCR and Flap Assay Oligonucleotides:

CAPN2 Forward Primer:  5'TGATGTTTAGGGGTTCGCG3' (SEQ ID NO:55)
CAPN2 Reverse Primer:  5'CGAAACTTCAAAAATACGAAACCCGA3' (SEQ ID NO:56)
CAPN2 Flap oligo.:  5'CGCCGAGGGCGGTTTTACGG/3C6/ (SEQ ID NO:57)

FIG. 1 (cont'd)

chr5_132 Target DNA: (SEQ ID NO:58)

5'CCGGAGCACTCGCGCGCCTGCGCGCCCTGAAGCCGCTGGCGGTAGGCGGCCCTCGAGGCCGCGGCCTGGGCGGCTC
GGCAGCCTGGCGCCGGGCCTCCGCGCCTCGGCGCCGCCAGC3'

Bisulfite-converted Target DNA: (SEQ ID NO:59)

5'TCGGAGTATTCGTCGTTGCGCGTTTTGAAGTCGTTGGCGGTAGGCGGTTTTCGAGGTCGGCGGGGGTTGGGCGGTTC
GGTAGTTTGCGTCGGGGTTTTCGTTTCGGTCGTTAGT3'

PCR and Flap Assay Oligonucleotides:

chr5_132 Forward Primer:     5'GTATTCGTCGTTGCGCG3' (SEQ ID NO:60)

chr5_132 Reverse Primer:     5'CCTCGAAAACCGCCTACC3' (SEQ ID NO:61)

chr5_132 Flap oligo.:        5'CCACGGACGCGCCAACGACTT/3C6/ (SEQ ID NO:62)

FIG. 1 (cont'd)

chr7_636 Target DNA: (SEQ ID NO:63)

5'CGCCGTGAGTGTTATAGTTCTTAAAGGCGGCCGTGTCCGGAGTTTCTTCCTTCTGGTGGGGTTCGTGGTCTCGCCG
GCTCAGGAGTGAAGCTGCAGATCTTCGCGGTGAGTGTTACAGCTCCTAAGGCGGGCGCAT3'

Bisulfite-converted Target DNA: (SEQ ID NO:64)

5'CGTCGTGAGTGTTATAGTTTTTAAAGGCGGTCGTGTTCGGAGTTTTTTTTTTTGGTGGGGTTCGTGGTTTCGTCG
GTTTAGGAGTGAAGTTGTAGATTTTCGCGGTGAGTGTTATAGTTTTTATAGTTTTTAAGGCGGGCGTAT3'

PCR and Flap Assay Oligonucleotides:

chr7_636_HM Forward Primer:    5'TAAAGGCGGCCGTGTTCG3' (SEQ ID NO:65)

chr7_636_HM Reverse Primer:    5'CAACTTCACTCCTAAACCGAC3' (SEQ ID NO:66)

chr7_636_HM Flap oligo.:       5'CCACGGACGCGAAACCACGAA/3C6/ (SEQ ID NO:67)

FIG. 1 (cont'd)

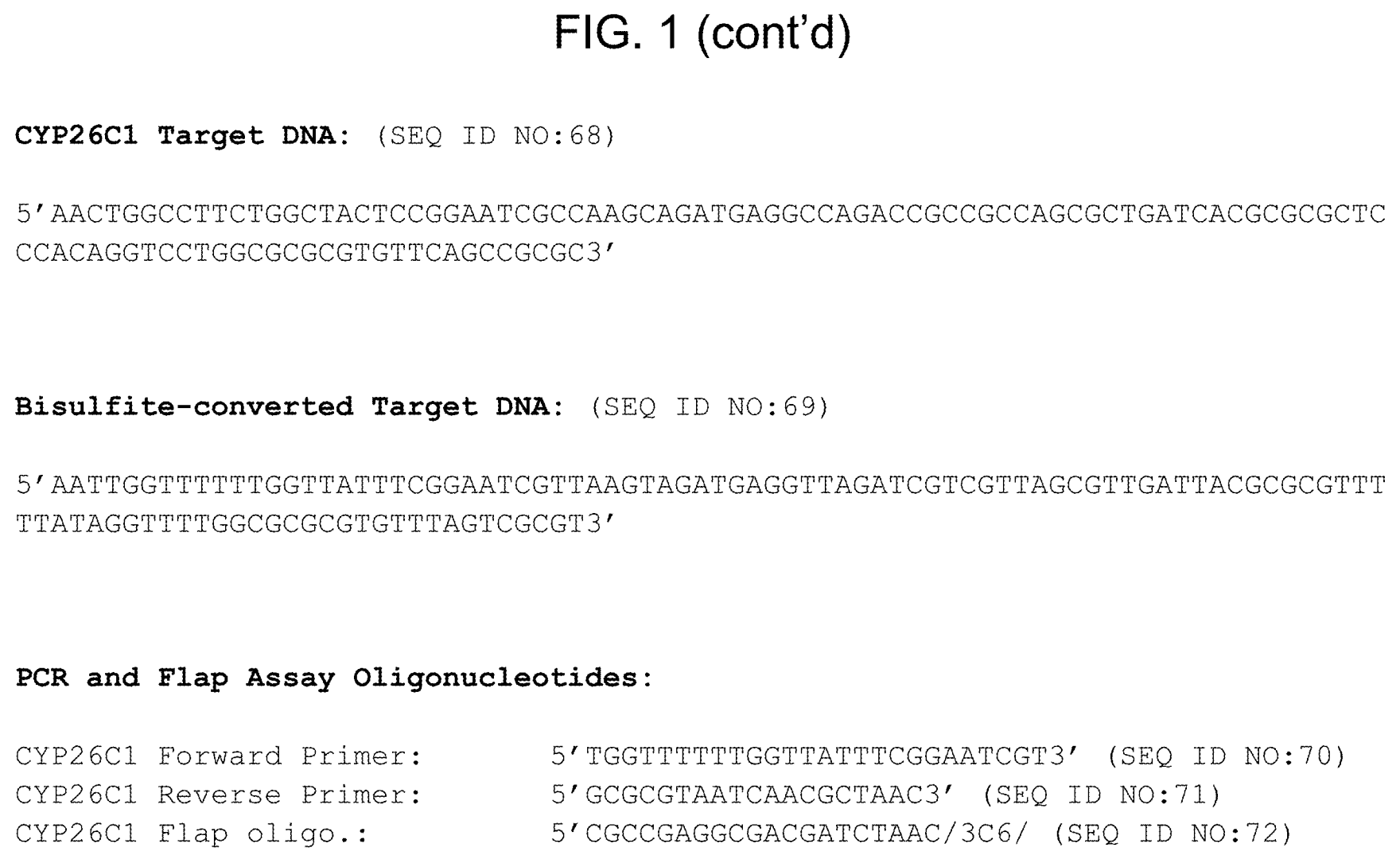

CYP26C1 Target DNA: (SEQ ID NO:68)

5'AACTGGCCTTCTGGCTACTCCGGAATCGCCAAGCAGATGAGGCCAGACCGCGCCGCCAGCCGCTGATCACGCGCGCTC
CCACAGGTCCTGGCGGGCGGTGTTCAGCCGCGC3'

Bisulfite-converted Target DNA: (SEQ ID NO:69)

5'AATTGGTTTTTTGGTTATTCCGGAATCGTTAAGTAGAGATGAGGTTAGATCGTCGTTAGCGTTGATTACGCGCGTTT
TTATAGGTTTTGGCGCGCGGTGTTTAGTCGCGT3'

PCR and Flap Assay Oligonucleotides:

CYP26C1 Forward Primer:     5'TGGTTTTTTTGGTTATTTCGGAATCGT3' (SEQ ID NO:70)

CYP26C1 Reverse Primer:     5'GCGCGTAATCAACGCTAAC3' (SEQ ID NO:71)

CYP26C1 Flap oligo.:     5'CGCCGAGGCGACGATCTAAC/3C6/ (SEQ ID NO:72)

FIG. 1 (cont'd)

DID01 Target DNA: (SEQ ID NO:73)

5′GGAGCGGGGCAGAGAGGAGGAGCCCAGCGCCGAGGCGCGCCCCCGCCCTCGCCCCTCCCCGTGCCCCTCCCC
GCTGCTCCCC3′

Bisulfite-converted Target DNA: (SEQ ID NO:74)

5′GGAGCGGGTAGAGGAGGAGTTTAGCGTCGAGGTTTAGGCGCGTTTCGTTTTTTTTTCGTGTTTTTTTTC
GTTGTTTTT3′

PCR and Flap Assay Oligonucleotides:

DID01 Forward Primer:     5′GAGGAGGAGTTTAGCGTCG3′ (SEQ ID NO:75)

DID01 Reverse Primer:     5′CACGAAAAAAACGAAAACGAAAACGAAAC3′ (SEQ ID NO:76)

DID01 Flap oligo.:     5′CGCCGAGGCGCCTAAACC/3C6/ (SEQ ID NO:77)

FIG. 1 (cont'd)

DLX4 Target DNA: (SEQ ID NO:78)

5′GCGGTCTATCACGGGCACCCCTAACACTTGGTGAGTGCGCAGTGCTCTCGGCGCAGTCTCTGGGCTCCATACGATGC
CTACCGCACGCCCTAGCAGAGGAGGTCTCTGT3′

Bisulfite-converted Target DNA: (SEQ ID NO:79)

5′GCGGTTTATTACGGGTATTTTTAATATTTGGTGAGTGCGTAGTGTTTTCGGTAGTGTTTTTGGGTTTTATACGATGT
TTATCGTACGTTTTAGTAGAGGAGGTTTTTGT3′

PCR and Flap Assay Oligonucleotides:

DLX4 Forward Primer:              5′TGAGTGCGTAGTGTGTTTTCGG3′ (SEQ ID NO:80)
DLX4 Reverse Primer:              5′CTCCTCTACTAAAACGTACGATAAAACA3′ (SEQ ID NO:81)
DLX4 Flap oligo.:                 5′CGCCGAGGATCGTATAAAAC/3C6/ (SEQ ID NO:82)

DLX4 Forward Primer Universal:    5′ATATTTGGTGAGTGCGTAGTG3′ (SEQ ID NO:83)
DLX4 Reverse Primer Universal:    5′ACGTACGATAAACATCGTATAAAACC3′ (SEQ ID NO:84)
DLX4 Flap oligo. Universal:       5′CGCCGAGGGTTTTCGGTAGT/3C6/(SEQ ID NO:85)

FIG. 1 (cont'd)

DMRTA2 Target DNA: (SEQ ID NO:86)

5'TACTCCACTGCCGGCTTGGTGCCGCCCACCCATGGACTACGCCCTTTAGCGGATCTCATGCGT
GACCGGCTCGGCGCCGCCGCTGCTGGGGGCGGTGCACAAGGAGCCGACCT3'

Bisulfite-converted Target DNA: (SEQ ID NO:87)

5'TATTTTATTGTCGGTTTGGTGTTGTTTACGTTCGGTTTTCGTTTATTTATGGATTACGTTTTTTAGCGGATTTTATGCGT
GATCGTTCGGTCGTTGTTGCGGGCGGTGTATAAGGAGTCGATTT3'

PCR and Flap Assay Oligonucleotides:

DMRTA2 Forward Primer:  5'TGGTGTGTTTACGTTCGGTTTTCGT3' (SEQ ID NO:88)

DMRTA2 Reverse Primer:  5'CCGCAACAACGACGACC3' (SEQ ID NO:89)

DMRTA2 Flap oligo.:  5'CGCCGAGGCGAACGATCACG/3C6/ (SEQ ID NO:90)

FIG. 1 (cont'd)

DNMT3A Target DNA: (SEQ ID NO:91)

5'AGGCCGGTCACGAACAAAGCGCTGGCGCGCCGAGTGCGCGCCCGCCGCCACGCGCGACAGGTGCCCGCGACAAGAGACGCCCCGT
CCCCGCCCACGCGCGCCCCGCGGGGGCTGAGCC3'

Bisulfite-converted Target DNA: (SEQ ID NO:92)

5'AGGTCGGTTACGAATAAAGCGTTGGCGCGTTCGTTTACGCGCGTATAGGTGTTCGCGATAAGACGTTTCGT
TTTCGTTTACGCGCGTTTTCGCGGGGTTGAGTT3'

PCR and Flap Assay Oligonucleotides:

DNMT3A Forward Primer:     5'GTTACGAATAAAGCGTTGGCG3' (SEQ ID NO:93)

DNMT3A Reverse Primer:     5'AACGAAACGTCTTATCCGCGA3' (SEQ ID NO:94)

DNMT3A Flap oligo.:     5'CCACGGACGGAGTGCGCGGTTC/3C6/ (SEQ ID NO:95)

FIG. 1 (cont'd)

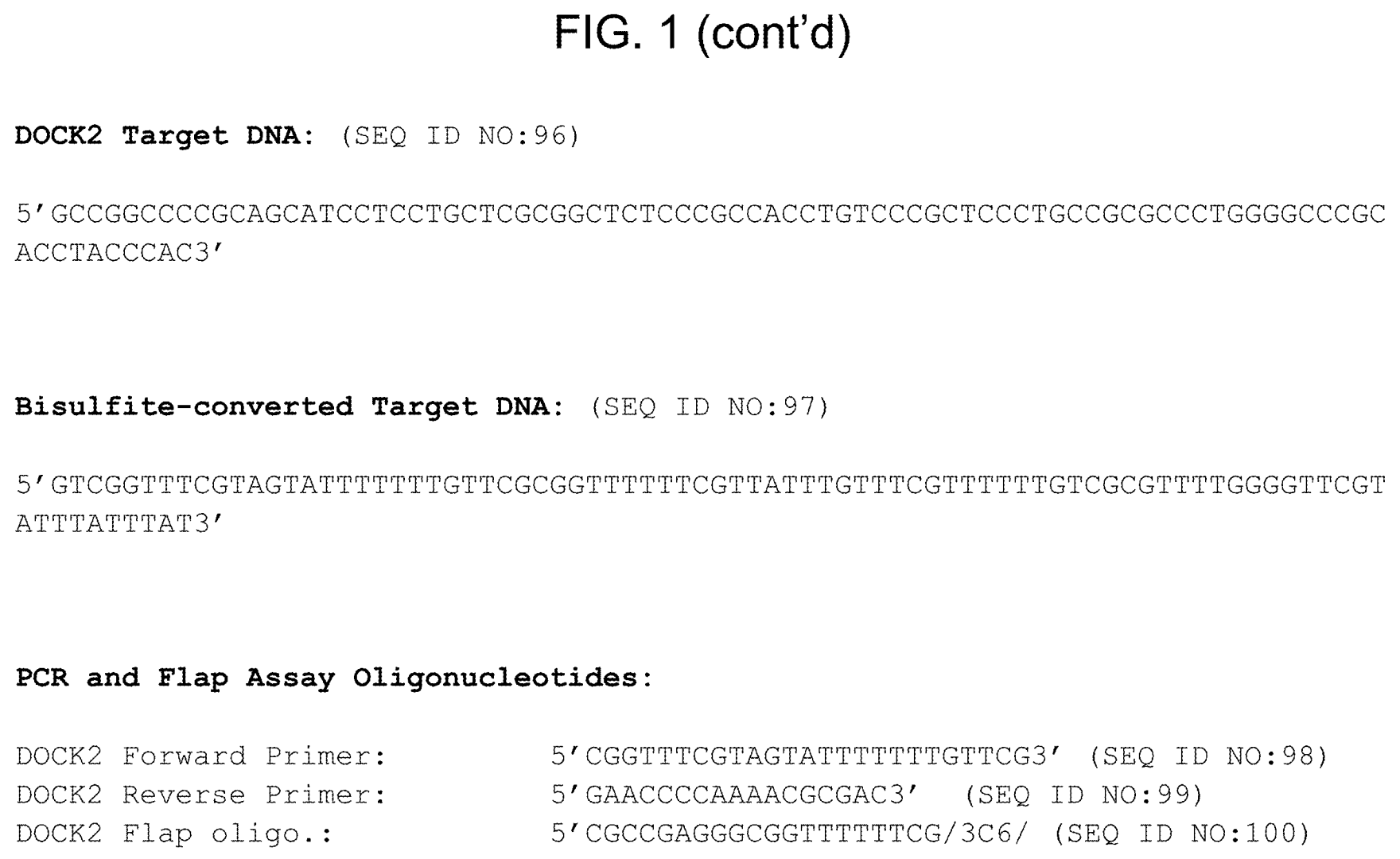

DOCK2 Target DNA: (SEQ ID NO:96)

5'GCCGGCCCGCAGCATCCTCCTGCTCGCGGCTCTCCCGCCACCTGTCCCGCTCCCGCCCCGCCCCTGGGGCCCGC
ACCTACCCAC3'

Bisulfite-converted Target DNA: (SEQ ID NO:97)

5'GTCGGTTTCGTAGTATTTTTTTTGTTCGCGGTTTTTTCGTTATTTGTTTCGTTTTTTTTGTTCGCGGTTTTGGGGTTCGT
ATTTATTTAT3'

PCR and Flap Assay Oligonucleotides:

DOCK2 Forward Primer:     5'CGGTTTCGTAGTATTTTTTTTGTTCG3' (SEQ ID NO:98)
DOCK2 Reverse Primer:     5'GAACCCCAAAAACGCGGAC3' (SEQ ID NO:99)
DOCK2 Flap oligo.:     5'CGCCGAGGGCGGTTTTTTCG/3C6/ (SEQ ID NO:100)

FIG. 1 (cont'd)

DTX1 Target DNA: (SEQ ID NO:101)

5'CGCCTCCTGGGCTCCCCCCGGAGTGGGAGGGAGCCGCGGTCCCGCGCCTCCGCGCCGTTCCCTCCCAGGCCCCTCG
GCCGCGGCCGAGCTTTCCGCGCGTGGACAGACTGCCCGGCCCGACGGACGGCCAGG3'

Bisulfite-converted Target DNA: (SEQ ID NO:102)

5'CGTTTTTTTGGGTTTTTTTTCGGAGTGGGAGGGAGTCGCGGTTTCGTTTTCGCGTTCGTTTTTTTTTAGGTTTTTCG
GTTCGTCGGTTCGAGTTTTTCGCGCGTGGATAGATTGTTCGGTTCGGACGGACGACGTAGG3'

PCR and Flap Assay Oligonucleotides:

DTX1 Forward Primer:_49         5'GAGTCGCGGGTTTCGTTTTC3'  (SEQ ID NO:103)
DTX1 Reverse Primer:_Ver2        5'GACGCGACGACCGAAAAAC3'  (SEQ ID NO:104)
DTX1 Flap oligo.:_S_49           5'CGCCGAGGCGCGTTCGTTTT/3C6/ (SEQ ID NO:105)

FIG. 1 (cont'd)

EMX1 Target DNA: (SEQ ID NO:106)

5'TCCGGGCGCGCGTTTTCTAGAGAACCGGGTCTCAGCGGATGCTCATTTCAGCCCCGTCTTAATGCAACAAACGAAA
CCCCACGAACGAAAAGGAACACATGTCTGCGCT3'

Bisulfite-converted Target DNA: (SEQ ID NO:107)

5'TCGGGCGTCGCGTTTTTTAGAGAATCGGGTTTTTAGCGGATGTTTATTTTCGTTTTTAATGTAATAAACGAAAT
TTTATACGAACGAAAAGGAATATGTTTGCGTT3'

PCR and Flap Assay Oligonucleotides:

EMX1 Forward Primer:   5'GGCGTCGCGTTTTTTTAGAGAA3'  (SEQ ID NO:108)

EMX1 Reverse Primer:   5'TTCCTTTTCGTTCGTATAAAATTTCGTT3'  (SEQ ID NO:109)

EMX1 Flap oligo.:5'CCACGGACGATCGGGTTTTAG/3C6/ (SEQ ID NO:110)

FIG. 1 (cont'd)

FAM59B Target DNA: (SEQ ID NO:111)

5'GGGCCTGCTGGCCGGGGACCCGCGCGTGGCGCGGCCTCGAGCGCGCCTCCTACTGCCGCGAGCGCTTCGA
CCCGACGAGTACTCCACGGCGGCCGTGCGCGAGGCGCCAGCGGCTCGCCGAAG3'

Bisulfite-converted Target DNA: (SEQ ID NO:112)

5'GGGTTTGTTGGTCGGGGATTCGCGCGTTTGGTGCGCGGCGATAGCGCGTTTTTTTATTGTCGCGAGCGTTTCGA
TTTCGACGAGTATTTTACGGTCGTGCGCGAGGCGTTAGCGGCGGAGTTCGTCGAAG3'

PCR and Flap Assay Oligonucleotides:

FAM59B Forward Primer:     5'CGATAGCGCGTTTTTTTATTGTCGCG3'   (SEQ ID NO:113)

FAM59B Reverse Primer:     5'GCACGACCGTAAAATACTCGTC3'   (SEQ ID NO:114)

FAM59B Flap oligo.:     5'CCACGGACGCGAAATCGAAAC/3C6/  (SEQ ID NO:115)

FIG. 1 (cont'd)

FERMT3 Target DNA: (SEQ ID NO:116)

5'TAGCAGCAGCCGCAGCCATGGCGGGGATGAAGAGACAGCCTCCGGGGACTACATCGACTCGTCATGGGAGCTGCGGG
TGTTTGTGGGAGAGGAGGACCCAGAGGCCGAGTCGGTCACCCTGCGGGTCACTGGGGAGTCGCAC3'

Bisulfite-converted Target DNA: (SEQ ID NO:117)

5'TAGTAGTAGTCGTAGTTATGGGCGGGGATGAAGAGATAGTTTTCGGGGATTATATCGATTCGTTATGGGAGTTGCGGG
TGTTTGTGGGAGAGGAGGATTTAGAGGTCGGTTATTTTGCGGGTTATTGGGGAGTCGTAT3'

PCR and Flap Assay Oligonucleotides:

FERMT3 Forward Primer:    5'GTTTTTCGGGGATTATATCGATTCG3'   (SEQ ID NO:118)
FERMT3 Reverse Primer:    5'CCCAATAACCCGCAAAATAACC3'   (SEQ ID NO:119)
FERMT3 Flap oligo.:    5'CGCCGAGGCGACTCGACCTC/3C6/   (SEQ ID NO:120)

FIG. 1 (cont'd)

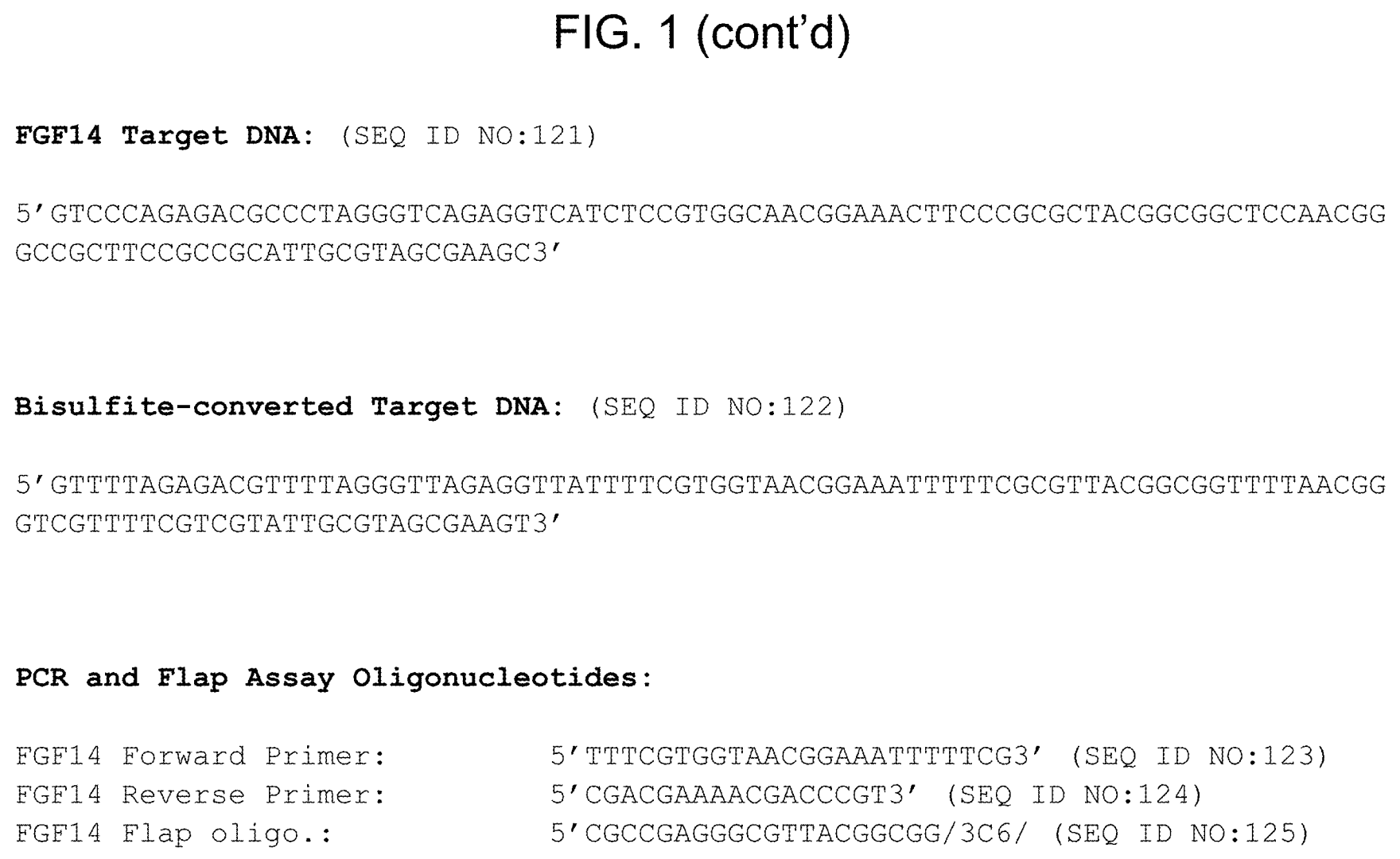

FGF14 Target DNA: (SEQ ID NO:121)

5'GTCCCAGAGACGCCCTAGGGTCAGAGGTCATCTCCGTGGCAACGGAAACTTCCCGCGCTACGGGCGGCTCCAACGG
GCCGCTTCCGCCGCATTGCGTAGCGAAGC3'

Bisulfite-converted Target DNA: (SEQ ID NO:122)

5'GTTTTAGAGACGTTTTAGGGTTAGAGGTTATTTTCGTGGTAACGGAAATTTTTCGCGTTACGGGCGGTTTTAACGG
GTCGTTTTCGTCGTATTGCGTAGCGAAGT3'

PCR and Flap Assay Oligonucleotides:

FGF14 Forward Primer:    5'TTTCGTGGTAACGGAAATTTTTCG3'    (SEQ ID NO:123)

FGF14 Reverse Primer:    5'CGACGAAAACGACCCGT3'    (SEQ ID NO:124)

FGF14 Flap oligo.:    5'CGCCGAGGGCGGTTACGGCGG/3C6/    (SEQ ID NO:125)

FIG. 1 (cont'd)

FLJ34208 Target DNA: (SEQ ID NO:126)

5'GCGCCCCGCGGCCGCAGGCGGAGGACAGGGAGGAGGCGCACACGAGAAAGCTCCCACGCGCCCGCGCGCCTCGCGCCTCCGA
CGGGAAGGCGCCTCTTCCGACCGTCCTGGATG3'

Bisulfite-converted Target DNA: (SEQ ID NO:127)

5'GCGTTTCGGTCGTAGGCGGGAGGATAGGGAGGAGGCGTATACGAGAAAGTTTTTACGCGTTCGCGCGTTTCGTTTTCGA
CGGGAAGGCGTTTTTTTTCGATCGTTTTGGATG3'

PCR and Flap Assay Oligonucleotides:

FLJ34208 Forward Primer:     5'GAGCGTATACGAGAAAGTTTTTACG (SEQ ID NO:128)

FLJ34208 Reverse Primer:     5'AACGCCTTCCCGTCGAA (SEQ ID NO:129)

FLJ34208 Flap oligo.:     5'CCACGGACGGCGTTCGCGCGTTT/3C6/ (SEQ ID NO:130)

FIG. 1 (cont'd)

FLJ45983 Target DNA: (SEQ ID NO:131)

5′ CGAGAGGGCGCGAGCACAGCCGAGGCCATGGAGGTGACGGCGCGGCGGGAGCCAGCCGCGCTGGGTGAGCCACCACCACCCC
GCCGTGCTCAACGGGGCAGCACCCGGACACGCAC3′

Bisulfite-converted Target DNA: (SEQ ID NO:132)

5′ CGAGAGGGCGCGAGTATAGTCGAGGTTATGGAGGTGACGGCGCGGCGGGATTAGTCGCGTTGGGTGAGTTATTATTATTTC
GTCGTGTTTAACGGGTAGTATTCGGATACGTAT3′

PCR and Flap Assay Oligonucleotides:

FLJ45983 Forward Primer:      5′GGGCGCGGAGTATAGTCG3′ (SEQ ID NO:133)

FLJ45983 Reverse Primer:      5′CAACGCGACTAATCCGC3′ (SEQ ID NO:134)

FLJ45983 Flap oligo.:      5′CGCCGAGGCCGTCACCTCCA/3C6/ (SEQ ID NO:135)

FIG. 1 (cont'd)

GRIN2D Target DNA: (SEQ ID NO:136)

5'CGCCCCCTCACCTCCCGATCATCATGCCGTTCCAGAGACGCCATCGATCTTCTTTCCGTGCTTGCCATTGGTGACCAGG
TAGAGGTCGTAGCTGAAGCCGATGGTATGCGCGCCAGCCGCTTCAGAAATGTCGATGCAGAAACCCTTG3'

Bisulfite-converted Target DNA: (SEQ ID NO:137)

5'CGTTTTTTTATTTTTTCGATTATGTCGTTTTTAGACGTTATCGATTTTTTTTTTCGTGTGTTTGTTATTGGTGATTAGG
TAGAGGTCGTAGTTGAAGTCGATGGTATGCGCGTTAGTTCGTTTTAGAAATGTCGATGTAGAAATTTTTG3'

PCR and Flap Assay Oligonucleotides:

GRIN2D Forward Primer:    5'TCGATTATGTCGTTTTTAGACGTTATCG3' (SEQ ID NO:138)
GRIN2D Reverse Primer:    5'TCTACATCGACATTCTAAAACGACTAAC3' (SEQ ID NO:139)
GRIN2D Flap oligo.:       5'CCACGGACGCGCATACCATCG/3C6/(SEQ ID NO:140)

FIG. 1 (cont'd)

HIST1H2BE Target DNA: (SEQ ID NO:141)

5′CGGCGAGGCTTCCCGCCTGGCGCATTACAACAAGCGCTCGACCATCACCTCCAGGGAGATCCAGACGGCCGTGCG CCTGCTGCTTCCCGGGGA3′

Bisulfite-converted Target DNA: (SEQ ID NO:142)

5′CGGCGAGGTTTTTCGTTTGGGCGTATTATAATAAGCGTTCGATTATTATTTTTAGGGAGATTTAGACGGTCGTGCG TTTGTTGTTTTTCGGGGA3′

PCR and Flap Assay Oligonucleotides:

HIST1H2BE Forward Primer:     5′TGGCGTATTATAATAAGCGTTCG3′   (SEQ ID NO:143)
HIST1H2BE Reverse Primer:     5′AACAACAAACGCACGACC3′   (SEQ ID NO:144)
HIST1H2BE Flap oligo.:        5′CCACGGACGCGTCTAAATCTC/3C6/ (SEQ ID NO:145)

FIG. 1 (cont'd)

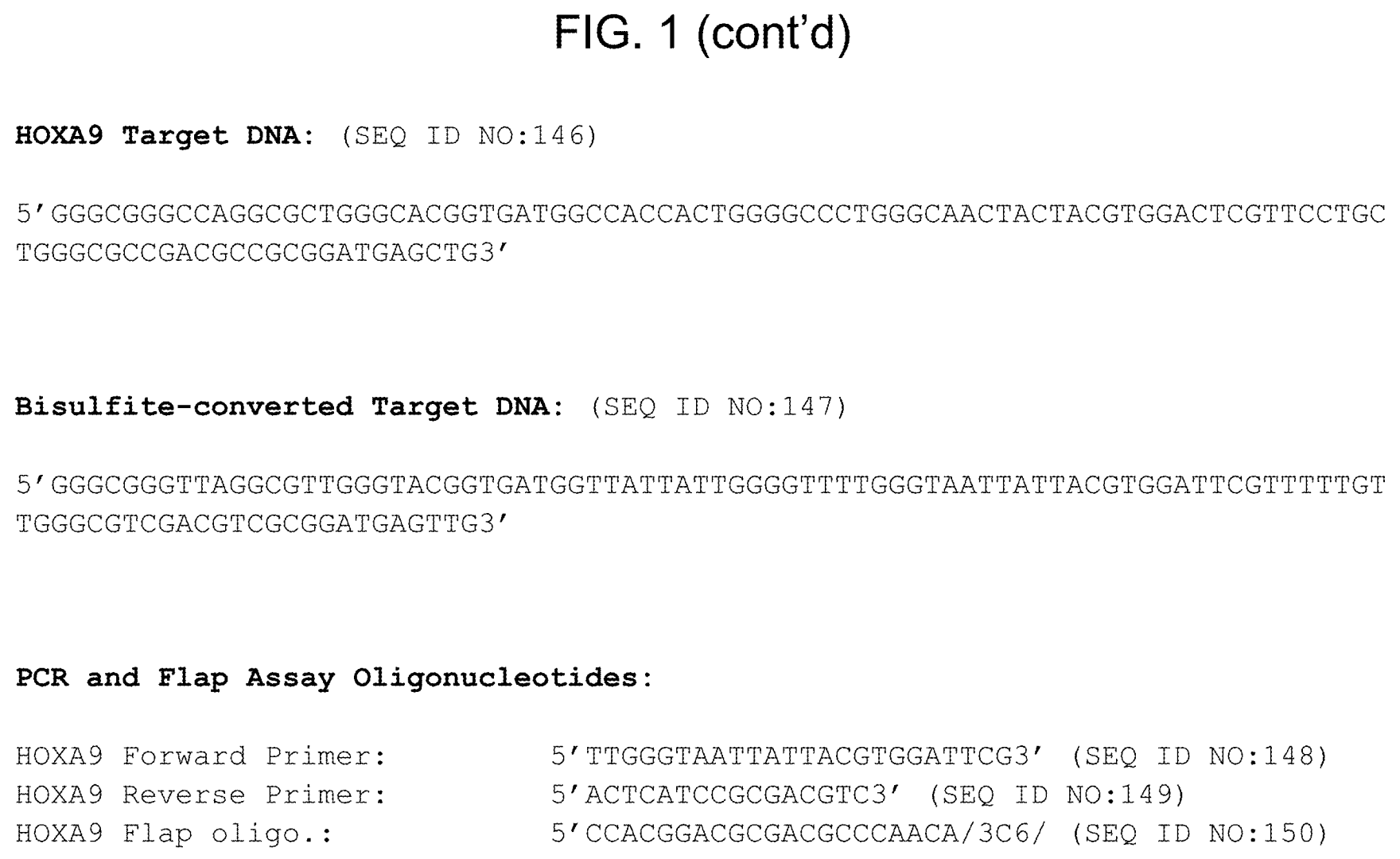

HOXA9 Target DNA: (SEQ ID NO:146)

5'GGGCGGGGCCAGGCGCTGGGCACGGTGATGGCCACCACTGGGGCCCTGGGCAACTACTACGTGGACTCGTTCCTGC
TGGGCGGCCGACGCGCGGGGATGAGCTG3'

Bisulfite-converted Target DNA: (SEQ ID NO:147)

5'GGGCGGGGTTAGGCGTTGGGTACGGTGATGGTTATTATTGGGGTTTTGGGTAATTATTACGTGGATTCGTTTTTGT
TGGGCGGTCGACGTCGCGGGATGAGTTG3'

PCR and Flap Assay Oligonucleotides:

HOXA9 Forward Primer:    5'TTGGGTAATTATTACGTGGATTCG3' (SEQ ID NO:148)
HOXA9 Reverse Primer:    5'ACTCATCCGCGACGTC3' (SEQ ID NO:149)
HOXA9 Flap oligo.:       5'CCACGGACGCGACGCCCAACA/3C6/ (SEQ ID NO:150)

FIG. 1 (cont'd)

HOXB2 Target DNA: (SEQ ID NO:151)

5'GGGCCATTGCCAGAAGACGTCTTCTCGGGGCGCCAGGATTCACCTTTCCTTCCCGACCTCAACTTCTTCGCGGCC
GACTCCTGTCTCCAGCTATC3'

Bisulfite-converted Target DNA: (SEQ ID NO:152)

5'GGGTTATTGTTAGAAGACGTTTTTTCGGGGCGTTAGGATTTATTTTTTTTTTTCGATTTAATTTTTTTCGCGGTC
GATTTTTGTTTTTTAGTTATT3'

PCR and Flap Assay Oligonucleotides:

HOXB2 Forward Primer:  5'GTTAGAAGACGTTTTTTCGGGG3' (SEQ ID NO:153)
HOXB2 Reverse Primer:  5'AAAACAAAAATCGACCGCGA3' (SEQ ID NO:154)
HOXB2 Flap oligo.:  5'CGCCGAGGGCGTTAGGATTT/3C6/ (SEQ ID NO:155)

FIG. 1 (cont'd)

KLHDC7B.chr22.50987185-50987290 Target DNA: (SEQ ID NO:156)

5'GGCCCCGGAAGCCCAGCTCCCGGGCCCTGGAGCCCCGCCACGGCGGCGGCAGCCCTGCGCGGCGGCTGGACCTGGGCA
GTTGCCTGGACGTGCTGGCCTTTGCCCAGCA3'

Bisulfite-converted Target DNA: (SEQ ID NO:157)

5'GGTTTCGGAAGTTTAGTTTTCGGGTTTTTGGAGTTCGTTCGTTACGGCGGCGGTAGTTTTGCGCGGCGGCGGTTGGATTTGGGTA
GTTGTTTGGACGTGTTGGTTTTTGTTTAGTA3'

PCR and Flap Assay Oligonucleotides:

KLHDC7B Forward Primer:    5'AGTTTTTCGGGTTTTTGGAGTTCGTTA3'  (SEQ ID NO:158)

KLHDC7B Reverse Primer:    5'CCAAATCCAACCGCCGC3'  (SEQ ID NO:159)

KLHDC7B Flap oligo.:    5'CGCCGAGGACGCGGGTAGTT/3C6/  (SEQ ID NO:160)

FIG. 1 (cont'd)

LOC100129726 Target DNA: (SEQ ID NO:161)

5'GGCGGCGCCGGCGGCTGCGCGGGGGGCGCCAGGCCCTGCTGCTGCTGACTGCGGGTAGTAGGCGGCG GCGGCCACGGGCGGCAAAGTTGTGGGTCTGGA

Bisulfite-converted Target DNA: (SEQ ID NO:162)

5'GGCGGGCGTCGGCGGTTGCGCGGGGGGCGTTAGGTTTTTGTTGTTGTTGTTGATTGCGGGTAGTAGGCGGCG GCGGTTACGGGCGGTAAAGTTGTGGGTTTGGA

PCR and Flap Assay Oligonucleotides:

LOC100129726 Forward Primer:    5'TTGATTGCGGTAGTAGGCG3'    (SEQ ID NO:163)

LOC100129726 Reverse Primer:    5'AACCCACAACTTTACCGCC3'    (SEQ ID NO:164)

LOC100129726 Flap oligo.:    5'CGCCGAGGCGGTAACCGCCGC/3C6/(SEQ ID NO:165)

FIG. 1 (cont'd)

MATK Target DNA: (SEQ ID NO:166)

5'GGTTTCCCCCACCCCGGCCTCGGGGTCTCTCCACGTCTCCCCGCCGACGTGCTCACCTGCTCAGGGGGCGCCCC
CGAGCCGCGGCCCCGCGCCCGCGCCCCAGGAGGGCCTCCGCGGAGCCGGCCTGCACACCCCGAGGGCGGTCCCGGCTGCACA
AC3'

Bisulfite-converted Target DNA: (SEQ ID NO:167)

5'GGTTTTTTTTTTATTTCGGTTTCGGGGTTTTTTTTTTTACGTTTTTTTTCGTCGACGTGTTTATTTGTTTAGGGGGCGTTTT
CGAGTCGCGGTTTTCGCGTTCGCGTTTTTTAGGAGGGTTTTCGCGAGTCGGTTGTATATTTCGAGGGCGGTTTCGGTTGTATA
AT3'

PCR and Flap Assay Oligonucleotides:

MATK Forward Primer:     5'GTTTCGGGGGTTTTTTTTTACGTTTTTTCG3' (SEQ ID NO:168)

MATK Reverse Primer:     5'AAACGCGACTCGAAAAACGC3' (SEQ ID NO:169)

MATK Flap oligo.:     5'CGCCGAGGGTCGACGTGTTT/3C6/ (SEQ ID NO:170)

FIG. 1 (cont'd)

MAX.chr10.22541891-22541946 Target DNA: (SEQ ID NO:171)

5′CTCCGGTTTTCGCGGTTCTCAGCGATATTAGGCGCGGCCAGTGTCTGAAAGCTCCTCGGGGTTACGTCCTGGGGC
GACTGGAGGCGGGCTCACGAC3′

Bisulfite-converted Target DNA: (SEQ ID NO:172)

5′TTTCGGTTTTCGCGGTTTTTAGCGATATTAGGCGCGGTTAGTGTTTGAAAGTTTTTCGGGGTTACGTTTTGGGGC
GATTGGAGGCGGGTTACGAT3′

PCR and Flap Assay Oligonucleotides:

MAX_Chr10.225 Forward Primer: 5′CGGTTTTTAGGCGATATTAGGCG3′ (SEQ ID NO:173)
MAX_Chr10.225 Reverse Primer: 5′CCCAAAACGTAACCCCGA3′ (SEQ ID NO:174)
MAX_Chr10.225 Flap oligo.: 5′CGCCGAGGCGGGTTAGTGTT/3C6/(SEQ ID NO:175)

FIG. 1 (cont'd)

MAX.chr10.22624430-22624544 Target DNA: (SEQ ID NO:176)

5'CGACGGCCGCGGAGGAGGAAGGCCAGGGGGGAAATTTGCATTTCGTAAAACCGCGGTTAAGAAATGACGATGCCAC
GTAGACAAGCCAGTTGTGACGTTCAGCACAACGTGCTACTGAACTACCGAGATCCGCCACCAAATGGC3'

Bisulfite-converted Target DNA: (SEQ ID NO:177)

5'CGACGGTCGCGGAGGAGGAAGGTTAGGGGGGAAATTTGTATTTCGTAAAATCGCGGTTAAGAAATGACGATGTTAC
GTAGATAAGTTAGTTGTGACGTTTAGTTAGTATAACGTGTTATTGAATTATCGAGATTCGTTATTAAATGGT3'

PCR and Flap Assay Oligonucleotides:

MAX_Chr10.226 Forward Primer: 5'GGGAAATTTGTATTTCGTAAAATCG3' (SEQ ID NO:178)
MAX_Chr10.226 Reverse Primer: 5'ACAACTAACTTATCTACGTAACATCGT3'(SEQ ID NO:179)
MAX_Chr10.226 Flap oligo.: 5'CCACGGACGCGGTTAAGAAA/3C6/ (SEQ ID NO:180)

FIG. 1 (cont'd)

MAX.chr12.52652268-52652362 Target DNA: (SEQ ID NO:181)

5'GGCTTGGGGGTCCAGCCGCGCCCGCCCCTGCCGCCACCGCCACCATGTCCTGCCCTCTACTCCCGCCTCAGCGCGCCCCCTG
CGGGGTCCGCGCGCCTTCAGCTGCATCTCGGCCTGCGGGGCCCC3'

Bisulfite-converted Target DNA: (SEQ ID NO:182)

5'GGTTTGGGGGTTTAGTCGTTCGTTTTTGTCGTTATCGTATTATGTTTTGTTTTTATTTTTCGTTTTTAGCGTTTTTTG
CGGGGTTCGCGTTTTTTAGTTGTATTGTATTTCGGGTTTGCGGGTTTT3'

PCR and Flap Assay Oligonucleotides:

MAX.chr12.52 Forward Primer:    5'TCGTTCGTTTTTTGTCGTTATCG3'  (SEQ ID NO:183)

MAX.chr12.52 Reverse Primer:    5'AACCGAAATACAACTAAAAACGC3'(SEQ ID NO:184)

MAX.chr12.52 Flap oligo.:    5'CCACGACGCGAACCCCGCAA/3C6/(SEQ ID NO:185)

FIG. 1 (cont'd)

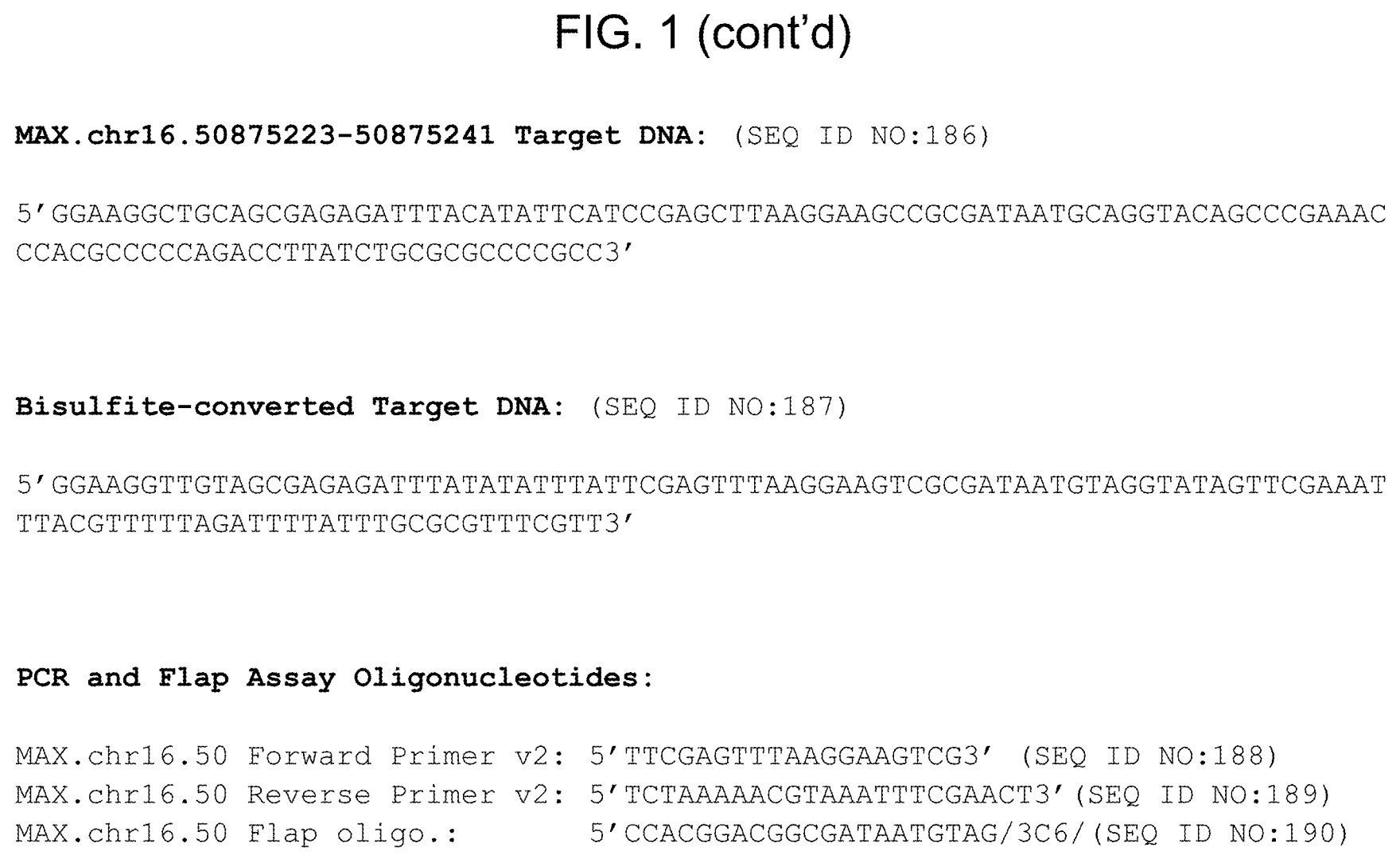

MAX.chr16.50875223-50875241 Target DNA: (SEQ ID NO:186)

5'GGAAGGCTGCAGCGAGAGATTTACATATTCATCCGAGCTTAAGGAAGCCGCGATAATGCAGGTACAGCCCGAAAC
CCACGCCCCCAGACCTTATCTGCGCGCCCCGCC3'

Bisulfite-converted Target DNA: (SEQ ID NO:187)

5'GGAAGGTTGTAGCGAGAGATTTATATATTTATTCGAGTTTAAGGAAGTCGCGATAATGTAGGTATAGTTCGAAAT
TTACGTTTTTAGATTTTATTTGCGCGTTTCGTT3'

PCR and Flap Assay Oligonucleotides:

MAX.chr16.50 Forward Primer v2:   5'TTCGGAGTTTAAGGAAGTCG3' (SEQ ID NO:188)

MAX.chr16.50 Reverse Primer v2:   5'TCTAAAAACGTAAATTTCGAACT3' (SEQ ID NO:189)

MAX.chr16.50 Flap oligo.:   5'CCACGGACGCGGCGATAATGTAG/3C6/(SEQ ID NO:190)

FIG. 1 (cont'd)

MAX.chr19.16394489-16394575 Target DNA: (SEQ ID NO:191)

5'GGAGTTATTTTTAACCATCGGCCTCCCAGAACATTACGGAGCTTCCTCTCTCCAACACGCAGGAAACCCTACTTGG
CTGTGCTTCCTGCTAACACGAGGCCCTGCGATTGCTGAGAACAACAGCCCCGAGACTGCGCG3'

Bisulfite-converted Target DNA: (SEQ ID NO:192)

5'GGAGTTATTTTTTAATTATCGTTTTTTTAGAATATTACGGAGCTTTTTTTTTTTTAATACGTAGGAAATTTTATTTGG
TTGTGTTTTTTGTTAATACGAGGTTTTGCGATTGTTGAGAATAATAGTTTCGAGATTGCGCG3'

PCR and Flap Assay Oligonucleotides:

MAX.chr19.16 For. Primer:    5'TTTAATTATCGTTTTTTTAGAATATTACGGA3'(SEQ ID NO:193)
MAX.chr19.16 Reverse Primer: 5'ACTATTATTCTCAACAATCGCAAAAC3'(SEQ ID NO:194)
MAX.chr19.16 Flap oligo.:    5'CCACGGACGCCTCGTATTAAC/3C6/(SEQ ID NO:195)

FIG. 1 (cont'd)

MAX.chr19.37288426-37288480 Target DNA: (SEQ ID NO:196)

5′GGCGGGGCGCTTGGCCAAACAGCCCAAGACTGCGGAATCACACTCGCCACTGTGTACCTGGACGCGCCATCTGCAGAC
CCAGCGCCTGCGGGGATTCCGGAAACGGGAGCGGGCTTCC3′

Bisulfite-converted Target DNA: (SEQ ID NO:197)

5′GGCGGGGCGTTTGGTTAAATAGTTTAAGATTGCGGAATTATATTCGTTATTGTGTATTTGGACGTTATTTGTAGAT
TTAGCGTTTGCGGGGATTTCGGAAACGGGAGCGGGTTTTT3′

PCR and Flap Assay Oligonucleotides:

MAX.chr19.37 For. Primer_v2:    5′AGTTTAAGATTGCGGAATTATATTCGT3′ (SEQ ID NO:198)

MAX.chr19.37 Reverse Primer:    5′TTCCGAAATCCCCGCAA3′ (SEQ ID NO:199)

MAX.chr19.37 Flap oligo.:    5′CGCCGAGGAACGCTAAATCT/3C6/ (SEQ ID NO:200)

FIG. 1 (cont'd)

MAX.chr8.1241173236-1241173370 Target DNA: (SEQ ID NO:201)

5'CGCAGGCTGAGGCCCTCGGGTCCCCAGCGGGTCCTCGCCATCAGTCACTCTCTACGGGCCAGGCCTCGGGGGTCAC
GGCCTGCAGGAGCCTCCCTGCGCGGCCCCACTCCCTCATCTGCGACCCCGTGGGGAGGCGACCCTGACCACCCTCGT
TCCG3'

Bisulfite-converted Target DNA: (SEQ ID NO:202)

5'CGTAGGTTGAGGTTTTCGGGTTTTTTAGCGGGTTTTCGTTATTAGTTAGTTATTTTTTACGGGTTAGGTTTGGGGGTTAC
GGTTTGTAGGAGTTTTTTTGCGCGGTTTTATTTTTTTATTTGCGATTTCGTGGGGAGGCGATTTTGATTATTTTCGT
TTCG3'

PCR and Flap Assay Oligonucleotides:

MAX_Chr8.124 Forward Primer:    5'GGTTGAGGTTTTCGGGTTTTTAG3'  (SEQ ID NO:203)
MAX_Chr8.124 Reverse Primer:    5'CCTCCCCACGAAATCGC3'  (SEQ ID NO:204)
MAX_Chr8.124 Flap oligo.:       5'CGCCGAGGGCGGGTTTTCGT/3C6/  (SEQ ID NO:205)

MAX_Chr8.124 Forward Primer v2: 5'AGGAGTTTTTTTGCGCGGG3'  (SEQ ID NO:206)
MAX_Chr8.124 Reverse Primer v2: 5'ACGAAAAATAATCAAAATCGCCTCC3'  (SEQ ID NO:207)
MAX_Chr8.124 Flap oligo. v2:    5'CGCCGAGGCCCACGAAATCG/3C6/  (SEQ ID NO:208)

FIG. 1 (cont'd)

MAX.chr8.145105646-145105653 Target DNA (SEQ ID NO:209)

5'CGGGGGAGGGCGGCATCAGCCAGAGCCTCAGCCGACGGCGCTCCCCAGGTCCCACTTCCCGCTCCGATACCCTCCC
CCTAAGCACGATACCCAGGGCCCAGGGCTGCTCTTGGGCG3'

Bisulfite-converted Target DNA: (SEQ ID NO:210)

5'CGGGGGAGGGCGGTATTAGTTAGAGTTTTAGTCGACGGCGCGTTTTTTAGGTTTATTTTTCGTTTCGATATTTTTT
TTTAAGTACGATATTTAGGGTTTAGGGTTGTTTTTGGGCG3'

PCR and Flap Assay Oligonucleotides:

MAX_Chr8.145 Forward Primer:   5'GCGGTATTAGTTAGAGTTTTAGTCG3'   (SEQ ID NO:211)

MAX_Chr8.145 Reverse Primer:   5'ACAAACCCTAAACCCTAAATATCGT3'   (SEQ ID NO:212)

MAX_Chr8.145 Flap oligo.:   5'CCACGGACGCGGACGCGGCGTTTTT/3C6/   (SEQ ID NO:213)

FIG. 1 (cont'd)

MAX_Chr1.110 (MAX.chr1.110627198-110627213) Target DNA: (SEQ ID NO:214)

5'CTCCGCTCCCCGCCAGGCCTGGCCGCGCGACGGGCACCCAGCGGGTTGTTATCAATTATTCAGGCCCCAAGTTCAC GGGCACTGCATCCATTTCCCTCGCGTGCGCCC3'

Bisulfite-converted Target DNA: (SEQ ID NO:215)

5'TTTCGTTTTTCGTAGGTTTGGTTCGCGCGACGGGTATTTAGCGGGTTGTTATTAATTATTTAGGTTTTTAAGTTTAC GGGTATTGTATTTATTTTTTTTCGCGTGCGTTT3'

PCR and Flap Assay Oligonucleotides:

MAX_Chr1.110 Forward Primer:     5'TTTCGTAGGTTTGGTTCGCG3' (SEQ ID NO:216)

MAX_Chr1.110 Reverse Primer:     5'AACCTAAATAATTAATAACAACCCGC3' (SEQ ID NO:217)

MAX_Chr1.110 Flap oligo.: 5'CCACGGACGGCGACGGGTATT/3C6/(SEQ ID NO:218)

FIG. 1 (cont'd)

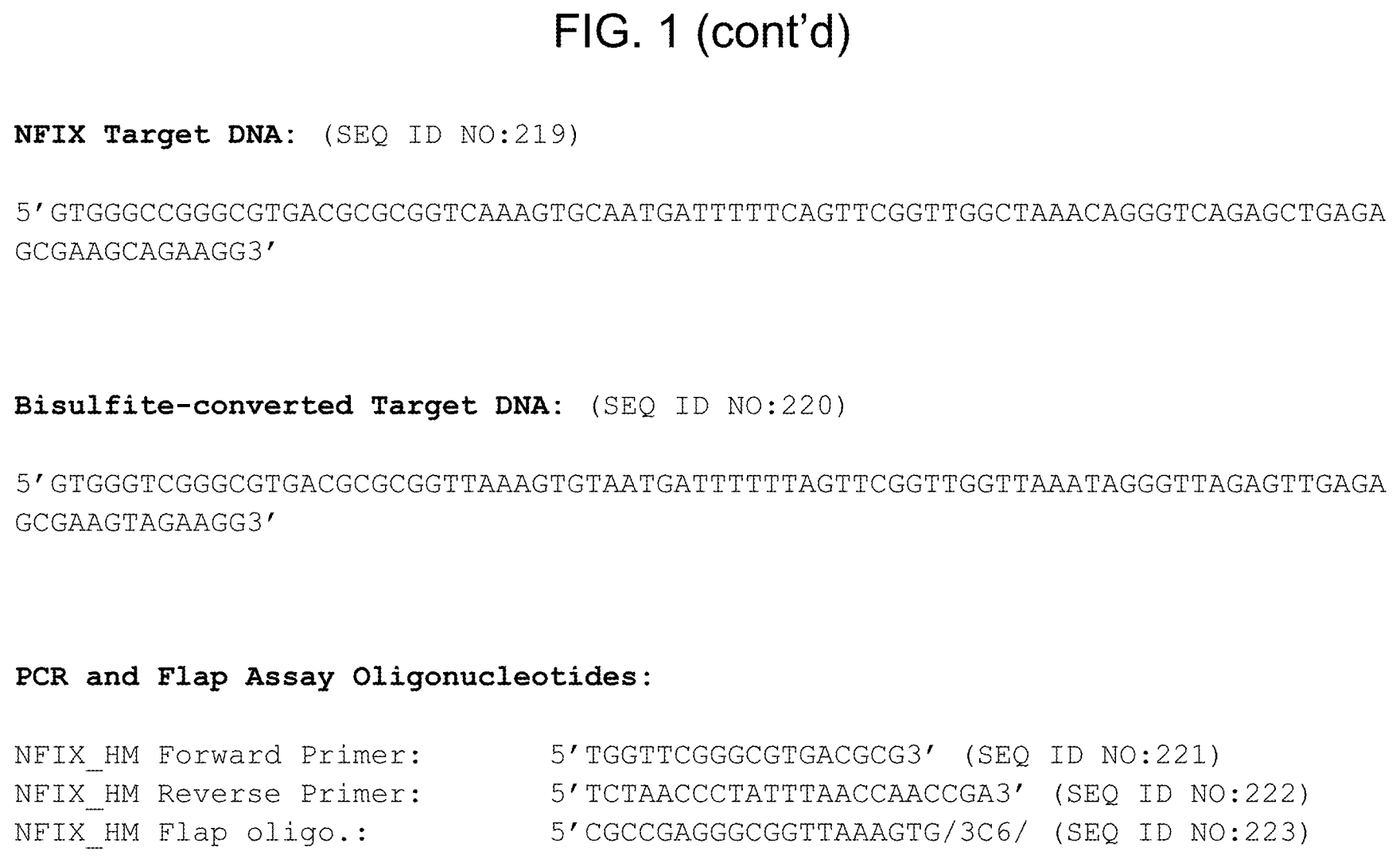

NFIX Target DNA: (SEQ ID NO:219)

5′GTGGGCCGGCGGCGGTGACGCGCGGGTCAAAGTGCAATGATTTTTCAGTTCGGTTGGCTAAACAGGGTCAGAGCTGAGAGCGAAGCAGAAGG3′

Bisulfite-converted Target DNA: (SEQ ID NO:220)

5′GTGGGTCGGGCGGTGACGCGCGGGTTAAAGTGTAATGATTTTTTAGTTCGGTTGGTTAAATAGGGTTAGAGTTGAGAGCGAAGTAGAAGG3′

PCR and Flap Assay Oligonucleotides:

NFIX_HM Forward Primer:   5′TGGTTCGGGCGGTGACGCGCG3′ (SEQ ID NO:221)
NFIX_HM Reverse Primer:   5′TCTAACCCTATTTAACCAACCGA3′ (SEQ ID NO:222)
NFIX_HM Flap oligo.:   5′CGCCGAGGGCGGGTTAAAGTG/3C6/ (SEQ ID NO:223)

FIG. 1 (cont'd)

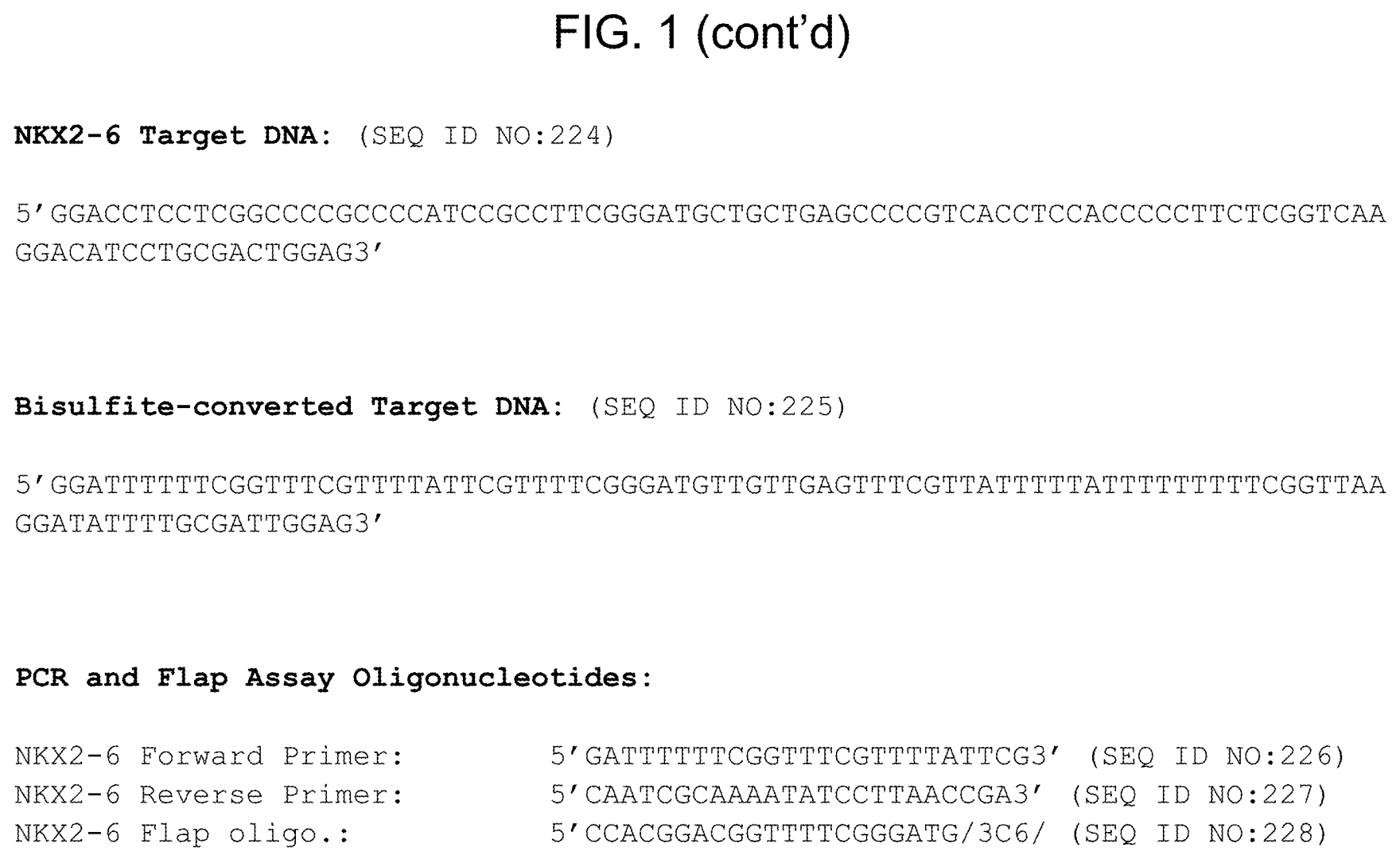

NKX2-6 Target DNA:  (SEQ ID NO:224)

5'GGACCTCCTCGGCCCCGCCCCATCCGCCCTTCGGGATGCTGCTGAGCCCCGTCACCTCCAACCCCCTTCTCGGTCAA
GGACATCCTGCGACTGGGAG3'

Bisulfite-converted Target DNA:  (SEQ ID NO:225)

5'GGATTTTTTCGGTTTCGTTTTATTCGTTTTTCGGGATGTTGTTGAGTTTCGTTTATTTTTATTTTTTTTCGGTTAA
GGATATTTTGCGATTGGGAG3'

PCR and Flap Assay Oligonucleotides:

NKX2-6 Forward Primer:    5'GATTTTTTTCGGTTTTCGTTTTATTCG3'    (SEQ ID NO:226)
NKX2-6 Reverse Primer:    5'CAATCGCAAAATATCCTTAACCGA3'    (SEQ ID NO:227)
NKX2-6 Flap oligo.:    5'CCACGGACGGTTTTCGGGATG/3C6/    (SEQ ID NO:228)

FIG. 1 (cont'd)

OPLAH Target DNA: (SEQ ID NO:229)

5′CTGTCAGTGCTGACCGAGCGCCGGCGCCTTCCGGCCATACGGGCTCCACGGTGCGCGGTTCCCCAGCCCTCGCGGC
CCTCCCCGCCCCG3′

Bisulfite-converted Target DNA: (SEQ ID NO:230)

5′TTGTTAGTGTTGATCGAGCGTCGGCGTTTTTCGGTTATACGGGTTTTTACGGTGCGCGGTTTTTAGTTTTCGCGGT
TTTTTTCGTTTTTCG3′

PCR and Flap Assay Oligonucleotides:

OPLAH Forward Primer:     5′CGTCGCGGTTTTTTCGGTTATACG3′ (SEQ ID NO:231)

OPLAH Reverse Primer:     5′CGCGAAAACTAAAAAACCGCG3′ (SEQ ID NO:232)

OPLAH Flap oligo.:     5′CCACGGACGCGACCGTAAAAC/3C6/ (SEQ ID NO:233)

FIG. 1 (cont'd)

PARP15 Target DNA: (SEQ ID NO:234)

5'CGGAGTATGGTGAGGAGCGCGGGGGAAGGGGACAGGGTGCGGGAAGGGGACAGCAGGGCCTGAGCCTGGGGCCCGCAAGACCC
AGCAGCCCGAGCGGGGGGCGCAGAGACCCCACGCCACGCACA3'

Bisulfite-converted Target DNA: (SEQ ID NO:235)

5'CGGAGTATGGTGAGGAGCGCGGGGGAAGGGGACAGGGTGCGGGAAGGGGATAGTAGGGTTGAGTTTGGGGTTCGTAAGATTT
AGTAGTTCGAGCGGGGGGCGTAGAGATTTACGTTACGTATA3'

PCR and Flap Assay Oligonucleotides:

PARP15 Forward Primer:    5'GGTTGAGTTTGGGGTTCG3' (SEQ ID NO:236)

PARP15 Reverse Primer:    5'CGTAACGTAAAATCTCTACGCCC3' (SEQ ID NO:237)

PARP15 Flap oligo.:    5'CCACGGACGCGCTCGAACTAC/3C6/ (SEQ ID NO:238)

FIG. 1 (cont'd)

PRDM14 Target DNA: (SEQ ID NO:239)

5'GGAGAGCAGCCCGCAGAACCTGGCCGCGCGTACTACACGCCCTTCCCGTCCTATGGACACTACAGAAACAGCCTGGC
CACCGTGGAGGAAGACTTCC3'

Bisulfite-converted Target DNA: (SEQ ID NO:240)

5'GGAGAGTAGTTCGTAGAATTTGGTCGCGCGTATTATACGTTTTTTTCGTTTTATGGATATTATAGAAATAGTTTGGT
TATCGTGGAGGAAGATTTT3'

PCR and Flap Assay Oligonucleotides:

PRDM14 Forward Primer:      5'GAGTAGTTCGTAGAATTTGGTCG3' (SEQ ID NO:241)
PRDM14 Reverse Primer v2: 5'CCACGATAACCAAACTATTTCTATAATATCC3' (SEQ ID NO:242)
PRDM14 Flap oligo.:         5'CCACGGACGGCGTATTATACG/3C6/(SEQ ID NO:243)

PRDM14 Forward Primer v3: 5'GGAGAGTAGTTCGTAGAATTTGG3' (SEQ ID NO:244)
PRDM14 Rev. Primer v3: 5'CTATTTCTATAATATCCATAAAACGAAAAAAACGT3' (SEQ ID NO:245)
PRDM14 Flap oligo. v3: 5'CCACGGACGGTCGCGTATTAT/3C6/ (SEQ ID NO:246)

FIG. 1 (cont'd)

PRKCB_28 Target DNA: (SEQ ID NO:247)

5'GGGAAGGTGCCCTGCGCGGCGCGCTCACCAGAGATGAAGTCGGTGGCTGCAGAAGTGGGCTGCTTGAAGA
AGCGGGGCGGTGAATTTG3'

Bisulfite-converted Target DNA: (SEQ ID NO:248)

5'GGGAAGGTGTTTTGCGGCGCGCGTTTATTAGATGAAGTCGGTGGTTGTAGAAGTGGGTTGTTTGAAGA
AGCGGGGCGGTGAATTTG3'

PCR and Flap Assay Oligonucleotides:

PRKCB_28 Forward Primer:    5'GGAAGGTGTTTTGCGGCG3' (SEQ ID NO:249)
PRKCB_28 Reverse Primer:    5'CTTCTACAACCACTACACCGA3' (SEQ ID NO:250)
PRKCB_28 Flap oligo.:    5'CCACGGACGCGGCCGCGTTTAT/3C6/ (SEQ ID NO:251)

FIG. 1 (cont'd)

PTGDR Target DNA: (SEQ ID NO:252)

5'GCCTCGGGGCCCGGGGACTCACAATTACGGGCAGAGAACACATAGTGAAGAGAGCACGGTCATCAGCGGCCAGCAGCA
GGAGGTGATCCAGCTCCTCCAGGGGCTGAGGG3'

Bisulfite-converted Target DNA: (SEQ ID NO:253)

5'GTTTCGGGGTTCGGGGATTTATAATTACGGGTAGAGAATATATAGTGAAGAGAGTACGGTTATTAGCGGTTAGTAGTA
GGAGGTGATTTAGTTTTTTTAGGGGTTGAGGG3'

PCR and Flap Assay Oligonucleotides:

PTGDR Forward Primer:    5'GGGTTCGGGGGATTTATAATTACGGG3'  (SEQ ID NO:254)

PTGDR Reverse Primer:    5'CCTCCTACTACTAACGCTAATAACC3'   (SEQ ID NO:255)

PTGDR Flap oligo.:       5'CCACGGACGCGTACTCTTCAC/3C6/  (SEQ ID NO:256)

FIG. 1 (cont'd)

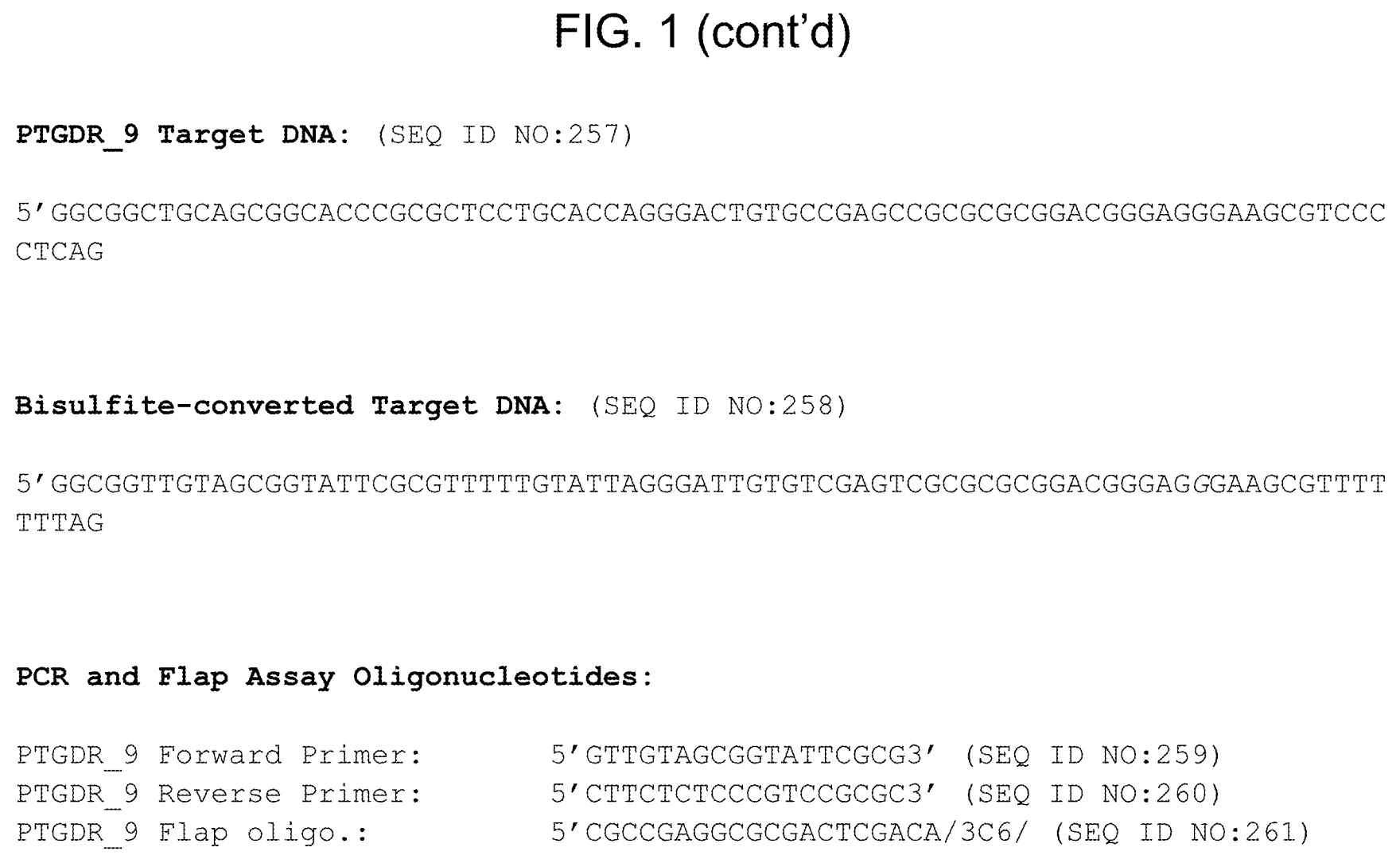

PTGDR_9 Target DNA: (SEQ ID NO:257)

5'GGCGGGCTGCAGCGGCACCCGCGCTCCTGCACCAGGGACTGTGCCGAGCCGCGCGGGACGGGAGGGAAGCGTCCC
CTCAG

Bisulfite-converted Target DNA: (SEQ ID NO:258)

5'GGCGGGTTGTAGCGGGTATTCGCGTTTTTGTATTAGGGATTGTGTCGAGTCGCGCGGGACGGGAGGGAAGCGTTTT
TTTAG

PCR and Flap Assay Oligonucleotides:

PTGDR_9 Forward Primer:     5'GTTGTAGCGGGTATTCGCG3' (SEQ ID NO:259)
PTGDR_9 Reverse Primer:     5'CTTCTCCCGTCCGCGC3' (SEQ ID NO:260)
PTGDR_9 Flap oligo.:     5'CGCCGAGGCGGCGACTCGACA/3C6/ (SEQ ID NO:261)

FIG. 1 (cont'd)

Human RASSF1 Target DNA: (SEQ ID NO:262)

5'TCCAGAAACACGGGTATCTCCGCGTGGTGCTTTGCGGTCGCCGTCGTTGTGGCCGTCCGGGGGTGGGGTGTGAGGA
GGGGACGGAGGAGGGAAGGGCAAGGGCAAGGGCGGGGGGGCTCTGCGAGAGCGCGCCCAGCCCCGCCTTC3'

Bisulfite-converted Target DNA: (SEQ ID NO:263)

5'TTTAGAAATACGGGTATTTTCGCGTGTGTTTGCGGTCGTCGTCGTTGTGGTCGTTGTGGTCGTTGTGGTGTGAGGA
GGGGACGGAGGAGGGAAGGGGTAAGGGCGGGGGGGTTTTGCGAGAGCGCGTTTAGTTTCGTTTTT3'

PCR and Flap Assay Oligonucleotides:

Human RASSF1 Forward Primer v2:     5'AGAAATACGGGTATTTTCGCG3' (SEQ ID NO:264)

Human RASSF1 Reverse Primer v2:     5'CCACAACGACGACGACGACC3' (SEQ ID NO:265)

Human RASSF1 Flap oligo. V2:     5'CCACGGACGCGCGCAAAACACCA/3C6/(SEQ ID NO:266)

FIG. 1 (cont'd)

SHOX2 Target DNA: (SEQ ID NO:267)

5'CGGTCGGGCAGGCGGGACGGGAGATTACCTGGCTGTCCAGGGGACCCTTATGCAGGGTTTGGCCCGAGCCCAGGGGC
AGCGAGGGGCGTCTGCGGGATGCGGGCTCCCCTGTGCGGCACAAACACC3'

Bisulfite-converted Target DNA: (SEQ ID NO:268)

5'CGGTCGGGTAGGCGGGACGGGAGATTATTTGGTTGTTTAGGGGATTTTATGTAGGGTTTGGTTCGAGTTTAGGGGT
AGCGAGGGGCGTTTGCGGGATGCGGGTTTTTTGTGCGGTATAATATT3'

PCR and Flap Assay Oligonucleotides:

SHOX2 Forward Primer:    5'GTTCGAGTTTAGGGGTAGGCG3' (SEQ ID NO:269)
SHOX2 Reverse Primer:    5'CCGCACAAAAAACCCGCA3' (SEQ ID NO:270)
SHOX2 Flap oligo.:       5'CCACGGACGATCCGCAAACGC/3C6/ (SEQ ID NO:271)

FIG. 1 (cont'd)

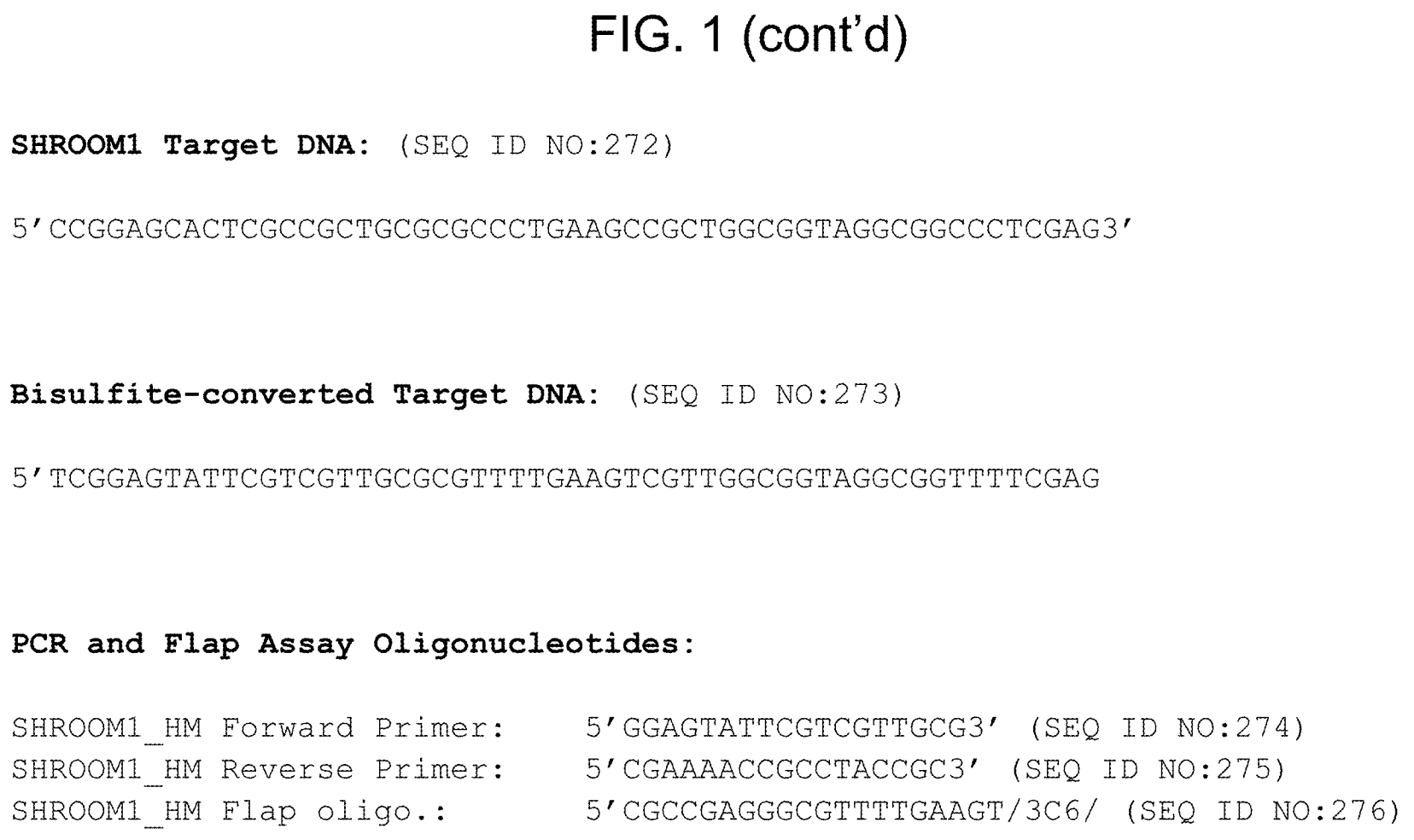

SHROOM1 Target DNA: (SEQ ID NO:272)

5' CCGGAGCACTCGCCGCGGCTGCGCGCCCTGAAGCCGCTGGCGGGTAGGCGGCCCTCGAG3'

Bisulfite-converted Target DNA: (SEQ ID NO:273)

5' TCGGAGTATTCGTCGTTGCGCGTTTTGAAGTCGTTGGCGGGTAGGCGGTTTTCGAG

PCR and Flap Assay Oligonucleotides:

SHROOM1_HM Forward Primer:      5'GGAGTATTCGTCGTTGCG3'  (SEQ ID NO:274)

SHROOM1_HM Reverse Primer:      5'CGAAAACCGCCTACCGC3'  (SEQ ID NO:275)

SHROOM1_HM Flap oligo.:      5'CGCCGAGGGCGTTTTGAAGT/3C6/ (SEQ ID NO:276)

FIG. 1 (cont'd)

SKI Target DNA: (SEQ ID NO:277)

5'CCCGGGCCTACGGTCCTCCCGCCACCTCCACGGGGGCGGCTGTGTTGGGGCCCCACCAGGCAGAGCCGTGTTCTCAGG
CGTTGGCTCTCATGGAGGTGG3'

Bisulfite-converted Target DNA: (SEQ ID NO:278)

5'TTCGGGTTTACGGTTTTTTTCGTTATTTTTTACGGGGGCGGTTGTGTTGGGGGTTTTATTAGGTAGAGTCGTGTTTTTAGG
CGTTGGTTTTTATGGAGGTGG3'

PCR and Flap Assay Oligonucleotides:

SKI Forward Primer:  5'ACGGTTTTTTTCGTTATTTTTTACGGG3'  (SEQ ID NO:279)

SKI Reverse Primer:  5'CAACGCCTAAAAAACACGACTC3'  (SEQ ID NO:280)

SKI Flap oligo.:  5'CGCCGAGGGCGGGTTGTTGG/3C6/  (SEQ ID NO:281)

FIG. 1 (cont'd)

S1PR4 Target DNA: (SEQ ID NO:282)

5'GGGCCTGTCCCGTTCCCTGCTCCCCATACAGGCGAGGCTGCGTGCACACAGCTTCCTGTACCCCAGGAGGGCCTG
CCTGGCACGCACCCGGTGGCTGCCACCATCCACACGCAAGACTGCAACTTCAGATGCTCCGCACGCTGGAGATG3'

Bisulfite-converted Target DNA: (SEQ ID NO:283)

5'GGGTTTGTTTCGTTTTTTGTTTTTTATATAGGCGAGGTTGCGTGTATATAGTTTTTTGTATTTTAGGAGGGTTTG
TTTGGTACGTATTCGGTGGTTGTATTATTTATACGTAAGATTGTAATTTTAGATGTTTCGTACGTTGGAGATG3'

PCR and Flap Assay Oligonucleotides:

S1PR4_HM Forward Primer:     5'TTATATAGGCGAGGTTGCGT3'  (SEQ ID NO:284)

S1PR4_HM Reverse Primer:     5'CTTACGTATAAATAATACAACCACCGAATA3'  (SEQ ID NO:285)

S1PR4_HM Flap oligo.:        5'CCACGGACGACGTACCAAACA/3C6/(SEQ ID NO:286)

FIG. 1 (cont'd)

SLC12A8 Target DNA: (SEQ ID NO:287)

5'CGGAGCTAGGAGGGTGGGGCTCCGGAGGGCGCAGGAAGAGCGGCTCTGCGAGGAAAGGAGAGGCCGCTTC
TGGGAAGGGACCC3'

Bisulfite-converted Target DNA: (SEQ ID NO:288)

5'CGGAGTTAGGAGGGTGGGGGTTCCGGAGGGCGTAGGAAGAGCGGTTTTGCGAGGAAAGGAGAGAGGTCGTTTT
TGGGAAGGGATTT3'

PCR and Flap Assay Oligonucleotides:

SLC12A8 Forward Primer:    5'TTAGGAGGGTGGGGTTCG3'    (SEQ ID NO:289)

SLC12A8 Reverse Primer:    5'CTTTCCTCGCAAAACCGC3'    (SEQ ID NO:290)

SLC12A8 Flap oligo.:    5'CCACGACGGGAGGGCGTAGG/3C6/ (SEQ ID NO:291)

FIG. 1 (cont'd)

SOBP Target DNA: (SEQ ID NO:292)

5'GCCCCGGCGGGCCCCGAGGGGCGCGGCGCCTGCAACGTCATCGTGAACGGCACGCGCGGG3'

Bisulfite-converted Target DNA: (SEQ ID NO:293)

5'GTTTCGGCGGGGTTTCGAGGCGGTCGCGCGGTTTGTAACGTTATCGTGAACGGTACGCGCGGG3'

PCR and Flap Assay Oligonucleotides:

SOBP_HM Forward Primer:     5'TTTCGGCGGGGTTTCGAG3' (SEQ ID NO:294)

SOBP_HM Reverse Primer:     5'CGTACCGTTCACGATAACGT3' (SEQ ID NO:295)

SOBP_HM Flap oligo.:        5'CGCCGAGGGGCGGGTCGCGGT/3C6/ (SEQ ID NO:296)

SOBP_HM Flap oligo. v2:     5'CGCCGAGGTTACAAACCGCG/3C6/ (SEQ ID NO:297)

FIG. 1 (cont'd)

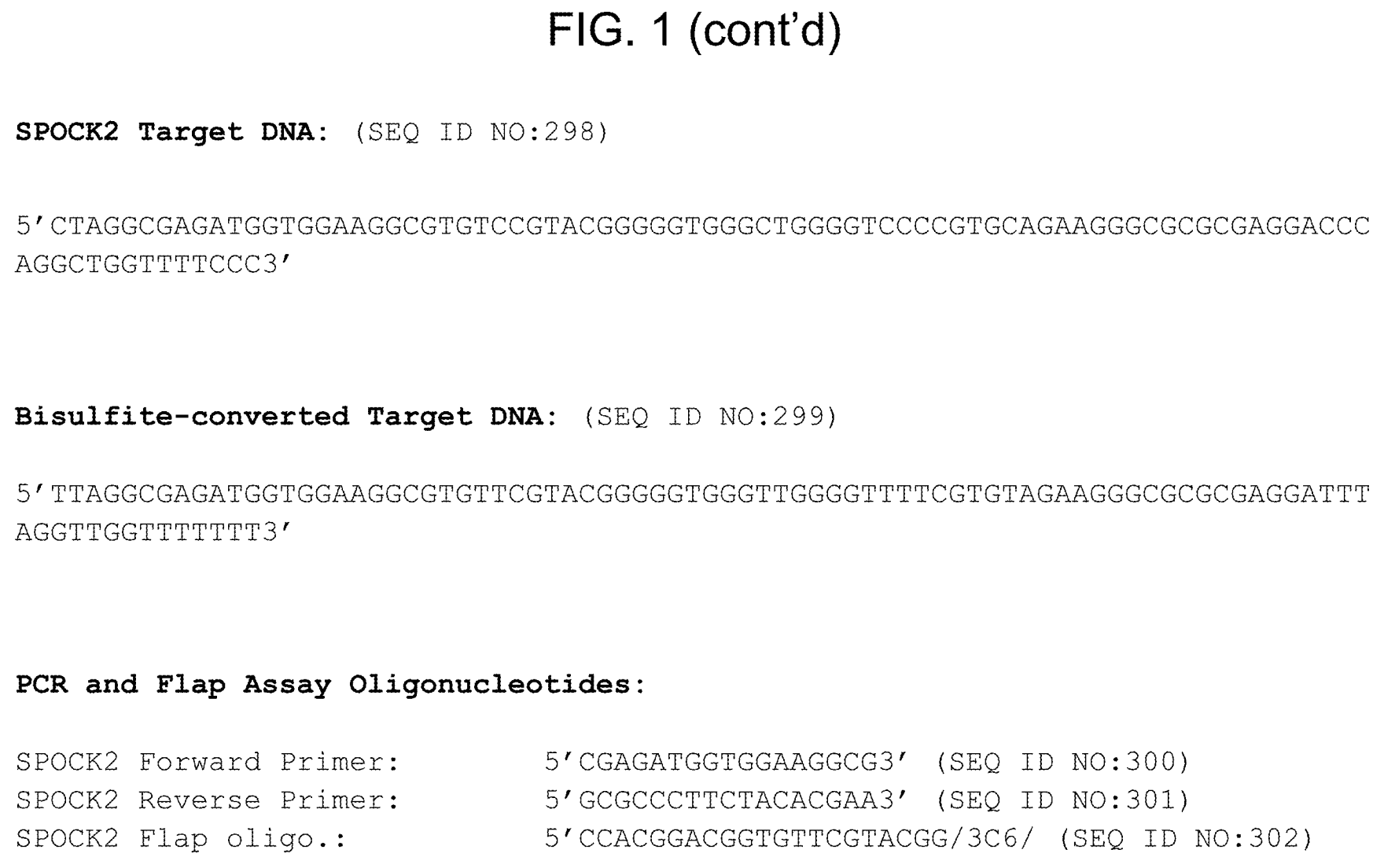

SPOCK2 Target DNA: (SEQ ID NO:298)

5′CTAGGCGAGATGGTGGAAGGCGTGTCCGTACGGGGGGTGGGGCTGGGGTCCCCGTGCAGAAGGGCGCGGAGGACCC
AGGCTGGTTTTCCC3′

Bisulfite-converted Target DNA: (SEQ ID NO:299)

5′TTAGGCGAGATGGTGGAAGGCGTGTTCGTACGGGGGGTGGGGTTGGGGTTTTCGTGTAGAAGGGCGCGGAGGATTT
AGGTTGGTTTTTT3′

PCR and Flap Assay Oligonucleotides:

SPOCK2 Forward Primer:     5′CGAGATGGTGGAAGGGCG3′ (SEQ ID NO:300)

SPOCK2 Reverse Primer:     5′GCGCCCTTCTACACGAA3′ (SEQ ID NO:301)

SPOCK2 Flap oligo.:     5′CCACGGACGGTGTTCGTACGG/3C6/ (SEQ ID NO:302)

FIG. 1 (cont'd)

ST8SIA1 Target DNA: (SEQ ID NO:303)

5′GCGCTGCTGCGCCGCCAGGCAAGGCGAGGGCTCCGGGAGAAGGCTCGGCTCCCTCCTAAACATGTGGCCCGTGGCG
TCCCCTTGTCCCCTCCGAGCGATGCTCCTGCGCCCTCCCCGCGCCTCGCGCCTGCGCGCGCCAGGCAA3′

Bisulfite-converted Target DNA: (SEQ ID NO:304)

5′GGCGAGGGTTCGGGAGAAGGTTCGGTTTTTTTTAAATATGTGGTTCGTGGCGTTTTTTTGTTTTTTTTCGAGCGA
TGTTTTTGCGTTTTTCGTTTTTTTCGCGTTGTTGCGTCGTTAGGTAA3′

PCR and Flap Assay Oligonucleotides:

ST8SIA1 Forward Primer:    5′AAATATGTGGTTCGTGGCGGGTT3′    (SEQ ID NO:305)

ST8SIA1 Reverse Primer:    5′ACGCAACAACGCGAAAAAAC3′    (SEQ ID NO:306)

ST8SIA1 Flap oligo.:    5′CGCCGAGGCGACGAAAAAACG/3C6/    (SEQ ID NO:307)

FIG. 1 (cont'd)

ST8SIA1_22 Target DNA: (SEQ ID NO:308)

5'ACGAGAAAGAGATCGTGCTGCAGGGGTGCAACAGGGCACGGCGCGTGGAGGAGGAACCAGACCGCGGCCAGAGCGT
TCAGGTACTCCTGCCCTCGCGGCTCCTCCCCCTCTAGCGTCCTTCCTCCCCGAGTGCAGAGG3'

Bisulfite-converted Target DNA: (SEQ ID NO:309)

5'ACGAGAAAGAGATCGTGTTGTAGGGGTGTTGTAATAGGGTACGGCGCGTGGAGGAGGAATTAGATCGCGGTTAGAGCGT
TTAGGTATTTTTGTTTTCGCGGTTTTTTTTTTTTTAGCGTTTTTTTTTTTTTCGAGTGTAGAGG3'

PCR and Flap Assay Oligonucleotides:

ST8SIA1_22 Forward Primer:     5'GGGGTGTTGTTGTAATAGGGTACG3'  (SEQ ID NO:310)
ST8SIA1_22 Reverse Primer:     5'CTAAACGCTCTAACCGCGA3'  (SEQ ID NO:311)
ST8SIA1_22 Flap oligo.:        5'CCACGGACGGGCGGTGGAGGAG/3C6/  (SEQ ID NO:312)

FIG. 1 (cont'd)

SP9 Target DNA: (SEQ ID NO:313)

5'CGCGCCGTTGGTCACCTCGCCGCCGCCAGCCGTCGAATGGAAGCCCGACTTGTACCAGGACTCGTACGGGTGCGC
CATGCCCACGCGCGGGTACAGCCCGTCGGCTGCCGTCGTCGTG3'

Bisulfite-converted Target DNA: (SEQ ID NO:314)

5'CGCGTCGTTGGTTATTTCGTCGGTCGTTAGCGTCGAATGGAAGTTCGATTTGTATTAGGATTCGTACGGGTGCGT
TATGTTTACGCGCGGGTATAGTTCGTCGGTTGTCGTCGTGTG3'

PCR and Flap Assay Oligonucleotides:

SP9 Forward Primer:           5'TAGCCGTCGAATGGAAGTTCGA3' (SEQ ID NO:315)

SP9 Reverse Primer:           5'GCGCGTAAACATAACGCACC3' (SEQ ID NO:317)

SP9 Flap oligo.:           `5'CCACGGACGCCGTACGAATCC/3C6/ (SEQ ID NO:318)

SP9 Forward Primer Universal: 5'GGTCGTTAGCGTCGAATG3' (SEQ ID NO:316)

SP9 Reverse Primer:           5'GCGCGTAAACATAACGCACC3' (SEQ ID NO:317)

SP9 Flap oligo.:           5'CCACGGACGCCGTACGAATCC/3C6/ (SEQ ID NO:318)

FIG. 1 (cont'd)

SUCLG2 Target DNA: (SEQ ID NO:319)

5'GGTTCCTTCCCGTGGGTTCTTAATCGTCTCGCTGACTTCCAGAATGAAAACTGCAGACCCTCGCGGTAAAGATGGC
GTGACCAGAA3'

Bisulfite-converted Target DNA: (SEQ ID NO:320)

5'GGTTTTTTTCGTGGGTTTTTAATCGTTTCGTTGATTTTTAGAATGAAATTGTAGATTTTCGCGGTAAAGATGGC
GTGATTAGAA3'

PCR and Flap Assay Oligonucleotides:

SUCLG2_HM Forward Primer:          5'TCGTGGGTTTTTAATCGTTTCG3' (SEQ ID NO:321)

SUCLG2_HM Reverse Primer:          5'TCACGCCATCTTTACCGC3' (SEQ ID NO:322)

SUCLG2_HM Flap oligo.: 5'CCACGGACGCGAAAATCTACA/3C6/ (SEQ ID NO:323)

SUCLG2_HM For. Primer Univ.:   5'GGTTTTTTTCGTGGGTTTTTAATCG3' (SEQ ID NO:324)

SUCLG2_HM Rev. Primer Univ.:   5'CTAATCACGCCATCTTTACCG3'(SEQ ID NO:325)

SUCLG2_HM Flap oligo. Univ.:   5'CCACGGACGGGTTTCGTTGATT/3C6/(SEQ ID NO:326)

FIG. 1 (cont'd)

TBX15 Target DNA Region 1: (SEQ ID NO:327)

5'GGAGTGAGTGCCTACAACGCGCAGGCCGGACTGATCCCCCGTTGCTGCAGGTTGGTGCCCAAGCTGCGGGTGCT
CGGGCGCCAACTAAAGCCAGCTCTGTCCAGACGCGGAAAG3'

Bisulfite-converted Target DNA: (SEQ ID NO:328)

5'GGAGTGAGTGTTTATAACGCGTAGGTCGGATTGATTTTTCGTTGTTGTAGGTTGGTGTTTAAGTTGCGGGTGTT
CGGGCGTTAATTAAAGTTAGTTTTGTTTAGACGCGGAAAG3'

PCR and Flap Assay Oligonucleotides:

| | |
|---|---|
| TBX15 Forward Primer: | 5'CGTAGGTCGGATTGATTTTTCGT3' (SEQ ID NO:329) |
| TBX15 Reverse Primer: | 5'TCTAAACAAAACTAACTTTAATTAACGCCC3' (SEQ ID NO:330) |
| TBX15 Flap oligo.: | 5'CCACGGACGGCGAACACCCGCA/3C6/ (SEQ ID NO:331) |

FIG. 1 (cont'd)

TBX15 Target DNA Region 2: (SEQ ID NO:403)

5'GGAAGGAAATTGCGGGGTTCCCGTCTGCCTTGTCTCCAGCTTCTCTGCTGAAGCCCGGTAGCAGTGAATGGCGCT
GACTTTCAGCGACGACTCCTGGAAGCAACGCCA3'

Bisulfite-converted Target DNA: (SEQ ID NO:404)

5'GGAAGGAAATTGCGGGGTTTTCGTTTGTTTTTTGTTTTTAGTTTTTTTTTGTTGAAGTTCGGTAGTAGTGAATGGCGTT
GATTTTTAGCGACGATTTTTGGAAGTAACGTTA3'

PCR and Flap Assay Oligonucleotides:

TBX15 Reg. 2 Forward Primer:    5' AGGAAATTGCGGGGTTTTCG3' (SEQ ID NO:332)
TBX15 Reg. 2 Forward Primer Univ.:5'GGAAGGAAATTGCGGGTTTTC3' (SEQ ID NO:333)
TBX15 Reg. 2 Reverse Primer:    5'CCAAAAATCGTCGCTAAAAAATCAAC3' (SEQ ID NO:334)
TBX15 Reg. 2 Flap oligo.:    5'CCACGGACGCGCGCCATTCACT/3C6/ (SEQ ID NO:335)

FIG. 1 (cont'd)

TRH Target DNA: (SEQ ID NO:336)

5'GGCGGCCGGCGACCCCTCCCCGCTGACCTCACTCGAGCCGCCCTGGCGCAGATATAAGCGGGCGGCCCATCTGAA
GAGGGCTCGGCGCAGGCGCCCGGGGTC3'

Bisulfite-converted Target DNA with primer and Flap oligo. sites
(SEQ ID NO:337)

5'GGCGGTCGCGATTTTTTTTCGTTGATTTTATTCGAGTCGTCGTTTGGCGTAGATATAAGCGGGCGGTTTATTTGAA
GAGGGTTCGGTAGGCGTTCGGGGTT3'

PCR and Flap Assay Oligonucleotides:

TRH Forward Primer:     5'TTTCGTTGATTTTATTCGAGTCG3' (SEQ ID NO:338)

TRH Reverse Primer:     5'TCTTCAAATAAACCGCCGC3' (SEQ ID NO:339)

TRH Flap oligo.:     5'CGCCGAGGGTCGTTTGGCGT/3C6/ (SEQ ID NO:340)

FIG. 1 (cont'd)

TSC22D4 Target DNA: (SEQ ID NO:341)

5'CGGGTGGTGAAGCTGCCCCACGGCCTGGGAGAGCCTTATCGCCGCGGTCGCTGGACGTGTGTGGATGTTTATGAG
CGAGACCTGGAGCCCCACAGCTTCGGCGGACTCCCTGGAGGGAA3'

Bisulfite-converted Target DNA: (SEQ ID NO:342)

5'CGGGTGGTGAAGTTGTTTTACGGTTTGGGAGAGTTTTATCGTCGCGGTCGTTGGACGTGTGTGGATGTTTATGAG
CGAGATTTGGAGTTTTATAGTTTCGGCGGATTTTTGGAGGGAA3'

PCR and Flap Assay Oligonucleotides:

TSC22D4 Forward Primer:    5'GTTTGGGAGAGTTTTATCGTCG3' (SEQ ID NO:343)

TSC22D4 Reverse Primer:    5'CCTCCAAAAATCCGCCGA3' (SEQ ID NO:344)

TSC22D4 Flap oligo.:    5'CGCCGAGGGCGGTCGTTGGA/3C6/ (SEQ ID NO:345)

FIG. 1 (cont'd)

ZDHHC1-zincfinger, DHHC-typecontaining1 Target DNA: (SEQ ID NO:346)

5'GGGGCGGGGCCGACAGCCCACGCTGGCGGCGGCAGGCGGCTGGCGGCCGCGCCGCGTTTTCGTGAGCCCGAGCAG3'

Bisulfite-converted Target DNA: (SEQ ID NO:347)

5'GGGGTCGGGGTCGATAGTTTACGTTGGGCGGCGGTAGGCGGCGTTCGTCGTTTTCGTGAGTTCGAGTAG3'

PCR and Flap Assay Oligonucleotides:

ZDHHC1 Forward Primer:        5'GTCGGGGGTCGATAGTTTACG3' (SEQ ID NO:348)

ZDHHC1 Reverse Primer_v3:        5'ACTCGAACTCACGAAAACG3' (SEQ ID NO:349)

ZDHHC1 Flap oligo.:        5'CGCCGAGGGACGAACGCCACG/3C6/ (SEQ ID NO:350)

FIG. 1 (cont'd)

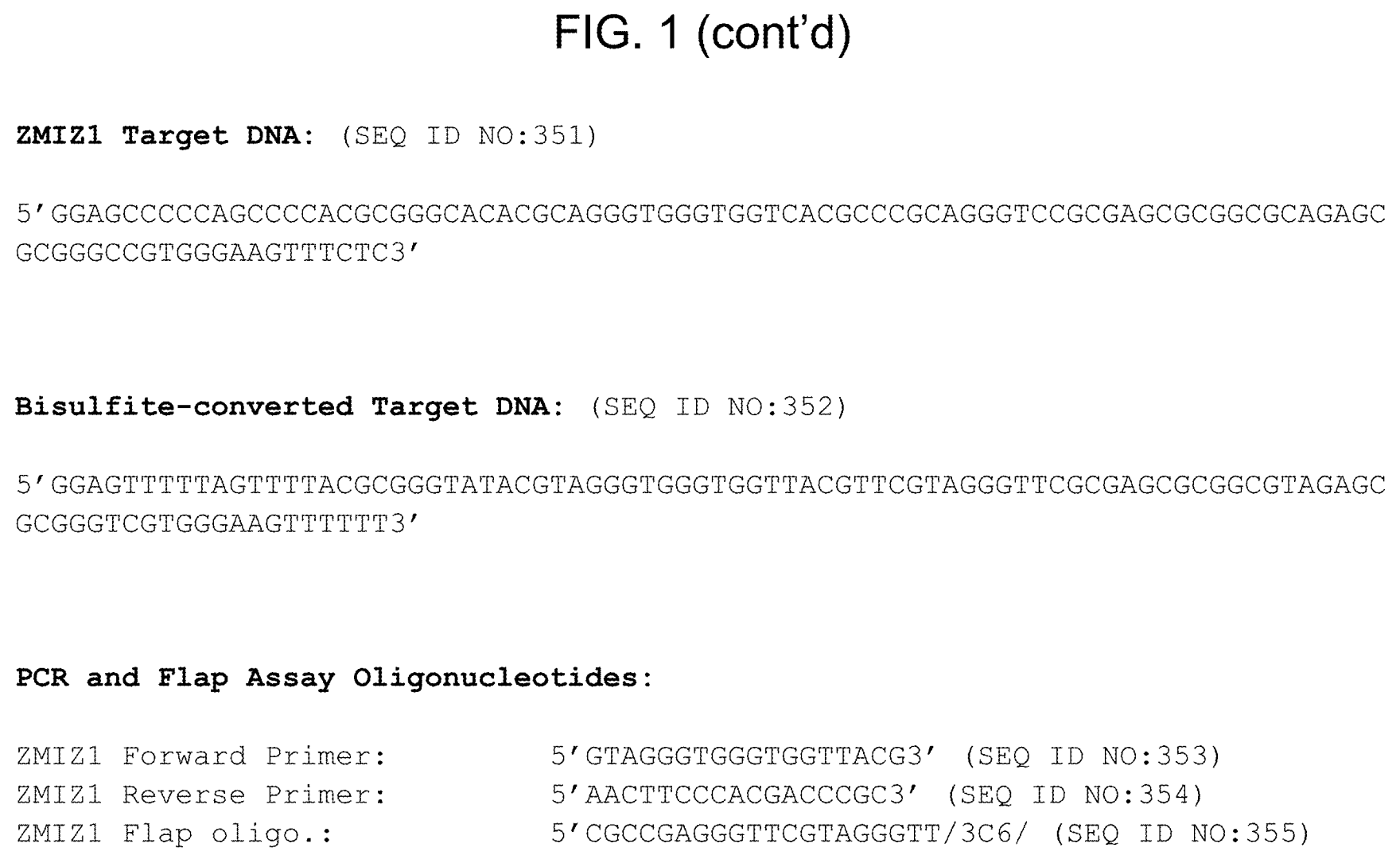

ZMIZ1 Target DNA: (SEQ ID NO:351)

5'GGAGCCCCCAGCCCCACGCGGGCACACGCAGGGTGGGTCACGCCCGCAGGTCCGCGAGCGGGCGCAGAGC
GCGGGCCGTGGGAAGTTTCTC3'

Bisulfite-converted Target DNA: (SEQ ID NO:352)

5'GGAGTTTTTAGTTTTACGCGGGTATACGTAGGGTGGGTGGGTTACGTTCGCGAGCGGGCGCGTAGAGC
GCGGGTCGTGGGAAGTTTTT3'

PCR and Flap Assay Oligonucleotides:

ZMIZ1 Forward Primer:      5'GTAGGGTGGGTGGGTGGTTACG3' (SEQ ID NO:353)
ZMIZ1 Reverse Primer:      5'AACTTCCCACGACCCGC3' (SEQ ID NO:354)
ZMIZ1 Flap oligo.:         5'CGCCGAGGGTTCGTAGGGTT/3C6/ (SEQ ID NO:355)

FIG. 1 (cont'd)

ZNF132 Target DNA: (SEQ ID NO:356)

5'GGCGCCGCCATTGCGGTCCTCATTTTGCTGCTGGTGGGCTACAGCAGGCCTCTGGAGCCACACCAGGGCA
CGGGAGTGGGTGCAGGGACCGTCACCGCGCCTTCACACGCACCATAGTGCCC3'

Bisulfite-converted Target DNA: (SEQ ID NO:357)

5'GGCGTCGTTATTGCGGTTTTTATTTTGTTGCTGGTGGGTTATAGTAGGTTTTTGGAGTTATATTAGGGTA
CGGGAGTGGGTGTAGGGATCGTTATCGCGTTTTTATACGTATTATAGTGTTT3'

PCR and Flap Assay Oligonucleotides:

ZNF132 Forward Primer v2: 5'TGGAGTTATATTAGGGTACGGGA3' (SEQ ID NO:358)

ZNF132 Reverse Primer: 5'ACACTATAATAACGTATAAAAACGCGATA3' (SEQ ID NO:359)

ZNF132 Flap oligo.: 5'CCACGGACGAACGATCCCTAC/3C6/ (SEQ ID NO:360)

FIG. 1 (cont'd)

ZNF329 Target DNA: (SEQ ID NO:361)

5' GGCGGGCGAGGGGCGCGTCCGCGGGTGGGTTTCACCTGGGTGGTGGCATGTGGGGCCCGCTAGGGCGGAGGGTCTG
GCCAGGGGCGTAGTTCTCCCTGGTGGGTGGGGACGCGCTCCCGTGGGCGATTGGGGGTCACTCCTCTGAGG3'

Bisulfite-converted Target DNA: (SEQ ID NO:362)

5' GGCGGGCGAGGGGCGCGTTCGCGGGTGGGTTTTATTTGGGTGGTGGGGTATGTGGGGTTCGTTAGGGCGGAGGGTTTG
GTTAGGGGCGTAGTTTTTTTGGTGGGTGGGGACGTTTCGTGGGCGATTGGGGGTTATTTTTTGAGG3'

PCR and Flap Assay Oligonucleotides:

ZNF329 Forward Primer:    5' GGTGGTGGGTATGTCGG3' (SEQ ID NO:363)
ZNF329 Reverse Primer:    5' CCAATCGCCACGAAACG3' (SEQ ID NO:364)
ZNF329 Flap oligo.:       5' CCACGACGGGTTCGTTAGGG/3C6/ (SEQ ID NO:365)

FIG. 1 (cont'd)

ZNF671 Target DNA: (SEQ ID NO:366)

5′CCGTGGGCGCGGACAGCTGCCGGGAGCGGCAGGCGTCTCGATCCGGGGACGCAGGCACTTCCGTCCCTGCAGAGCA
TCAGAGCGCGTCTCGGGACACTGGGACAACATCTCCTCCGCG3′

Bisulfite-converted Target DNA: (SEQ ID NO:367)

5′TCGTGGGGCGCGGATAGTTGTCGGGAGCGGCGTTTCGATCCGGGGACGTAGGCGTATTTTCGTTTTTGTAGAGTA
TTAGACGCGTTTCGGGATATTGGGATAATATTTTTTTCGCG3′

PCR and Flap Assay Oligonucleotides:

ZNF671 Forward Primer:  5′GTTGTCGGGGAGCGGCGTAGG3′ (SEQ ID NO:368)
ZNF671 Reverse Primer:  5′CCAATATCCCGAAACGCCGTCT3′ (SEQ ID NO:369)
ZNF671 Flap oligo.:  5′CCACGGACGCCGTTTCGATCG/3C6/ (SEQ ID NO:370)

FIG. 1 (cont'd)

ZNF781:Chr19:38183137-38183018(GRCh37/hg19) Target DNA: (SEQ ID NO:371)

5'AAGCTGCGCCCGGAGACGTGGGAGCCGTTCTCTTGTTTTCCGAGTGCGCGGACTCATCGGGTCACAGTTTATGCTT
TTATGACGCGGGTGAGTCCAGCCACTGATTCCTAACGGTTTAGAGT3'

Bisulfite-converted Target DNA: (SEQ ID NO:372)

5'AAGTTGCGTTCGGAGACGTGGGAGCCGTTTTTTTGTTTTTTCGAGTGCGCGGATTTATCGGGTTATAGTTTATGTTT
TTATGACGCGGGTGAGTTTAGTTATTGATTTTTAACGGTTTAGAGT3'

PCR and Flap Assay Oligonucleotides:

ZNF781 Forward Primer:    5'CGTTTTTTTTGTTTTTCGAGTGCG3'    (SEQ ID NO:373)
ZNF781 Reverse Primer:    5'TCAATAACTAAACTCACCGCGTC3'    (SEQ ID NO:374)
ZNF781 Flap oligo.:    5'CCACGCGACGGGCGGATTTATCG/3C6/ (SEQ ID NO:375)

FIG. 2

| Adenocarcinoma marker region ref. # | Chromosome | Start position | Stop position | mean BC island | mean lung,normal, island | mean Adenocarcinoma Lung island | mean Large cell Lung island | mean Small cell Lung island | mean Squamous Lung island | mean undefined cancer Lung island | Norm/BC | Ad/BC | LC/BC | SC/BC | SQ/BC | UND/BC |
|---|---|---|---|---|---|---|---|---|---|---|---|---|---|---|---|---|
| AC1 | 10 | 81002926 | 81002992 | 0% | 1% | 21% | 15% | 22% | 8% | 32% | 1.31 | 42.51 | 30.95 | 45.31 | 15.74 | 64.67 |
| AC2 | 2 | 73147720 | 73147790 | 1% | 3% | 24% | 36% | 50% | 28% | 59% | 3.25 | 26.10 | 38.89 | 54.76 | 30.96 | 64.51 |
| AC3 | 20 | 37435530 | 37435681 | 1% | 1% | 21% | 6% | 5% | 9% | 8% | 1.55 | 33.32 | 9.43 | 7.37 | 15.07 | 12.88 |
| AC4 | 19 | 3785837 | 3785923 | 0% | 1% | 19% | 20% | 5% | 7% | 56% | 4.69 | 66.90 | 68.62 | 19.25 | 26.13 | 195.13 |
| AC5 | 2 | 74726554 | 74726617 | 1% | 4% | 38% | 47% | 68% | 31% | 49% | 3.10 | 27.46 | 34.21 | 49.28 | 22.18 | 35.41 |
| AC6 | 12 | 25056015 | 25056162 | 0% | 1% | 10% | 18% | 25% | 10% | 35% | 1.51 | 27.62 | 50.51 | 68.55 | 27.10 | 95.52 |
| AC7 | 12 | 52400959 | 52401020 | 1% | 1% | 12% | 19% | 3% | 1% | 19% | 1.59 | 24.05 | 36.73 | 5.80 | 2.58 | 36.73 |
| AC8 | 1 | 156863477 | 156863554 | 1% | 3% | 24% | 19% | 32% | 14% | 13% | 2.42 | 20.38 | 15.89 | 26.82 | 11.70 | 10.87 |
| AC9 | 8 | 145106353 | 145106439 | 0% | 2% | 24% | 29% | 9% | 25% | 26% | 4.89 | 59.66 | 71.50 | 22.47 | 62.77 | 65.19 |
| AC10 | 7 | 27135634 | 27135679 | 0% | 0% | 10% | 10% | 7% | 1% | 40% | 1.74 | 44.26 | 42.10 | 28.73 | 4.44 | 172.75 |
| AC11 | 7 | 27135772 | 27135823 | 0% | 1% | 15% | 21% | 7% | 2% | 44% | 4.72 | 91.85 | 132.84 | 43.76 | 10.27 | 270.65 |
| AC12 | 8 | 145106742 | 145106827 | 0% | 2% | 26% | 34% | 10% | 21% | 14% | 5.40 | 81.76 | 108.02 | 31.02 | 68.54 | 45.26 |
| AC13 | 11 | 830323 | 830382 | 0% | 1% | 16% | 9% | 7% | 1% | 2% | 3.56 | 60.14 | 31.27 | 24.44 | 3.55 | 5.83 |
| AC14 | 3 | 124860573 | 124860665 | 0% | 1% | 12% | 34% | 12% | 37% | 39% | 1.55 | 29.73 | 84.15 | 28.68 | 91.45 | 97.00 |
| AC15 | 2 | 97193509 | 97193639 | 1% | 1% | 14% | 7% | 16% | 13% | 16% | 2.04 | 26.57 | 14.00 | 30.21 | 23.54 | 29.84 |
| AC16 | 1 | 65731423 | 65731507 | 0% | 1% | 14% | 20% | 7% | 6% | 5% | 4.05 | 40.31 | 57.98 | 20.18 | 17.71 | 15.74 |
| AC17 | 1 | 968477 | 968584 | 1% | 1% | 25% | 22% | 2% | 12% | 9% | 2.07 | 40.71 | 35.38 | 3.80 | 18.61 | 15.35 |
| AC18 | 14 | 101033514 | 101033620 | 0% | 2% | 18% | 7% | 40% | 5% | 14% | 4.29 | 36.37 | 14.15 | 82.74 | 10.45 | 29.35 |
| AC19 | 17 | 274467359 | 27467467 | 0% | 0% | 10% | 7% | 28% | 4% | 5% | 2.69 | 61.89 | 42.49 | 170.64 | 26.04 | 31.95 |
| AC20 | 8 | 145105570 | 145105675 | 1% | 3% | 30% | 26% | 9% | 29% | 23% | 3.15 | 29.77 | 25.41 | 9.23 | 28.54 | 22.59 |
| AC21 | 9 | 88137543 | 88137628 | 1% | 1% | 13% | 9% | 3% | 7% | 13% | 1.79 | 24.24 | 16.71 | 5.68 | 13.54 | 22.96 |

FIG. 2 (cont'd)

| Adenocarcinoma marker region ref. # | Chromosome | Gene | Transcript | Strand | In Exon | Tss Distance | In CpG Island | Entrez ID | Gene title |
|---|---|---|---|---|---|---|---|---|---|
| AC1 | 10 | ZMIZ1 | NM_020338 | + | 0 | 174135 | 1 | 57178 | zinc finger, MIZ-type containing 1 |
| AC2 | 2 | EMX1 | NM_004097 | + | 0 | 3117 | 1 | 2016 | empty spiracles homeobox 1 |
| AC3 | 20 | PPP1R16B | NM_001172735;NM_015568 | + | 0 | 1183;1183 | 1 | 26051 | protein phosphatase 1, regulatory (inhibitor) subunit 16B |
| AC4 | 19 | MATK | NM_002378;NM_139355;NM_139354 | - | 0 | 15973;578;578 | 1 | 4145 | megakaryocyte-associated tyrosine kinase |
| AC5 | 2 | LBX2 | NM_001009812 | - | 0 | 3889 | 1 | 85474 | ladybird homeobox 2 |
| AC6 | 12 | BCAT1 | NM_001178092;NM_005504;NM_001178094;NM_001178091;NM_001178093 | - | 0 | 46378;46378;-693;46378;-6 | 1 | 586 | branched chain amino-acid transaminase 1, cytosolic |
| AC7 | 12 | GRASP | NM_181711 | + | 1 | 212 | 1 | 160622 | GRP1 (general receptor for phosphoinositides 1)-associated scaffold protein |
| AC8 | 1 | PEAR1 | NM_001080471 | + | 0 | -45 | 1 | 375033 | platelet endothelial aggregation receptor 1 |
| AC9 | 8 | OPLAH | NM_017570 | - | 1 | 9231 | 1 | 26873 | 5-oxoprolinase (ATP-hydrolysing) |
| AC10 | 7 | HOXA1 | NM_005522;NM_153620 | - | 0 | -9;-9 | 1 | 3198 | homeobox A1 |
| AC11 | 7 | HOXA1 | NM_005522;NM_153620 | - | 0 | -147;-147 | 1 | 3198 | homeobox A1 |
| AC12 | 8 | OPLAH | NM_017570 | - | 0 | 8842 | 1 | 26873 | 5-oxoprolinase (ATP-hydrolysing) |
| AC13 | 11 | CD151 | NM_004357;NM_139029;NM_139030;NM_001039490 | + | 1 | -2628;-2628;-2628;-2628 | 1 | 977 | CD151 molecule (Raph blood group) |
| AC14 | 3 | SLC12A8 | NM_001195483;NM_024628 | - | 0 | 69670;71036 | 1 | 84561 | solute carrier family 12 (potassium/chloride transporters), member 8 |
| AC15 | 2 | MAX.chr2.97193509-97193639 | - | - | 0 | - | 0 | - | - |
| AC16 | 1 | DNAJC6 | NM_014787 | + | 0 | 994 | 1 | 9829 | DnaJ (Hsp40) homolog, subfamily C, member 6 |
| AC17 | 1 | AGRN | NM_198576 | + | 0 | 12975 | 1 | 375790 | agrin |
| AC18 | 14 | BEGAIN | NM_001159531;NM_020836 | - | 0 | 893;2617 | 0 | 57596 | brain-enriched guanylate kinase-associated homolog (rat) |
| AC19 | 17 | MYO18A | NM_078471;NM_203318 | - | 0 | 40048;40048 | 0 | 399687 | myosin XVIIIA |
| AC20 | 8 | MAX.chr8.145105570-145105675 | - | - | 0 | - | 1 | - | - |
| AC21 | 9 | MAX.chr9.88137543-88137628 | - | - | 0 | - | 0 | - | - |

FIG. 2 (cont'd)

| Adenocarcinoma marker region ref. # | Chromosome | Start position | Stop position | mean BC.island | mean lung,normal, island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| AC22 | 19 | 369909350 | 369909447 | 0% | 1% | 11% | 15% | 2% | 8% | 0% | 1.86 | 29.45 | 41.75 | 5.10 | 22.88 | 1.28 |
| AC23 | 2 | 96991058 | 96991212 | 0% | 1% | 15% | 6% | 4% | 7% | 4% | 6.00 | 176.53 | 76.85 | 44.00 | 81.37 | 50.29 |
| AC24 | 1 | 2165937 | 2166058 | 0% | 0% | 12% | 17% | 64% | 6% | 16% | 1.37 | 45.20 | 63.35 | 232.04 | 20.22 | 59.05 |
| AC25 | 19 | 58661757 | 58661861 | 1% | 1% | 20% | 12% | 9% | 7% | 4% | 2.71 | 36.53 | 22.37 | 17.50 | 12.26 | 8.10 |
| AC26 | 2 | 97193166 | 97193253 | 0% | 1% | 13% | 8% | 18% | 12% | 21% | 1.71 | 42.20 | 25.79 | 55.43 | 37.48 | 67.24 |
| AC27 | 8 | 145013661 | 145013775 | 0% | 0% | 26% | 6% | 32% | 2% | 10% | 5.69 | 361.21 | 80.01 | 444.31 | 30.71 | 144.38 |
| AC28 | 17 | 26699039 | 26699117 | 0% | 1% | 13% | 14% | 6% | 1% | 12% | 10.25 | 110.62 | 119.15 | 55.00 | 11.44 | 105.40 |
| AC29 | 19 | 58661880 | 58662026 | 1% | 1% | 15% | 6% | 7% | 3% | 4% | 2.75 | 27.79 | 11.93 | 12.58 | 5.88 | 7.42 |
| AC30 | 12 | 502978879 | 502979912 | 1% | 2% | 17% | 20% | 4% | 7% | 19% | 2.26 | 22.36 | 27.00 | 5.77 | 9.22 | 24.93 |
| AC31 | 1 | 322337695 | 322337880 | 1% | 3% | 22% | 25% | 44% | 10% | 14% | 2.78 | 22.43 | 25.97 | 45.37 | 10.13 | 14.59 |
| AC32 | 1 | 65731622 | 65731666 | 1% | 2% | 27% | 35% | 11% | 12% | 17% | 2.00 | 31.36 | 39.95 | 13.18 | 14.20 | 19.04 |
| AC33 | 16 | 23847586 | 23847684 | 0% | 2% | 15% | 23% | 18% | 2% | 26% | 12.77 | 119.07 | 189.49 | 148.49 | 13.87 | 209.78 |
| AC34 | 7 | 1000075307 | 1000075425 | 0% | 2% | 21% | 18% | 54% | 15% | 16% | 3.87 | 45.55 | 39.16 | 116.74 | 32.72 | 34.94 |
| AC35 | 1 | 44031599 | 44031658 | 0% | 2% | 24% | 18% | 21% | 21% | 18% | 4.80 | 75.23 | 56.94 | 66.66 | 64.67 | 56.57 |
| AC36 | 16 | 23847871 | 23847925 | 0% | 1% | 10% | 11% | 6% | 2% | 19% | #DIV/0! | #DIV/0! | #DIV/0! | #DIV/0! | #DIV/0! | #DIV/0! |
| AC37 | 16 | 23847938 | 23848020 | 0% | 1% | 15% | 12% | 10% | 2% | 15% | 25.58 | 293.90 | 237.97 | 199.65 | 41.02 | 298.01 |
| AC38 | 19 | 3785977 | 3786032 | 0% | 1% | 14% | 24% | 3% | 5% | 34% | 5.84 | 54.36 | 93.77 | 12.00 | 19.42 | 135.15 |
| AC39 | 19 | 37288523 | 37288615 | 1% | 2% | 19% | 22% | 26% | 18% | 30% | 2.72 | 25.92 | 30.28 | 34.88 | 24.73 | 40.51 |
| AC40 | 13 | 1030046898 | 1030046982 | 0% | 0% | 14% | 10% | 1% | 1% | 13% | 1.60 | 47.29 | 32.21 | 2.55 | 1.96 | 41.48 |
| AC41 | 2 | 25439185 | 25439264 | 0% | 1% | 10% | 11% | 31% | 3% | 7% | 2.31 | 25.89 | 26.41 | 77.49 | 6.89 | 18.37 |
| AC42 | 20 | 61638472 | 61638536 | 0% | 1% | 15% | 11% | 1% | 5% | 17% | 5.21 | 56.31 | 41.95 | 4.97 | 19.39 | 63.96 |
| AC43 | 1 | 322337893 | 322337998 | 1% | 2% | 19% | 29% | 52% | 10% | 27% | 2.51 | 24.19 | 36.61 | 65.03 | 12.62 | 34.40 |
| AC44 | 3 | 503378496 | 503378540 | 0% | 1% | 13% | 14% | 62% | 6% | 16% | 6.77 | 84.98 | 89.94 | 406.60 | 38.31 | 101.31 |

FIG. 2 (cont'd)

| Adenocarcinoma marker region ref. # | Chromosome | Gene | Transcript | Strand | In Exon | Tss Distance | In CpG Island | Entrez ID | Gene title |
|---|---|---|---|---|---|---|---|---|---|
| AC22 | 19 | LOC644189 | NR_033748 | + | 0 | -3088 | 1 | 644189 | acyl-CoA thioesterase 4 pseudogene |
| AC23 | 2 | ITPRIPL1 | NM_178495;NM_001163524;NM_01008949;NM_001163523 | + | 0 | -876;-886;-3;-10 | 1 | 150771 | inositol 1,4,5-triphosphate receptor interacting protein-like 1 |
| AC24 | 1 | SKI | NM_003036 | + | 0 | 5804 | 0 | 6497 | v-ski sarcoma viral oncogene homolog (avian) |
| AC25 | 19 | ZNF329 | NM_024620 | - | 0 | 391 | 1 | 79673 | zinc finger protein 329 |
| AC26 | 2 | MAX.chr2.97193166-97193253 | - | - | 0 | - | 1 | - | - |
| AC27 | 8 | PLEC | NM_201381;NM_201383;NM_0004 45;NM_201378;NM_201380;NM_20 1384;NM_201382;NM_201379 | - | 1 | 5244;3031;37252;340 36;11383;97;4449,144 27 | 0 | 5339 | plectin |
| AC28 | 17 | SARM1 | NM_015077 | + | 1 | 53 | 1 | 23098 | sterile alpha and TIR motif containing 1 |
| AC29 | 19 | ZNF329 | NM_024620 | - | 0 | 268 | 1 | 79673 | zinc finger protein 329 |
| AC30 | 12 | FAIM2 | NM_012306 | - | 0 | -159 | 1 | 23017 | Fas apoptotic inhibitory molecule 2 |
| AC31 | 1 | MAX.chr1.32237695-32237880 | - | - | 0 | - | 0 | - | - |
| AC32 | 1 | DNAJC6 | NM_014787 | + | 0 | 1193 | 1 | 9829 | DnaJ (Hsp40) homolog, subfamily C, member 6 |
| AC33 | 16 | PRKCB | NM_002738;NM_212535 | + | 1 | 287;287 | 1 | 5579 | protein kinase C, beta |
| AC34 | 7 | TSC22D4 | NM_030935 | - | 1 | 1595 | 1 | 81628 | TSC22 domain family, member 4 |
| AC35 | 1 | PTPRF | NM_002840;NM_130440 | + | 0 | 35053;35053 | 1 | 5792 | protein tyrosine phosphatase, receptor type, F |
| AC36 | 16 | PRKCB | NM_002738;NM_212535 | + | 0 | 572;572 | 1 | 5579 | protein kinase C, beta |
| AC37 | 16 | PRKCB | NM_002738;NM_212535 | + | 0 | 639;639 | 1 | 5579 | protein kinase C, beta |
| AC38 | 19 | MATK | NM_002378;NM_139355;NM_1393 54 | - | 0 | 15833;438;438 | 1 | 4145 | megakaryocyte-associated tyrosine kinase |
| AC39 | 19 | MAX.chr19.37288523-37288615 | - | - | 0 | - | 1 | - | - |
| AC40 | 13 | FGF14 | NM_175929 | - | 0 | 7226 | 1 | 2259 | fibroblast growth factor 14 |
| AC41 | 2 | MAX.chr2.25439185-25439264 | - | - | 0 | - | 1 | - | - |
| AC42 | 20 | BHLHE23 | NM_080606 | - | 0 | -85 | 1 | 128408 | basic helix-loop-helix family, member e23 |
| AC43 | 1 | MAX.chr1.32237893-32237998 | - | - | 0 | - | 1 | - | - |
| AC44 | 3 | RASSF1 | NM_170714;NM_007182;NM_1707 12;NM_170713 | - | 0 | -129;-129;-2832;-3601 | 1 | 11186 | Ras association (RalGDS/AF-6) domain family member 1 |

FIG. 2 (cont'd)

| Adenocarcinoma marker region ref. # | Chromosome | Start position | Stop position | mean BC.island | mean lung.normal. island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| AC45 | 8 | 99439151 | 99439192 | 0% | 1% | 14% | 18% | 4% | 1% | 26% | 1.44 | 31.01 | 40.63 | 8.77 | 1.90 | 57.44 |
| AC46 | 19 | 37288426 | 37288510 | 0% | 1% | 15% | 22% | 30% | 19% | 27% | 1.79 | 39.22 | 55.94 | 78.85 | 49.81 | 69.01 |
| AC47 | 9 | 96715209 | 96715360 | 1% | 3% | 24% | 15% | 29% | 10% | 6% | 3.21 | 29.13 | 17.97 | 35.67 | 11.96 | 6.87 |
| AC48 | 15 | 65116396 | 65116440 | 0% | 1% | 11% | 21% | 5% | 25% | 2% | 5.61 | 51.82 | 98.18 | 22.13 | 114.94 | 10.41 |
| AC49 | 17 | 17627469 | 17627534 | 1% | 1% | 17% | 7% | 0% | 19% | 11% | 0.77 | 21.31 | 8.72 | 0.57 | 23.63 | 14.12 |

FIG. 2 (cont'd)

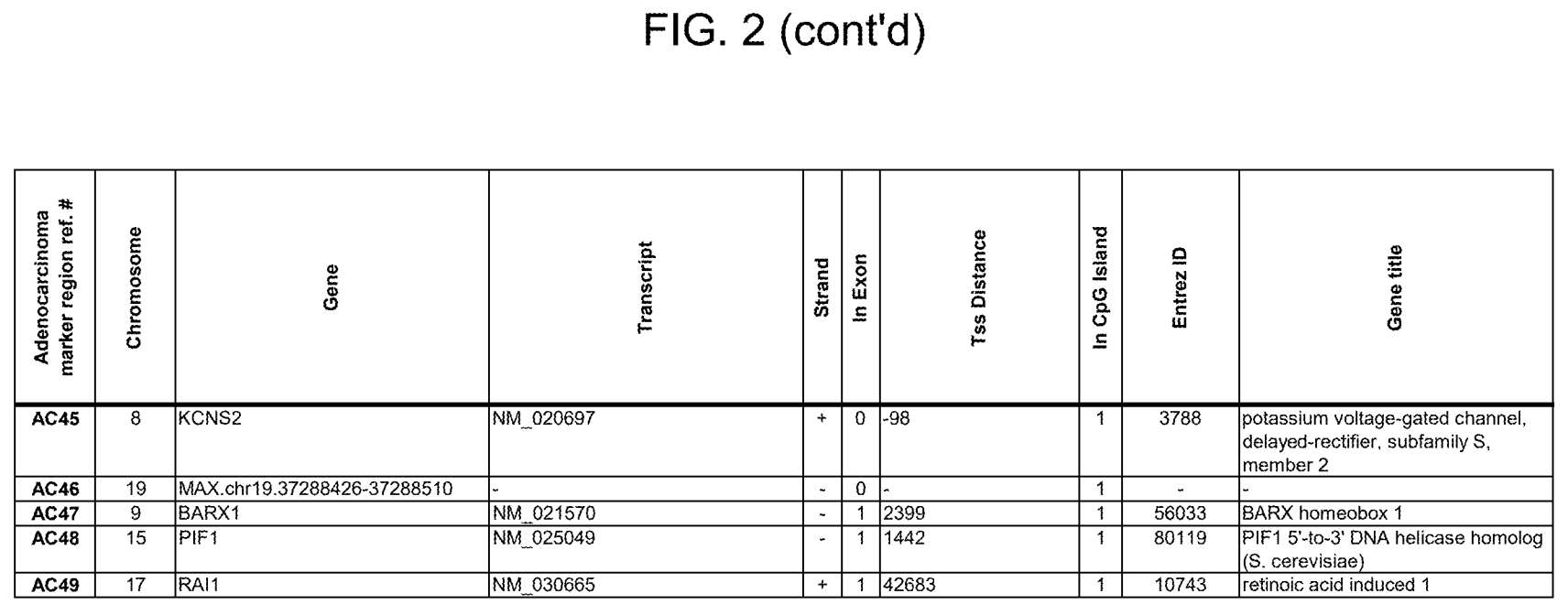

| Adenocarcinoma marker region ref. # | Chromosome | Gene | Transcript | Strand | In Exon | Tss Distance | In CpG Island | Entrez ID | Gene title |
|---|---|---|---|---|---|---|---|---|---|
| AC45 | 8 | KCNS2 | NM_020697 | + | 0 | -98 | 1 | 3788 | potassium voltage-gated channel, delayed-rectifier, subfamily S, member 2 |
| AC46 | 19 | MAX.chr19.37288426-37288510 | , | , | 0 | , | 1 | , | , |
| AC47 | 9 | BARX1 | NM_021570 | , | 1 | 2399 | 1 | 56033 | BARX homeobox 1 |
| AC48 | 15 | PIF1 | NM_025049 | - | 1 | 1442 | 1 | 80119 | PIF1 5'-to-3' DNA helicase homolog (S. cerevisiae) |
| AC49 | 17 | RAI1 | NM_030665 | + | 1 | 42683 | 1 | 10743 | retinoic acid induced 1 |

FIG. 3

| Large cell marker region ref. # | Chromosome | Start position | Stop position | mean BC_island | mean lung_normal.island | mean Adenocarcinoma Lung_island | mean Large cell Lung_island | mean Small cell Lung_island | mean Squamous Lung_island | mean undefined cancer Lung_island | Norm/BC | Ad/BC | LC/BC | SC/BC | SQ/BC | UND/BC |
|---|---|---|---|---|---|---|---|---|---|---|---|---|---|---|---|---|
| LC1 | 16 | 23847871 | 23847925 | 0% | 1% | 10% | 11% | 6% | 2% | 19% | #DIV/0! | #DIV/0! | #DIV/0! | #DIV/0! | #DIV/0! | #DIV/0! |
| LC2 | 5 | 169064343 | 169064446 | 0% | 1% | 10% | 11% | 40% | 2% | 13% | 29.90 | 255.47 | 295.59 | 1054.27 | 55.31 | 339.16 |
| LC3 | 5 | 42992328 | 42992393 | 0% | 4% | 27% | 38% | 43% | 23% | 50% | 29.14 | 179.62 | 252.75 | 288.47 | 156.43 | 334.25 |
| LC4 | 7 | 37488072 | 37488105 | 0% | 0% | 3% | 19% | 6% | 1% | 16% | 5.21 | 36.35 | 238.74 | 72.25 | 9.26 | 203.41 |
| LC5 | 16 | 23847938 | 23848020 | 0% | 1% | 15% | 12% | 10% | 2% | 15% | 25.58 | 293.90 | 237.97 | 199.65 | 41.02 | 298.01 |
| LC6 | 19 | 17346461 | 17346549 | 0% | 2% | 9% | 21% | 0% | 14% | 26% | 17.37 | 84.73 | 202.32 | 0.58 | 132.88 | 247.58 |
| LC7 | 16 | 23847586 | 23847684 | 0% | 2% | 15% | 23% | 18% | 2% | 26% | 12.77 | 119.07 | 189.49 | 148.49 | 13.87 | 209.78 |
| LC8 | 5 | 42995328 | 42995393 | 0% | 4% | 12% | 28% | 50% | 30% | 55% | 24.55 | 77.50 | 185.42 | 325.38 | 198.95 | 362.13 |
| LC9 | 19 | 58238816 | 58238942 | 0% | 1% | 8% | 15% | 24% | 17% | 33% | 8.09 | 94.63 | 175.66 | 277.57 | 203.93 | 390.90 |
| LC10 | 7 | 37488118 | 37488163 | 0% | 0% | 2% | 11% | 2% | 0% | 12% | 2.85 | 29.53 | 155.86 | 33.00 | 6.18 | 159.79 |
| LC11 | 5 | 42995477 | 42995528 | 0% | 5% | 20% | 35% | 60% | 39% | 62% | 18.40 | 82.13 | 141.62 | 245.53 | 158.96 | 254.67 |
| LC12 | 1 | 110627264 | 110627325 | 0% | 1% | 5% | 28% | 52% | 8% | 31% | 3.49 | 23.92 | 137.94 | 259.29 | 39.55 | 152.65 |
| LC13 | 19 | 58011421 | 58011488 | 0% | 1% | 3% | 22% | 12% | 6% | 0% | 3.89 | 17.87 | 129.28 | 71.80 | 35.25 | 1.25 |
| LC14 | 12 | 49484143 | 49484184 | 0% | 1% | 5% | 15% | 5% | 2% | 9% | 6.92 | 36.99 | 121.11 | 43.30 | 15.20 | 72.91 |
| LC15 | 17 | 26699039 | 26699117 | 0% | 1% | 13% | 14% | 6% | 1% | 12% | 10.25 | 110.62 | 119.15 | 55.00 | 11.44 | 105.40 |
| LC16 | 20 | 47443870 | 47443961 | 0% | 1% | 6% | 10% | 4% | 2% | 9% | 8.85 | 64.06 | 110.72 | 46.66 | 17.90 | 96.24 |
| LC17 | 17 | 46675164 | 46675237 | 0% | 1% | 8% | 20% | 6% | 7% | 11% | 4.38 | 43.34 | 109.94 | 35.52 | 37.61 | 58.29 |
| LC18 | 8 | 145106742 | 145106827 | 0% | 2% | 26% | 34% | 10% | 21% | 14% | 5.40 | 81.76 | 108.02 | 31.02 | 68.54 | 45.26 |
| LC19 | 17 | 75447560 | 75447708 | 0% | 0% | 2% | 15% | 2% | 0% | 5% | 1.28 | 17.71 | 107.93 | 17.41 | 2.23 | 37.60 |
| LC20 | 4 | 102711879 | 102711959 | 0% | 2% | 8% | 23% | 12% | 11% | 19% | 8.25 | 32.43 | 99.18 | 50.15 | 48.17 | 80.58 |
| LC21 | 11 | 14926886 | 14926955 | 0% | 3% | 6% | 29% | 78% | 21% | 20% | 8.70 | 18.97 | 99.05 | 266.28 | 70.91 | 68.97 |
| LC22 | 17 | 42287927 | 42287988 | 0% | 0% | 11% | 15% | 26% | 18% | 32% | 1.27 | 71.79 | 95.09 | 167.27 | 117.62 | 206.97 |
| LC23 | 19 | 3785977 | 3786032 | 0% | 1% | 14% | 24% | 3% | 5% | 34% | 5.84 | 54.36 | 93.77 | 12.00 | 19.42 | 135.15 |
| LC24 | 2 | 182322274 | 182322403 | 0% | 1% | 9% | 11% | 10% | 2% | 8% | 7.64 | 78.53 | 92.41 | 84.05 | 18.74 | 72.85 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC1 | 16 | PRKCB | NM_002738;NM_212535 | + | 0 | 572;572 | 1 | 5579 | protein kinase C, beta |
| LC2 | 5 | DOCK2 | NM_004946 | + | 1 | 93 | 1 | 1794 | dedicator of cytokinesis 2 |
| LC3 | 5 | MAX.chr5.42992328-42992393 | - | - | 0 | - | 1 | - | - |
| LC4 | 7 | ELMO1 | NM_014800 | - | 0 | 439 | 1 | 9844 | engulfment and cell motility 1 |
| LC5 | 16 | PRKCB | NM_002738;NM_212535 | + | 0 | 639;639 | 1 | 5579 | protein kinase C, beta |
| LC6 | 19 | NR2F6 | NM_005234 | - | 1 | 9690 | 1 | 2063 | nuclear receptor subfamily 2, group F, member 6 |
| LC7 | 16 | PRKCB | NM_002738;NM_212535 | + | 1 | 287;287 | 1 | 5579 | protein kinase C, beta |
| LC8 | 5 | MAX.chr5.42995328-42995393 | - | - | 0 | - | 1 | - | - |
| LC9 | 19 | ZNF671 | NM_024833 | - | 1 | 179 | 1 | 79891 | zinc finger protein 671 |
| LC10 | 7 | ELMO1 | NM_014800 | - | 0 | 393 | 1 | 9844 | engulfment and cell motility 1 |
| LC11 | 5 | MAX.chr5.42995477-42995528 | - | - | 0 | - | 0 | - | - |
| LC12 | 1 | MAX.chr1.110627264-110627325 | - | - | 0 | - | 1 | - | - |
| LC13 | 19 | ZNF773 | NM_198542 | + | 1 | 113 | 1 | 374928 | zinc finger protein 773 |
| LC14 | 12 | DHH | NM_021044 | - | 1 | 4459 | 1 | 50846 | desert hedgehog |
| LC15 | 17 | SARM1 | NM_015077 | + | 1 | 53 | 1 | 23098 | sterile alpha and TIR motif containing 1 |
| LC16 | 20 | PREX1 | NM_020820 | - | 0 | 550 | 1 | 57580 | phosphatidylinositol-3,4,5-trisphosphate-dependent Rac exchange factor 1 |
| LC17 | 17 | HOXB5 | NM_002147 | - | 1 | -4061 | 1 | 3215 | homeobox B5 |
| LC18 | 8 | OPLAH | NM_017570 | - | 0 | 8842 | 1 | 26873 | 5-oxoprolinase (ATP-hydrolysing) |
| LC19 | 17 | sep9 | NM_066640;NM_001113494;NM_001113496;NM_001113492;NM_001113493;NM_001113491 | + | 0 | 131964;75396;948;1635 88;78289;170069 | 1 | 10801 | septin 9 |
| LC20 | 4 | BANK1 | NM_017935;NM_001127507 | + | 1 | 116;116 | 1 | 55024 | B-cell scaffold protein with ankyrin repeats 1 |
| LC21 | 11 | MAX.chr11.149268886-149269955 | - | - | 0 | - | 1 | - | - |
| LC22 | 17 | UBTF | NM_001076684;NM_001076683;NM_014233 | - | 0 | 8997;10323;7737 | 1 | 7343 | upstream binding transcription factor, RNA polymerase I |
| LC23 | 19 | MATK | NM_002378;NM_139355;NM_139354 | - | 0 | 15833;438;438 | 1 | 4145 | megakaryocyte-associated tyrosine kinase |
| LC24 | 2 | ITGA4 | NM_000885 | + | 1 | 656 | 1 | 3676 | integrin, alpha 4 (antigen CD49D, alpha 4 subunit of VLA-4 receptor) |

FIG. 3 (cont'd)

| Large cell marker region ref. # | Chromosome | Start position | Stop position | mean BC.island | mean lung.normal.island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| LC25 | 3 | 50378496 | 50378540 | 0% | 1% | 13% | 14% | 62% | 6% | 16% | 6.77 | 84.98 | 89.94 | 406.60 | 38.31 | 101.31 |
| LC26 | 5 | 157098339 | 157098381 | 0% | 1% | 9% | 18% | 11% | 2% | 13% | 5.53 | 45.71 | 89.03 | 53.16 | 11.52 | 64.27 |
| LC27 | 8 | 124173236 | 124173386 | 0% | 1% | 11% | 15% | 49% | 14% | 29% | 7.50 | 63.79 | 86.89 | 276.90 | 78.49 | 166.63 |
| LC28 | 4 | 42153564 | 42153601 | 0% | 0% | 5% | 13% | 6% | 1% | 10% | 2.47 | 36.03 | 85.84 | 37.84 | 7.67 | 70.13 |
| LC29 | 19 | 17346401 | 17346450 | 0% | 1% | 5% | 15% | 2% | 6% | 14% | 5.69 | 25.74 | 84.33 | 13.37 | 34.47 | 78.56 |
| LC30 | 3 | 124860573 | 124860665 | 0% | 1% | 12% | 34% | 12% | 37% | 39% | 1.55 | 29.73 | 84.15 | 28.68 | 91.45 | 97.00 |
| LC31 | 7 | 37488225 | 37488303 | 0% | 0% | 4% | 15% | 4% | 1% | 13% | 2.22 | 22.77 | 82.00 | 24.55 | 6.84 | 70.81 |
| LC32 | 12 | 250055873 | 250055997 | 0% | 1% | 10% | 22% | 29% | 12% | 40% | 4.32 | 36.00 | 77.51 | 103.02 | 44.17 | 140.87 |
| LC33 | 3 | 194118747 | 194118919 | 0% | 2% | 13% | 26% | 43% | 19% | 41% | 6.97 | 38.31 | 74.49 | 125.02 | 55.43 | 117.27 |
| LC34 | 8 | 145106353 | 145106439 | 0% | 2% | 24% | 29% | 9% | 25% | 26% | 4.89 | 59.66 | 71.50 | 22.47 | 62.77 | 65.19 |
| LC35 | 17 | 46620564 | 46620622 | 1% | 1% | 11% | 34% | 21% | 12% | 29% | 2.90 | 22.12 | 70.90 | 43.06 | 25.10 | 59.41 |
| LC36 | 2 | 173099757 | 173099817 | 0% | 1% | 4% | 16% | 7% | 4% | 3% | 3.23 | 17.04 | 69.46 | 30.54 | 19.33 | 11.52 |
| LC37 | 19 | 3785837 | 3785923 | 0% | 1% | 19% | 20% | 5% | 7% | 56% | 4.69 | 66.90 | 68.62 | 19.25 | 26.13 | 195.13 |
| LC38 | 7 | 37487776 | 37487893 | 0% | 1% | 3% | 12% | 6% | 0% | 11% | 3.09 | 17.32 | 66.89 | 32.54 | 1.97 | 64.09 |
| LC39 | 6 | 6004298 | 6004338 | 1% | 5% | 21% | 40% | 58% | 34% | 61% | 7.31 | 33.74 | 64.23 | 93.83 | 54.50 | 99.42 |
| LC40 | 10 | 22541891 | 22541996 | 0% | 2% | 13% | 22% | 49% | 18% | 24% | 5.71 | 36.56 | 63.36 | 141.74 | 52.16 | 69.90 |
| LC41 | 1 | 2165937 | 2166058 | 0% | 0% | 12% | 17% | 64% | 6% | 16% | 1.37 | 45.20 | 63.35 | 232.04 | 20.22 | 59.05 |
| LC42 | 1 | 223936868 | 223936997 | 0% | 1% | 7% | 18% | 45% | 16% | 28% | 2.13 | 26.29 | 63.20 | 158.81 | 57.13 | 99.50 |
| LC43 | 5 | 1295194 | 1295314 | 0% | 1% | 8% | 12% | 26% | 2% | 14% | 3.69 | 41.84 | 62.47 | 142.53 | 9.07 | 77.02 |
| LC44 | 11 | 128564667 | 128564773 | 0% | 0% | 3% | 13% | 7% | 3% | 25% | 2.36 | 15.22 | 60.67 | 32.31 | 14.64 | 120.57 |
| LC45 | 1 | 65731423 | 65731507 | 0% | 1% | 14% | 20% | 7% | 6% | 5% | 4.05 | 40.31 | 57.98 | 20.18 | 17.71 | 15.74 |
| LC46 | 7 | 142494769 | 142494904 | 0% | 1% | 7% | 11% | 5% | 2% | 23% | 5.22 | 34.83 | 57.90 | 28.83 | 12.03 | 123.00 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC25 | 3 | RASSF1 | NM_170714;NM_007182;NM_1707 12;NM_170713 | - | 0 | -129;-129;-2832;-3601 | 1 | 11186 | Ras association (RalGDS/AF-6) domain family member 1 |
| LC26 | 5 | C5orf52 | NM_001145132 | + | 0 | -221 | 1 | 100190949 | chromosome 5 open reading frame 52 |
| LC27 | 8 | MAX.chr8.124173236-124173386 | . | - | 0 | . | 1 | . | . |
| LC28 | 4 | BEND4 | NM_0011159547;NM_207406 | - | 0 | 1331;1331 | 1 | 389206 | BEN domain containing 4 |
| LC29 | 19 | NR2F6 | NM_005234 | - | 1 | 9750 | 1 | 2063 | nuclear receptor subfamily 2, group F, member 6 |
| LC30 | 3 | SLC12A8 | NM_0011195483;NM_024628 | - | 0 | 69670;71036 | 1 | 84561 | solute carrier family 12 (potassium/chloride transporters), member 8 |
| LC31 | 7 | ELMO1 | NM_014800 | - | 0 | 286 | 1 | 9844 | engulfment and cell motility 1 |
| LC32 | 12 | BCAT1 | NM_001178092;NM_005504;NM_0 011178094;NM_001178091;NM_001 178093 | - | 0 | 46520;46520;- 551;46520;136 | 1 | 586 | branched chain amino-acid transaminase 1, cytosolic |
| LC33 | 3 | GP5 | NM_004488 | - | 1 | 1248 | 1 | 2814 | glycoprotein V (platelet) |
| LC34 | 8 | OPLAH | NM_017570 | - | 1 | 9231 | 1 | 26873 | 5-oxoprolinase (ATP-hydrolysing) |
| LC35 | 17 | HOXB2 | NM_002145 | - | 1 | 1829 | 1 | 3212 | homeobox B2 |
| LC36 | 2 | MAX.chr2.173099757-173099817 | . | - | 0 | . | 1 | . | . |
| LC37 | 19 | MATK | NM_002378;NM_139355;NM_1393 54 | - | 0 | 15973;578;578 | 1 | 4145 | megakaryocyte-associated tyrosine kinase |
| LC38 | 7 | ELMO1 | NM_014800 | - | 0 | 735 | 1 | 9844 | engulfment and cell motility 1 |
| LC39 | 6 | NRN1 | NM_016588 | - | 0 | 3335 | 1 | 51299 | neuritin 1 |
| LC40 | 10 | MAX.chr10.225441891-225441996 | . | - | 0 | . | 1 | . | . |
| LC41 | 1 | SKI | NM_003036 | + | 0 | 5804 | 0 | 6497 | v-ski sarcoma viral oncogene homolog (avian) |
| LC42 | 1 | CAPN2 | NM_001146068;NM_001748 | + | 0 | 47574;36750 | 1 | 824 | calpain 2, (m/II) large subunit |
| LC43 | 5 | TERT | NM_001193376;NM_198253 | - | 0 | -32;-32 | 1 | 7015 | telomerase reverse transcriptase |
| LC44 | 11 | FLI1 | NM_002017;NM_001167681 | + | 0 | 855;2279 | 1 | 2313 | Friend leukemia virus integration 1 |
| LC45 | 1 | DNAJC6 | NM_014787 | + | 0 | 994 | 1 | 9829 | DnaJ (Hsp40) homolog, subfamily C, member 6 |
| LC46 | 7 | MAX.chr7.142494769-142494904 | . | - | 0 | . | 1 | . | . |

FIG. 3 (cont'd)

| Large cell marker region ref. # | Chromosome | Start position | Stop position | mean BC Island | mean lung-normal, Island | mean Adenocarcinoma Lung Island | mean Large cell Lung Island | mean Small cell Lung Island | mean Squamous Lung Island | mean undefined Lung cancer Island | Norm/BC | Ad/BC | LC/BC | SC/BC | SQ/BC | UND/BC |
|---|---|---|---|---|---|---|---|---|---|---|---|---|---|---|---|---|
| LC47 | 1 | 161275664 | 161275801 | 0% | 0% | 3% | 11% | 0% | 6% | 0% | 2.20 | 15.83 | 57.68 | 1.19 | 32.84 | 2.04 |
| LC48 | 1 | 32237619 | 32237654 | 1% | 5% | 32% | 35% | 60% | 14% | 28% | 7.65 | 53.16 | 57.57 | 100.17 | 23.82 | 46.87 |
| LC49 | 1 | 44031599 | 44031658 | 0% | 2% | 24% | 18% | 21% | 21% | 18% | 4.80 | 75.23 | 56.94 | 66.66 | 64.67 | 56.57 |
| LC50 | 20 | 61560692 | 61560749 | 0% | 1% | 6% | 13% | 62% | 19% | 28% | 5.65 | 24.19 | 56.55 | 258.74 | 79.08 | 115.84 |
| LC51 | 3 | 122296709 | 122296828 | 0% | 3% | 17% | 23% | 65% | 25% | 61% | 5.87 | 39.97 | 54.78 | 151.39 | 57.49 | 143.28 |
| LC52 | 8 | 145104291 | 145104342 | 0% | 1% | 6% | 13% | 3% | 12% | 10% | 3.80 | 26.23 | 54.77 | 13.90 | 49.84 | 41.94 |
| LC53 | 4 | 140201231 | 140201277 | 1% | 2% | 7% | 34% | 11% | 7% | 21% | 3.04 | 10.87 | 54.63 | 18.35 | 12.07 | 33.86 |
| LC54 | 4 | 15780145 | 15780191 | 0% | 2% | 5% | 16% | 19% | 8% | 19% | 5.10 | 17.13 | 53.63 | 61.39 | 27.48 | 61.88 |
| LC55 | 1 | 111217635 | 111217682 | 0% | 1% | 8% | 18% | 3% | 4% | 28% | 2.24 | 22.91 | 52.55 | 9.59 | 10.61 | 83.04 |
| LC56 | 3 | 124860704 | 124860798 | 0% | 1% | 10% | 21% | 9% | 35% | 22% | 1.98 | 23.37 | 51.32 | 20.78 | 84.00 | 51.80 |
| LC57 | 12 | 25056015 | 25056162 | 0% | 1% | 10% | 18% | 25% | 10% | 35% | 1.51 | 27.62 | 50.51 | 68.55 | 27.10 | 95.52 |
| LC58 | 17 | 48042562 | 48042606 | 1% | 3% | 24% | 47% | 56% | 25% | 44% | 3.67 | 25.97 | 50.24 | 59.12 | 26.78 | 46.42 |
| LC59 | 12 | 107713157 | 107713254 | 0% | 2% | 6% | 24% | 2% | 3% | 17% | 3.60 | 12.28 | 49.38 | 4.01 | 5.33 | 34.97 |
| LC60 | 19 | 37464151 | 37464219 | 0% | 1% | 6% | 20% | 19% | 17% | 40% | 2.12 | 15.10 | 47.57 | 43.26 | 38.92 | 93.33 |
| LC61 | 12 | 65218381 | 65218413 | 0% | 0% | 1% | 11% | 4% | 1% | 8% | 1.99 | 6.49 | 47.47 | 17.50 | 5.10 | 35.85 |
| LC62 | 10 | 94834101 | 94834171 | 0% | 1% | 4% | 14% | 3% | 1% | 9% | 2.24 | 13.39 | 46.30 | 10.38 | 4.51 | 27.46 |
| LC63 | 5 | 169064211 | 169064314 | 0% | 1% | 9% | 15% | 30% | 2% | 22% | 3.71 | 29.12 | 46.14 | 93.41 | 5.35 | 71.09 |
| LC64 | 12 | 4273887 | 4274003 | 0% | 1% | 8% | 17% | 9% | 3% | 6% | 3.02 | 22.67 | 45.94 | 24.63 | 7.65 | 17.15 |
| LC65 | 12 | 25055634 | 25055804 | 1% | 3% | 14% | 27% | 30% | 17% | 50% | 5.65 | 23.18 | 44.87 | 51.11 | 28.60 | 83.14 |
| LC66 | 3 | 13115009 | 13115073 | 1% | 2% | 46% | 40% | 16% | 3% | 42% | 2.26 | 51.11 | 44.54 | 17.94 | 2.82 | 47.14 |

FIG. 3 (cont'd)

| Large cell marker region ref. # | Chromosome | Gene | Transcript | Strand | In Exon | Tss Distance | In CpG island | Entrez ID | Gene title |
|---|---|---|---|---|---|---|---|---|---|
| LC47 | 1 | MPZ | NM_000530 | - | 1 | 4098 | 0 | 4359 | myelin protein zero |
| LC48 | 1 | MAX.chr1.32237619-32237654 | | - | 0 | | 0 | - | |
| LC49 | 1 | PTPRF | NM_002840;NM_130440 | + | 0 | 35053;35053 | 1 | 5792 | protein tyrosine phosphatase, receptor type, F |
| LC50 | 20 | DIDO1 | NM_033081;NM_001193369;NM_0 22105;NM_080797;NM_001193370; NM_080796 | - | 0 | 8612;-2789;8612;8612;- 2789;-2789 | 1 | 11083 | death inducer-obliterator 1 |
| LC51 | 3 | PARP15 | NM_001113523 | + | 0 | 261 | 1 | 165631 | poly (ADP-ribose) polymerase family, member 15 |
| LC52 | 8 | MAX.chr8.145104291-145104342 | - | - | 0 | | 1 | - | |
| LC53 | 4 | C4orf49 | NM_032623 | - | 1 | 261 | 1 | 84709 | chromosome 4 open reading frame 49 |
| LC54 | 4 | CD38 | NM_001775 | + | 1 | 215 | 1 | 952 | CD38 molecule |
| LC55 | 1 | KCNA3 | NM_002232 | - | 1 | 20 | 1 | 3738 | potassium voltage-gated channel, shaker-related subfamily, member 3 |
| LC56 | 3 | SLC12A8 | NM_001195483;NM_024628 | - | 0 | 69539;70905 | 1 | 84561 | solute carrier family 12 (potassium/chloride transporters), member 8 |
| LC57 | 12 | BCAT1 | NM_001178092;NM_005504;NM_0 01178094;NM_001178091;NM_001 178093 | - | 0 | 46378;46378;- 693;46378;-6 | 1 | 586 | branched chain amino-acid transaminase 1, cytosolic |
| LC58 | 17 | DLX4 | NM_138281 | + | 0 | -3999 | 1 | 1748 | distal-less homeobox 4 |
| LC59 | 12 | BTBD11 | NM_001018072 | - | 0 | 961 | 1 | 121551 | BTB (POZ) domain containing 11 |
| LC60 | 19 | MAX.chr19.37464151-37464219 | - | - | 0 | | 1 | - | |
| LC61 | 12 | TBC1D30 | NM_015279 | + | 1 | 30 | 1 | 23329 | TBC1 domain family, member 30 |
| LC62 | 10 | CYP26A1 | NM_000783;NM_057157 | + | 1 | 455;870 | 1 | 1592 | cytochrome P450, family 26, subfamily A, polypeptide 1 |
| LC63 | 5 | DOCK2 | NM_004946 | + | 0 | -39 | 0 | 1794 | dedicator of cytokinesis 2 |
| LC64 | 12 | MAX.chr12.4273887-4274003 | - | - | 0 | | 1 | - | |
| LC65 | 12 | BCAT1 | NM_001178092;NM_005504;NM_0 01178094;NM_001178091;NM_001 178093 | - | 0 | 46759;46759;- 312;46759;375 | 1 | 586 | branched chain amino-acid transaminase 1, cytosolic |
| LC66 | 3 | IQSEC1 | NM_001134382 | - | 0 | -392 | 1 | 9922 | IQ motif and Sec7 domain 1 |

FIG. 3 (cont'd)

| Large cell marker region ref. # | Chromosome | Start position | Stop position | mean BC.island | mean lung.normal, island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| LC67 | 20 | 37434670 | 37434793 | 0% | 1% | 7% | 10% | 1% | 1% | 10% | 2.23 | 31.25 | 44.50 | 2.57 | 3.70 | 43.59 |
| LC68 | 7 | 100273764 | 100273857 | 0% | 0% | 2% | 11% | 0% | 9% | 10% | 0.72 | 7.67 | 44.09 | 0.23 | 37.98 | 38.77 |
| LC69 | 2 | 118981859 | 118981945 | 1% | 3% | 14% | 33% | 42% | 28% | 29% | 4.14 | 18.40 | 42.45 | 53.71 | 35.86 | 36.89 |
| LC70 | 8 | 70981960 | 70982028 | 1% | 4% | 26% | 36% | 65% | 28% | 58% | 5.02 | 30.29 | 41.91 | 74.59 | 32.63 | 66.72 |
| LC71 | 20 | 61638221 | 61638352 | 0% | 1% | 7% | 15% | 1% | 2% | 18% | 2.59 | 20.85 | 40.85 | 3.78 | 6.32 | 50.89 |
| LC72 | 5 | 77266624 | 77268718 | 1% | 2% | 12% | 22% | 34% | 7% | 21% | 3.72 | 21.82 | 40.13 | 61.10 | 12.77 | 38.23 |
| LC73 | 1 | 657731622 | 657731666 | 1% | 2% | 27% | 35% | 11% | 12% | 17% | 2.00 | 31.36 | 39.95 | 13.18 | 14.20 | 19.04 |
| LC74 | 1 | 78511734 | 78511827 | 1% | 2% | 15% | 32% | 24% | 15% | 51% | 2.91 | 18.47 | 39.63 | 29.28 | 18.15 | 62.64 |
| LC75 | 7 | 100075307 | 100075425 | 0% | 2% | 21% | 18% | 54% | 15% | 16% | 3.87 | 45.55 | 39.16 | 116.74 | 32.72 | 34.94 |
| LC76 | 17 | 73073700 | 73073810 | 0% | 0% | 0% | 15% | 8% | 17% | 0% | 1.26 | 1.07 | 39.05 | 21.72 | 46.29 | 0.42 |
| LC77 | 2 | 73147720 | 73147790 | 1% | 3% | 24% | 36% | 50% | 28% | 59% | 3.25 | 26.10 | 38.89 | 54.76 | 30.96 | 64.51 |
| LC78 | 12 | 103352075 | 103352138 | 0% | 1% | 3% | 10% | 1% | 4% | 16% | 2.48 | 12.32 | 38.77 | 3.39 | 15.06 | 62.03 |
| LC79 | 10 | 22624410 | 22624553 | 1% | 2% | 7% | 30% | 63% | 11% | 58% | 2.80 | 9.42 | 38.62 | 82.32 | 14.11 | 75.75 |
| LC80 | 8 | 98290125 | 98290161 | 0% | 1% | 5% | 18% | 10% | 5% | 17% | 2.98 | 10.47 | 38.51 | 20.42 | 10.93 | 35.54 |
| LC81 | 2 | 66808687 | 66808728 | 1% | 7% | 24% | 48% | 74% | 37% | 80% | 5.37 | 19.49 | 38.15 | 58.88 | 29.21 | 63.62 |
| LC82 | 15 | 84748786 | 84748909 | 1% | 1% | 9% | 19% | 1% | 5% | 13% | 2.55 | 16.56 | 36.80 | 1.01 | 8.97 | 25.40 |
| LC83 | 12 | 52400959 | 524010020 | 1% | 1% | 12% | 19% | 3% | 1% | 19% | 1.59 | 24.05 | 36.73 | 5.80 | 2.58 | 36.73 |
| LC84 | 1 | 322237893 | 322237998 | 1% | 2% | 19% | 29% | 52% | 10% | 27% | 2.51 | 24.19 | 36.61 | 65.03 | 12.62 | 34.40 |
| LC85 | 7 | 27205013 | 27205081 | 1% | 7% | 29% | 50% | 83% | 42% | 48% | 5.20 | 20.79 | 36.52 | 60.30 | 30.77 | 35.13 |
| LC86 | 4 | 8859253 | 8859363 | 0% | 1% | 4% | 14% | 14% | 7% | 18% | 3.88 | 9.54 | 36.29 | 35.88 | 18.16 | 46.41 |
| LC87 | 20 | 47444641 | 47444682 | 0% | 1% | 7% | 15% | 2% | 1% | 5% | 3.03 | 16.83 | 36.12 | 5.94 | 2.12 | 11.01 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC67 | 20 | PPP1R16B | NM_001172735;NM_015568 | + | 0 | 323;323 | 1 | 26051 | protein phosphatase 1, regulatory (inhibitor) subunit 16B |
| LC68 | 7 | GNB2 | NM_005273 | + | 0 | 2402 | 1 | 2783 | guanine nucleotide binding protein (G protein), beta polypeptide 2 |
| LC69 | 2 | MAX.chr2.118981859-118981945 | - | - | 0 | - | 1 | - | - |
| LC70 | 8 | PRDM14 | NM_024504 | - | 1 | 1602 | 1 | 63978 | PR domain containing 14 |
| LC71 | 20 | BHLHE23 | NM_080606 | - | 1 | 166 | 1 | 128408 | basic helix-loop-helix family, member e23 |
| LC72 | 5 | MAX.chr5.77268624-77268718 | - | - | 0 | - | 1 | - | - |
| LC73 | 1 | DNAJC6 | NM_014787 | + | 0 | 1193 | 1 | 9829 | DnaJ (Hsp40) homolog, subfamily C, member 6 |
| LC74 | 1 | GIPC2 | NM_017655 | + | 1 | 146 | 1 | 54810 | GIPC PDZ domain containing family, member 2 |
| LC75 | 7 | TSC22D4 | NM_030935 | - | 1 | 1595 | 1 | 81628 | TSC22 domain family, member 4 |
| LC76 | 17 | MAX.chr17.730073700-730073810 | - | - | 0 | - | 1 | - | - |
| LC77 | 2 | EMX1 | NM_004097 | + | 0 | 3117 | 1 | 2016 | empty spiracles homeobox 1 |
| LC78 | 12 | ASCL1 | NM_004316 | + | 1 | 624 | 1 | 429 | achaete-scute complex homolog 1 (Drosophila) |
| LC79 | 10 | MAX.chr10.226244410-226624553 | - | - | 0 | - | 1 | - | - |
| LC80 | 8 | TSPYL5 | NM_033512 | - | 1 | 51 | 1 | 85453 | TSPY-like 5 |
| LC81 | 2 | MAX.chr2.66808687-66808728 | - | - | 0 | - | 1 | - | - |
| LC82 | 15 | LOC648809 | NR_036652 | + | 0 | -152 | 1 | 648809 | elongation factor Tu GTP-binding domain-containing protein 1 pseudogene |
| LC83 | 12 | GRASP | NM_181711 | + | 1 | 212 | 1 | 160622 | GRP1 (general receptor for phosphoinositides 1)-associated scaffold protein |
| LC84 | 1 | MAX.chr1.32237893-32237998 | - | - | 0 | - | 1 | - | - |
| LC85 | 7 | HOXA9 | NM_152739 | - | 1 | 136 | 1 | 3205 | homeobox A9 |
| LC86 | 4 | MAX.chr4.8859253-8859363 | - | - | 0 | - | 1 | - | - |
| LC87 | 20 | PREX1 | NM_020820 | - | 0 | -221 | 1 | 57580 | phosphatidylinositol-3,4,5-trisphosphate-dependent Rac exchange factor 1 |

FIG. 3 (cont'd)

| Large cell marker region ref. # | Chromosome | Start position | Stop position | mean BC.island | mean lung,normal. island | mean Adenocarcinoma Lung.island | mean Large cell Lung.island | mean Small cell Lung.island | mean Squamous Lung.island | mean undefined Lung.island cancer | Norm/BC | Ad/BC | LC/BC | SC/BC | SQ/BC | UND/BC |
|---|---|---|---|---|---|---|---|---|---|---|---|---|---|---|---|---|
| LC88 | 19 | 54486055 | 54486134 | 1% | 2% | 11% | 21% | 10% | 3% | 34% | 2.95 | 18.45 | 36.01 | 16.74 | 5.84 | 57.48 |
| LC89 | 2 | 26407721 | 26407876 | 0% | 1% | 2% | 11% | 47% | 18% | 16% | 2.39 | 8.36 | 36.01 | 160.15 | 60.97 | 56.07 |
| LC90 | 7 | 27196035 | 27196154 | 1% | 3% | 21% | 31% | 37% | 18% | 56% | 3.72 | 24.32 | 35.89 | 42.10 | 20.22 | 64.49 |
| LC91 | 7 | 158937376 | 158937476 | 1% | 2% | 8% | 20% | 9% | 5% | 21% | 3.81 | 14.17 | 35.70 | 16.30 | 8.28 | 37.29 |
| LC92 | 12 | 103352229 | 103352268 | 0% | 1% | 2% | 14% | 2% | 3% | 25% | 2.42 | 5.87 | 35.68 | 4.29 | 6.57 | 62.78 |
| LC93 | 1 | 968477 | 968584 | 1% | 1% | 25% | 22% | 2% | 12% | 9% | 2.07 | 40.71 | 35.38 | 3.80 | 18.61 | 15.35 |
| LC94 | 7 | 157483370 | 157483425 | 0% | 1% | 9% | 14% | 1% | 3% | 23% | 3.36 | 22.18 | 35.26 | 3.79 | 7.43 | 58.67 |
| LC95 | 5 | 1789575576 | 1789576695 | 1% | 2% | 15% | 18% | 41% | 17% | 24% | 3.97 | 29.20 | 34.94 | 78.81 | 31.81 | 45.24 |
| LC96 | 17 | 46675383 | 46675464 | 0% | 1% | 4% | 11% | 3% | 5% | 3% | 1.83 | 12.26 | 34.87 | 9.04 | 14.87 | 8.78 |
| LC97 | 19 | 51831114 | 51831160 | 1% | 2% | 17% | 20% | 26% | 4% | 26% | 4.03 | 29.10 | 34.38 | 43.50 | 6.23 | 44.43 |
| LC98 | 2 | 74726554 | 74726617 | 1% | 4% | 38% | 47% | 68% | 31% | 49% | 3.10 | 27.46 | 34.21 | 49.28 | 22.18 | 35.41 |
| LC99 | 14 | 70654555 | 70654616 | 0% | 1% | 9% | 15% | 1% | 5% | 7% | 3.08 | 19.47 | 33.99 | 3.28 | 12.22 | 15.29 |
| LC100 | 5 | 134879621 | 134879709 | 1% | 2% | 5% | 21% | 40% | 6% | 35% | 3.43 | 8.06 | 33.63 | 65.55 | 9.28 | 56.82 |
| LC101 | 12 | 107715041 | 107715084 | 0% | 1% | 5% | 11% | 2% | 1% | 19% | 2.19 | 16.32 | 33.62 | 5.06 | 2.98 | 57.40 |
| LC102 | 14 | 52734489 | 52734592 | 0% | 1% | 7% | 13% | 5% | 3% | 24% | 3.42 | 16.75 | 33.53 | 12.05 | 7.48 | 59.56 |
| LC103 | 1 | 101004818 | 101004860 | 0% | 1% | 10% | 16% | 3% | 2% | 23% | 3.10 | 20.44 | 33.24 | 5.47 | 4.02 | 49.05 |
| LC104 | 4 | 13524253 | 13524378 | 1% | 2% | 7% | 21% | 28% | 11% | 23% | 3.50 | 10.37 | 32.37 | 43.87 | 17.49 | 36.14 |
| LC105 | 10 | 81002926 | 81002992 | 0% | 1% | 21% | 15% | 22% | 8% | 32% | 1.31 | 42.51 | 30.95 | 45.31 | 15.74 | 64.67 |
| LC106 | 11 | 14926627 | 14926716 | 1% | 1% | 5% | 16% | 62% | 16% | 11% | 1.78 | 10.57 | 30.66 | 119.53 | 31.77 | 21.41 |
| LC107 | 2 | 176945102 | 176945135 | 1% | 2% | 7% | 18% | 7% | 7% | 38% | 2.93 | 11.98 | 30.46 | 10.98 | 11.55 | 63.00 |
| LC108 | 1 | 248020671 | 248020722 | 1% | 4% | 31% | 40% | 63% | 33% | 63% | 3.31 | 23.46 | 30.04 | 47.26 | 24.66 | 47.74 |
| LC109 | 11 | 31820365 | 31820418 | 1% | 4% | 19% | 39% | 74% | 21% | 59% | 3.41 | 14.93 | 30.02 | 57.24 | 16.07 | 45.33 |
| LC110 | 17 | 26699373 | 26699456 | 1% | 2% | 14% | 20% | 8% | 2% | 8% | 2.84 | 21.52 | 29.85 | 12.44 | 3.28 | 12.27 |
| LC111 | 1 | 214158912 | 214158969 | 1% | 4% | 20% | 33% | 50% | 18% | 46% | 3.39 | 17.95 | 29.64 | 45.85 | 16.83 | 41.54 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC88 | 19 | CACNG8 | NM_031895 | + | 1 | 19766 | 1 | 59283 | calcium channel, voltage-dependent, gamma subunit 8 |
| LC89 | 2 | FAM59B | NM_001191033;NM_001168241 | + | 1 | 4137;11762 | 1 | 150946 | family with sequence similarity 59, member B |
| LC90 | 7 | HOXA7 | NM_006896 | - | 1 | 261 | 1 | 3204 | homeobox A7 |
| LC91 | 7 | VIPR2 | NM_003382 | - | 0 | 273 | 1 | 7434 | vasoactive intestinal peptide receptor 2 |
| LC92 | 12 | ASCL1 | NM_004316 | + | 1 | 778 | 1 | 429 | achaete-scute complex homolog 1 (Drosophila) |
| LC93 | 1 | AGRN | NM_198576 | + | 0 | 12975 | 1 | 375790 | agrin |
| LC94 | 7 | PTPRN2 | NM_130842;NM_002847;NM_130843 | - | 0 | 897112;897112;897112 | 1 | 5799 | protein tyrosine phosphatase, receptor type, N polypeptide 2 |
| LC95 | 5 | MAX.chr5.178957576-178957695 | - | - | 0 | - | 1 | - | - |
| LC96 | 17 | HOXB5 | NM_002147 | - | 1 | -4280 | 1 | 3215 | homeobox B5 |
| LC97 | 19 | IGLON5 | NM_001101372 | + | 1 | 16013 | 1 | 402665 | IgLON family member 5 |
| LC98 | 2 | LBX2 | NM_001009812 | - | 0 | 3889 | 1 | 85474 | ladybird homeobox 2 |
| LC99 | 14 | SLC8A3 | NM_183002;NM_058240;NM_182932;NM_033262 | - | 0 | 1232;1232;1232;1232 | 0 | 6547 | solute carrier family 8 (sodium/calcium exchanger), member 3 |
| LC100 | 5 | MAX.chr5.134879621-134879709 | - | - | 0 | - | 1 | - | - |
| LC101 | 12 | BTBD11 | NM_001018072 | + | 0 | 2845 | 0 | 121551 | BTB (POZ) domain containing 11 |
| LC102 | 14 | PTGDR | NM_000953 | + | 1 | 59 | 1 | 5729 | prostaglandin D2 receptor (DP) |
| LC103 | 4 | GPR88 | NM_022049 | + | 1 | 1091 | 1 | 54112 | G protein-coupled receptor 88 |
| LC104 | 4 | MAX.chr4.13524253-13524378 | - | - | 0 | - | 1 | - | - |
| LC105 | 10 | ZMIZ1 | NM_020338 | + | 0 | 174135 | 1 | 57178 | zinc finger, MIZ-type containing 1 |
| LC106 | 11 | MAX.chr11.14926627-14926716 | - | - | 0 | - | 1 | - | - |
| LC107 | 2 | EVX2 | NM_001080458 | - | 1 | 3588 | 1 | 344191 | even-skipped homeobox 2 |
| LC108 | 1 | TRIM58 | NM_015431 | + | 1 | 171 | 1 | 25893 | tripartite motif-containing 58 |
| LC109 | 11 | PAX6 | NM_000280;NM_001604;NM_001127612 | - | 0 | 12514;12514;19144 | 1 | 5080 | paired box 6 |
| LC110 | 17 | SARM1 | NM_015077 | + | 1 | 387 | 1 | 23098 | sterile alpha and TIR motif containing 1 |
| LC111 | 1 | PROX1 | NM_002763 | + | 0 | -2947 | 1 | 5629 | prospero homeobox 1 |

FIG. 3 (cont'd)

| Large cell marker region ref. # | Chromosome | Start position | Stop position | mean BC island | mean lung,normal, island | mean Adenocarcinoma Lung island | mean Large cell Lung island | mean Small cell Lung island | mean Squamous Lung island | mean undefined cancer Lung island | Norm/BC | Ad/BC | LC/BC | SC/BC | SQ/BC | UND/BC |
|---|---|---|---|---|---|---|---|---|---|---|---|---|---|---|---|---|
| LC112 | 11 | 13984886 | 13984972 | 1% | 3% | 14% | 25% | 6% | 11% | 31% | 3.40 | 16.30 | 29.63 | 7.65 | 12.51 | 36.31 |
| LC113 | 5 | 134879362 | 134879483 | 0% | 1% | 5% | 13% | 35% | 5% | 17% | 3.15 | 10.56 | 29.38 | 80.54 | 10.94 | 39.68 |
| LC114 | 4 | 8859990 | 8860023 | 1% | 3% | 13% | 31% | 21% | 15% | 34% | 2.85 | 12.04 | 28.82 | 19.00 | 14.14 | 31.74 |
| LC115 | 14 | 52735425 | 52735485 | 1% | 3% | 15% | 29% | 18% | 15% | 63% | 3.09 | 15.29 | 28.53 | 17.82 | 14.71 | 61.82 |
| LC116 | 18 | 12254306 | 12254366 | 0% | 1% | 3% | 10% | 1% | 2% | 5% | 2.01 | 9.00 | 28.44 | 3.39 | 4.24 | 14.73 |
| LC117 | 6 | 2903614 | 2903705 | 0% | 1% | 2% | 13% | 21% | 2% | 1% | 1.58 | 3.90 | 28.42 | 45.90 | 4.89 | 1.60 |
| LC118 | 8 | 72755971 | 72756053 | 1% | 1% | 17% | 25% | 6% | 2% | 23% | 1.61 | 19.29 | 28.37 | 7.16 | 1.82 | 25.68 |
| LC119 | 8 | 23564059 | 23564136 | 1% | 2% | 12% | 23% | 30% | 12% | 50% | 2.76 | 14.60 | 27.91 | 36.65 | 14.91 | 61.08 |
| LC120 | 19 | 30017795 | 30017896 | 1% | 1% | 13% | 19% | 10% | 3% | 14% | 1.80 | 18.06 | 27.33 | 13.50 | 4.20 | 20.21 |
| LC121 | 12 | 25056183 | 25056246 | 1% | 5% | 19% | 37% | 54% | 29% | 64% | 4.03 | 13.60 | 27.03 | 39.72 | 21.36 | 47.09 |
| LC122 | 12 | 50297879 | 50297912 | 1% | 2% | 17% | 20% | 4% | 7% | 19% | 2.26 | 22.36 | 27.00 | 5.77 | 9.22 | 24.93 |
| LC123 | 14 | 52735223 | 52735373 | 1% | 2% | 12% | 22% | 14% | 7% | 62% | 2.15 | 14.58 | 26.97 | 17.16 | 8.92 | 74.66 |
| LC124 | 2 | 25439185 | 25439264 | 0% | 1% | 10% | 11% | 31% | 3% | 7% | 2.31 | 25.89 | 26.41 | 77.49 | 6.89 | 18.37 |
| LC125 | 1 | 32237695 | 32237880 | 1% | 3% | 22% | 25% | 44% | 10% | 14% | 2.78 | 22.43 | 25.97 | 45.37 | 10.13 | 14.59 |
| LC126 | 5 | 327713586 | 327713669 | 2% | 5% | 25% | 42% | 17% | 11% | 33% | 3.07 | 15.16 | 25.58 | 10.49 | 6.68 | 20.46 |
| LC127 | 8 | 145105570 | 145105675 | 1% | 3% | 30% | 26% | 9% | 29% | 23% | 3.15 | 29.77 | 25.41 | 9.23 | 28.54 | 22.59 |
| LC128 | 12 | 52401041 | 52401138 | 1% | 1% | 12% | 16% | 1% | 2% | 12% | 1.36 | 19.11 | 25.37 | 2.04 | 2.89 | 19.80 |
| LC129 | 7 | 271195748 | 271195829 | 1% | 5% | 25% | 36% | 38% | 24% | 69% | 3.68 | 17.21 | 25.20 | 26.39 | 16.93 | 48.45 |
| LC130 | 2 | 99439270 | 99439356 | 1% | 3% | 24% | 31% | 81% | 32% | 56% | 2.54 | 19.21 | 25.16 | 66.32 | 26.30 | 45.23 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC112 | 11 | SPON1 | NM_006108 | + | 0 | 973 | 1 | 10418 | spondin 1, extracellular matrix protein |
| LC113 | 5 | MAX.chr5.134879362-134879483 | - | - | 0 | - | 0 | - | - |
| LC114 | 4 | MAX.chr4.8859990-8860023 | - | - | 0 | - | 1 | - | - |
| LC115 | 14 | PTGDR | NM_000953 | + | 0 | 995 | 1 | 5729 | prostaglandin D2 receptor (DP) |
| LC116 | 18 | CIDEA | NM_001279;NR_036468 | + | 0 | -11;-53 | 1 | 1149 | cell death-inducing DFFA-like effector a |
| LC117 | 6 | SERPINB9 | NM_004155 | - | 0 | -69 | 1 | 5272 | serpin peptidase inhibitor, clade B (ovalbumin), member 9 |
| LC118 | 8 | LOC100132891 | NR_033651;NR_033652 | + | 1 | -379;614 | 1 | 100132891 | hypothetical LOC100132891 |
| LC119 | 8 | NKX2-6 | NM_001136271 | - | 0 | -137 | 1 | 137814 | NK2 transcription factor related, locus 6 (Drosophila) |
| LC120 | 19 | VSTM2B | NM_001146339 | + | 0 | 305 | 1 | 342865 | V-set and transmembrane domain containing 2B |
| LC121 | 12 | BCAT1 | NM_001178092;NM_005504;NM_001178094;NM_001178091;NM_001178093 | - | 0 | 46210;46210;-861;46210;-174 | 1 | 586 | branched chain amino-acid transaminase 1, cytosolic |
| LC122 | 12 | FAIM2 | NM_012306 | - | 0 | -159 | 1 | 23017 | Fas apoptotic inhibitory molecule 2 |
| LC123 | 14 | PTGDR | NM_000953 | + | 1 | 793 | 1 | 5729 | prostaglandin D2 receptor (DP) |
| LC124 | 2 | MAX.chr2.25439185-25439264 | - | - | 0 | - | 1 | - | - |
| LC125 | 1 | MAX.chr1.32237695-32237880 | - | - | 0 | - | 0 | - | - |
| LC126 | 5 | NPR3 | NM_000908 | + | 0 | 1922 | 1 | 4883 | natriuretic peptide receptor C/guanylate cyclase C (atrionatriuretic peptide receptor C) |
| LC127 | 8 | MAX.chr8.145105570-145105675 | - | - | 0 | - | 1 | - | - |
| LC128 | 12 | GRASP | NM_181711 | + | 1 | 294 | 1 | 160622 | GRP1 (general receptor for phosphoinositides 1)-associated scaffold protein |
| LC129 | 7 | HOXA7 | NM_006896 | - | 0 | 548 | 1 | 3204 | homeobox A7 |
| LC130 | 2 | C2orf55 | NM_207362 | - | 1 | 113414 | 1 | 343990 | chromosome 2 open reading frame 55 |

FIG. 3 (cont'd)

| Large cell marker region ref. # | Chromosome | Start position | Stop position | mean BC.island | mean lung,normal. island | mean Adenocarcinoma Lung island | mean Large cell Lung island | mean Small cell Lung island | mean Squamous Lung island | mean undefined cancer Lung island | Norm/BC | Ad/BC | LC/BC | SC/BC | SQ/BC | UND/BC |
|---|---|---|---|---|---|---|---|---|---|---|---|---|---|---|---|---|
| LC131 | 10 | 124910562 | 124910715 | 1% | 3% | 7% | 31% | 26% | 11% | 16% | 2.57 | 5.42 | 24.87 | 20.86 | 8.77 | 13.03 |
| LC132 | 7 | 35293717 | 35293754 | 2% | 6% | 21% | 44% | 37% | 17% | 55% | 3.29 | 11.74 | 24.80 | 21.20 | 9.72 | 31.02 |
| LC133 | 1 | 161275580 | 161275649 | 1% | 1% | 6% | 20% | 1% | 12% | 2% | 1.19 | 7.61 | 24.72 | 1.32 | 14.12 | 2.90 |
| LC134 | 17 | 448967701 | 44896855 | 0% | 1% | 5% | 11% | 5% | 6% | 2% | 1.54 | 10.77 | 24.70 | 10.80 | 12.84 | 3.79 |
| LC135 | 6 | 108440646 | 108440760 | 1% | 3% | 23% | 30% | 56% | 23% | 29% | 2.73 | 19.07 | 24.47 | 45.83 | 18.68 | 23.23 |
| LC136 | 6 | 2903051 | 2903104 | 1% | 1% | 2% | 16% | 9% | 3% | 0% | 1.13 | 2.43 | 24.28 | 13.65 | 4.40 | 0.45 |
| LC137 | 12 | 576188791 | 576188831 | 2% | 4% | 21% | 37% | 78% | 30% | 61% | 2.91 | 13.94 | 23.92 | 50.79 | 19.55 | 39.93 |
| LC138 | 21 | 36042030 | 36042110 | 1% | 2% | 4% | 22% | 41% | 13% | 55% | 1.88 | 3.80 | 23.37 | 43.13 | 13.73 | 57.60 |
| LC139 | 2 | 233352635 | 233352699 | 1% | 1% | 8% | 18% | 3% | 3% | 18% | 1.40 | 9.63 | 22.92 | 3.72 | 3.82 | 21.94 |
| LC140 | 14 | 52536106 | 52536240 | 1% | 2% | 15% | 21% | 17% | 9% | 42% | 2.36 | 16.40 | 22.80 | 18.91 | 10.21 | 46.04 |
| LC141 | 10 | 105036730 | 105036777 | 1% | 2% | 17% | 25% | 14% | 6% | 53% | 2.01 | 15.78 | 22.74 | 12.57 | 5.11 | 48.13 |
| LC142 | 1 | 110627121 | 110627221 | 1% | 3% | 7% | 25% | 39% | 7% | 33% | 2.37 | 6.55 | 22.73 | 36.30 | 6.54 | 30.81 |
| LC143 | 8 | 1435922229 | 143592285 | 1% | 1% | 8% | 12% | 5% | 2% | 16% | 2.49 | 15.63 | 22.64 | 9.72 | 4.31 | 29.27 |
| LC144 | 7 | 158938047 | 158938133 | 1% | 4% | 9% | 30% | 14% | 7% | 29% | 3.07 | 6.84 | 22.63 | 10.90 | 5.54 | 22.04 |
| LC145 | 17 | 433392264 | 43339345 | 1% | 1% | 4% | 11% | 41% | 12% | 11% | 1.45 | 8.50 | 22.19 | 82.48 | 23.48 | 21.17 |
| LC146 | 10 | 1193129219 | 1193312997 | 1% | 3% | 15% | 26% | 28% | 5% | 11% | 2.57 | 12.66 | 22.08 | 23.61 | 4.33 | 9.25 |
| LC147 | 17 | 771779798 | 771779841 | 1% | 1% | 12% | 22% | 3% | 4% | 26% | 1.14 | 11.60 | 21.93 | 3.21 | 3.68 | 26.04 |
| LC148 | 4 | 1554122291 | 1554122375 | 1% | 1% | 5% | 12% | 6% | 2% | 10% | 2.01 | 10.12 | 21.79 | 11.77 | 3.65 | 19.36 |
| LC149 | 8 | 70947017 | 70947084 | 1% | 2% | 19% | 31% | 46% | 19% | 38% | 1.50 | 13.80 | 21.67 | 32.73 | 13.18 | 26.96 |
| LC150 | 15 | 651116474 | 651116558 | 1% | 1% | 9% | 15% | 9% | 18% | 1% | 1.58 | 12.74 | 21.62 | 13.62 | 26.30 | 1.26 |
| LC151 | 14 | 525535777 | 525535870 | 1% | 2% | 6% | 14% | 6% | 4% | 21% | 2.36 | 8.67 | 21.61 | 8.65 | 6.18 | 32.65 |
| LC152 | 12 | 1033352291 | 1033352323 | 1% | 1% | 3% | 26% | 3% | 7% | 31% | 1.13 | 2.73 | 21.57 | 2.19 | 5.76 | 25.28 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC131 | 10 | BUB3 | NM_001007793;NM_004725 | + | 0 | -3197;-3197 | 1 | 9184 | budding uninhibited by benzimidazoles 3 homolog (yeast) |
| LC132 | 7 | TBX20 | NM_001166220;NM_001077653 | - | 0 | -6;-6 | 1 | 57057 | T-box 20 |
| LC133 | 1 | MPZ | NM_000530 | - | 1 | 4182 | 0 | 4359 | myelin protein zero |
| LC134 | 17 | WNT3 | NM_030753 | - | 0 | -619 | 1 | 7473 | wingless-type MMTV integration site family, member 3 |
| LC135 | 6 | MAX.chr6.1084406646-1084407660 | - | - | 0 | - | 1 | - | - |
| LC136 | 6 | SERPINB9 | NM_004155 | - | 0 | 494 | 0 | 5272 | serpin peptidase inhibitor, clade B (ovalbumin), member 9 |
| LC137 | 12 | NXPH4 | NM_007224 | + | 1 | 8214 | 1 | 11247 | neurexophilin 4 |
| LC138 | 21 | CLIC6 | NM_053277 | + | 1 | 343 | 1 | 54102 | chloride intracellular channel 6 |
| LC139 | 2 | ECEL1 | NM_004826 | - | 0 | -103 | 1 | 9427 | endothelin converting enzyme-like 1 |
| LC140 | 14 | NID2 | NM_007361 | - | 0 | -160 | 1 | 22795 | nidogen 2 (osteonidogen) |
| LC141 | 10 | INA | NM_032727 | + | 0 | -189 | 1 | 9118 | internexin neuronal intermediate filament protein, alpha |
| LC142 | 1 | MAX.chr1.110627121-110627221 | - | - | 0 | - | 1 | - | - |
| LC143 | 8 | BAI1 | NM_001702 | + | 0 | 46853 | 1 | 575 | brain-specific angiogenesis inhibitor 1 |
| LC144 | 7 | VIPR2 | NM_003382 | - | 0 | -398 | 1 | 7434 | vasoactive intestinal peptide receptor 2 |
| LC145 | 17 | C17orf46 | NM_152343 | - | 0 | 215 | 1 | 124783 | chromosome 17 open reading frame 46 |
| LC146 | 10 | MAX.chr10.119312919-119312997 | - | - | 0 | - | 1 | - | - |
| LC147 | 17 | RBFOX3 | NM_001082575 | - | 0 | 298765 | 1 | 146713 | RNA binding protein, fox-1 homolog (C. elegans) 3 |
| LC148 | 4 | DCHS2 | NM_001142552;NM_001142553 | - | 1 | 586;639 | 1 | 54798 | dachsous 2 (Drosophila) |
| LC149 | 8 | MAX.chr8.70947017-70947084 | - | 0 | - | 1 | - | - | - |
| LC150 | 15 | PIF1 | NM_025049 | - | 1 | 1364 | 1 | 80119 | PIF1 5'-to-3' DNA helicase homolog (S. cerevisiae) |
| LC151 | 14 | NID2 | NM_007361 | - | 1 | 169 | 1 | 22795 | nidogen 2 (osteonidogen) |
| LC152 | 12 | ASCL1 | NM_004316 | + | 1 | 840 | 1 | 429 | achaete-scute complex homolog 1 (Drosophila) |

FIG. 3 (cont'd)

| Large cell marker region ref. # | Chromosome | Start position | Stop position | mean BC.island | mean lung.normal. island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| LC153 | 9 | 114075 | 114141 | 1% | 1% | 7% | 14% | 6% | 3% | 10% | 1.46 | 11.00 | 21.51 | 9.66 | 4.36 | 14.91 |
| LC154 | 2 | 26407567 | 26407639 | 1% | 1% | 5% | 12% | 62% | 27% | 16% | 1.73 | 9.78 | 21.33 | 112.60 | 49.01 | 28.67 |
| LC155 | 17 | 80329497 | 80329526 | 2% | 4% | 15% | 35% | 15% | 7% | 18% | 2.19 | 9.12 | 21.26 | 9.30 | 4.01 | 11.06 |
| LC156 | 2 | 946378 | 946438 | 1% | 1% | 10% | 13% | 4% | 3% | 20% | 2.16 | 16.72 | 21.25 | 7.07 | 5.17 | 32.61 |
| LC157 | 2 | 87088958 | 87088997 | 2% | 4% | 23% | 42% | 10% | 8% | 34% | 2.06 | 11.42 | 21.20 | 4.83 | 4.08 | 16.97 |
| LC158 | 1 | 78511892 | 78512047 | 1% | 2% | 5% | 21% | 12% | 10% | 16% | 2.00 | 4.64 | 21.05 | 12.33 | 10.20 | 15.52 |
| LC159 | 17 | 46832435 | 46832494 | 2% | 4% | 18% | 51% | 64% | 10% | 45% | 1.74 | 7.35 | 20.82 | 26.15 | 4.19 | 18.31 |
| LC160 | 5 | 1876308 | 1876340 | 2% | 3% | 21% | 42% | 5% | 24% | 30% | 1.64 | 10.14 | 20.71 | 2.63 | 11.89 | 14.89 |
| LC161 | 4 | 88590049 | 8859184 | 1% | 1% | 6% | 14% | 12% | 6% | 23% | 2.12 | 8.57 | 20.70 | 18.12 | 9.42 | 34.78 |
| LC162 | 1 | 8277482 | 8277571 | 1% | 2% | 10% | 22% | 48% | 31% | 59% | 1.59 | 9.26 | 20.67 | 45.68 | 29.57 | 56.50 |
| LC163 | 5 | 10563569 | 10563607 | 1% | 2% | 6% | 16% | 9% | 2% | 23% | 2.00 | 7.48 | 20.66 | 12.20 | 2.30 | 30.00 |
| LC164 | 2 | 74726082 | 74726257 | 1% | 1% | 5% | 19% | 13% | 7% | 22% | 1.42 | 5.07 | 20.56 | 13.46 | 7.60 | 23.48 |
| LC165 | 9 | 129377645 | 129377714 | 1% | 1% | 2% | 12% | 2% | 7% | 4% | 1.91 | 3.68 | 20.35 | 3.27 | 11.71 | 7.54 |
| LC166 | 12 | 106979840 | 106979932 | 2% | 3% | 13% | 32% | 4% | 11% | 39% | 1.93 | 7.96 | 20.27 | 2.45 | 7.05 | 24.97 |
| LC167 | 3 | 170137371 | 170137439 | 2% | 5% | 15% | 34% | 49% | 33% | 62% | 2.78 | 9.08 | 20.26 | 29.02 | 19.46 | 36.27 |
| LC168 | 2 | 74726270 | 74726331 | 1% | 1% | 6% | 24% | 22% | 9% | 22% | 1.27 | 5.44 | 20.19 | 19.04 | 7.96 | 18.84 |
| LC169 | 7 | 50343331 | 50343395 | 1% | 2% | 6% | 20% | 11% | 3% | 16% | 2.36 | 5.94 | 20.12 | 11.47 | 2.74 | 15.82 |
| LC170 | 8 | 687683 | 687729 | 2% | 4% | 29% | 46% | 31% | 24% | 58% | 1.75 | 12.72 | 20.04 | 13.43 | 10.27 | 25.10 |

FIG. 3 (cont'd)

| Large cell marker region ref. # | Chromosome | Gene | Transcript | Strand | In Exon | Tss Distance | In CpG Island | Entrez ID | Gene title |
|---|---|---|---|---|---|---|---|---|---|
| LC153 | 9 | MAX.chr9.114075-114141 | - | - | 0 | - | 1 | - | - |
| LC154 | 2 | FAM59B | NM_001191033;NM_001168241 | + | 1 | 3983;11608 | 1 | 150946 | family with sequence similarity 59, member B |
| LC155 | 17 | UTS2R | NM_018949 | + | 0 | -2703 | 1 | 2837 | urotensin 2 receptor |
| LC156 | 2 | SNTG2 | NM_018968 | + | 0 | -175 | 1 | 54221 | syntrophin, gamma 2 |
| LC157 | 2 | CD8B | NM_004931;NM_172102;NM_00117 8100;NM_172213;NM_172101 | - | 1 | 89;89;89;89;89 | 1 | 926 | CD8b molecule |
| LC158 | 1 | GIPC2 | NM_017655 | + | 1 | 304 | 1 | 54810 | GIPC PDZ domain containing family, member 2 |
| LC159 | 17 | MAX.chr17.46832435-46832494 | - | - | 0 | - | 1 | - | - |
| LC160 | 5 | MAX.chr5.1876308-1876340 | - | - | 0 | - | 1 | - | - |
| LC161 | 4 | MAX.chr4.8859049-8859184 | - | - | 0 | - | 1 | - | - |
| LC162 | 1 | MAX.chr1.8277482-8277571 | - | - | 0 | - | 1 | - | - |
| LC163 | 5 | ANKRD33B | NM_001164440 | + | 0 | -865 | 1 | 651746 | ankyrin repeat domain 33B |
| LC164 | 2 | LBX2 | NM_0010009812 | - | 0 | 4361 | 1 | 85474 | ladybird homeobox 2 |
| LC165 | 9 | LMX1B | NM_002316;NM_001174146;NM_0 01174147 | + | 0 | 924;924;924 | 1 | 4010 | LIM homeobox transcription factor 1, beta |
| LC166 | 12 | RFX4 | NM_213594 | + | 0 | 2808 | 1 | 5992 | regulatory factor X, 4 (influences HLA class II expression) |
| LC167 | 3 | CLDN11 | NM_001185056;NM_005602 | + | 0 | -1656;719 | 1 | 5010 | claudin 11 |
| LC168 | 2 | LBX2 | NM_0010009812 | - | 0 | 4173 | 1 | 85474 | ladybird homeobox 2 |
| LC169 | 7 | IKZF1 | NM_006060 | + | 0 | -1046 | 1 | 10320 | IKAROS family zinc finger 1 (Ikaros) |
| LC170 | 8 | MAX.chr8.687683-687729 | - | - | 0 | - | 1 | - | - |

FIG. 4

| Small Cell marker region ref. # | Chromosome | Start position | Stop position | mean BC.island | mean lung.normal, normal.island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC1 | 5 | 42995102 | 42995171 | 0% | 4% | 8% | 21% | 43% | 32% | 59% | 37.37 | 88.00 | 220.17 | 459.69 | 335.17 | 627.38 |
| SC2 | 11 | 14926886 | 14926955 | 0% | 3% | 6% | 29% | 78% | 21% | 20% | 8.70 | 18.97 | 99.05 | 266.28 | 70.91 | 68.97 |
| SC3 | 11 | 14926795 | 14926853 | 0% | 2% | 9% | 26% | 78% | 27% | 10% | 6.70 | 27.57 | 84.20 | 249.90 | 86.19 | 33.11 |
| SC4 | 5 | 42995477 | 42995528 | 0% | 5% | 20% | 35% | 60% | 39% | 62% | 18.40 | 82.13 | 141.62 | 245.53 | 158.96 | 254.67 |
| SC5 | 9 | 124132797 | 124132861 | 0% | 3% | 6% | 8% | 49% | 10% | 55% | 15.58 | 27.54 | 37.71 | 217.46 | 45.00 | 246.29 |
| SC6 | 17 | 27467359 | 27467467 | 0% | 0% | 10% | 7% | 28% | 4% | 5% | 2.69 | 61.89 | 42.49 | 170.64 | 26.04 | 31.95 |
| SC7 | 11 | 14926995 | 14927132 | 0% | 4% | 6% | 16% | 66% | 14% | 13% | 10.65 | 16.01 | 42.26 | 168.75 | 35.65 | 33.15 |
| SC8 | 6 | 149803478 | 149803586 | 0% | 4% | 6% | 16% | 48% | 19% | 25% | 14.98 | 19.63 | 54.98 | 164.84 | 66.15 | 87.14 |
| SC9 | 19 | 17403238 | 174032270 | 0% | 2% | 3% | 4% | 46% | 5% | 22% | 8.35 | 9.57 | 14.66 | 154.96 | 15.55 | 74.38 |
| SC10 | 3 | 122296709 | 122296828 | 0% | 3% | 17% | 23% | 65% | 25% | 61% | 5.87 | 39.97 | 54.78 | 151.39 | 57.49 | 143.28 |
| SC11 | 10 | 22541891 | 22541996 | 0% | 2% | 13% | 22% | 49% | 18% | 24% | 5.71 | 36.56 | 63.36 | 141.74 | 52.16 | 69.90 |
| SC12 | 8 | 72754556 | 72754648 | 1% | 4% | 18% | 23% | 65% | 21% | 50% | 8.04 | 33.54 | 42.57 | 119.67 | 39.04 | 91.67 |
| SC13 | 7 | 100075307 | 100075425 | 0% | 2% | 21% | 18% | 54% | 15% | 16% | 3.87 | 45.55 | 39.16 | 116.74 | 32.72 | 34.94 |
| SC14 | 8 | 144328573 | 144328649 | 0% | 2% | 10% | 13% | 32% | 7% | 22% | 5.38 | 32.52 | 41.01 | 101.81 | 21.45 | 68.46 |
| SC15 | 9 | 96721507 | 96721564 | 1% | 3% | 11% | 22% | 77% | 19% | 28% | 2.86 | 11.67 | 24.03 | 83.04 | 20.71 | 29.71 |
| SC16 | 10 | 22624410 | 22624553 | 1% | 2% | 7% | 30% | 63% | 11% | 58% | 2.80 | 9.42 | 38.62 | 82.32 | 14.11 | 75.75 |
| SC17 | 8 | 709881960 | 70982028 | 1% | 4% | 26% | 36% | 65% | 28% | 58% | 5.02 | 30.29 | 41.91 | 74.59 | 32.63 | 66.72 |
| SC18 | 3 | 138658597 | 138658705 | 1% | 4% | 15% | 29% | 50% | 25% | 58% | 6.02 | 21.20 | 39.97 | 68.59 | 34.74 | 79.20 |
| SC19 | 2 | 99439270 | 99439356 | 1% | 3% | 24% | 31% | 81% | 32% | 56% | 2.54 | 19.21 | 25.16 | 66.32 | 26.30 | 45.23 |
| SC20 | 14 | 33402226 | 33402304 | 1% | 4% | 24% | 21% | 71% | 15% | 49% | 3.48 | 22.10 | 19.50 | 64.55 | 13.58 | 45.05 |
| SC21 | 1 | 239936705 | 239936773 | 1% | 4% | 15% | 30% | 65% | 24% | 31% | 4.19 | 14.48 | 28.80 | 62.06 | 22.68 | 29.92 |
| SC22 | 7 | 272205013 | 27205081 | 1% | 7% | 29% | 50% | 83% | 42% | 48% | 5.20 | 20.79 | 36.52 | 60.30 | 30.77 | 35.13 |
| SC23 | 17 | 48042562 | 48042606 | 1% | 3% | 24% | 47% | 56% | 25% | 44% | 3.67 | 25.97 | 50.24 | 59.12 | 26.78 | 46.42 |
| SC24 | 11 | 31820365 | 31820418 | 1% | 4% | 19% | 39% | 74% | 21% | 59% | 3.41 | 14.93 | 30.02 | 57.24 | 16.07 | 45.33 |
| SC25 | 2 | 711116233 | 711116269 | 1% | 4% | 14% | 24% | 62% | 15% | 51% | 4.02 | 12.56 | 21.37 | 55.76 | 13.59 | 46.07 |
| SC26 | 2 | 239140226 | 239140351 | 1% | 2% | 7% | 16% | 42% | 5% | 15% | 2.14 | 8.36 | 19.00 | 51.66 | 6.30 | 17.68 |
| SC27 | 18 | 55095158 | 55095201 | 1% | 5% | 11% | 31% | 64% | 13% | 42% | 3.65 | 9.00 | 23.92 | 50.49 | 10.38 | 32.83 |
| SC28 | 15 | 89914730 | 89914776 | 1% | 3% | 4% | 10% | 59% | 18% | 16% | 2.44 | 3.73 | 8.26 | 49.97 | 15.08 | 13.65 |
| SC29 | 2 | 747265554 | 747266617 | 1% | 4% | 38% | 47% | 68% | 31% | 49% | 3.10 | 27.46 | 34.21 | 49.28 | 22.18 | 35.41 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC1 | 5 | MAX.chr5.42995102-42995171 | - | - | 0 | | 0 | - | - |
| SC2 | 11 | MAX.chr11.14926886-14926955 | - | - | 0 | | 1 | - | - |
| SC3 | 11 | MAX.chr11.14926795-14926853 | - | - | 0 | | 1 | - | - |
| SC4 | 5 | MAX.chr5.42995477-42995528 | - | - | 0 | | 0 | - | - |
| SC5 | 9 | STOM | NM_198194;NM_004099 | - | 0 | -252;-252 | 1 | 2040 | stomatin |
| SC6 | 17 | MYO18A | NM_078471;NM_203318 | - | 0 | 40048;40048 | 0 | 399687 | myosin XVIIIA |
| SC7 | 11 | MAX.chr11.14926995-14927132 | - | - | 0 | | 1 | - | - |
| SC8 | 6 | ZC3H12D | NM_207360 | - | 0 | 2670 | 0 | 340152 | zinc finger CCCH-type containing 12D |
| SC9 | 19 | ABHD8 | NM_024527 | - | 1 | 11044 | 1 | 79575 | abhydrolase domain containing 8 |
| SC10 | 3 | PARP15 | NM_001113523 | + | 0 | 261 | 1 | 165631 | poly (ADP-ribose) polymerase family, member 15 |
| SC11 | 10 | MAX.chr10.22541891-22541996 | - | - | 0 | | 1 | - | - |
| SC12 | 8 | LOC100132891 | NR_033651;NR_033652 | + | 1 | -1794;-801 | 1 | 100132891 | hypothetical LOC100132891 |
| SC13 | 7 | TSC22D4 | NM_030935 | + | 0 | 1585 | 1 | 81628 | TSC22 domain family, member 4 |
| SC14 | 8 | ZFP41 | NM_173832 | + | 0 | -535 | 1 | 286128 | zinc finger protein 41 homolog (mouse) |
| SC15 | 9 | BARX1 | NM_021570 | - | 0 | -3899 | 1 | 56033 | BARX homeobox 1 |
| SC16 | 10 | MAX.chr10.22624410-22624553 | - | - | 0 | | 1 | - | - |
| SC17 | 8 | PRDM14 | NM_024504 | - | 1 | 1602 | 1 | 63978 | PR domain containing 14 |
| SC18 | 3 | MAX.chr3.138658597-138658705 | - | - | 0 | | 1 | - | - |
| SC19 | 2 | C2orf55 | NM_207362 | - | 1 | 113414 | 1 | 343990 | chromosome 2 open reading frame 55 |
| SC20 | 14 | MAX.chr14.33402226-33402304 | - | - | 0 | | 1 | - | - |
| SC21 | 1 | CAPN2 | NM_001146068;NM_001748 | + | 0 | 47411;36587 | 1 | 824 | calpain 2, (m/II) large subunit |
| SC22 | 7 | HOXA9 | NM_152739 | - | 1 | 136 | 1 | 3205 | homeobox A9 |
| SC23 | 17 | DLX4 | NM_138281 | + | 0 | -3999 | 1 | 1748 | distal-less homeobox 4 |
| SC24 | 11 | PAX6 | NM_000280;NM_001604;NM_001127612 | - | 0 | 12514;12514;19144 | 1 | 5080 | paired box 6 |
| SC25 | 2 | MAX.chr2.71116233-71116269 | - | - | 0 | | 1 | - | - |
| SC26 | 2 | LOC151174 | NR_026926;NR_026925 | - | 1 | 92;92 | 1 | 151174 | hypothetical LOC151174 |
| SC27 | 18 | MAX.chr18.55095158-55095201 | - | - | 0 | | 1 | - | - |
| SC28 | 15 | MAX.chr15.89914730-89914776 | - | - | 0 | | 1 | - | - |
| SC29 | 2 | LBX2 | NM_001009812 | - | 0 | 3889 | 1 | 85474 | ladybird homeobox 2 |

FIG. 4 (cont'd)

| Small Cell marker region ref. # | Chromosome | Start position | Stop position | mean BC island | mean lung-normal. island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC30 | 12 | 133481464 | 133481521 | 1% | 5% | 25% | 28% | 54% | 26% | 49% | 4.21 | 22.69 | 24.67 | 48.26 | 23.58 | 43.20 |
| SC31 | 10 | 22624260 | 22624375 | 1% | 2% | 6% | 21% | 53% | 13% | 56% | 1.91 | 5.10 | 18.41 | 47.17 | 11.24 | 50.06 |
| SC32 | 20 | 61560462 | 61560635 | 2% | 3% | 9% | 19% | 72% | 30% | 26% | 1.81 | 5.48 | 11.30 | 42.16 | 17.75 | 15.47 |
| SC33 | 1 | 151811410 | 151811523 | 2% | 8% | 20% | 39% | 68% | 16% | 34% | 4.65 | 12.47 | 24.13 | 42.10 | 9.64 | 20.83 |
| SC34 | 5 | 1295444 | 1295496 | 2% | 3% | 16% | 28% | 76% | 15% | 58% | 1.93 | 8.89 | 15.80 | 42.04 | 8.35 | 32.46 |
| SC35 | 7 | 8482598 | 8482670 | 2% | 4% | 19% | 34% | 80% | 14% | 54% | 2.23 | 9.82 | 17.57 | 41.49 | 7.09 | 27.92 |
| SC36 | 9 | 96722680 | 96722762 | 2% | 4% | 13% | 18% | 81% | 18% | 54% | 1.81 | 6.40 | 9.21 | 40.62 | 9.17 | 27.11 |
| SC37 | 19 | 13617166 | 13617235 | 2% | 3% | 16% | 24% | 79% | 7% | 42% | 1.52 | 7.95 | 12.14 | 40.60 | 3.55 | 21.30 |
| SC38 | 11 | 31825851 | 31825955 | 1% | 5% | 12% | 28% | 56% | 18% | 49% | 3.29 | 8.47 | 20.02 | 40.60 | 12.92 | 35.78 |
| SC39 | 1 | 47696594 | 47696674 | 1% | 4% | 13% | 16% | 46% | 9% | 51% | 3.76 | 10.92 | 13.85 | 39.04 | 7.83 | 43.54 |
| SC40 | 5 | 1295519 | 1295587 | 2% | 4% | 17% | 28% | 72% | 11% | 60% | 2.15 | 9.27 | 15.05 | 38.74 | 6.15 | 32.15 |
| SC41 | 19 | 16394457 | 16394575 | 1% | 2% | 18% | 14% | 52% | 21% | 23% | 1.72 | 13.16 | 10.15 | 38.09 | 15.47 | 17.08 |
| SC42 | 14 | 101033663 | 101033775 | 1% | 2% | 12% | 8% | 32% | 4% | 15% | 1.82 | 13.80 | 9.61 | 37.74 | 5.12 | 17.01 |
| SC43 | 2 | 71116047 | 71116131 | 2% | 5% | 20% | 37% | 73% | 21% | 66% | 2.54 | 10.30 | 19.16 | 37.51 | 11.04 | 34.09 |
| SC44 | 3 | 157821297 | 157821378 | 2% | 5% | 15% | 35% | 77% | 33% | 48% | 2.18 | 7.42 | 16.95 | 37.26 | 15.88 | 23.32 |
| SC45 | 20 | 39597822 | 39597893 | 1% | 5% | 8% | 7% | 50% | 8% | 38% | 3.36 | 5.53 | 5.14 | 36.66 | 5.59 | 27.57 |
| SC46 | 8 | 23564059 | 23564136 | 1% | 2% | 12% | 23% | 30% | 12% | 50% | 2.76 | 14.60 | 27.91 | 36.65 | 14.91 | 61.08 |
| SC47 | 20 | 250061836 | 250611911 | 1% | 4% | 19% | 19% | 54% | 8% | 55% | 2.39 | 12.78 | 12.56 | 36.50 | 5.35 | 36.91 |
| SC48 | 2 | 171678927 | 171678966 | 2% | 5% | 23% | 43% | 83% | 36% | 56% | 2.35 | 10.01 | 18.83 | 36.28 | 15.71 | 24.53 |
| SC49 | 1 | 165323561 | 165323624 | 2% | 5% | 18% | 29% | 62% | 19% | 60% | 2.83 | 10.55 | 16.83 | 35.93 | 10.85 | 34.56 |
| SC50 | 4 | 27765684 | 27765768 | 2% | 5% | 13% | 20% | 73% | 13% | 44% | 2.44 | 6.44 | 9.67 | 35.86 | 6.17 | 21.87 |
| SC51 | 14 | 38724873 | 38724946 | 2% | 5% | 26% | 28% | 54% | 28% | 39% | 3.19 | 17.27 | 18.37 | 35.74 | 18.39 | 25.84 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC30 | 12 | MAX.chr12.133481464-133481521 | - | - | 0 | - | 0 | - | - |
| SC31 | 10 | MAX.chr10.22624260-22624375 | - | - | 0 | - | 1 | - | - |
| SC32 | 20 | DIDO1 | NM_033081;NM_001193369;NM_0 22105;NM_080797;NM_001193370; NM_080796 | - | 0 | 8842;-2559;8842;8842; 2559;-2559 | 1 | 11083 | death inducer-obliterator 1 |
| SC33 | 1 | C2CD4D | NM_001136003 | - | 1 | 1623 | 1 | 100191040 | C2 calcium-dependent domain containing 4D |
| SC34 | 5 | TERT | NM_001193376;NM_198253 | - | 0 | -282;-282 | 1 | 7015 | telomerase reverse transcriptase |
| SC35 | 7 | NXPH1 | NM_152745 | + | 0 | 9014 | 1 | 30010 | neurexophilin 1 |
| SC36 | 9 | MAX.chr9.96722680-96722762 | - | - | 0 | - | 1 | - | - |
| SC37 | 19 | CACNA1A | NM_001127222;NM_023035;NM_0 01127221;NM_000068;NM_001174 080 | - | 1 | 108;108;108;108;108 | 1 | 773 | calcium channel, voltage-dependent. P/Q type, alpha 1A subunit |
| SC38 | 11 | PAX6 | NM_000280;NM_001604;NM_0011 27612 | - | 0 | 7028;7028;13658 | 1 | 5080 | paired box 6 |
| SC39 | 1 | TAL1 | NM_003189 | - | 0 | -1151 | 1 | 6886 | T-cell acute lymphocytic leukemia 1 |
| SC40 | 5 | TERT | NM_001193376;NM_198253 | - | 0 | -357;-357 | 1 | 7015 | telomerase reverse transcriptase |
| SC41 | 19 | MAX.chr19.16394457-16394575 | - | - | 0 | - | 1 | - | - |
| SC42 | 14 | BEGAIN | NM_001159531;NM_020836 | - | 0 | 744;2468 | 0 | 57596 | brain-enriched guanylate kinase-associated homolog (rat) |
| SC43 | 2 | MAX.chr2.71116047-71116131 | - | - | 0 | - | 1 | - | - |
| SC44 | 3 | SHOX2 | NM_001163678;NM_006884;NM_0 03030 | - | 0 | 2655;2655;2655 | 1 | 6474 | short stature homeobox 2 |
| SC45 | 20 | MAX.chr20.39597822-39597893 | - | - | 0 | - | 0 | - | - |
| SC46 | 8 | NKX2-6 | NM_001136271 | - | 0 | -137 | 1 | 137814 | NK2 transcription factor related, locus 6 (Drosophila) |
| SC47 | 20 | VSX1 | NM_014588;NM_199425 | - | 0 | 931;931 | 1 | 30813 | visual system homeobox 1 |
| SC48 | 2 | GAD1 | NM_000817;NM_013445 | + | 0 | 5728;5728 | 1 | 2571 | glutamate decarboxylase 1 (brain, 67kDa) |
| SC49 | 1 | LMX1A | NM_001174069;NM_177398 | - | 0 | 1917;2391 | 1 | 4009 | LIM homeobox transcription factor 1, alpha |
| SC50 | 4 | MAX.chr4.27655684-27655768 | - | - | 0 | - | 1 | - | - |
| SC51 | 14 | CLEC14A | NM_175060 | - | 1 | 701 | 1 | 161198 | C-type lectin domain family 14, member A |

FIG. 4 (cont'd)

| Small Cell marker region ref. # | Chromosome | Start position | Stop position | mean BC.island | mean lung.normal. island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC52 | 14 | 57275051 | 57275128 | 2% | 5% | 23% | 23% | 69% | 33% | 62% | 2.46 | 12.11 | 12.16 | 35.71 | 17.08 | 32.11 |
| SC53 | 1 | 119527180 | 119527255 | 2% | 5% | 18% | 33% | 66% | 26% | 59% | 2.62 | 9.32 | 17.22 | 34.40 | 13.57 | 30.76 |
| SC54 | 17 | 37321375 | 37321560 | 1% | 2% | 14% | 16% | 46% | 20% | 28% | 1.69 | 10.17 | 11.26 | 33.55 | 14.38 | 20.12 |
| SC55 | 19 | 22825989 | 22882652 | 2% | 4% | 17% | 18% | 70% | 8% | 34% | 1.95 | 8.09 | 8.43 | 33.32 | 3.73 | 16.12 |
| SC56 | 14 | 57275166 | 57275267 | 2% | 3% | 17% | 15% | 58% | 23% | 58% | 1.81 | 9.89 | 8.63 | 33.21 | 12.99 | 32.92 |
| SC57 | 8 | 70947017 | 70947084 | 1% | 2% | 19% | 31% | 46% | 19% | 38% | 1.50 | 13.80 | 21.67 | 32.73 | 13.18 | 26.96 |
| SC58 | 17 | 37321636 | 37321779 | 2% | 4% | 25% | 28% | 56% | 24% | 35% | 2.13 | 14.57 | 16.29 | 32.47 | 13.78 | 20.19 |
| SC59 | 7 | 156796836 | 156796900 | 2% | 6% | 34% | 35% | 65% | 13% | 44% | 3.16 | 16.78 | 17.33 | 32.09 | 6.32 | 22.05 |
| SC60 | 13 | 112708072 | 112708131 | 2% | 4% | 16% | 19% | 60% | 29% | 52% | 2.28 | 8.17 | 9.98 | 30.61 | 15.09 | 26.55 |
| SC61 | 15 | 60287478 | 60287520 | 3% | 3% | 7% | 24% | 75% | 11% | 56% | 1.34 | 2.93 | 9.22 | 29.60 | 4.15 | 21.93 |
| SC62 | 2 | 176964778 | 176964812 | 3% | 5% | 29% | 35% | 80% | 40% | 78% | 1.72 | 10.48 | 12.64 | 28.72 | 14.52 | 27.93 |
| SC63 | 17 | 59529752 | 59529199 | 2% | 4% | 8% | 8% | 64% | 27% | 19% | 1.93 | 3.71 | 12.10 | 28.70 | 11.98 | 8.64 |
| SC64 | 16 | 79623678 | 79623752 | 2% | 4% | 14% | 9% | 60% | 12% | 31% | 1.67 | 6.46 | 4.23 | 28.57 | 5.92 | 14.79 |
| SC65 | 9 | 37002603 | 37002649 | 3% | 4% | 18% | 31% | 74% | 17% | 51% | 1.40 | 6.83 | 11.99 | 28.51 | 6.44 | 19.72 |
| SC66 | 17 | 35299945 | 35299975 | 3% | 7% | 34% | 41% | 70% | 30% | 67% | 2.75 | 13.34 | 15.98 | 27.54 | 11.92 | 26.15 |
| SC67 | 9 | 96714376 | 96714430 | 3% | 5% | 22% | 26% | 84% | 23% | 35% | 1.73 | 7.31 | 8.50 | 27.40 | 7.43 | 11.57 |
| SC68 | 8 | 23564008 | 23564050 | 1% | 4% | 16% | 23% | 33% | 14% | 48% | 2.96 | 12.99 | 19.51 | 27.33 | 11.90 | 40.25 |
| SC69 | 2 | 162280520 | 162280586 | 2% | 5% | 25% | 32% | 61% | 22% | 48% | 2.23 | 11.24 | 14.21 | 27.13 | 9.78 | 21.69 |
| SC70 | 17 | 353300794 | 353300829 | 2% | 6% | 17% | 32% | 62% | 19% | 36% | 2.40 | 6.98 | 13.40 | 26.28 | 7.88 | 14.98 |
| SC71 | 14 | 609552425 | 609552483 | 2% | 4% | 16% | 17% | 57% | 16% | 53% | 1.86 | 7.61 | 7.86 | 26.23 | 7.50 | 24.42 |
| SC72 | 7 | 156814766 | 156814822 | 2% | 2% | 10% | 17% | 47% | 7% | 25% | 1.21 | 5.45 | 9.24 | 25.65 | 3.68 | 13.51 |
| SC73 | 17 | 46711207 | 46711240 | 2% | 7% | 27% | 33% | 61% | 22% | 46% | 2.92 | 11.03 | 13.61 | 24.97 | 8.80 | 18.91 |
| SC74 | 11 | 74178467 | 74178613 | 2% | 3% | 4% | 8% | 50% | 5% | 10% | 1.26 | 2.15 | 4.04 | 24.88 | 2.51 | 5.18 |
| SC75 | 5 | 42993534 | 42993659 | 2% | 5% | 10% | 21% | 53% | 18% | 49% | 2.27 | 4.60 | 9.88 | 24.87 | 8.31 | 22.95 |
| SC76 | 5 | 72595672 | 72595716 | 3% | 6% | 21% | 29% | 73% | 17% | 66% | 2.06 | 7.13 | 9.82 | 24.53 | 5.88 | 22.18 |
| SC77 | 19 | 13617366 | 13617505 | 3% | 4% | 14% | 12% | 70% | 6% | 34% | 1.32 | 4.91 | 4.33 | 24.48 | 2.22 | 11.85 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC52 | 14 | OTX2 | NM_172337;NM_021728 | - | 0 | -2706;2133 | 1 | 5015 | orthodenticle homeobox 2 |
| SC53 | 1 | TBX15 | NM_152380 | - | 0 | 4999 | 1 | 6913 | T-box 15 |
| SC54 | 17 | ARL5C | NM_001143968 | - | 1 | 1039 | 0 | 390790 | ADP-ribosylation factor-like 5C |
| SC55 | 19 | C19orf35 | NM_198532 | - | 0 | -408 | 0 | 374872 | chromosome 19 open reading frame 35 |
| SC56 | 14 | OTX2 | NM_172337;NM_021728 | - | 0 | -2821;2018 | 1 | 5015 | orthodenticle homeobox 2 |
| SC57 | 8 | MAX.chr8.70947017-70947084 | - | - | 0 | - | 1 | - | , |
| SC58 | 17 | ARL5C | NM_001143968 | - | 0 | 778 | 1 | 390790 | ADP-ribosylation factor-like 5C |
| SC59 | 7 | MAX.chr7.156796836-156796900 | - | - | 0 | - | 1 | - | , |
| SC60 | 13 | MAX.chr13.112708072-112708131 | - | - | 0 | - | 1 | - | , |
| SC61 | 15 | MAX.chr15.60287478-60287520 | - | + | 0 | - | 1 | - | , |
| SC62 | 2 | HOXD12 | NM_021193 | + | 1 | 249 | 1 | 3238 | homeobox D12 |
| SC63 | 17 | TBX4 | NM_018488 | + | 0 | -4654 | 1 | 9496 | T-box 4 |
| SC64 | 16 | MAX.chr16.79623678-79623752 | - | - | 0 | - | 1 | - | , |
| SC65 | 9 | PAX5 | NM_016734 | - | 0 | 31873 | 1 | 5079 | paired box 5 |
| SC66 | 17 | LHX1 | NM_005568 | + | 0 | 5174 | 1 | 3975 | LIM homeobox 1 |
| SC67 | 9 | BARX1 | NM_021570 | - | 1 | 3232 | 1 | 56033 | BARX homeobox 1 |
| SC68 | 8 | NKX2-6 | NM_001136271 | - | 0 | -86 | 1 | 137814 | NK2 transcription factor related, locus 6 (Drosophila) |
| SC69 | 2 | TBR1 | NM_006593 | + | 1 | 7901 | 1 | 10716 | T-box, brain, 1 |
| SC70 | 17 | LHX1 | NM_005568 | + | 1 | 6023 | 1 | 3975 | LIM homeobox 1 |
| SC71 | 14 | C14orf39 | NM_174978 | - | 0 | 339 | 1 | 317761 | chromosome 14 open reading frame 39 |
| SC72 | 7 | MAX.chr7.156814766-156814822 | - | - | 0 | - | 0 | - | , |
| SC73 | 17 | MIR196A1 | NR_029582 | - | 0 | -1286 | 1 | 406972 | microRNA 196a-1 |
| SC74 | 11 | KCNE3 | NM_005472 | - | 1 | 133 | 1 | 10008 | potassium voltage-gated channel, Isk-related family, member 3 |
| SC75 | 5 | MAX.chr5.42993534-42993659 | - | - | 0 | - | 0 | - | , |
| SC76 | 5 | MAX.chr5.72595672-72595716 | - | - | 0 | - | 1 | - | , |
| SC77 | 19 | CACNA1A | NM_001127222;NM_023035;NM_011127221;NM_000068;NM_001174080 | - | 0 | -92;-92;-92;-92;-92 | 0 | 773 | calcium channel, voltage-dependent, P/Q type, alpha 1A subunit |

FIG. 4 (cont'd)

| Small Cell marker region ref. # | Chromosome | Start position | Stop position | mean BC island | mean lung,normal island | mean Adenocarcinoma Lung island | mean Large cell Lung island | mean Small cell Lung island | mean Squamous Lung island | mean undefined Lung cancer island | Norm/BC | Ad/BC | LC/BC | SC/BC | SQ/BC | UND/BC |
|---|---|---|---|---|---|---|---|---|---|---|---|---|---|---|---|---|
| SC78 | 11 | 74178305 | 74178408 | 2% | 2% | 4% | 9% | 49% | 5% | 13% | 1.05 | 2.00 | 4.30 | 23.91 | 2.45 | 6.46 |
| SC79 | 1 | 50885167 | 50885250 | 3% | 5% | 19% | 22% | 79% | 31% | 60% | 1.35 | 5.67 | 6.59 | 23.78 | 9.13 | 18.04 |
| SC80 | 3 | 138659030 | 138659082 | 2% | 8% | 27% | 27% | 59% | 25% | 36% | 3.18 | 10.80 | 10.88 | 23.77 | 10.05 | 14.63 |
| SC81 | 6 | 45631289 | 45631363 | 3% | 6% | 14% | 34% | 59% | 20% | 74% | 2.29 | 5.52 | 13.60 | 23.49 | 8.10 | 29.57 |
| SC82 | 6 | 10421453 | 10421550 | 3% | 6% | 14% | 28% | 68% | 23% | 50% | 2.12 | 4.84 | 9.60 | 23.21 | 7.79 | 17.17 |
| SC83 | 11 | 20627327 | 20627367 | 3% | 5% | 15% | 16% | 74% | 11% | 43% | 1.49 | 4.59 | 5.07 | 23.06 | 3.31 | 13.58 |
| SC84 | 9 | 37030436 | 37030506 | 3% | 4% | 9% | 11% | 71% | 7% | 24% | 1.33 | 2.87 | 3.44 | 22.93 | 2.40 | 7.84 |
| SC85 | 3 | 138658429 | 138658507 | 2% | 5% | 15% | 35% | 43% | 23% | 52% | 2.49 | 8.08 | 18.45 | 22.68 | 12.15 | 27.67 |
| SC86 | 7 | 8482447 | 8482526 | 3% | 6% | 22% | 35% | 70% | 17% | 55% | 1.84 | 7.01 | 11.06 | 22.36 | 5.51 | 17.36 |
| SC87 | 7 | 157478020 | 157478086 | 4% | 6% | 19% | 28% | 80% | 17% | 63% | 1.53 | 5.18 | 7.78 | 22.02 | 4.63 | 17.28 |
| SC88 | 1 | 149672262 | 149672714 | 2% | 4% | 12% | 20% | 50% | 19% | 33% | 1.78 | 5.42 | 8.91 | 21.77 | 8.39 | 14.44 |
| SC89 | 9 | 96588741 | 96588774 | 4% | 5% | 23% | 24% | 76% | 18% | 60% | 1.40 | 6.54 | 6.62 | 21.42 | 5.00 | 16.79 |
| SC90 | 6 | 106429477 | 106429533 | 3% | 6% | 14% | 25% | 55% | 17% | 37% | 2.21 | 5.42 | 9.91 | 21.29 | 6.62 | 14.36 |
| SC91 | 9 | 96714225 | 96714363 | 3% | 4% | 14% | 17% | 58% | 15% | 20% | 1.50 | 5.03 | 6.36 | 21.29 | 5.43 | 7.33 |
| SC92 | 17 | 35300086 | 35300164 | 3% | 6% | 23% | 44% | 67% | 23% | 66% | 1.90 | 7.45 | 13.87 | 21.26 | 7.40 | 20.98 |
| SC93 | 15 | 89914568 | 89914681 | 3% | 4% | 9% | 15% | 70% | 26% | 25% | 1.31 | 2.63 | 4.57 | 20.96 | 7.72 | 7.48 |
| SC94 | 11 | 31827697 | 31827758 | 3% | 4% | 10% | 39% | 68% | 21% | 16% | 1.29 | 2.95 | 11.78 | 20.63 | 6.35 | 4.88 |
| SC95 | 2 | 239140132 | 239140170 | 3% | 5% | 19% | 21% | 57% | 11% | 26% | 1.73 | 6.70 | 7.55 | 20.48 | 4.03 | 9.37 |
| SC96 | 2 | 177001697 | 177001736 | 3% | 5% | 21% | 34% | 60% | 29% | 67% | 1.62 | 6.93 | 11.53 | 20.37 | 9.82 | 22.55 |
| SC97 | 2 | 175193478 | 175193572 | 3% | 5% | 7% | 18% | 59% | 25% | 32% | 1.64 | 2.40 | 6.03 | 20.11 | 8.41 | 10.89 |
| SC98 | 2 | 176931886 | 176931980 | 4% | 6% | 24% | 32% | 75% | 36% | 66% | 1.63 | 6.52 | 8.48 | 20.07 | 9.48 | 17.58 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC78 | 11 | KCNE3 | NM_005472 | - | 0 | 295 | 1 | 10008 | potassium voltage-gated channel, Isk-related family, member 3 |
| SC79 | 1 | DMRTA2 | NM_032110 | - | 1 | 3974 | 1 | 63950 | DMRT-like family A2 |
| SC80 | 3 | MAX.chr3.138659030-138659082 | - | - | 0 | - | 1 | - | - |
| SC81 | 6 | MAX.chr6.45631289-45631363 | - | - | 0 | - | 1 | - | - |
| SC82 | 6 | TFAP2A | NM_001042425 | - | 0 | -1656 | 1 | 7020 | transcription factor AP-2 alpha (activating enhancer binding protein 2 alpha) |
| SC83 | 11 | SLC6A5 | NM_004211 | + | 0 | 6382 | 0 | 9152 | solute carrier family 6 (neurotransmitter transporter, glycine), member 5 |
| SC84 | 9 | PAX5 | NM_016734 | - | 0 | 4040 | 0 | 5079 | paired box 5 |
| SC85 | 3 | MAX.chr3.138658429-138658507 | - | - | 0 | - | 1 | - | - |
| SC86 | 7 | NXPH1 | NM_152745 | + | 0 | 8863 | 1 | 30010 | neurexophilin 1 |
| SC87 | 7 | PTPRN2 | NM_130842;NM_002847;NM_1308 43 | - | 0 | 902462;902462;902462 | 1 | 5799 | protein tyrosine phosphatase, receptor type, N polypeptide 2 |
| SC88 | 1 | MAX.chr1.149672622-149672714 | - | - | 0 | - | 1 | - | - |
| SC89 | 9 | MAX.chr9.96588741-96588774 | - | - | 0 | - | 1 | - | - |
| SC90 | 6 | MAX.chr6.106429477-106429533 | - | - | 0 | - | 1 | - | - |
| SC91 | 9 | BARX1 | NM_021570 | - | 1 | 3383 | 1 | 56033 | BARX homeobox 1 |
| SC92 | 17 | LHX1 | NM_005568 | + | 1 | 5315 | 1 | 3975 | LIM homeobox 1 |
| SC93 | 15 | MAX.chr15.89914568-89914681 | - | - | 0 | - | 1 | - | - |
| SC94 | 11 | PAX6 | NM_000280;NM_001604;NM_0011 27612 | - | 0 | 5182;5182;11812 | 1 | 5080 | paired box 6 |
| SC95 | 2 | LOC151174 | NR_026926;NR_026925 | - | 1 | 186;186 | 1 | 151174 | hypothetical LOC151174 |
| SC96 | 2 | MAX.chr2.177001697-177001736 | - | - | 0 | - | 1 | - | - |
| SC97 | 2 | MAX.chr2.175193478-175193572 | - | - | 0 | - | 1 | - | - |
| SC98 | 2 | MAX.chr2.176931886-176931980 | - | - | 0 | - | 1 | - | - |

FIG. 4 (cont'd)

| Small Cell marker region ref. # | Chromosome | Start position | Stop position | mean BC.island | mean lung.normal, island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SG/BC | UND/BC |
|---|---|---|---|---|---|---|---|---|---|---|---|---|---|---|---|---|
| SC99 | 14 | 60852634 | 60952756 | 3% | 5% | 14% | 20% | 57% | 15% | 59% | 1.90 | 4.95 | 7.09 | 20.00 | 5.23 | 20.49 |
| SC100 | 11 | 14926627 | 14926716 | 1% | 1% | 5% | 16% | 62% | 16% | 11% | 1.78 | 10.57 | 30.66 | 119.53 | 31.77 | 21.41 |
| SC101 | 2 | 66666637 | 66666685 | 1% | 7% | 32% | 35% | 66% | 28% | 67% | 5.39 | 24.98 | 27.27 | 51.35 | 22.00 | 51.95 |
| SC102 | 1 | 6269157 | 6269209 | 1% | 7% | 26% | 22% | 61% | 23% | 61% | 5.21 | 19.42 | 15.89 | 45.08 | 17.31 | 44.99 |
| SC103 | 17 | 72353079 | 72353146 | 2% | 3% | 20% | 32% | 84% | 10% | 74% | 1.79 | 10.73 | 17.31 | 44.61 | 5.54 | 39.28 |
| SC104 |  | 39980533 | 39980614 | 2% | 6% | 18% | 13% | 68% | 13% | 77% | 3.63 | 10.23 | 7.34 | 39.03 | 7.64 | 44.50 |
| SC105 | 10 | 8097914 | 8097973 | 1% | 1% | 6% | 31% | 54% | 21% | 52% | 3.35 | 12.62 | 20.86 | 36.48 | 14.17 | 35.54 |
| SC106 | 17 | 27038627 | 27038718 | 1% | 1% | 4% | 4% | 23% | 6% | 12% | 1.91 | 8.68 | 5.96 | 35.81 | 9.42 | 17.97 |
| SC107 | 9 | 972186 | 972250 | 3% | 5% | 10% | 31% | 63% | 14% | 39% | 1.89 | 3.69 | 11.26 | 22.88 | 4.95 | 14.22 |
| SC108 | 8 | 76316557 | 76316616 | 2% | 4% | 16% | 17% | 42% | 19% | 48% | 1.88 | 8.48 | 8.63 | 22.16 | 9.85 | 25.03 |
| SC109 | 4 | 155663905 | 155663938 | 2% | 4% | 21% | 28% | 32% | 13% | 31% | 2.76 | 13.76 | 18.57 | 21.03 | 8.54 | 20.27 |
| SC110 | 17 | 27940477 | 27940568 | 0% | 1% | 5% | 9% | 59% | 22% | 25% | 3.44 | 21.98 | 34.20 | 238.86 | 87.69 | 99.96 |
| SC111 | 1 | 2165761 | 2165877 | 1% | 2% | 14% | 17% | 58% | 9% | 21% | 3.72 | 23.15 | 27.86 | 92.49 | 13.90 | 33.78 |
| SC112 | 10 | 94822422 | 94822464 | 1% | 8% | 11% | 30% | 63% | 19% | 54% | 5.15 | 7.55 | 20.17 | 42.86 | 13.14 | 37.12 |
| SC113 | 19 | 31842678 | 31842822 | 1% | 2% | 10% | 17% | 27% | 7% | 9% | 2.58 | 10.59 | 19.10 | 30.03 | 7.96 | 9.88 |
| SC114 | 12 | 54812201 | 54812346 | 1% | 3% | 14% | 15% | 28% | 8% | 13% | 2.51 | 13.59 | 13.91 | 26.63 | 7.20 | 12.05 |
| SC115 | 1 | 1110626702 | 1110626798 | 0% | 2% | 12% | 17% | 59% | 11% | 48% | 5.10 | 25.49 | 36.85 | 129.67 | 24.94 | 105.67 |
| SC116 | 14 | 65007294 | 65007341 | 0% | 0% | 0% | 3% | 31% | 3% | 45% | 0.68 | 0.87 | 8.06 | 84.42 | 7.09 | 121.70 |
| SC117 | 12 | 104609954 | 104610035 | 1% | 3% | 19% | 19% | 68% | 10% | 23% | 5.01 | 3.26 | 30.04 | 104.45 | 14.99 | 35.53 |
| SC118 | 22 | 97193509 | 97193639 | 0% | 1% | 14% | 7% | 16% | 13% | 16% | 2.04 | 26.57 | 14.00 | 30.21 | 23.54 | 29.84 |
| SC119 | 22 | 19754481 | 19754550 | 0% | 6% | 18% | 24% | 48% | 33% | 46% | 16.82 | 56.38 | 72.02 | 146.30 | 101.74 | 140.35 |
| SC120 | 7 | 121950506 | 121950608 | 1% | 1% | 8% | 11% | 44% | 15% | 35% | 0.98 | 5.54 | 7.95 | 30.55 | 10.22 | 24.53 |
| SC121 | 19 | 17791129 | 17791220 | 0% | 0% | 2% | 1% | 53% | 1% | 15% | 1.35 | 4.63 | 4.30 | 158.54 | 2.85 | 45.50 |
| SC122 | 22 | 28198280 | 28198349 | 0% | 1% | 4% | 3% | 22% | 3% | 16% | 2.42 | 11.11 | 8.66 | 64.31 | 7.42 | 45.69 |
| SC123 | 2 | 97193166 | 97193253 | 0% |  | 13% | 8% | 18% | 12% | 21% | 1.71 | 42.20 | 25.79 | 55.43 | 37.48 | 67.24 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC99 | 14 | C14orf39 | NM_174978 | - | 0 | 130 | 1 | 317761 | chromosome 14 open reading frame 39 |
| SC100 | 11 | MAX.chr11.14926627-14926716 | - | - | 0 | - | 1 | - | - |
| SC101 | 2 | MEIS1 | NM_002398 | + | 0 | 4106 | 0 | 4211 | Meis homeobox 1 |
| SC102 | 1 | RNF207 | NM_207396 | + | 0 | 2969 | 1 | 388591 | ring finger protein 207 |
| SC103 | 17 | BTBD17 | NM_001080466 | - | 1 | 4879 | 1 | 388419 | BTB (POZ) domain containing 17 |
| SC104 | 1 | BMP8A | NM_181809 | + | 0 | 23216 | 1 | 353500 | bone morphogenetic protein 8a |
| SC105 | 10 | FLJ45983 | NR_024255;NR_024256 | - | 1 | -2467;-2467 | 1 | 399717 | hypothetical LOC399717 |
| SC106 | 17 | PROCA1 | NM_152465 | - | 1 | 245 | 1 | 147011 | protein interacting with cyclin A1 |
| SC107 | 9 | DMRT3 | NM_021240 | + | 0 | -4777 | 1 | 58524 | doublesex and mab-3 related transcription factor 3 |
| SC108 | 8 | MAX.chr8.76316557-76316616 | - | - | 0 | - | 0 | - | - |
| SC109 | 4 | LRAT | NM_004744 | + | 0 | -1257 | 1 | 9227 | lecithin retinol acyltransferase (phosphatidylcholine--retinol O-acyltransferase) |
| SC110 | 17 | ANKRD13B | NM_152345 | + | 1 | 19951 | 1 | 124930 | ankyrin repeat domain 13B |
| SC111 | 1 | SKI | NM_003036 | + | 0 | 5628 | 0 | 6497 | v-ski sarcoma viral oncogene homolog (avian) |
| SC112 | 10 | CYP26C1 | NM_183374 | + | 0 | 1402 | 1 | 340665 | cytochrome P450, family 26, subfamily C, polypeptide 1 |
| SC113 | 19 | TSHZ3 | NM_020856 | - | 0 | -2488 | 1 | 57616 | teashirt zinc finger homeobox 3 |
| SC114 | 12 | ITGA5 | NM_002205 | - | 0 | 849 | 1 | 3678 | integrin, alpha 5 (fibronectin receptor, alpha polypeptide) |
| SC115 | 1 | MAX.chr1.110626702-110626798 | - | - | 0 | - | 1 | - | - |
| SC116 | 14 | HSPA2 | NM_021979 | + | 1 | 109 | 1 | 3306 | heat shock 70kDa protein 2 |
| SC117 | 12 | TXNRD1 | NM_001093771 | + | 0 | 396 | 1 | 7296 | thioredoxin reductase 1 |
| SC118 | 2 | MAX.chr2.97193509-97193639 | - | - | 0 | - | 0 | - | - |
| SC119 | 22 | TBX1 | NM_005992;NM_080647;NM_080646 | + | 1 | 10256;10256;10256 | 1 | 6899 | T-box 1 |
| SC120 | 7 | MAX.chr7.121950506-121950608 | - | - | 0 | - | 1 | - | - |
| SC121 | 19 | UNC13A | NM_001080421 | - | 0 | 7879 | 1 | 23025 | unc-13 homolog A (C. elegans) |
| SC122 | 22 | MN1 | NM_002430 | - | 0 | -794 | 1 | 4330 | meningioma (disrupted in balanced translocation) 1 |
| SC123 | 2 | MAX.chr2.97193166-97193253 | - | - | 0 | - | 1 | - | - |

FIG. 4 (cont'd)

| Small Cell marker region ref. # | Chromosome | Start position | Stop position | mean BC.island | mean lung.normal.island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC124 | 6 | 1620240 | 1620379 | 1% | 6% | 4% | 10% | 45% | 21% | 12% | 4.88 | 2.92 | 8.66 | 36.89 | 17.72 | 10.09 |
| SC125 | 6 | 27064644 | 27064775 | 1% | 3% | 11% | 11% | 38% | 6% | 23% | 2.23 | 7.75 | 7.75 | 25.78 | 4.29 | 15.70 |
| SC126 | 8 | 145013661 | 145013775 | 0% | 0% | 26% | 6% | 32% | 2% | 10% | 5.69 | 361.21 | 80.01 | 444.31 | 30.71 | 144.38 |
| SC127 | 14 | 101033514 | 101033620 | 0% | 2% | 18% | 7% | 40% | 5% | 14% | 4.29 | 36.37 | 14.15 | 82.74 | 10.45 | 29.35 |
| SC128 | 1 | 32237893 | 32237998 | 1% | 2% | 19% | 29% | 52% | 10% | 27% | 2.51 | 24.19 | 36.61 | 65.03 | 12.62 | 34.40 |
| SC129 | 17 | 58217191 | 58217358 | 1% | 1% | 6% | 9% | 30% | 1% | 20% | 1.26 | 5.55 | 8.49 | 27.20 | 1.31 | 18.28 |
| SC130 | 17 | 72350351 | 72350446 | 2% | 2% | 10% | 8% | 54% | 11% | 21% | 1.36 | 5.77 | 4.55 | 31.81 | 6.33 | 12.32 |
| SC131 | 19 | 46380017 | 46380063 | 1% | 2% | 7% | 13% | 43% | 8% | 20% | 2.99 | 8.59 | 17.60 | 57.01 | 10.67 | 26.25 |
| SC132 | 2 | 118982155 | 118982248 | 2% | 6% | 24% | 41% | 60% | 34% | 51% | 2.62 | 11.31 | 19.18 | 28.19 | 15.99 | 23.95 |
| SC133 | 2 | 85361426 | 85361486 | 2% | 3% | 6% | 9% | 42% | 15% | 22% | 1.26 | 3.07 | 4.62 | 20.61 | 7.25 | 10.58 |
| SC134 | 9 | 131007357 | 131007440 | 1% | 2% | 7% | 10% | 20% | 5% | 11% | 1.66 | 7.04 | 9.96 | 20.01 | 5.36 | 11.03 |
| SC135 | 9 | 35675856 | 35675991 | 1% | 1% | 9% | 10% | 23% | 7% | 23% | 1.38 | 11.08 | 12.62 | 28.05 | 8.69 | 28.17 |
| SC136 | 8 | 124173236 | 124173386 | 0% | 1% | 11% | 15% | 49% | 14% | 29% | 7.50 | 63.79 | 86.89 | 276.90 | 78.49 | 166.63 |
| SC137 | 8 | 108509567 | 108509637 | 1% | 1% | 14% | 3% | 62% | 7% | 58% | 1.01 | 15.24 | 3.44 | 67.53 | 8.05 | 63.61 |
| SC138 | 8 | 72754380 | 72754425 | 1% | 6% | 31% | 30% | 74% | 31% | 62% | 4.73 | 24.20 | 23.17 | 57.79 | 24.17 | 48.85 |
| SC139 | 9 | 123631470 | 123631561 | 0% | 1% | 0% | 2% | 37% | 2% | 6% | 1.90 | 1.41 | 6.49 | 124.61 | 6.16 | 20.92 |
| SC140 | 12 | 57618791 | 57618831 | 2% | 4% | 21% | 37% | 78% | 30% | 61% | 2.91 | 13.94 | 23.92 | 50.79 | 19.55 | 39.93 |
| SC141 | 19 | 17958807 | 17958893 | 0% | 3% | 10% | 10% | 22% | 9% | 14% | 42.72 | 161.42 | 159.54 | 345.13 | 136.09 | 214.13 |
| SC142 | 2 | 43451713 | 43451822 | 0% | 2% | 4% | 11% | 61% | 9% | 14% | 8.52 | 18.71 | 44.66 | 258.11 | 38.21 | 56.72 |
| SC143 | 12 | 1906517 | 1906559 | 0% | 1% | 0% | 6% | 27% | 1% | 7% | 7.16 | 3.35 | 49.38 | 217.21 | 10.98 | 54.50 |
| SC144 | 9 | 21965528 | 21965573 | 1% | 1% | 2% | 11% | 75% | 13% | 27% | 1.65 | 2.60 | 13.05 | 89.72 | 16.03 | 31.66 |
| SC145 | 10 | 94822484 | 94822576 | 1% | 5% | 8% | 22% | 58% | 16% | 31% | 4.97 | 7.48 | 20.48 | 53.91 | 15.39 | 29.40 |
| SC146 | 19 | 39993535 | 39993600 | 1% | 2% | 8% | 10% | 76% | 9% | 43% | 1.71 | 5.62 | 6.73 | 53.20 | 5.98 | 29.81 |
| SC147 | 6 | 163837552 | 163837584 | 1% | 1% | 1% | 1% | 37% | 1% | 2% | 0.73 | 0.85 | 1.06 | 47.13 | 0.91 | 2.76 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC124 | 6 | MAX.chr6.1620240-1620379 | . | - | 0 | . | 1 | - | . |
| SC125 | 6 | MAX.chr6.27064644-27064775 | . | - | 0 | . | 1 | - | plectin |
| SC126 | 8 | PLEC | NM_201381;NM_201383;NM_0004 45;NM_201378;NM_201380;NM_20 1384;NM_201382;NM_201379 | - | 1 | 5244;3031;37252;3403 6;11383;97;4449;14427 | 0 | 5339 | plectin |
| SC127 | 14 | BEGAIN | NM_001159531;NM_020836 | - | 0 | 893;2617 | 0 | 57596 | brain-enriched guanylate kinase-associated homolog (rat) |
| SC128 | 1 | MAX.chr1.32237893-32237998 | . | - | 0 | . | 1 | - | . |
| SC129 | 17 | MAX.chr17.58217191-58217358 | . | - | 0 | . | 1 | - | . |
| SC130 | 17 | KIF19 | NM_153209 | + | 1 | 28001 | 1 | 124602 | kinesin family member 19 |
| SC131 | 19 | MAX.chr19.46380017-46380063 | . | - | 0 | . | 1 | - | . |
| SC132 | 2 | MAX.chr2.118982155-118982248 | . | - | 0 | . | 1 | - | . |
| SC133 | 2 | TCF7L1 | NM_031283 | + | 0 | 844 | 1 | 83439 | transcription factor 7-like 1 (T-cell specific, HMG-box) |
| SC134 | 9 | DNM1 | NM_001005336;NM_004408 | + | 0 | 41695;41695 | 0 | 1759 | dynamin 1 |
| SC135 | 9 | CA9 | NM_001216 | + | 1 | 1942 | 1 | 768 | carbonic anhydrase IX |
| SC136 | 8 | MAX.chr8.124173236-124173386 | . | - | 0 | . | 1 | - | . |
| SC137 | 8 | ANGPT1 | NM_001146;NM_001199859 | - | 1 | 687;687 | 0 | 284 | angiopoietin 1 |
| SC138 | 8 | LOC100132891 | NR_033651;NR_033652 | + | 1 | -1970;-977 | 1 | 100132891 | hypothetical LOC100132891 |
| SC139 | 9 | PHF19 | NM_015651 | - | 1 | 8136 | 1 | 26147 | PHD finger protein 19 |
| SC140 | 12 | NXPH4 | NM_007224 | + | 1 | 8214 | 1 | 11247 | neurexophilin 4 |
| SC141 | 19 | JAK3 | NM_000215 | - | 1 | 34 | 1 | 3718 | Janus kinase 3 |
| SC142 | 2 | LOC100129726 | NR_027251 | + | 1 | -2636 | 1 | 100129726 | hypothetical LOC100129726 |
| SC143 | 12 | CACNA2D4 | NM_172364 | - | 0 | 121353 | 1 | 93589 | calcium channel, voltage-dependent, alpha 2/delta subunit 4 |
| SC144 | 9 | C9orf53 | NR_024274 | + | 0 | -1609 | 1 | 51198 | chromosome 9 open reading frame 53 |
| SC145 | 10 | CYP26C1 | NM_183374 | + | 1 | 1464 | 1 | 340665 | cytochrome P450, family 26, subfamily C, polypeptide 1 |
| SC146 | 19 | DLL3 | NM_016941;NM_203486 | + | 1 | 3979;3979 | 1 | 10683 | delta-like 3 (Drosophila) |
| SC147 | 6 | LOC100526820 | NR_037593 | - | 0 | -2570 | 0 | - | . |

FIG. 4 (cont'd)

| Small Cell marker region ref. # | Chromosome | Start position | Stop position | mean BC.island | mean lung.normal.island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC148 | 6 | 108440646 | 108440760 | 1% | 3% | 23% | 30% | 56% | 23% | 29% | 2.73 | 19.07 | 24.47 | 45.83 | 18.68 | 23.23 |
| SC149 | 3 | 184099224 | 184099335 | 1% | 4% | 18% | 10% | 59% | 26% | 24% | 2.97 | 13.39 | 7.63 | 43.10 | 19.14 | 17.55 |
| SC150 | 14 | 92980747 | 92980787 | 2% | 3% | 3% | 4% | 50% | 7% | 17% | 1.85 | 2.10 | 2.30 | 32.86 | 4.78 | 10.93 |
| SC151 | 3 | 128201932 | 128202122 | 1% | 7% | 21% | 18% | 60% | 22% | 40% | 4.99 | 15.77 | 13.22 | 44.94 | 16.26 | 29.75 |
| SC152 | 11 | 518925 | 518978 | 0% | 1% | 1% | 1% | 28% | 3% | 7% | 3.52 | 2.42 | 3.68 | 135.42 | 14.75 | 33.97 |
| SC153 | 10 | 102497213 | 102497267 | 2% | 4% | 11% | 23% | 33% | 19% | 21% | 2.47 | 6.79 | 14.51 | 20.88 | 12.23 | 13.18 |
| SC154 | 20 | 61560692 | 61560749 | 0% | 1% | 6% | 13% | 62% | 19% | 28% | 5.65 | 24.19 | 56.55 | 258.74 | 79.08 | 115.84 |
| SC155 | 12 | 1906566 | 1906598 | 0% | 2% | 1% | 7% | 32% | 1% | 8% | 8.47 | 4.68 | 33.66 | 163.92 | 7.51 | 38.65 |
| SC156 | 19 | 15695457 | 15695579 | 1% | 1% | 3% | 2% | 41% | 1% | 40% | 1.76 | 5.19 | 3.78 | 77.31 | 2.65 | 76.95 |
| SC157 | 1 | 17215983 | 17216025 | 1% | 2% | 3% | 13% | 34% | 11% | 17% | 1.88 | 3.55 | 15.12 | 38.96 | 12.50 | 19.16 |
| SC158 | 5 | 10565409 | 10565490 | 1% | 2% | 24% | 22% | 50% | 7% | 31% | 1.84 | 17.95 | 16.36 | 37.52 | 5.45 | 23.84 |
| SC159 | 17 | 72353261 | 72353424 | 2% | 4% | 13% | 24% | 58% | 9% | 59% | 2.30 | 7.21 | 13.50 | 32.83 | 5.34 | 33.27 |
| SC160 | 5 | 72732853 | 72732891 | 0% | 3% | 7% | 12% | 43% | 9% | 44% | 8.51 | 21.79 | 35.57 | 125.15 | 26.22 | 126.99 |
| SC161 | 17 | 37856733 | 37856801 | 2% | 1% | 2% | 1% | 67% | 2% | 17% | 0.76 | 1.07 | 0.73 | 41.58 | 0.98 | 10.58 |
| SC162 | 2 | 26407721 | 26407876 | 0% | 1% | 2% | 11% | 47% | 18% | 16% | 2.39 | 8.36 | 36.01 | 160.15 | 60.97 | 56.07 |
| SC163 | 19 | 13950008 | 13950055 | 1% | 0% | 6% | 4% | 40% | 7% | 21% | 0.28 | 8.91 | 6.93 | 63.59 | 10.57 | 33.61 |
| SC164 | 1 | 203236695 | 203236828 | 0% | 0% | 1% | 2% | 11% | 3% | 2% | 0.95 | 1.76 | 6.71 | 35.95 | 8.17 | 6.07 |
| SC165 | 16 | 70771681 | 70771770 | 1% | 3% | 17% | 18% | 53% | 17% | 28% | 4.46 | 24.22 | 25.13 | 76.49 | 23.80 | 39.51 |
| SC166 | 12 | 58021623 | 58021670 | 1% | 7% | 16% | 30% | 68% | 27% | 26% | 5.02 | 11.65 | 22.46 | 50.71 | 20.53 | 19.86 |
| SC167 | 16 | 54971076 | 54971118 | 2% | 5% | 7% | 19% | 62% | 27% | 27% | 2.10 | 2.81 | 7.63 | 25.26 | 10.87 | 11.18 |
| SC168 | 14 | 38724686 | 38724772 | 2% | 4% | 22% | 23% | 44% | 18% | 28% | 1.89 | 11.29 | 11.83 | 22.26 | 9.16 | 14.44 |
| SC169 | 17 | 72462912 | 72462993 | 2% | 8% | 31% | 36% | 50% | 18% | 23% | 3.54 | 12.93 | 15.09 | 20.99 | 7.48 | 9.78 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC148 | 6 | MAX.chr6.108440646-108440760 | , | , | 0 | , | 1 | , | , |
| SC149 | 3 | CHRD | NM_003741 | + | 0 | 1364 | 1 | 8646 | chordin |
| SC150 | 14 | RIN3 | NM_024832 | + | 0 | 623 | 1 | 79890 | Ras and Rab interactor 3 |
| SC151 | 3 | GATA2 | NM_001145662;NM_032638;NM_001145661 | - | 0 | 4832;10098;5441 | 0 | 2624 | GATA binding protein 2 |
| SC152 | 11 | MAX.chr11.518925-518978 | , | , | 0 | , | 1 | , | , |
| SC153 | 10 | MAX.chr10.102497213-102497267 | , | , | 0 | , | 1 | , | , |
| SC154 | 20 | DIDO1 | NM_033081;NM_001193369;NM_022105;NM_080797;NM_001193370;NM_080796 | - | 0 | 8612;-2789;8612;8612;-2789;-2789 | 1 | 11083 | death inducer-obliterator 1 |
| SC155 | 12 | CACNA2D4 | NM_172364 | - | 0 | 121304 | 1 | 93589 | calcium channel, voltage-dependent, alpha 2/delta subunit 4 |
| SC156 | 19 | MAX.chr19.15695457-15695579 | , | , | 0 | , | 1 | , | , |
| SC157 | 1 | MAX.chr1.17215983-17216025 | , | , | 0 | , | 1 | , | , |
| SC158 | 5 | ANKRD33B | NM_001164440 | + | 0 | 975 | 1 | 651746 | ankyrin repeat domain 33B |
| SC159 | 17 | BTBD17 | NM_001080466 | - | 1 | 4697 | 1 | 388419 | BTB (POZ) domain containing 17 |
| SC160 | 5 | MAX.chr5.72732853-72732891 | , | , | 0 | , | 1 | , | , |
| SC161 | 17 | ERBB2 | NM_001005862;NM_004448 | + | 0 | 12341;480 | 1 | 2064 | v-erb-b2 erythroblastic leukemia viral oncogene homolog 2, neuro/glioblastoma derived oncogene homolog (avian) |
| SC162 | 2 | FAM59B | NM_001191033;NM_001168241 | + | 1 | 4137;11762 | 1 | 150946 | family with sequence similarity 59, member B |
| SC163 | 19 | LOC284454 | NR_036515 | - | 0 | -2905 | 0 | 284454 | hypothetical LOC284454 |
| SC164 | 1 | MAX.chr1.203236695-203236828 | , | , | 0 | , | 0 | , | , |
| SC165 | 16 | VAC14 | NM_018052 | - | 0 | 63380 | 0 | 55697 | Vac14 homolog (S. cerevisiae) |
| SC166 | 12 | B4GALNT1 | NM_001478 | , | 1 | 5362 | 1 | 2583 | beta-1,4-N-acetyl-galactosaminyl transferase 1 |
| SC167 | 16 | MAX.chr16.54971076-54971118 | , | , | 0 | , | 1 | , | , |
| SC168 | 14 | CLEC14A | NM_175060 | , | 1 | 888 | 1 | 161198 | C-type lectin domain family 14, member A |
| SC169 | 17 | CD300A | NM_007261 | + | 0 | 391 | 0 | 11314 | CD300a molecule |

FIG. 4 (cont'd)

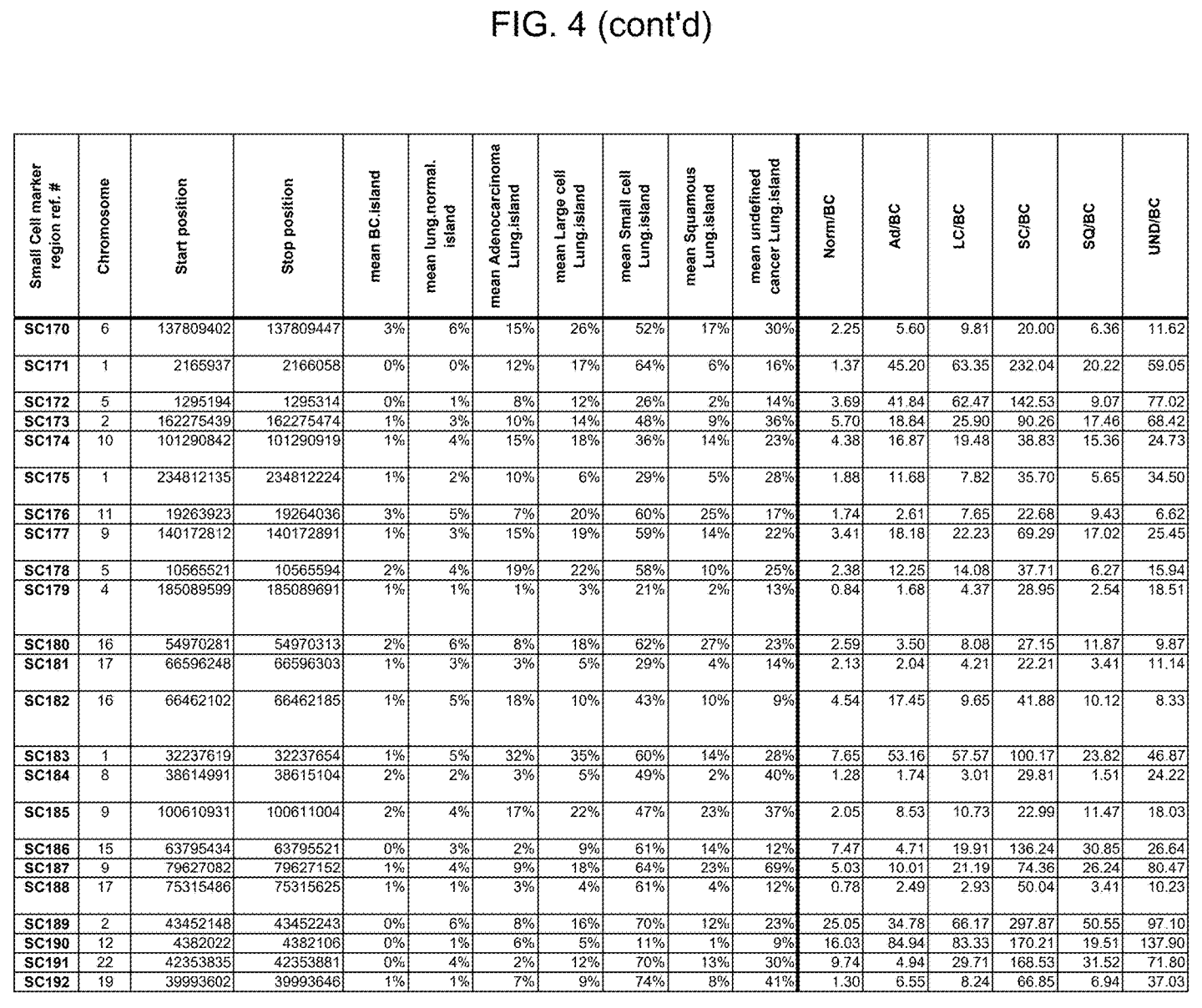

| Small Cell marker region ref. # | Chromosome | Start position | Stop position | mean BC island | mean lung.normal. island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC170 | 6 | 137809402 | 137809447 | 3% | 6% | 15% | 26% | 52% | 17% | 30% | 2.25 | 5.60 | 9.81 | 20.00 | 6.36 | 11.62 |
| SC171 | 1 | 2165937 | 2166058 | 0% | 0% | 12% | 17% | 64% | 6% | 16% | 1.37 | 45.20 | 63.35 | 232.04 | 20.22 | 59.05 |
| SC172 | 5 | 1295194 | 1295314 | 0% | 1% | 8% | 12% | 26% | 2% | 14% | 3.69 | 41.84 | 62.47 | 142.53 | 9.07 | 77.02 |
| SC173 | 2 | 162275439 | 162275474 | 1% | 3% | 10% | 14% | 48% | 9% | 36% | 5.70 | 18.84 | 25.90 | 90.26 | 17.46 | 68.42 |
| SC174 | 10 | 101290842 | 101290919 | 1% | 4% | 15% | 18% | 36% | 14% | 23% | 4.38 | 16.87 | 19.48 | 38.83 | 15.36 | 24.73 |
| SC175 | 1 | 234812135 | 234812224 | 1% | 2% | 10% | 6% | 29% | 5% | 28% | 1.88 | 11.68 | 7.82 | 35.70 | 5.65 | 34.50 |
| SC176 | 11 | 19263923 | 19264036 | 3% | 5% | 7% | 20% | 60% | 25% | 17% | 1.74 | 2.61 | 7.65 | 22.68 | 9.43 | 6.62 |
| SC177 | 9 | 140172812 | 140172891 | 1% | 3% | 15% | 19% | 59% | 14% | 22% | 3.41 | 18.18 | 22.23 | 69.29 | 17.02 | 25.45 |
| SC178 | 5 | 10565521 | 10565594 | 2% | 4% | 19% | 22% | 58% | 10% | 25% | 2.38 | 12.25 | 14.08 | 37.71 | 6.27 | 15.94 |
| SC179 | 4 | 185089599 | 185089691 | 1% | 1% | 1% | 3% | 21% | 2% | 13% | 0.84 | 1.68 | 4.37 | 28.95 | 2.54 | 18.51 |
| SC180 | 16 | 54970281 | 54970313 | 2% | 6% | 8% | 18% | 62% | 27% | 23% | 2.59 | 3.50 | 8.08 | 27.15 | 11.87 | 9.87 |
| SC181 | 17 | 66596248 | 66596303 | 1% | 3% | 3% | 5% | 29% | 4% | 14% | 2.13 | 2.04 | 4.21 | 22.21 | 3.41 | 11.14 |
| SC182 | 16 | 66462102 | 66462185 | 1% | 5% | 18% | 10% | 43% | 10% | 9% | 4.54 | 17.45 | 9.65 | 41.88 | 10.12 | 8.33 |
| SC183 | 1 | 32237619 | 32237654 | 1% | 5% | 32% | 35% | 60% | 14% | 28% | 7.65 | 53.16 | 57.57 | 100.17 | 23.82 | 46.87 |
| SC184 | 8 | 38614991 | 38615104 | 2% | 2% | 3% | 5% | 49% | 2% | 40% | 1.28 | 1.74 | 3.01 | 29.81 | 1.51 | 24.22 |
| SC185 | 9 | 100610931 | 100611004 | 2% | 4% | 17% | 22% | 47% | 23% | 37% | 2.05 | 8.53 | 10.73 | 22.99 | 11.47 | 18.03 |
| SC186 | 15 | 63795434 | 63795521 | 0% | 3% | 2% | 9% | 61% | 14% | 12% | 7.47 | 4.71 | 19.91 | 136.24 | 30.85 | 26.64 |
| SC187 | 9 | 79277082 | 79277152 | 1% | 4% | 9% | 18% | 64% | 23% | 69% | 5.03 | 10.01 | 21.19 | 74.36 | 26.24 | 80.47 |
| SC188 | 17 | 75315486 | 75315625 | 1% | 1% | 3% | 4% | 61% | 4% | 12% | 0.78 | 2.49 | 2.93 | 50.04 | 3.41 | 10.23 |
| SC189 | 2 | 43452148 | 43452243 | 0% | 6% | 8% | 16% | 70% | 12% | 23% | 25.05 | 34.78 | 66.17 | 297.87 | 50.55 | 97.10 |
| SC190 | 12 | 4382022 | 4382106 | 0% | 1% | 6% | 5% | 11% | 1% | 9% | 16.03 | 84.94 | 83.33 | 170.21 | 19.51 | 137.90 |
| SC191 | 22 | 42353835 | 42353881 | 0% | 4% | 2% | 12% | 70% | 13% | 30% | 9.74 | 4.94 | 29.71 | 168.53 | 31.52 | 71.80 |
| SC192 | 19 | 39993602 | 39993646 | 1% | 1% | 7% | 9% | 74% | 8% | 41% | 1.30 | 6.55 | 8.24 | 66.85 | 6.94 | 37.03 |

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC170 | 6 | MAX.chr6.137809402-137809447 | - | - | 0 | - | 1 | - | - |
| SC171 | 1 | SKI | NM_003036 | + | 0 | 5804 | 0 | 6497 | v-ski sarcoma viral oncogene homolog (avian) |
| SC172 | 5 | TERT | NM_001193376;NM_198253 | - | 0 | -32;-32 | 1 | 7015 | telomerase reverse transcriptase |
| SC173 | 2 | TBR1 | NM_006593 | + | 1 | 2820 | 1 | 10716 | T-box, brain, 1 |
| SC174 | 10 | NKX2-3 | NM_145285 | + | 0 | -1847 | 1 | 159296 | NK2 transcription factor related, locus 3 (Drosophila) |
| SC175 | 1 | MAX.chr1.234812135-234812224 | - | - | 0 | - | 0 | - | - |
| SC176 | 11 | E2F8 | NM_024680 | - | 0 | -1416 | 1 | 79733 | E2F transcription factor 8 |
| SC177 | 9 | C9orf167 | NM_017723 | + | 0 | 533 | 1 | 54863 | chromosome 9 open reading frame 167 |
| SC178 | 5 | ANKRD33B | NM_001164440 | + | 0 | 1087 | 1 | 651746 | ankyrin repeat domain 33B |
| SC179 | 4 | ENPP6 | NM_153343 | - | 0 | 49515 | 0 | 133121 | ectonucleotide pyrophosphatase/phosphodiesterase 6 |
| SC180 | 16 | MAX.chr16.54970281-54970313 | - | - | 0 | - | 0 | - | - |
| SC181 | 17 | FAM20A | NM_017565 | - | 0 | 847 | 1 | 54757 | family with sequence similarity 20, member A |
| SC182 | 16 | BEAN1 | NM_001178020;NM_001197225;NM_001136106;NM_001197224 | + | 0 | 1287;-1287;1287;1287 | 1 | 146227 | brain expressed, associated with NEDD4, 1 |
| SC183 | 1 | MAX.chr1.322376919-322237654 | - | - | 0 | - | 0 | - | - |
| SC184 | 8 | TACC1 | NM_001146216 | + | 0 | 29288 | 1 | 6867 | transforming, acidic coiled-coil containing protein 1 |
| SC185 | 9 | FOXE1 | NM_004473 | + | 0 | -4605 | 1 | 2304 | forkhead box E1 (thyroid transcription factor 2) |
| SC186 | 15 | USP3 | NM_006537 | + | 0 | -1375 | 0 | 9960 | ubiquitin specific peptidase 3 |
| SC187 | 9 | MAX.chr9.79627082-79627152 | - | - | 0 | - | 0 | - | - |
| SC188 | 17 | 9-Sep | NM_006640;NM_001113492;NM_001113491 | + | 0 | -110;31514,37995 | 0 | 10801 | septin 9 |
| SC189 | 2 | LOC100129726 | NR_027251 | + | 1 | -2201 | 1 | 100129726 | hypothetical LOC100129726 |
| SC190 | 12 | CCND2 | NM_001759 | + | 0 | -879 | 1 | 894 | cyclin D2 |
| SC191 | 22 | LOC339674 | NR_024355 | + | 1 | 5645 | 1 | 339674 | hypothetical LOC339674 |
| SC192 | 19 | DLL3 | NM_016941;NM_203486 | + | 1 | 4046;4046 | 1 | 10683 | delta-like 3 (Drosophila) |

FIG. 4 (cont'd)

| Small Cell marker region ref. # | Chromosome | Start position | Stop position | mean BC,island | mean lung,normal, island | mean Adenocarcinoma Lung,island | mean Large cell Lung,island | mean Small cell Lung,island | mean Squamous Lung,island | mean undefined cancer Lung,island | Norm/BC | Ad/BC | LC/BC | SC/BC | SQ/BC | UND/BC |
|---|---|---|---|---|---|---|---|---|---|---|---|---|---|---|---|---|
| SC193 | 5 | 10333588 | 10333742 | 1% | 1% | 4% | 6% | 38% | 5% | 25% | 1.25 | 5.09 | 8.20 | 51.82 | 6.55 | 34.37 |
| SC194 | 14 | 24808727 | 24808770 | 1% | 4% | 3% | 11% | 32% | 7% | 8% | 5.37 | 4.89 | 16.21 | 46.37 | 10.19 | 11.60 |
| SC195 | 1 | 32237695 | 32237880 | 1% | 3% | 22% | 25% | 44% | 10% | 14% | 2.78 | 22.43 | 25.97 | 45.37 | 10.13 | 14.59 |
| SC196 | 14 | 95234712 | 95234849 | 2% | 4% | 8% | 18% | 43% | 8% | 27% | 2.56 | 5.27 | 11.66 | 27.79 | 5.40 | 17.45 |
| SC197 | 19 | 14667596 | 14667671 | 0% | 1% | 1% | 1% | 24% | 5% | 5% | 1.51 | 2.28 | 3.41 | 60.37 | 13.55 | 13.44 |
| SC198 | 15 | 28352738 | 28352817 | 1% | 5% | 12% | 21% | 58% | 11% | 21% | 3.25 | 8.34 | 14.55 | 40.37 | 7.29 | 14.34 |
| SC199 | 16 | 10480178 | 10480238 | 0% | 1% | 2% | 4% | 19% | 3% | 28% | 6.60 | 11.96 | 26.48 | 116.02 | 15.18 | 166.59 |
| SC200 | 22 | 19742789 | 19742857 | 2% | 5% | 10% | 14% | 47% | 17% | 13% | 2.51 | 5.00 | 7.01 | 24.29 | 8.86 | 6.63 |
| SC201 | 5 | 42995328 | 42995393 | 0% | 4% | 12% | 28% | 50% | 30% | 55% | 24.55 | 77.50 | 185.42 | 325.38 | 198.95 | 362.13 |
| SC202 | 5 | 42993267 | 42993312 | 0% | 6% | 15% | 22% | 45% | 18% | 55% | 20.06 | 48.10 | 71.60 | 147.07 | 59.74 | 178.70 |
| SC203 | 12 | 58021483 | 58021536 | 1% | 8% | 12% | 26% | 69% | 17% | 29% | 11.91 | 18.78 | 39.87 | 106.60 | 27.11 | 44.27 |
| SC204 | 12 | 25055873 | 25055997 | 0% | 1% | 10% | 22% | 29% | 12% | 40% | 4.32 | 36.00 | 77.51 | 103.02 | 44.17 | 140.87 |
| SC205 | 2 | 43451937 | 43452012 | 1% | 4% | 5% | 8% | 57% | 9% | 13% | 5.93 | 7.65 | 11.58 | 84.17 | 13.31 | 19.60 |
| SC206 | 6 | 1620122 | 1620172 | 1% | 7% | 6% | 15% | 72% | 41% | 31% | 5.87 | 5.36 | 12.51 | 60.18 | 34.60 | 25.88 |
| SC207 | 9 | 37037883 | 37037949 | 1% | 6% | 17% | 14% | 66% | 5% | 56% | 3.77 | 11.52 | 9.77 | 44.81 | 3.27 | 38.35 |
| SC208 | 5 | 10333749 | 10333885 | 1% | 1% | 2% | 6% | 43% | 6% | 23% | 1.04 | 1.70 | 5.02 | 36.10 | 5.17 | 18.80 |
| SC209 | 8 | 55367295 | 55367420 | 1% | 3% | 10% | 21% | 39% | 10% | 42% | 3.21 | 9.56 | 19.77 | 35.89 | 9.58 | 38.62 |
| SC210 | 2 | 100721771 | 100721847 | 1% | 1% | 4% | 6% | 26% | 1% | 5% | 1.18 | 4.71 | 7.92 | 33.23 | 1.92 | 6.91 |
| SC211 | 13 | 533313456 | 533313530 | 1% | 5% | 16% | 24% | 46% | 9% | 47% | 3.27 | 10.97 | 16.69 | 31.99 | 6.61 | 32.97 |
| SC212 | 2 | 95401460 | 95401490 | 2% | 5% | 25% | 30% | 53% | 30% | 59% | 3.06 | 14.07 | 17.04 | 30.20 | 16.81 | 33.42 |
| SC213 | 2 | 177017228 | 177017277 | 2% | 5% | 21% | 16% | 46% | 26% | 16% | 3.06 | 12.85 | 10.12 | 28.49 | 16.05 | 9.69 |
| SC214 | 5 | 10333423 | 10333478 | 2% | 6% | 11% | 25% | 48% | 15% | 30% | 2.97 | 5.20 | 11.92 | 22.61 | 7.11 | 14.28 |
| SC215 | 9 | 139024776 | 139024933 | 2% | 4% | 12% | 15% | 48% | 5% | 32% | 1.71 | 5.77 | 6.96 | 22.15 | 2.28 | 14.73 |
| SC216 | 15 | 68125482 | 68125550 | 1% | 4% | 15% | 20% | 52% | 17% | 26% | 3.44 | 13.77 | 18.50 | 47.09 | 15.83 | 23.80 |
| SC217 | 17 | 72352858 | 72352916 | 2% | 4% | 9% | 14% | 52% | 7% | 42% | 1.79 | 4.18 | 6.40 | 23.41 | 3.14 | 18.93 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC193 | 5 | MAX.chr5.10333588-10333742 | - | - | 0 | - | 1 | - | - |
| SC194 | 14 | ADCY4 | NM_139247;NM_001198592;NM_001198568 | - | 1 | -4450;-4450;-4450 | 1 | 196883 | adenylate cyclase 4 |
| SC195 | 1 | MAX.chr1.32237695-32237880 | - | - | 0 | - | 0 | - | - |
| SC196 | 14 | GSC | NM_173849 | - | 0 | 1787 | 1 | 145258 | goosecoid homeobox |
| SC197 | 19 | TECR | NM_138501 | + | 0 | 27215 | 0 | 9524 | trans-2,3-enoyl-CoA reductase |
| SC198 | 15 | MAX.chr15.28352738-28352817 | - | - | 0 | - | 1 | - | - |
| SC199 | 16 | MAX.chr16.10480178-10480238 | - | - | 0 | - | 1 | - | - |
| SC200 | 22 | TBX1 | NM_005992;NM_080647;NM_080646 | + | 0 | -1436;-1436;-1436 | 0 | 6899 | T-box 1 |
| SC201 | 5 | MAX.chr5.42995328-42995393 | - | - | 0 | - | 1 | - | - |
| SC202 | 5 | MAX.chr5.42993267-42993312 | - | - | 0 | - | 0 | - | - |
| SC203 | 12 | B4GALNT1 | NM_001478 | - | 1 | 5502 | 1 | 2583 | beta-1,4-N-acetyl-galactosaminyl transferase 1 |
| SC204 | 12 | BCAT1 | NM_001178092;NM_005504;NM_011178094;NM_001178091;NM_001178093 | - | 0 | 46520;46520;-551;46520;136 | 1 | 586 | branched chain amino-acid transaminase 1, cytosolic |
| SC205 | 2 | LOC100129726 | NR_027251 | + | 1 | -2412 | 1 | 100129726 | hypothetical LOC100129726 |
| SC206 | 6 | MAX.chr6.1620122-1620172 | - | - | 0 | - | 1 | - | - |
| SC207 | 9 | PAX5 | NM_016734 | - | 0 | -3407 | 1 | 5079 | paired box 5 |
| SC208 | 5 | MAX.chr5.10333749-10333885 | - | - | 0 | - | 1 | - | - |
| SC209 | 8 | SOX17 | NM_022454 | + | 0 | -3199 | 1 | 64321 | SRY (sex determining region Y)-box 17 |
| SC210 | 2 | AFF3 | NM_002285;NM_001025108 | - | 0 | 37266;274 | 0 | 3899 | AF4/FMR2 family, member 3 |
| SC211 | 13 | LECT1 | NM_007015;NM_001011705 | - | 0 | 491;491 | 1 | 11061 | leukocyte cell derived chemotaxin 1 |
| SC212 | 2 | MAX.chr2.95401460-95401490 | - | - | 0 | - | 1 | - | - |
| SC213 | 2 | HOXD4 | NM_014621 | + | 0 | 1116 | 0 | 3233 | homeobox D4 |
| SC214 | 5 | MAX.chr5.10333423-10333478 | - | - | 0 | - | 1 | - | - |
| SC215 | 9 | MAX.chr9.139024776-139024933 | - | - | 0 | - | 1 | - | - |
| SC216 | 15 | SKOR1 | NM_001031807 | + | 0 | 7542 | 0 | 390598 | SKI family transcriptional corepressor 1 |
| SC217 | 17 | BTBD17 | NM_001080466 | - | 1 | 5100 | 1 | 388419 | BTB (POZ) domain containing 17 |

FIG. 4 (cont'd)

| Small Cell marker region ref. # | Chromosome | Start position | Stop position | mean BC.island | mean lung.normal. island | mean Adenocarcinoma Lung.island | mean Large cell Lung.island | mean Small cell Lung.island | mean Squamous Lung.island | mean undefined Lung cancer island | Norm/BC | Ad/BC | LC/BC | SC/BC | SQ/BC | UND/BC |
|---|---|---|---|---|---|---|---|---|---|---|---|---|---|---|---|---|
| SC218 | 6 | 2903614 | 2903705 | 0% | 1% | 2% | 13% | 21% | 2% | 1% | 1.58 | 3.90 | 28.42 | 45.90 | 4.89 | 1.60 |
| SC219 | 1 | 108506611 | 108506701 | 0% | 1% | 8% | 10% | 21% | 4% | 19% | 6.54 | 35.25 | 44.05 | 91.51 | 18.41 | 82.35 |
| SC220 | 10 | 124910491 | 124910540 | 2% | 4% | 9% | 32% | 57% | 15% | 24% | 2.62 | 5.68 | 19.94 | 35.80 | 9.12 | 15.29 |
| SC221 | 5 | 100240192 | 100240273 | 0% | 5% | 8% | 11% | 63% | 13% | 10% | 41.36 | 62.03 | 86.85 | 479.51 | 95.95 | 77.29 |
| SC222 | 14 | 60976754 | 60976830 | 3% | 6% | 31% | 26% | 64% | 28% | 64% | 2.07 | 10.76 | 9.12 | 22.28 | 9.82 | 22.57 |
| SC223 | 1 | 221052041 | 221052157 | 1% | 5% | 11% | 27% | 39% | 5% | 29% | 7.04 | 15.55 | 37.83 | 54.48 | 7.03 | 40.64 |
| SC224 | 12 | 250556634 | 250555804 | 1% | 3% | 14% | 27% | 30% | 17% | 50% | 5.65 | 23.18 | 44.87 | 51.11 | 28.60 | 83.14 |
| SC225 | 12 | 4140345 | 4140422 | 0% | 1% | 2% | 3% | 11% | 1% | 4% | 2.43 | 6.24 | 9.50 | 39.21 | 4.13 | 15.23 |
| SC226 | 1 | 47698051 | 47698082 | 1% | 4% | 24% | 18% | 51% | 16% | 48% | 4.25 | 22.37 | 17.39 | 47.95 | 15.43 | 45.65 |
| SC227 | 2 | 30453799 | 30453967 | 0% | 2% | 15% | 17% | 21% | 7% | 22% | 7.67 | 47.98 | 55.02 | 69.82 | 24.31 | 72.43 |
| SC228 | 2 | 26408004 | 26408041 | 1% | 2% | 3% | 9% | 44% | 15% | 17% | 3.91 | 5.50 | 18.17 | 87.75 | 29.51 | 34.54 |
| SC229 | 4 | 88593253 | 88593363 | 0% | 1% | 4% | 14% | 14% | 7% | 18% | 3.88 | 9.54 | 36.29 | 35.88 | 18.16 | 46.41 |
| SC230 | 10 | 52177880 | 52177955 | 0% | 0% | 1% | 1% | 35% | 7% | 7% | 0.41 | 1.18 | 2.25 | 71.20 | 13.46 | 14.52 |
| SC231 | 8 | 999960542 | 999960654 | 1% | 3% | 10% | 20% | 44% | 29% | 24% | 2.42 | 9.58 | 18.79 | 40.90 | 26.85 | 22.50 |
| SC232 | 12 | 250556183 | 250562246 | 1% | 5% | 19% | 37% | 54% | 29% | 64% | 4.03 | 13.60 | 27.03 | 39.72 | 21.36 | 47.09 |
| SC233 | 14 | 85996211 | 85996331 | 1% | 2% | 6% | 5% | 46% | 6% | 37% | 1.50 | 4.65 | 3.78 | 34.78 | 4.76 | 28.13 |
| SC234 | 14 | 78108294 | 78108420 | 1% | 3% | 2% | 13% | 42% | 6% | 25% | 1.94 | 1.38 | 8.93 | 29.33 | 4.53 | 17.37 |
| SC235 | 6 | 26273748 | 26273836 | 2% | 3% | 4% | 28% | 39% | 9% | 34% | 1.84 | 2.40 | 17.99 | 25.11 | 5.70 | 22.17 |
| SC236 | 17 | 72209156 | 72209196 | 0% | 1% | 1% | 3% | 27% | 1% | 9% | 2.15 | 1.82 | 7.56 | 73.90 | 3.66 | 25.72 |
| SC237 | 6 | 137809670 | 137809791 | 2% | 4% | 11% | 18% | 44% | 10% | 18% | 1.83 | 5.96 | 9.48 | 22.78 | 5.22 | 9.41 |
| SC238 | 6 | 28175437 | 28175586 | 1% | 2% | 7% | 16% | 23% | 6% | 14% | 3.23 | 9.57 | 21.74 | 31.93 | 8.81 | 19.25 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC218 | 6 | SERPINB9 | NM_004155 | - | 0 | -69 | 1 | 5272 | serpin peptidase inhibitor, clade B (ovalbumin), member 9 |
| SC219 | 1 | VAV3 | NM_006113 | - | 0 | 934 | 0 | 10451 | vav 3 guanine nucleotide exchange factor |
| SC220 | 10 | BUB3 | NM_001007793;NM_004725 | + | 0 | -3268;-3268 | 1 | 9184 | budding uninhibited by benzimidazoles 3 homolog (yeast) |
| SC221 | 5 | ST8SIA4 | NM_005668;NM_175052 | - | 0 | -1205;-1222 | 0 | 7903 | ST8 alpha-N-acetyl-neuraminide alpha-2,8-sialyltransferase 4 |
| SC222 | 14 | SIX6 | NM_007374 | + | 0 | 817 | 1 | 4990 | SIX homeobox 6 |
| SC223 | 1 | HLX | NM_021958 | + | 0 | -701 | 1 | 3142 | H2.0-like homeobox |
| SC224 | 12 | BCAT1 | NM_001178092;NM_005504;NM_0 011780094;NM_001178091;NM_001 178093 | - | 0 | 46759;46759;-312;46759;375 | 1 | 586 | branched chain amino-acid transaminase 1, cytosolic |
| SC225 | 12 | MAX.chr12.4140345-4140422 | - | - | 0 | - | 0 | - | - |
| SC226 | 1 | TAL1 | NM_003189 | - | 0 | -2608 | 1 | 6886 | T-cell acute lymphocytic leukemia 1 |
| SC227 | 2 | LBH | NM_030915 | + | 0 | -597 | 1 | 81606 | limb bud and heart development homolog (mouse) |
| SC228 | 2 | FAM59B | NM_001191033;NM_001168241 | + | 1 | 4420;12045 | 1 | 150946 | family with sequence similarity 59, member B |
| SC229 | 4 | MAX.chr4.8859253-8859363 | - | - | 0 | - | 1 | - | - |
| SC230 | 10 | SGMS1 | NM_147156 | - | 0 | 205857 | 1 | 259230 | sphingomyelin synthase 1 |
| SC231 | 8 | OSR2 | NM_001142462;NM_053001 | + | 0 | 3912;3912 | 1 | 116039 | odd-skipped related 2 (Drosophila) |
| SC232 | 12 | BCAT1 | NM_001178092;NM_005504;NM_0 011780094;NM_001178091;NM_001 178093 | - | 0 | 46210;46210;-861;46210;-174 | 1 | 586 | branched chain amino-acid transaminase 1, cytosolic |
| SC233 | 14 | FLRT2 | NM_013231 | + | 0 | -276 | 0 | 23768 | fibronectin leucine rich transmembrane protein 2 |
| SC234 | 14 | MAX.chr14.78108294-78108420 | - | - | 0 | - | 1 | - | - |
| SC235 | 6 | HIST1H3G | NM_003534 | - | 0 | -2136 | 0 | 8355 | histone cluster 1, H3g |
| SC236 | 17 | MGC16275 | NR_026914 | - | 1 | 304 | 0 | 85001 | hypothetical protein MGC16275 |
| SC237 | 6 | MAX.chr6.137809670-137809791 | - | - | 0 | - | 1 | - | - |
| SC238 | 6 | MAX.chr6.28175437-28175586 | - | - | 0 | - | 1 | - | - |

FIG. 4 (cont'd)

| Small Cell marker region ref. # | Chromosome | Start position | Stop position | mean BC.island | mean lung.normal, island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SC239 | 4 | 175135937 | 175135997 | 2% | 4% | 5% | 22% | 35% | 7% | 37% | 2.24 | 3.27 | 13.71 | 22.01 | 4.52 | 23.04 |
| SC240 | 9 | 94444034 | 94444124 | 2% | 7% | 6% | 17% | 44% | 14% | 48% | 3.20 | 2.74 | 8.49 | 21.68 | 6.85 | 23.33 |
| SC241 | 11 | 19263815 | 19263912 | 2% | 4% | 5% | 16% | 54% | 17% | 13% | 2.43 | 2.71 | 9.32 | 31.54 | 10.14 | 7.44 |
| SC242 | 22 | 31481121 | 31481159 | 0% | 1% | 5% | 9% | 59% | 6% | 28% | 2.63 | 15.70 | 26.55 | 170.11 | 15.93 | 81.64 |
| SC243 | 6 | 27059752 | 27059869 | 0% | 2% | 4% | 4% | 38% | 3% | 40% | 4.64 | 10.35 | 10.26 | 104.70 | 8.90 | 110.25 |
| SC244 | 7 | 22539866 | 22539943 | 1% | 1% | 3% | 3% | 13% | 5% | 10% | 1.05 | 4.46 | 5.80 | 20.78 | 8.83 | 16.46 |
| SC245 | 11 | 518684 | 518729 | 0% | 0% | 0% | 0% | 24% | 6% | 3% | 1.94 | 2.51 | 2.30 | 138.27 | 36.98 | 15.71 |
| SC246 | 22 | 31481428 | 31481510 | 1% | 2% | 12% | 10% | 50% | 6% | 18% | 1.46 | 8.29 | 6.87 | 34.17 | 4.41 | 12.41 |
| SC247 | 17 | 48636503 | 48636608 | 1% | 2% | 3% | 5% | 21% | 5% | 6% | 2.71 | 3.51 | 6.21 | 24.43 | 5.92 | 7.43 |
| SC248 | 10 | 26727989 | 26728120 | 0% | 2% | 4% | 6% | 19% | 2% | 24% | 11.37 | 28.27 | 43.79 | 139.11 | 15.00 | 180.22 |
| SC249 | 7 | 2558594 | 2558664 | 1% | 1% | 6% | 5% | 47% | 3% | 16% | 1.38 | 5.78 | 5.37 | 45.60 | 2.76 | 15.89 |
| SC250 | 9 | 94444127 | 94444240 | 1% | 3% | 3% | 14% | 48% | 12% | 44% | 2.41 | 2.74 | 12.60 | 43.62 | 10.94 | 39.33 |
| SC251 | 17 | 37321144 | 37321212 | 0% | 1% | 2% | 3% | 16% | 6% | 4% | 1.92 | 6.27 | 9.79 | 58.67 | 21.36 | 16.09 |
| SC252 | 7 | 155302555 | 155302648 | 1% | 2% | 13% | 16% | 29% | 11% | 40% | 2.09 | 12.76 | 16.09 | 29.56 | 10.56 | 39.78 |
| SC253 | 1 | 156863477 | 156863554 | 1% | 3% | 24% | 19% | 32% | 14% | 13% | 2.42 | 20.38 | 15.89 | 26.82 | 11.70 | 10.87 |
| SC254 | 1 | 402368941 | 402370022 | 3% | 5% | 30% | 35% | 74% | 22% | 77% | 1.58 | 9.71 | 11.35 | 24.36 | 7.07 | 25.14 |
| SC255 | 2 | 200328930 | 200328964 | 2% | 6% | 13% | 20% | 42% | 14% | 45% | 2.95 | 6.68 | 10.18 | 21.87 | 7.45 | 23.16 |
| SC256 | 16 | 4422078 | 4422139 | 0% | 0% | 0% | 0% | 49% | 1% | 17% | 2.62 | 1.65 | 2.25 | 369.94 | 8.01 | 131.13 |
| SC257 | 19 | 139950379 | 139950468 | 1% | 3% | 9% | 4% | 37% | 9% | 16% | 2.62 | 9.53 | 4.40 | 37.32 | 8.87 | 16.23 |
| SC258 | 1 | 324410360 | 324410416 | 1% | 0% | 1% | 2% | 26% | 8% | 25% | 0.49 | 2.33 | 3.19 | 48.05 | 14.55 | 45.91 |
| SC259 | 17 | 58499109 | 58499183 | 0% | 1% | 1% | 5% | 35% | 18% | 8% | 4.22 | 4.26 | 17.93 | 124.48 | 63.79 | 28.58 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC239 | 4 | MAX.chr4.175135937-175135997 | - | - | 0 | - | 0 | - | - |
| SC240 | 9 | MAX.chr9.94444034-94444124 | - | - | 0 | - | 0 | - | - |
| SC241 | 11 | E2F8 | NM_024680 | - | 0 | -1308 | 1 | 79733 | E2F transcription factor 8 |
| SC242 | 22 | SMTN | NM_134269;NM_006932;NM_1342 70 | + | 0 | 3817;3817;3817 | 1 | 6525 | smoothelin |
| SC243 | 6 | MAX.chr6.27059752-27059869 | - | - | 0 | - | 0 | - | - |
| SC244 | 7 | MGC87042 | NM_207342;NM_001164460 | - | 1 | 35;35 | 1 | 256227 | STEAP family protein MGC87042 |
| SC245 | 11 | MAX.chr11.518684-518729 | - | - | 0 | - | 1 | - | - |
| SC246 | 22 | SMTN | NM_134269;NM_006932;NM_1342 70 | + | 0 | 4124;4124;4124 | 0 | 6525 | smoothelin |
| SC247 | 17 | CACNA1G | NM_018896;NM_198376;NM_1983 87;NM_198388;NM_198378;NM_19 8380;NM_198385;NM_198397;NM_ 198386;NM_198383;NM_198377;N M_198379;NM_198396;NM_198382 ;NM_198384 | + | 0 | -1945;-1945;-1945;- 1945;-1945;-1945;- 1945;-1945;-1945;- 1945;-1945;-1945;- 1945;-1945;-1945 | 1 | 8913 | calcium channel, voltage-dependent, T type, alpha 1G subunit |
| SC248 | 10 | APBB1IP | NM_019043 | + | 0 | 724 | 1 | 54518 | amyloid beta (A4) precursor protein-binding, family B, member 1 interacting protein |
| SC249 | 7 | LFNG | NM_001040167;NM_001166355;N M_001040168;NM_002304 | + | 0 | -884;6432;-884;1098 | 1 | 3955 | LFNG O-fucosylpeptide 3-beta-N-acetylglucosaminyltransferase |
| SC250 | 9 | MAX.chr9.94444127-94444240 | - | - | 0 | - | 0 | - | - |
| SC251 | 17 | ARL5C | NM_001143968 | - | 0 | 1270 | 0 | 390790 | ADP-ribosylation factor-like 5C |
| SC252 | 7 | CNPY1 | NM_001103176 | - | 0 | 23984 | 1 | 285888 | canopy 1 homolog (zebrafish) |
| SC253 | 1 | PEAR1 | NM_001080471 | + | 0 | -45 | 1 | 375033 | platelet endothelial aggregation receptor 1 |
| SC254 | 1 | BMP8B | NM_001720 | - | 1 | 17592 | 1 | 656 | bone morphogenetic protein 8b |
| SC255 | 2 | FLJ32063 | NR_026830 | + | 0 | -3890 | 1 | 150538 | hypothetical LOC150538 |
| SC256 | 16 | CORO7 | NM_024535 | - | 0 | 44561 | 1 | 79585 | coronin 7 |
| SC257 | 19 | LOC284454 | NR_036515 | - | 0 | -3276 | 0 | 284454 | hypothetical LOC284454 |
| SC258 | 1 | MAX.chr1.324103360-324103060-32410416 | - | - | 0 | - | 1 | - | - |
| SC259 | 17 | C17orf64 | NM_181707 | + | 0 | -755 | 1 | 124773 | chromosome 17 open reading frame 64 |

FIG. 4 (cont'd)

| Small Cell marker region ref. # | Chromosome | Start position | Stop position | mean BC island | mean lung,normal island | mean Adenocarcinoma Lung island | mean Large cell Lung island | mean Small cell Lung island | mean Squamous Lung island | mean undefined cancer Lung island | Norm/BC | Ad/BC | LC/BC | SC/BC | SQ/BC | UND/BC |
|---|---|---|---|---|---|---|---|---|---|---|---|---|---|---|---|---|
| SC260 | 12 | 251020040 | 251102115 | 1% | 1% | 2% | 7% | 30% | 6% | 46% | 0.98 | 1.54 | 6.05 | 24.87 | 5.12 | 37.73 |
| SC261 | 12 | 251101810 | 251101893 | 0% | 0% | 0% | 6% | 24% | 4% | 40% | 1.38 | 1.62 | 25.21 | 97.73 | 16.47 | 163.70 |
| SC262 | 5 | 169064211 | 169064314 | 0% | 1% | 9% | 15% | 30% | 2% | 22% | 3.71 | 29.12 | 46.14 | 93.41 | 5.35 | 71.09 |
| SC263 | 7 | 56357550 | 5635844 | 1% | 4% | 23% | 13% | 35% | 5% | 12% | 3.30 | 18.65 | 10.10 | 28.57 | 3.82 | 9.54 |
| SC264 | 20 | 44746681 | 44746768 | 1% | 2% | 5% | 6% | 25% | 3% | 7% | 1.71 | 5.43 | 6.36 | 26.47 | 3.23 | 6.91 |
| SC265 | 17 | 70216308 | 70216394 | 2% | 4% | 17% | 25% | 48% | 16% | 70% | 1.74 | 8.10 | 12.23 | 23.33 | 7.58 | 34.05 |
| SC266 | 2 | 25439185 | 25439264 | 0% | 1% | 10% | 11% | 31% | 3% | 7% | 2.31 | 25.89 | 26.41 | 77.49 | 6.89 | 18.37 |
| SC267 | 19 | 16022754 | 16022843 | 1% | 3% | 26% | 23% | 40% | 19% | 40% | 2.77 | 20.59 | 18.27 | 32.36 | 15.43 | 32.48 |
| SC268 | 6 | 157557573 | 157557649 | 2% | 3% | 5% | 25% | 66% | 16% | 33% | 1.63 | 2.76 | 12.83 | 34.25 | 8.20 | 17.06 |
| SC269 | 12 | 54812386 | 54812467 | 1% | 2% | 12% | 16% | 28% | 9% | 9% | 1.67 | 11.36 | 14.63 | 26.03 | 8.59 | 8.08 |
| SC270 | 17 | 36204463 | 36204540 | 2% | 4% | 6% | 12% | 44% | 9% | 44% | 2.57 | 3.62 | 7.26 | 25.84 | 5.35 | 26.21 |
| SC271 | 11 | 64108279 | 64108358 | 0% | 4% | 16% | 16% | 40% | 9% | 21% | 13.17 | 51.71 | 50.68 | 128.96 | 27.78 | 69.11 |
| SC272 | 5 | 105635501 | 105635540 | 1% | 4% | 11% | 20% | 30% | 3% | 29% | 4.01 | 11.13 | 19.49 | 30.32 | 2.98 | 28.82 |
| SC273 | 12 | 224868883 | 224487008 | 0% | 1% | 5% | 11% | 28% | 12% | 43% | 5.71 | 19.90 | 40.52 | 108.42 | 47.79 | 164.13 |
| SC274 | 19 | 58238816 | 58238942 | 0% | 1% | 8% | 15% | 24% | 17% | 33% | 8.09 | 94.63 | 175.66 | 277.57 | 203.93 | 390.80 |
| SC275 | 9 | 124132453 | 124132500 | 0% | 0% | 0% | 0% | 11% | 0% | 19% | 0.40 | 1.95 | 2.34 | 49.53 | 1.58 | 87.46 |
| SC276 | 5 | 37834916 | 37835022 | 1% | 5% | 9% | 28% | 55% | 37% | 42% | 4.35 | 7.78 | 25.11 | 49.26 | 33.19 | 37.95 |
| SC277 | 1 | 61519406 | 61519521 | 1% | 3% | 3% | 9% | 32% | 10% | 19% | 4.49 | 4.18 | 12.66 | 46.99 | 13.78 | 28.13 |
| SC278 | 19 | 1467153 | 1467216 | 2% | 4% | 11% | 25% | 53% | 15% | 42% | 2.08 | 5.76 | 12.88 | 26.95 | 7.57 | 21.46 |
| SC279 | 3 | 186648031 | 186648076 | 1% | 1% | 2% | 4% | 23% | 6% | 2% | 1.18 | 2.18 | 3.54 | 22.27 | 5.47 | 1.72 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC260 | 12 | BCAT1 | NM_001178092;NM_005504;NM_001178091 | - | 1 | 353;353;353 | 1 | 586 | branched chain amino-acid transaminase 1, cytosolic |
| SC261 | 12 | BCAT1 | NM_001178092;NM_005504;NM_001178091 | - | 0 | 583;583;583 | 1 | 586 | branched chain amino-acid transaminase 1, cytosolic |
| SC262 | 5 | DOCK2 | NM_004946 | + | 0 | -39 | 0 | 1794 | dedicator of cytokinesis 2 |
| SC263 | 7 | FSCN1 | NM_003088 | + | 0 | 3297 | 0 | 6624 | fascin homolog 1, actin-bundling protein (Strongylocentrotus purpuratus) |
| SC264 | 20 | CD40 | NM_001250;NM_152854 | + | 0 | -224;-224 | 0 | 958 | CD40 molecule, TNF receptor superfamily member 5 |
| SC265 | 17 | MAX.chr17.70216308-70216394 | - | - | 0 | - | 0 | - | . |
| SC266 | 2 | MAX.chr2.25439185-25439264 | - | - | 0 | - | 1 | - | . |
| SC267 | 19 | MAX.chr19.16022754-16022843 | - | - | 0 | - | 1 | - | . |
| SC268 | 6 | MAX.chr6.157557573-157557649 | - | - | 0 | - | 1 | - | . |
| SC269 | 12 | ITGA5 | NM_002205 | - | 0 | 664 | 0 | 3678 | integrin, alpha 5 (fibronectin receptor, alpha polypeptide) |
| SC270 | 17 | LOC284100 | NR_024178 | - | 0 | 39900 | 0 | 284100 | tyrosine 3-monooxygenase/tryptophan 5-monooxygenase activation protein, epsilon polypeptide pseudogene |
| SC271 | 11 | CCDC88B | NM_032251 | + | 0 | 590 | 0 | 283234 | coiled-coil domain containing 88B |
| SC272 | 5 | ANKRD33B | NM_001164440 | + | 0 | -933 | 1 | 651746 | ankyrin repeat domain 33B |
| SC273 | 12 | ST8SIA1 | NM_003034 | - | 0 | 765 | 1 | 6489 | ST8 alpha-N-acetyl-neuraminide alpha-2,8-sialyltransferase 1 |
| SC274 | 19 | ZNF671 | NM_024833 | - | 1 | 179 | 1 | 79891 | zinc finger protein 671 |
| SC275 | 9 | STOM | NM_198194;NM_004099 | - | 1 | 92;92 | 1 | 2040 | stomatin |
| SC276 | 5 | GDNF | NM_001190469;NM_001190468;NM_000514;NM_199231 | - | 1 | 1013;1013;4866;677 | 1 | 2668 | glial cell derived neurotrophic factor |
| SC277 | 1 | MAX.chr1.61519406-61519521 | - | - | 0 | - | 1 | - | . |
| SC278 | 19 | APC2 | NM_005883 | + | 1 | 17006 | 1 | 10297 | adenomatosis polyposis coli 2 |
| SC279 | 3 | ST6GAL1 | NM_173216;NM_173217 | + | 0 | -283;-283 | 0 | 6480 | ST6 beta-galactosamide alpha-2,6-sialyltranferase 1 |

FIG. 4 (cont'd)

| Small Cell marker region ref. # | Chromosome | Start position | Stop position | mean BC island | mean lung, normal island | mean Adenocarcinoma Lung island | mean Large cell Lung island | mean Small cell Lung island | mean Squamous Lung island | mean undefined cancer Lung island | Norm/BC | Ad/BC | LC/BC | SC/BC | SQ/BC | UND/BC |
|---|---|---|---|---|---|---|---|---|---|---|---|---|---|---|---|---|
| SC280 | 8 | 65490049 | 65490112 | 2% | 5% | 6% | 11% | 49% | 12% | 38% | 2.13 | 2.63 | 4.76 | 21.73 | 5.34 | 17.03 |
| SC281 | 9 | 96713572 | 96713746 | 1% | 2% | 1% | 6% | 49% | 9% | 13% | 1.43 | 1.30 | 5.34 | 45.71 | 8.18 | 12.40 |
| SC282 | 1 | 110627121 | 110627221 | 1% | 3% | 7% | 25% | 39% | 7% | 33% | 2.37 | 6.55 | 22.73 | 36.30 | 6.54 | 30.81 |
| SC283 | 21 | 44494923 | 44494962 | 1% | 4% | 13% | 10% | 41% | 12% | 16% | 3.28 | 10.92 | 8.29 | 34.30 | 9.61 | 13.41 |
| SC284 | 17 | 47073394 | 47073480 | 1% | 3% | 12% | 25% | 31% | 5% | 30% | 2.03 | 8.66 | 18.20 | 22.07 | 3.33 | 21.89 |
| SC285 | 9 | 96715505 | 96715595 | 2% | 5% | 27% | 26% | 56% | 22% | 13% | 2.12 | 12.92 | 12.09 | 26.40 | 10.29 | 6.21 |
| SC286 | 1 | 61519679 | 61519759 | 0% | 1% | 2% | 8% | 31% | 8% | 13% | 5.20 | 10.06 | 37.79 | 143.41 | 37.27 | 60.12 |
| SC287 | 6 | 157557374 | 157557528 | 1% | 1% | 1% | 11% | 36% | 9% | 15% | 2.32 | 2.11 | 18.24 | 61.73 | 15.37 | 26.63 |
| SC288 | 1 | 214158912 | 214158969 | 1% | 4% | 20% | 33% | 50% | 18% | 46% | 3.39 | 17.95 | 29.64 | 45.85 | 16.83 | 41.54 |
| SC289 | 6 | 1624797 | 1624838 | 1% | 5% | 13% | 9% | 39% | 13% | 24% | 4.95 | 13.39 | 9.22 | 38.66 | 12.89 | 24.01 |
| SC290 | 6 | 99295996 | 99296069 | 2% | 5% | 12% | 20% | 54% | 22% | 18% | 2.17 | 4.91 | 8.25 | 22.18 | 8.83 | 7.46 |
| SC291 | 6 | 6004298 | 6004338 | 1% | 5% | 21% | 40% | 58% | 34% | 61% | 7.31 | 33.74 | 64.23 | 93.83 | 54.50 | 99.42 |
| SC292 | 2 | 73147720 | 73147790 | 1% | 3% | 24% | 36% | 50% | 28% | 59% | 3.25 | 26.10 | 38.89 | 54.76 | 30.96 | 64.51 |
| SC293 | 1 | 248020671 | 248020722 | 1% | 4% | 31% | 40% | 63% | 33% | 63% | 3.31 | 23.46 | 30.04 | 47.26 | 24.66 | 47.74 |
| SC294 | 17 | 43339354 | 43339495 | 1% | 1% | 5% | 15% | 39% | 17% | 18% | 0.97 | 6.27 | 17.23 | 44.90 | 19.79 | 20.18 |
| SC295 | 13 | 53421299 | 53421350 | 2% | 6% | 30% | 32% | 64% | 24% | 65% | 3.20 | 16.30 | 17.38 | 34.40 | 12.80 | 34.96 |
| SC296 | 2 | 73147853 | 73147982 | 1% | 5% | 23% | 30% | 41% | 25% | 57% | 3.39 | 16.03 | 20.50 | 28.49 | 17.46 | 39.34 |
| SC297 | 6 | 137244467 | 137244587 | 3% | 6% | 16% | 23% | 55% | 22% | 55% | 2.34 | 6.29 | 9.20 | 21.68 | 8.65 | 21.76 |
| SC298 | 1 | 208132590 | 208132681 | 1% | 7% | 11% | 33% | 58% | 30% | 46% | 6.30 | 9.55 | 28.98 | 51.43 | 26.34 | 41.25 |
| SC299 | 5 | 37834716 | 37834762 | 2% | 4% | 16% | 25% | 51% | 36% | 36% | 2.51 | 9.42 | 14.77 | 30.36 | 21.39 | 21.50 |
| SC300 | 19 | 10406234 | 10406282 | 1% | 4% | 6% | 17% | 42% | 16% | 44% | 6.91 | 11.83 | 31.08 | 76.40 | 29.79 | 80.36 |
| SC301 | 9 | 96715384 | 96715473 | 1% | 3% | 19% | 19% | 53% | 19% | 8% | 2.78 | 16.47 | 17.08 | 47.26 | 17.24 | 6.84 |
| SC302 | 20 | 21493456 | 21493605 | 1% | 3% | 13% | 19% | 48% | 6% | 16% | 2.82 | 10.65 | 15.29 | 39.13 | 4.59 | 13.02 |
| SC303 | 1 | 61519535 | 61519667 | 0% | 1% | 2% | 9% | 35% | 8% | 17% | 2.03 | 3.47 | 17.58 | 71.29 | 15.47 | 34.29 |
| SC304 | 19 | 48983840 | 48983937 | 1% | 4% | 16% | 18% | 58% | 15% | 31% | 2.99 | 12.22 | 13.83 | 44.21 | 11.76 | 23.49 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC280 | 8 | BHLHE22 | NM_152414 | + | 0 | -2764 | 0 | 27319 | basic helix-loop-helix family, member e22 |
| SC281 | 9 | MAX.chr9.96713572-96713746 | - | - | 0 | - | 1 | - | - |
| SC282 | 1 | MAX.chr1.110627121-110627221 | - | - | 0 | - | 1 | - | - |
| SC283 | 21 | CBS | NM_001178008;NM_001178009;NM_000071 | - | 0 | 1549;1549;1117 | 1 | 875 | cystathionine-beta-synthase |
| SC284 | 17 | IGF2BP1 | NM_006546;NM_001160423 | + | 0 | -1379;-1379 | 1 | 10642 | insulin-like growth factor 2 mRNA binding protein 1 |
| SC285 | 9 | BARX1 | NM_021570 | - | 0 | 2103 | 1 | 56033 | BARX homeobox 1 |
| SC286 | 1 | MAX.chr1.61519679-61519759 | - | - | 0 | - | 1 | - | - |
| SC287 | 6 | MAX.chr6.157557374-157557528 | - | - | 0 | - | 1 | - | - |
| SC288 | 1 | PROX1 | NM_002763 | + | 0 | -2947 | 1 | 5629 | prospero homeobox 1 |
| SC289 | 6 | GMDS | NM_001500 | - | 0 | 621049 | 1 | 2762 | GDP-mannose 4,6-dehydratase |
| SC290 | 6 | MAX.chr6.99295996-99296069 | - | - | 0 | - | 1 | - | - |
| SC291 | 6 | NRN1 | NM_016588 | - | 0 | 3335 | 1 | 51299 | neuritin 1 |
| SC292 | 2 | EMX1 | NM_004097 | + | 0 | 3117 | 1 | 2016 | empty spiracles homeobox 1 |
| SC293 | 1 | TRIM58 | NM_015431 | + | 1 | 171 | 1 | 25893 | tripartite motif-containing 58 |
| SC294 | 17 | C17orf46 | NM_152343 | - | 0 | 125 | 1 | 124783 | chromosome 17 open reading frame 46 |
| SC295 | 13 | PCDH8 | NM_002590;NM_032949 | - | 1 | 1475;1475 | 1 | 5100 | protocadherin 8 |
| SC296 | 2 | EMX1 | NM_004097 | + | 0 | 3250 | 1 | 2016 | empty spiracles homeobox 1 |
| SC297 | 6 | SLC35D3 | NM_001008783 | + | 0 | 1066 | 1 | 340146 | solute carrier family 35, member D3 |
| SC298 | 1 | MAX.chr1.208132590-208132681 | - | - | 0 | - | 1 | - | - |
| SC299 | 5 | GDNF | NM_001190469;NM_001190468;NM_000514;NM_199231 | - | 0 | 1213;1213;5066;877 | 1 | 2668 | glial cell derived neurotrophic factor |
| SC300 | 19 | ICAM5 | NM_003259 | + | 1 | 5580 | 1 | 7087 | intercellular adhesion molecule 5, telencephalin |
| SC301 | 9 | BARX1 | NM_021570 | - | 1 | 2224 | 1 | 56033 | BARX homeobox 1 |
| SC302 | 20 | NKX2-2 | NM_002509 | - | 0 | 1208 | 1 | 4821 | NK2 homeobox 2 |
| SC303 | 1 | MAX.chr1.61519535-61519667 | - | - | 0 | - | 1 | - | - |
| SC304 | 19 | CYTH2 | NM_004228;NM_017457 | + | 1 | 11376;11376 | 1 | 9266 | cytohesin 2 |

FIG. 4 (cont'd)

| Small Cell marker region ref. # | Chromosome | Start position | Stop position | mean BC.island | mean lung.normal, island | mean Adenocarcinoma lung.island | mean Large cell lung.island | mean Small cell lung.island | mean Squamous lung.island | mean undefined cancer lung.island | Norm/BC | Ad/BC | LC/BC | SC/BC | SQ/BC | UND/BC |
|---|---|---|---|---|---|---|---|---|---|---|---|---|---|---|---|---|
| SC305 | 6 | 108490524 | 108490584 | 1% | 2% | 11% | 18% | 30% | 18% | 3% | 1.88 | 9.31 | 15.77 | 25.30 | 15.66 | 2.40 |
| SC306 | 5 | 149792249 | 149792285 | 0% | 3% | 1% | 5% | 29% | 13% | 17% | 17.71 | 6.75 | 24.08 | 147.62 | 64.65 | 85.42 |
| SC307 | 6 | 44119711 | 44119872 | 0% | 1% | 1% | 7% | 14% | 5% | 10% | 2.29 | 1.94 | 17.47 | 34.31 | 13.65 | 24.44 |
| SC308 | 19 | 38182957 | 38183121 | 1% | 2% | 18% | 13% | 26% | 17% | 28% | 1.78 | 16.97 | 11.59 | 24.34 | 15.34 | 25.69 |
| SC309 | 22 | 46263416 | 46263515 | 2% | 4% | 4% | 9% | 47% | 24% | 19% | 1.60 | 1.87 | 4.14 | 21.04 | 10.94 | 8.60 |
| SC310 | 1 | 248020410 | 248020517 | 2% | 4% | 20% | 28% | 42% | 15% | 46% | 2.26 | 11.28 | 15.61 | 22.96 | 8.22 | 25.33 |
| SC311 | 17 | 43339264 | 43339345 | 1% | 1% | 4% | 11% | 41% | 12% | 11% | 1.45 | 8.50 | 22.19 | 82.48 | 23.48 | 21.17 |
| SC312 | 5 | 134879362 | 134879483 | 0% | 1% | 5% | 13% | 35% | 5% | 17% | 3.15 | 10.56 | 29.38 | 80.54 | 10.94 | 39.68 |
| SC313 | 10 | 101300100 | 101300155 | 1% | 3% | 10% | 16% | 24% | 5% | 7% | 3.69 | 13.71 | 22.13 | 33.20 | 6.17 | 9.10 |
| SC314 | 5 | 37834845 | 37834910 | 2% | 5% | 13% | 29% | 50% | 39% | 33% | 3.22 | 8.38 | 18.64 | 32.37 | 25.14 | 21.61 |
| SC315 | 20 | 36013131 | 36013210 | 0% | 2% | 4% | 4% | 20% | 7% | 11% | 9.17 | 23.33 | 24.65 | 124.06 | 40.85 | 68.15 |
| SC316 | 3 | 16554363 | 16554496 | 0% | 0% | 0% | 3% | 11% | 4% | 2% | 3.51 | 1.43 | 26.47 | 107.49 | 36.66 | 15.44 |
| SC317 | 12 | 25056015 | 25056162 | 0% | 1% | 10% | 18% | 25% | 10% | 35% | 1.51 | 27.62 | 50.51 | 68.55 | 27.10 | 95.52 |
| SC318 | 6 | 157556780 | 157556850 | 1% | 3% | 3% | 17% | 49% | 11% | 11% | 2.07 | 1.73 | 11.91 | 33.83 | 7.40 | 7.57 |
| SC319 | 12 | 122231765 | 122231829 | 1% | 1% | 1% | 7% | 18% | 2% | 1% | 1.59 | 2.48 | 12.95 | 35.04 | 3.13 | 2.54 |
| SC320 | 3 | 182897149 | 182897232 | 1% | 1% | 3% | 4% | 24% | 1% | 10% | 0.83 | 4.11 | 5.33 | 32.87 | 1.36 | 13.04 |
| SC321 | 18 | 5891056 | 5891125 | 2% | 4% | 12% | 29% | 49% | 9% | 36% | 2.12 | 6.28 | 14.73 | 24.80 | 4.33 | 18.25 |
| SC322 | 11 | 76750814 | 76750881 | 1% | 8% | 30% | 27% | 52% | 16% | 64% | 10.48 | 41.11 | 36.46 | 70.66 | 22.09 | 86.31 |
| SC323 | 19 | 2251365 | 2251400 | 2% | 4% | 15% | 18% | 65% | 10% | 22% | 2.23 | 8.49 | 10.23 | 37.40 | 5.66 | 12.69 |

FIG. 4 (cont'd)

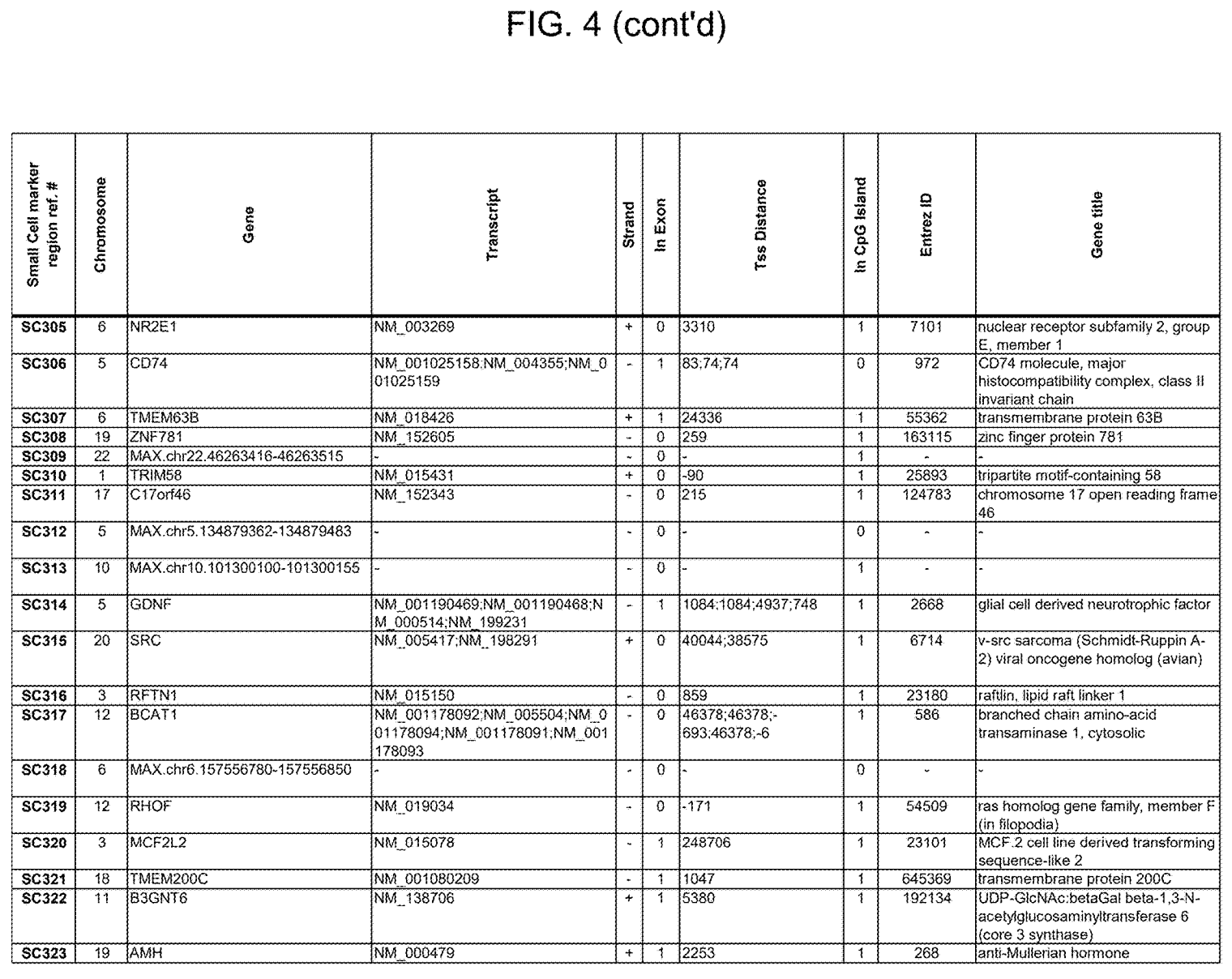

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC305 | 6 | NR2E1 | NM_003269 | + | 0 | 3310 | 1 | 7101 | nuclear receptor subfamily 2, group E, member 1 |
| SC306 | 5 | CD74 | NM_001025158;NM_004355;NM_001025159 | - | 1 | 83;74;74 | 0 | 972 | CD74 molecule, major histocompatibility complex, class II invariant chain |
| SC307 | 6 | TMEM63B | NM_018426 | + | 1 | 24336 | 1 | 55362 | transmembrane protein 63B |
| SC308 | 19 | ZNF781 | NM_152605 | - | 0 | 259 | 1 | 163115 | zinc finger protein 781 |
| SC309 | 22 | MAX.chr22.46263416-46263515 | - | - | 0 | - | 1 | - | - |
| SC310 | 1 | TRIM58 | NM_015431 | + | 0 | -90 | 1 | 25893 | tripartite motif-containing 58 |
| SC311 | 17 | C17orf46 | NM_152343 | - | 0 | 215 | 1 | 124783 | chromosome 17 open reading frame 46 |
| SC312 | 5 | MAX.chr5.134879362-134879483 | - | - | 0 | - | 0 | - | - |
| SC313 | 10 | MAX.chr10.101300100-101300155 | - | - | 0 | - | 1 | - | - |
| SC314 | 5 | GDNF | NM_001190469;NM_001190468;NM_000514;NM_199231 | - | 1 | 1084;1084;4937;748 | 1 | 2668 | glial cell derived neurotrophic factor |
| SC315 | 20 | SRC | NM_005417;NM_198291 | + | 0 | 40044;38575 | 1 | 6714 | v-src sarcoma (Schmidt-Ruppin A-2) viral oncogene homolog (avian) |
| SC316 | 3 | RFTN1 | NM_015150 | - | 0 | 859 | 1 | 23180 | raftlin, lipid raft linker 1 |
| SC317 | 12 | BCAT1 | NM_001178092;NM_005504;NM_001178094;NM_001178091;NM_001178093 | - | 0 | 46378;46378;-693;46378;-6 | 1 | 586 | branched chain amino-acid transaminase 1, cytosolic |
| SC318 | 6 | MAX.chr6.157556780-157556850 | - | - | 0 | - | 0 | - | - |
| SC319 | 12 | RHOF | NM_019034 | - | 0 | -171 | 1 | 54509 | ras homolog gene family, member F (in filopodia) |
| SC320 | 3 | MCF2L2 | NM_015078 | - | 1 | 248706 | 1 | 23101 | MCF.2 cell line derived transforming sequence-like 2 |
| SC321 | 18 | TMEM200C | NM_001080209 | - | 1 | 1047 | 1 | 645369 | transmembrane protein 200C |
| SC322 | 11 | B3GNT6 | NM_138706 | + | 1 | 5380 | 1 | 192134 | UDP-GlcNAc:betaGal beta-1,3-N-acetylglucosaminyltransferase 6 (core 3 synthase) |
| SC323 | 19 | AMH | NM_000479 | + | 1 | 2253 | 1 | 268 | anti-Mullerian hormone |

FIG. 4 (cont'd)

| Small Cell marker region ref. # | Chromosome | Start position | Stop position | mean BC.island | mean lung.normal, island | mean Adenocarcinoma Lung.island | mean Large cell Lung.island | mean Small cell Lung.island | mean Squamous Lung.island | mean undefined Lung cancer.island | Norm/BC | Ad/BC | LC/BC | SC/BC | SQ/BC | UND/BC |
|---|---|---|---|---|---|---|---|---|---|---|---|---|---|---|---|---|
| SC324 | 5 | 154026853 | 154026896 | 1% | 5% | 5% | 12% | 38% | 14% | 7% | 7.87 | 7.72 | 17.90 | 58.03 | 21.03 | 10.87 |
| SC325 | 1 | 167599734 | 167599813 | 0% | 1% | 5% | 11% | 13% | 3% | 16% | 7.00 | 23.21 | 52.79 | 62.19 | 15.82 | 79.50 |
| SC326 | 18 | 44526868 | 44526957 | 1% | 1% | 6% | 5% | 22% | 18% | 7% | 1.31 | 10.36 | 9.07 | 36.70 | 29.96 | 12.10 |
| SC327 | 19 | 48983735 | 48983826 | 2% | 5% | 20% | 17% | 47% | 10% | 25% | 1.94 | 8.78 | 7.43 | 20.22 | 4.38 | 10.74 |
| SC328 | 9 | 139159296 | 139159348 | 0% | 1% | 1% | 1% | 19% | 2% | 26% | 5.60 | 6.92 | 3.81 | 135.14 | 13.04 | 185.99 |
| SC329 | 5 | 132083179 | 132083223 | 1% | 1% | 2% | 6% | 30% | 2% | 5% | 1.53 | 1.67 | 6.35 | 32.19 | 2.49 | 5.46 |
| SC330 | 21 | 26934474 | 26934630 | 0% | 1% | 9% | 10% | 22% | 4% | 20% | 5.32 | 55.57 | 61.25 | 138.59 | 27.77 | 121.89 |
| SC331 | 6 | 1069608030 | 1069609025 | 0% | 2% | 2% | 7% | 50% | 4% | 23% | 3.36 | 4.28 | 15.50 | 108.22 | 9.22 | 49.69 |
| SC332 | 7 | 156701663 | 156701795 | 1% | 1% | 1% | 6% | 17% | 5% | 6% | 1.70 | 1.22 | 7.49 | 21.77 | 6.28 | 8.20 |
| SC333 | 1 | 47697788 | 47697839 | 1% | 4% | 15% | 16% | 35% | 12% | 52% | 4.93 | 18.42 | 19.77 | 42.61 | 14.00 | 63.25 |
| SC334 | 5 | 77140806 | 77140873 | 2% | 5% | 19% | 19% | 55% | 15% | 49% | 2.10 | 8.33 | 8.10 | 23.90 | 6.32 | 21.13 |
| SC335 | 15 | 28352323 | 28352494 | 1% | 1% | 4% | 8% | 15% | 2% | 20% | 1.47 | 6.11 | 12.78 | 24.57 | 2.78 | 31.63 |
| SC336 | 6 | 29521540 | 29521681 | 1% | 5% | 5% | 22% | 41% | 17% | 23% | 3.41 | 3.62 | 14.78 | 27.38 | 11.77 | 15.51 |
| SC337 | 14 | 92980637 | 92980695 | 0% | 0% | 1% | 1% | 22% | 1% | 9% | 0.63 | 3.61 | 1.60 | 91.32 | 3.10 | 36.73 |
| SC338 | 9 | 19127781 | 19127835 | 0% | 0% | 1% | 1% | 20% | 1% | 3% | 1.93 | 4.37 | 3.15 | 118.01 | 4.59 | 17.38 |
| SC339 | 1 | 6663497 | 6663545 | 0% | 1% | 1% | 1% | 15% | 4% | 8% | 2.59 | 3.84 | 3.13 | 64.79 | 19.15 | 35.96 |
| SC340 | 1 | 21336959 | 21337098 | 0% | 0% | 1% | 1% | 12% | 2% | 2% | 1.41 | 2.04 | 4.52 | 37.03 | 6.29 | 7.19 |
| SC341 | 21 | 36042030 | 36042110 | 1% | 2% | 4% | 22% | 41% | 13% | 55% | 1.88 | 3.80 | 23.37 | 43.13 | 13.73 | 57.60 |
| SC342 | 3 | 170137371 | 170137439 | 2% | 5% | 15% | 34% | 49% | 33% | 62% | 2.78 | 9.08 | 20.26 | 29.02 | 19.46 | 36.27 |
| SC343 | 6 | 158243942 | 158243981 | 1% | 1% | 1% | 2% | 33% | 2% | 13% | 1.38 | 1.60 | 2.72 | 36.48 | 1.68 | 14.51 |
| SC344 | 12 | 1255534296 | 1255534343 | 0% | 1% | 10% | 10% | 29% | 5% | 0% | 3.25 | 1.46 | 24.52 | 68.16 | 12.02 | 0.91 |
| SC345 | 12 | 1906061 | 1906126 | 0% | 0% | 0% | 8% | 23% | 0% | 4% | 0.76 | 0.41 | 20.08 | 57.07 | 0.76 | 9.54 |
| SC346 | 10 | 1193312919 | 1193312997 | 1% | 3% | 15% | 28% | 28% | 5% | 11% | 2.57 | 12.66 | 22.08 | 23.61 | 4.33 | 9.25 |
| SC347 | 13 | 25321012 | 25321114 | 1% | 2% | 2% | 6% | 26% | 16% | 26% | 2.12 | 2.30 | 7.65 | 31.63 | 19.72 | 31.63 |
| SC348 | 9 | 941183673 | 941183710 | 1% | 1% | 9% | 10% | 24% | 6% | 20% | 1.61 | 10.63 | 12.61 | 29.26 | 7.25 | 24.73 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC324 | 5 | MAX.chr5.154026853-154026896 | - | - | 0 | | 1 | - | - |
| SC325 | 1 | RCSD1 | NM_052862 | + | 0 | 261 | 1 | 92241 | RCSD domain containing 1 |
| SC326 | 18 | KATNAL2 | NM_031303 | + | 1 | 82 | 1 | 83473 | katanin p60 subunit A-like 2 |
| SC327 | 19 | CYTH2 | NM_004228;NM_017457 | + | 1 | 11271;11271 | 1 | 9266 | cytohesin 2 |
| SC328 | 9 | MAX.chr9.139159296-139159348 | - | - | 0 | | 0 | - | - |
| SC329 | 5 | CCNI2 | NM_001039780 | + | 1 | 43 | 1 | 645121 | cyclin I family, member 2 |
| SC330 | 21 | MIR155HG | NR_001458 | + | 1 | 18 | 1 | 114614 | MIR155 host gene (non-protein coding) |
| SC331 | 6 | AIM1 | NM_001624 | + | 1 | 1101 | 1 | 202 | absent in melanoma 1 |
| SC332 | 7 | MAX.chr7.156701663-156701795 | - | - | 0 | | 0 | - | - |
| SC333 | 1 | TAL1 | NM_003189 | - | 0 | -2345 | 1 | 6886 | T-cell acute lymphocytic leukemia 1 |
| SC334 | 5 | MAX.chr5.77140806-77140873 | - | - | 0 | | 1 | - | - |
| SC335 | 15 | MAX.chr15.28352323-28352494 | - | - | 0 | | 1 | - | - |
| SC336 | 6 | MAX.chr6.29521540-29521681 | - | - | 0 | | 1 | - | - |
| SC337 | 14 | RIN3 | NM_024832 | + | 0 | 513 | 1 | 79890 | Ras and Rab interactor 3 |
| SC338 | 9 | PLIN2 | NM_001122 | - | 0 | -208 | 1 | 123 | perilipin 2 |
| SC339 | 1 | KLHL21 | NM_014851 | - | 0 | -568 | 1 | 9903 | kelch-like 21 (Drosophila) |
| SC340 | 1 | C1orf86 | NM_001146310 | - | 0 | 2213 | 1 | 199990 | chromosome 1 open reading frame 86 |
| SC341 | 21 | CLIC6 | NM_053277 | + | 1 | 343 | 1 | 54102 | chloride intracellular channel 6 |
| SC342 | 3 | CLDN11 | NM_001185056;NM_005602 | + | 0 | -1656;719 | 1 | 5010 | claudin 11 |
| SC343 | 6 | SNX9 | NM_016224 | + | 0 | -351 | 1 | 51429 | sorting nexin 9 |
| SC344 | 12 | MAX.chr12.125534296-125534343 | - | - | 0 | | 1 | - | - |
| SC345 | 12 | CACNA2D4 | NM_172364 | - | 0 | 121809 | 1 | 93589 | calcium channel, voltage-dependent, alpha 2/delta subunit 4 |
| SC346 | 10 | MAX.chr10.119312919-119312997 | - | - | 0 | | 1 | - | - |
| SC347 | 13 | MAX.chr13.25321012-25321114 | - | - | 0 | | 1 | - | - |
| SC348 | 9 | NFIL3 | NM_005384 | - | 0 | 2471 | 1 | 4783 | nuclear factor, interleukin 3 regulated |

FIG. 4 (cont'd)

| Small Cell marker region ref. # | Chromosome | Start position | Stop position | mean BC.island | mean lung.normal. island | mean Adenocarcinoma.Lung.island | mean Large cell.Lung.island | mean Small cell.Lung.island | mean Squamous.Lung.island | mean undefined Lung.cancer island | Norm/BC | Ad/BC | LC/BC | SC/BC | SQ/BC | UND/BC |
|---|---|---|---|---|---|---|---|---|---|---|---|---|---|---|---|---|
| SC349 | 4 | 6660582 | 6660692 | 1% | 2% | 13% | 21% | 28% | 11% | 23% | 2.18 | 11.76 | 18.47 | 24.32 | 9.50 | 20.20 |
| SC350 | 5 | 77140667 | 77140774 | 2% | 2% | 10% | 15% | 35% | 9% | 24% | 1.33 | 5.81 | 8.99 | 20.78 | 5.24 | 14.34 |
| SC351 | 5 | 42952165 | 42952265 | 1% | 4% | 12% | 17% | 28% | 18% | 30% | 5.58 | 19.39 | 27.28 | 43.92 | 28.58 | 47.30 |
| SC352 | 3 | 194118747 | 194118919 | 0% | 2% | 13% | 26% | 43% | 19% | 41% | 6.97 | 38.31 | 74.49 | 125.02 | 55.43 | 117.27 |
| SC353 | 1 | 2989976 | 2990065 | 1% | 3% | 4% | 18% | 32% | 8% | 9% | 3.14 | 3.74 | 16.20 | 29.59 | 7.08 | 8.48 |
| SC354 | 17 | 41363552 | 41363612 | 0% | 0% | 0% | 2% | 21% | 6% | 15% | 0.76 | 0.60 | 4.16 | 55.55 | 15.12 | 39.77 |
| SC355 | 10 | 77168201 | 77168360 | 1% | 2% | 3% | 7% | 29% | 5% | 9% | 1.99 | 2.99 | 7.70 | 29.70 | 5.27 | 8.77 |
| SC356 | 11 | 129243348 | 129243401 | 2% | 5% | 17% | 29% | 49% | 41% | 66% | 2.48 | 8.04 | 13.91 | 22.93 | 19.19 | 31.01 |
| SC357 | 10 | 119296757 | 119296802 | 1% | 1% | 1% | 9% | 28% | 3% | 6% | 1.03 | 1.36 | 10.19 | 32.99 | 3.39 | 6.47 |
| SC358 | 18 | 21199523 | 21199632 | 0% | 1% | 10% | 8% | 17% | 5% | 6% | 4.06 | 33.90 | 26.89 | 56.35 | 15.34 | 21.73 |
| SC359 | 1 | 8277482 | 8277571 | 1% | 2% | 10% | 22% | 48% | 31% | 59% | 1.59 | 9.26 | 20.67 | 45.68 | 29.57 | 56.50 |
| SC360 | 1 | 2990151 | 2990207 | 1% | 3% | 5% | 18% | 32% | 10% | 16% | 3.23 | 4.95 | 19.48 | 34.02 | 10.98 | 17.06 |
| SC361 | 1 | 44031599 | 44031658 | 0% | 2% | 24% | 18% | 21% | 21% | 18% | 4.80 | 75.23 | 56.94 | 66.66 | 64.67 | 56.57 |
| SC362 | 7 | 27232734 | 27232792 | 2% | 5% | 12% | 21% | 46% | 20% | 34% | 2.43 | 6.01 | 10.74 | 23.94 | 10.31 | 18.04 |
| SC363 | 14 | 77591546 | 77591607 | 1% | 1% | 1% | 2% | 17% | 10% | 2% | 3.66 | 4.59 | 6.87 | 64.89 | 37.49 | 7.51 |
| SC364 | 5 | 42952414 | 42952472 | 2% | 5% | 20% | 25% | 43% | 35% | 57% | 2.78 | 10.31 | 13.24 | 22.51 | 17.99 | 29.67 |
| SC365 | 15 | 41787637 | 41787674 | 0% | 4% | 14% | 13% | 43% | 18% | 3% | 12.04 | 39.44 | 36.80 | 121.85 | 50.77 | 9.60 |
| SC366 | 13 | 33924448 | 33924560 | 1% | 2% | 4% | 12% | 37% | 5% | 11% | 1.75 | 2.62 | 8.62 | 26.18 | 3.24 | 7.69 |
| SC367 | 1 | 203598589 | 203596624 | 1% | 1% | 2% | 2% | 13% | 2% | 2% | 1.20 | 3.53 | 3.87 | 24.55 | 3.76 | 3.75 |
| SC368 | 19 | 503934424 | 503934465 | 1% | 3% | 11% | 4% | 25% | 6% | 40% | 4.96 | 18.14 | 6.73 | 42.96 | 10.89 | 68.93 |
| SC369 | 12 | 1255334190 | 1255334241 | 0% | 1% | 19% | 8% | 24% | 5% | 0% | 4.31 | 5.32 | 46.29 | 134.03 | 25.97 | 0.00 |
| SC370 | 15 | 41787438 | 41787549 | 1% | 4% | 15% | 11% | 45% | 16% | 2% | 3.98 | 19.46 | 11.22 | 47.23 | 16.68 | 1.89 |
| SC371 | 15 | 41787592 | 41787634 | 1% | 6% | 13% | 13% | 46% | 18% | 3% | 5.95 | 15.44 | 13.55 | 46.26 | 18.60 | 3.53 |
| SC372 | 8 | 383323572 | 383236853 | 0% | 1% | 4% | 1% | 10% | 6% | 6% | 2.27 | 17.67 | 2.23 | 46.12 | 26.23 | 27.48 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC349 | 4 | MAX.chr4.6660582-6660692 | - | - | 0 | - | 1 | - | - |
| SC350 | 5 | MAX.chr5.77140667-77140774 | - | - | 0 | - | 1 | - | - |
| SC351 | 5 | MAX.chr5.42952165-42952265 | - | - | 0 | - | 1 | - | - |
| SC352 | 3 | GP5 | NM_004488 | - | 1 | 1248 | 1 | 2814 | glycoprotein V (platelet) |
| SC353 | 1 | PRDM16 | NM_199454;NM_022114 | + | 0 | 4235;4235 | 0 | 63976 | PR domain containing 16 |
| SC354 | 17 | NBR1 | NM_031858;NM_031862;NM_005899 | + | 1 | 41042;41055;40307 | 0 | 4077 | neighbor of BRCA1 gene 1 |
| SC355 | 10 | NCRNA00245 | NR_024421;NR_024422 | + | 1 | 6916;4688 | 1 | 100131213 | non-protein coding RNA 245 |
| SC356 | 11 | BARX2 | NM_003658 | + | 0 | -2532 | 1 | 8538 | BARX homeobox 2 |
| SC357 | 10 | EMX2OS | NR_002791 | - | 0 | 7822 | 1 | 196047 | EMX2 opposite strand (non-protein coding) |
| SC358 | 18 | ANKRD29 | NM_173505 | - | 1 | 43326 | 1 | 147463 | ankyrin repeat domain 29 |
| SC359 | 1 | MAX.chr1.8277482-8277571 | - | - | 0 | - | 1 | - | - |
| SC360 | 1 | PRDM16 | NM_199454;NM_022114 | + | 0 | 4410;4410 | 1 | 63976 | PR domain containing 16 |
| SC361 | 1 | PTPRF | NM_002840;NM_130440 | + | 0 | 35053;35053 | 1 | 5792 | protein tyrosine phosphatase, receptor type, F |
| SC362 | 7 | MAX.chr7.27232734-27232792 | - | - | 0 | - | 1 | - | - |
| SC363 | 14 | MAX.chr14.77591546-77591607 | - | - | 0 | - | 0 | - | - |
| SC364 | 5 | MAX.chr5.42952414-42952472 | - | - | 0 | - | 1 | - | - |
| SC365 | 15 | ITPKA | NM_002220 | + | 0 | 1516 | 1 | 3706 | inositol 1,4,5-trisphosphate 3-kinase A |
| SC366 | 13 | MAX.chr13.33924448-33924560 | - | - | 0 | - | 1 | - | - |
| SC367 | 1 | ATP2B4 | NM_001001396;NM_001684 | + | 0 | 2662;2662 | 1 | 493 | ATPase, Ca++ transporting, plasma membrane 4 |
| SC368 | 19 | IL4I1 | NM_152899;NM_172374 | - | 1 | 6723;39338 | 1 | 259307 | interleukin 4 induced 1 |
| SC369 | 12 | MAX.chr12.125534190-125534241 | - | - | 0 | - | - | - | - |
| SC370 | 15 | ITPKA | NM_002220 | + | 0 | 1317 | 1 | 3706 | inositol 1,4,5-trisphosphate 3-kinase A |
| SC371 | 15 | ITPKA | NM_002220 | + | 0 | 1471 | 1 | 3706 | inositol 1,4,5-trisphosphate 3-kinase A |
| SC372 | 8 | FGFR1 | NM_001174064;NM_023105;NM_001174067;NM_015850;NM_001174063;NM_023110;NM_001174065;NM_001174066;NM_023106 | - | 0 | 2780;2780;1791;2780;2780;2780;1791;1791;2780 | 0 | 2260 | fibroblast growth factor receptor 1 |

FIG. 4 (cont'd)

| Small Cell marker region ref. # | Chromosome | Start position | Stop position | mean BC island | mean lung,normal, island | mean Adenocarcinoma Lung island | mean Large cell Lung island | mean Small cell Lung island | mean Squamous Lung island | mean undefined Lung cancer island | Norm/BC | Ad/BC | LC/BC | SC/BC | SQ/BC | UND/BC |
|---|---|---|---|---|---|---|---|---|---|---|---|---|---|---|---|---|
| SC373 | 22 | 42470432 | 42470495 | 0% | 1% | 2% | 1% | 11% | 6% | 1% | 1.87 | 4.62 | 2.75 | 31.95 | 19.18 | 2.56 |
| SC374 | 22 | 74782096 | 74782223 | 0% | 1% | 1% | 10% | 15% | 22% | 12% | 2.00 | 2.91 | 35.72 | 55.09 | 79.79 | 42.48 |
| SC375 | 1 | 203598746 | 203598782 | 0% | 0% | 2% | 3% | 17% | 2% | 3% | 1.78 | 8.34 | 14.03 | 90.60 | 9.86 | 16.53 |
| SC376 | 3 | 4910281 | 4910325 | 0% | 0% | 2% | 3% | 18% | 1% | 14% | 0.71 | 7.43 | 11.02 | 62.84 | 2.23 | 50.53 |
| SC377 | 14 | 24780133 | 24780195 | 1% | 2% | 12% | 9% | 29% | 11% | 2% | 1.26 | 8.92 | 6.65 | 21.77 | 8.09 | 1.18 |
| SC378 | 7 | 27196035 | 27196154 | 1% | 3% | 21% | 31% | 37% | 18% | 56% | 3.72 | 24.32 | 35.89 | 42.10 | 20.22 | 64.49 |
| SC379 | 1 | 6480815 | 6480859 | 1% | 3% | 11% | 8% | 40% | 5% | 11% | 4.03 | 17.19 | 12.38 | 61.31 | 7.48 | 17.22 |
| SC380 | 7 | 27195746 | 27195829 | 1% | 5% | 25% | 36% | 38% | 24% | 69% | 3.68 | 17.21 | 25.20 | 26.39 | 16.93 | 48.45 |
| SC381 | 5 | 178957576 | 178957695 | 1% | 2% | 15% | 18% | 41% | 17% | 24% | 3.97 | 29.20 | 34.94 | 78.81 | 31.81 | 45.24 |
| SC382 | 22 | 28198164 | 28198199 | 0% | 2% | 6% | 7% | 17% | 2% | 18% | 3.07 | 11.31 | 13.16 | 33.78 | 4.83 | 36.56 |
| SC383 | 5 | 77268624 | 77268718 | 1% | 2% | 12% | 22% | 34% | 7% | 21% | 3.72 | 21.82 | 40.13 | 61.10 | 12.77 | 38.23 |
| SC384 | 1 | 295866455 | 295866550 | 0% | 5% | 30% | 21% | 39% | 7% | 32% | 14.94 | 93.26 | 66.91 | 121.84 | 22.87 | 101.64 |
| SC385 | 4 | 13524253 | 13524378 | 1% | 2% | 7% | 21% | 28% | 11% | 23% | 3.50 | 10.37 | 32.37 | 43.87 | 17.49 | 36.14 |
| SC386 | 20 | 3052753 | 3052851 | 1% | 3% | 17% | 19% | 35% | 11% | 15% | 5.20 | 29.24 | 32.93 | 60.92 | 19.81 | 26.66 |
| SC387 | 1 | 78511734 | 78511827 | 1% | 2% | 15% | 32% | 24% | 15% | 51% | 2.91 | 18.47 | 39.63 | 29.28 | 18.15 | 62.64 |
| SC388 | 14 | 62217806 | 62217860 | 0% | 1% | 1% | 25% | 25% | 2% | 2% | 4.07 | 2.61 | 62.74 | 103.40 | 7.25 | 7.45 |
| SC389 | 1 | 232941214 | 232941254 | 0% | 0% | 2% | 10% | 10% | 1% | 1% | 1.43 | 5.41 | 34.37 | 33.30 | 4.75 | 4.09 |
| SC390 | 13 | 216649754 | 216649843 | 1% | 2% | 3% | 21% | 21% | 5% | 9% | 2.62 | 3.88 | 12.11 | 24.61 | 5.85 | 10.94 |
| SC391 | 18 | 5890808 | 5890841 | 1% | 2% | 1% | 9% | 35% | 4% | 16% | 1.59 | 0.97 | 8.79 | 34.81 | 3.53 | 15.72 |
| SC392 | 4 | 1161145 | 1161177 | 0% | 1% | 3% | 1% | 13% | 7% | 2% | 4.72 | 13.21 | 6.11 | 53.63 | 28.35 | 7.75 |
| SC393 | 5 | 1348790621 | 1348790709 | 1% | 2% | 5% | 21% | 40% | 6% | 35% | 3.43 | 8.06 | 33.63 | 65.55 | 9.28 | 56.82 |
| SC394 | 1 | 221052431 | 221052479 | 1% | 2% | 10% | 17% | 20% | 2% | 40% | 3.56 | 15.30 | 26.04 | 30.31 | 2.76 | 60.01 |
| SC395 | 2 | 232527285 | 232527325 | 1% | 3% | 4% | 5% | 32% | 9% | 17% | 3.87 | 5.99 | 6.44 | 43.13 | 11.79 | 23.75 |

FIG. 4 (cont'd)

| Small Cell marker region ref. # | Chromosome | Gene | Transcript | Strand | In Exon | Tss Distance | In CpG Island | Entrez ID | Gene title |
|---|---|---|---|---|---|---|---|---|---|
| SC373 | 22 | FAM109B | NM_001002034 | + | 0 | 178 | 1 | 150368 | family with sequence similarity 109, member B |
| SC374 | 2 | DOK1 | NM_001197260;NM_001381 | + | 0 | 5950;585 | 1 | 1796 | docking protein 1, 62kDa (downstream of tyrosine kinase 1) |
| SC375 | 1 | ATP2B4 | NM_001001396;NM_001684 | + | 0 | 2819;2819 | 1 | 493 | ATPase, Ca++ transporting, plasma membrane 4 |
| SC376 | 3 | MAX.chr3.4910281-4910325 | - | - | 0 | - | 1 | - | - |
| SC377 | 14 | CIDEB | NM_014430 | - | 1 | 443 | 1 | 27141 | cell death-inducing DFFA-like effector b |
| SC378 | 7 | HOXA7 | NM_006896 | - | 1 | 261 | 1 | 3204 | homeobox A7 |
| SC379 | 1 | ESPN | NM_031475 | + | 0 | -4032 | 1 | 83715 | espin |
| SC380 | 7 | HOXA7 | NM_006896 | - | 0 | 548 | 1 | 3204 | homeobox A7 |
| SC381 | 5 | MAX.chr5.178957576-178957695 | - | - | 0 | - | 1 | - | - |
| SC382 | 22 | MN1 | NM_002430 | - | 0 | -678 | 1 | 4330 | meningioma (disrupted in balanced translocation) 1 |
| SC383 | 5 | MAX.chr5.77268624-77268718 | - | - | 0 | - | 1 | - | - |
| SC384 | 1 | PTPRU | NM_133178;NM_133177;NM_0011 95001;NM_005704 | + | 1 | 23428;23428;23428;23 428 | 1 | 10076 | protein tyrosine phosphatase, receptor type, U |
| SC385 | 4 | MAX.chr4.13524253-13524378 | - | - | 0 | - | 1 | - | - |
| SC386 | 20 | OXT | NM_000915 | + | 1 | 488 | 1 | 5020 | oxytocin, prepropeptide |
| SC387 | 1 | GIPC2 | NM_017655 | + | 1 | 146 | 1 | 54810 | GIPC PDZ domain containing family, member 2 |
| SC388 | 14 | MAX.chr14.62217806-62217860 | - | - | 0 | - | 1 | - | - |
| SC389 | 1 | KIAA1383 | NM_019090 | + | 1 | 577 | 1 | 54627 | KIAA1383 |
| SC390 | 13 | MAX.chr13.21649754-21649843 | - | - | 0 | - | 0 | - | - |
| SC391 | 18 | TMEM200C | NM_001080209 | - | 1 | 1295 | 1 | 645369 | transmembrane protein 200C |
| SC392 | 4 | SPON2 | NM_012445;NM_001199021;NM_0 01128325 | - | 1 | 5512;41605;5854 | 1 | 10417 | spondin 2, extracellular matrix protein |
| SC393 | 5 | MAX.chr5.134879621-134879709 | - | - | 0 | - | 1 | - | - |
| SC394 | 1 | HLX | NM_021958 | + | 0 | -311 | 1 | 3142 | H2.0-like homeobox |
| SC395 | 2 | MAX.chr2.232527285-232527325 | - | - | 0 | - | 1 | - | - |

FIG. 5

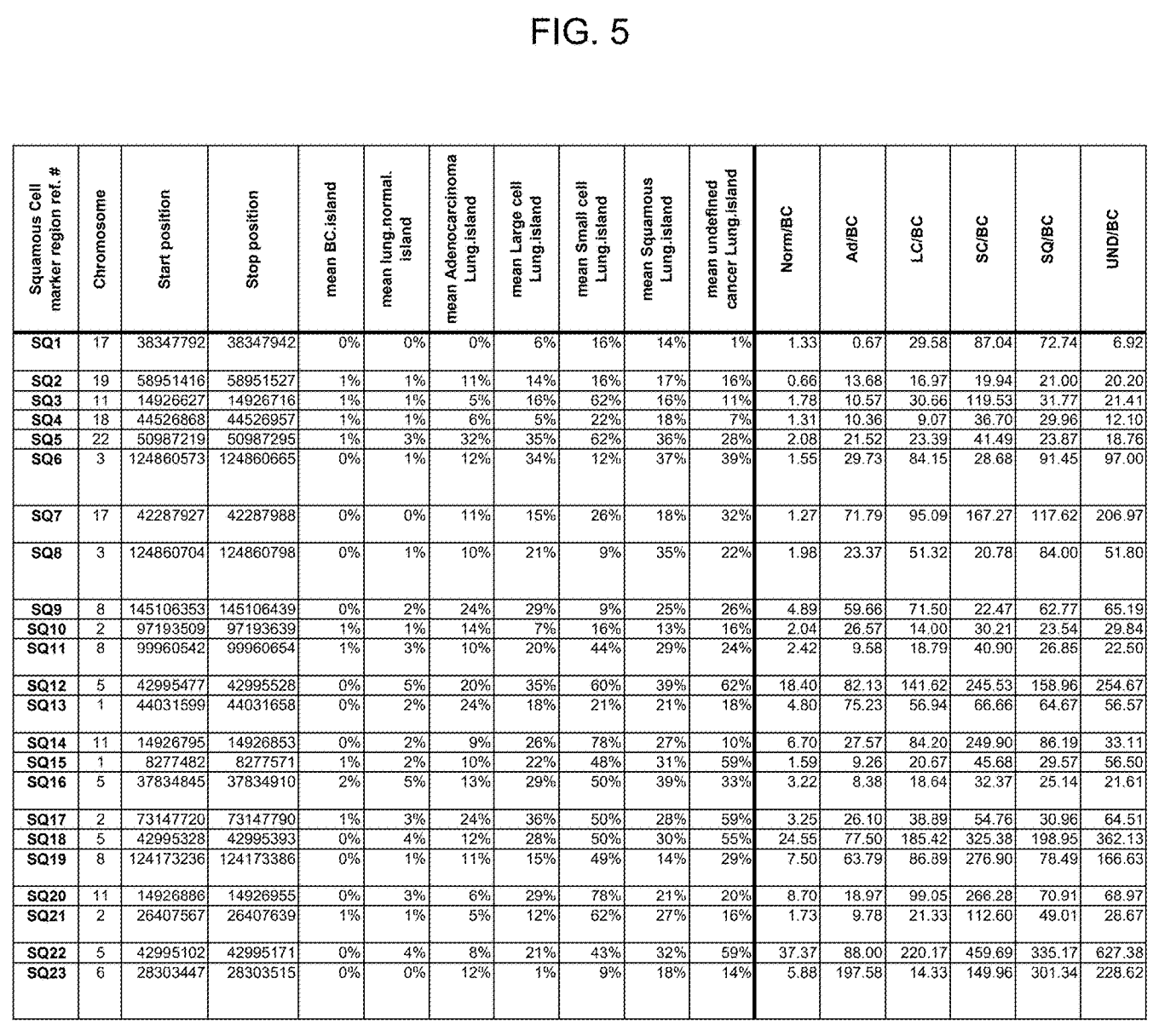

| Squamous Cell marker region ref. # | Chromosome | Start position | Stop position | mean BC.island | mean lung.normal. island | mean Adenocarcinoma Lung.island | mean Large cell Lung.island | mean Small cell Lung.island | mean Squamous Lung.island | mean undefined Lung cancer island | Norm/BC | Ad/BC | LC/BC | SC/BC | SQ/BC | UND/BC |
|---|---|---|---|---|---|---|---|---|---|---|---|---|---|---|---|---|
| SQ1 | 17 | 38347792 | 38347942 | 0% | 0% | 0% | 6% | 16% | 14% | 1% | 1.33 | 0.67 | 29.58 | 87.04 | 72.74 | 6.92 |
| SQ2 | 19 | 58951416 | 58951527 | 1% | 1% | 11% | 14% | 16% | 17% | 16% | 0.66 | 13.68 | 16.97 | 19.94 | 21.00 | 20.20 |
| SQ3 | 11 | 14926627 | 14926716 | 1% | 1% | 5% | 16% | 62% | 16% | 11% | 1.78 | 10.57 | 30.66 | 119.53 | 31.77 | 21.41 |
| SQ4 | 18 | 44526868 | 44526957 | 1% | 1% | 6% | 5% | 22% | 18% | 7% | 1.31 | 10.36 | 9.07 | 36.70 | 29.96 | 12.10 |
| SQ5 | 22 | 50987219 | 50987295 | 1% | 3% | 32% | 35% | 62% | 36% | 28% | 2.08 | 21.52 | 23.39 | 41.49 | 23.87 | 18.76 |
| SQ6 | 3 | 124860573 | 124860665 | 0% | 1% | 12% | 34% | 12% | 37% | 39% | 1.55 | 29.73 | 84.15 | 28.68 | 91.45 | 97.00 |
| SQ7 | 17 | 42287927 | 42287988 | 0% | 0% | 11% | 15% | 26% | 18% | 32% | 1.27 | 71.79 | 95.09 | 167.27 | 117.62 | 206.97 |
| SQ8 | 3 | 124860704 | 124860798 | 0% | 1% | 10% | 21% | 9% | 35% | 22% | 1.98 | 23.37 | 51.32 | 20.78 | 84.00 | 51.80 |
| SQ9 | 8 | 145106353 | 145106439 | 0% | 2% | 24% | 29% | 9% | 25% | 26% | 4.89 | 59.66 | 71.50 | 22.47 | 62.77 | 65.19 |
| SQ10 | 2 | 97193509 | 97193639 | 1% | 1% | 14% | 7% | 16% | 13% | 16% | 2.04 | 26.57 | 14.00 | 30.21 | 23.54 | 29.84 |
| SQ11 | 8 | 99960542 | 99960654 | 1% | 3% | 10% | 20% | 44% | 29% | 24% | 2.42 | 9.58 | 18.79 | 40.90 | 26.85 | 22.50 |
| SQ12 | 5 | 42995477 | 42995528 | 0% | 5% | 20% | 35% | 60% | 39% | 62% | 18.40 | 82.13 | 141.62 | 245.53 | 158.96 | 254.67 |
| SQ13 | 1 | 44031599 | 44031658 | 0% | 2% | 24% | 18% | 21% | 21% | 18% | 4.80 | 75.23 | 56.94 | 66.66 | 64.67 | 56.57 |
| SQ14 | 11 | 14926795 | 14926853 | 0% | 2% | 9% | 26% | 78% | 27% | 10% | 6.70 | 27.57 | 84.20 | 249.90 | 86.19 | 33.11 |
| SQ15 | 1 | 8277482 | 8277571 | 1% | 2% | 10% | 22% | 48% | 31% | 59% | 1.59 | 9.26 | 20.67 | 45.68 | 29.57 | 56.50 |
| SQ16 | 5 | 37834845 | 37834910 | 2% | 5% | 13% | 29% | 50% | 39% | 33% | 3.22 | 8.38 | 18.64 | 32.37 | 25.14 | 21.61 |
| SQ17 | 2 | 73147720 | 73147790 | 1% | 3% | 24% | 36% | 50% | 28% | 59% | 3.25 | 26.10 | 38.89 | 54.76 | 30.96 | 64.51 |
| SQ18 | 5 | 42995328 | 42995393 | 0% | 4% | 12% | 28% | 50% | 30% | 55% | 24.55 | 77.50 | 185.42 | 325.38 | 198.95 | 362.13 |
| SQ19 | 8 | 124173236 | 124173386 | 0% | 1% | 11% | 15% | 49% | 14% | 29% | 7.50 | 63.79 | 86.89 | 276.90 | 78.49 | 166.63 |
| SQ20 | 11 | 14926886 | 14926955 | 0% | 3% | 6% | 29% | 78% | 21% | 20% | 8.70 | 18.97 | 99.05 | 266.28 | 70.91 | 68.97 |
| SQ21 | 2 | 26407567 | 26407639 | 1% | 1% | 5% | 12% | 62% | 27% | 16% | 1.73 | 9.78 | 21.33 | 112.60 | 49.01 | 28.67 |
| SQ22 | 5 | 42995102 | 42995171 | 0% | 4% | 8% | 21% | 43% | 32% | 59% | 37.37 | 88.00 | 220.17 | 459.69 | 335.17 | 627.38 |
| SQ23 | 6 | 28303447 | 28303515 | 0% | 0% | 12% | 1% | 9% | 18% | 14% | 5.88 | 197.58 | 14.33 | 149.96 | 301.34 | 228.62 |

FIG. 5 (cont'd)

| Squamous Cell marker region ref. # | Chromosome | Gene | Transcript | Strand | In Exon | Tss Distance | In CpG Island | Entrez ID | Gene title |
|---|---|---|---|---|---|---|---|---|---|
| SQ1 | 17 | RAPGEFL1 | NM_016339 | + | 0 | 13551 | 0 | 51195 | Rap guanine nucleotide exchange factor (GEF)-like 1 |
| SQ2 | 19 | ZNF132 | NM_003433 | - | 1 | 173 | 1 | 7691 | zinc finger protein 132 |
| SQ3 | 11 | MAX.chr11.14926627-14926716 | - | - | 0 | - | 1 | - | - |
| SQ4 | 18 | KATNAL2 | NM_031303 | + | 1 | 82 | 1 | 83473 | katanin p60 subunit A-like 2 |
| SQ5 | 22 | KLHDC7B | NM_138433 | + | 1 | 758 | 1 | 113730 | kelch domain containing 7B |
| SQ6 | 3 | SLC12A8 | NM_001195483;NM_024628 | - | 0 | 69670;71036 | 1 | 84561 | solute carrier family 12 (potassium/chloride transporters), member 8 |
| SQ7 | 17 | UBTF | NM_001076684;NM_001076683;NM_014233 | - | 0 | 8997;10323;7737 | 1 | 7343 | upstream binding transcription factor, RNA polymerase I |
| SQ8 | 3 | SLC12A8 | NM_001195483;NM_024628 | - | 0 | 69539;70905 | 1 | 84561 | solute carrier family 12 (potassium/chloride transporters), member 8 |
| SQ9 | 8 | OPLAH | NM_017570 | - | 1 | 9231 | 1 | 26873 | 5-oxoprolinase (ATP-hydrolysing) |
| SQ10 | 2 | MAX.chr2.97193509-97193639 | - | - | 0 | - | 0 | - | - |
| SQ11 | 8 | OSR2 | NM_001142462;NM_053001 | + | 0 | 3912;3912 | 1 | 116039 | odd-skipped related 2 (Drosophila) |
| SQ12 | 5 | MAX.chr5.42995477-42995528 | - | - | 0 | - | 0 | - | - |
| SQ13 | 1 | PTPRF | NM_002840;NM_130440 | + | 0 | 35053;35053 | 1 | 5792 | protein tyrosine phosphatase, receptor type, F |
| SQ14 | 11 | MAX.chr11.14926795-14926853 | - | - | 0 | - | 1 | - | - |
| SQ15 | 1 | MAX.chr1.8277482-8277571 | - | - | 0 | - | 1 | - | - |
| SQ16 | 5 | GDNF | NM_001190469;NM_001190468;NM_000514;NM_199231 | - | 1 | 1084;1084;4937;748 | 1 | 2668 | glial cell derived neurotrophic factor |
| SQ17 | 2 | EMX1 | NM_004097 | + | 0 | 3117 | 1 | 2016 | empty spiracles homeobox 1 |
| SQ18 | 5 | MAX.chr5.42995328-42995393 | - | - | 0 | - | 1 | - | - |
| SQ19 | 8 | MAX.chr8.124173236-124173386 | - | - | 0 | - | 1 | - | - |
| SQ20 | 11 | MAX.chr11.14926886-14926955 | - | - | 0 | - | 1 | - | - |
| SQ21 | 2 | FAM59B | NM_001191033;NM_001168241 | + | 1 | 3983;11608 | 1 | 150946 | family with sequence similarity 59, member B |
| SQ22 | 5 | MAX.chr5.42995102-42995171 | - | - | 0 | - | 0 | - | - |
| SQ23 | 6 | ZNF323 | NM_145909;NR_024164;NM_0011 35216;NM_030899;NM_0011135215; NR_024165 | - | 0 | 18525;464;464;705;206 01;705 | 0 | 64288 | zinc finger protein 323 |

FIG. 5 (cont'd)

| Squamous Cell marker region ref. # | Chromosome | Start position | Stop position | mean BC.island | mean lung.normal,.island | mean Adenocarcinoma Lung.island | mean Large cell Lung.island | mean Small cell Lung.island | mean Squamous Lung.island | mean undefined Lung cancer island | Norm/BC | Ad/BC | LC/BC | SC/BC | SQ/BC | UND/BC |
|---|---|---|---|---|---|---|---|---|---|---|---|---|---|---|---|---|
| SQ24 | 19 | 37095829 | 37095999 | 1% | 1% | 23% | 23% | 19% | 19% | 41% | 1.82 | 28.94 | 28.12 | 23.98 | 23.78 | 50.92 |
| SQ25 | 8 | 145106742 | 145106827 | 0% | 2% | 26% | 34% | 10% | 21% | 14% | 5.40 | 81.76 | 108.02 | 31.02 | 68.54 | 45.26 |
| SQ26 | 5 | 37834716 | 37834762 | 2% | 4% | 16% | 25% | 51% | 36% | 36% | 2.51 | 9.42 | 14.77 | 30.36 | 21.39 | 21.50 |
| SQ27 | 2 | 99439270 | 99439356 | 1% | 3% | 24% | 31% | 81% | 32% | 56% | 2.54 | 19.21 | 25.16 | 66.32 | 26.30 | 45.23 |
| SQ28 | 1 | 248020671 | 248020722 | 1% | 4% | 31% | 40% | 63% | 33% | 63% | 3.31 | 23.46 | 30.04 | 47.26 | 24.66 | 47.74 |
| SQ29 | 17 | 383348024 | 383348072 | 0% | 0% | 1% | 7% | 7% | 15% | 0% | 0.84 | 2.22 | 14.28 | 13.90 | 29.67 | 0.00 |
| SQ30 | 20 | 61560692 | 61560749 | 0% | 1% | 6% | 13% | 62% | 19% | 28% | 5.65 | 24.19 | 56.55 | 258.74 | 79.08 | 115.84 |
| SQ31 | 3 | 122296709 | 122296828 | 0% | 3% | 17% | 23% | 65% | 25% | 61% | 5.87 | 39.97 | 54.78 | 151.39 | 57.49 | 143.28 |
| SQ32 | 2 | 26407721 | 26407876 | 0% | 1% | 2% | 11% | 47% | 18% | 16% | 2.39 | 8.36 | 36.01 | 160.15 | 60.97 | 56.07 |
| SQ33 | 10 | 22541891 | 225541996 | 0% | 2% | 13% | 22% | 49% | 18% | 24% | 5.71 | 36.56 | 63.36 | 141.74 | 52.16 | 69.90 |
| SQ34 | 8 | 145105570 | 145105675 | 1% | 3% | 30% | 26% | 9% | 29% | 23% | 3.15 | 29.77 | 25.41 | 9.23 | 28.54 | 22.59 |
| SQ35 | 15 | 65116396 | 65116440 | 0% | 1% | 11% | 21% | 5% | 25% | 2% | 5.61 | 51.82 | 98.18 | 22.13 | 114.94 | 10.41 |
| SQ36 | 2 | 74782325 | 74782452 | 0% | 2% | 1% | 10% | 12% | 21% | 12% | 20.45 | 11.21 | 82.60 | 106.15 | 183.80 | 103.64 |
| SQ37 | 5 | 37834916 | 37835022 | 1% | 5% | 9% | 28% | 55% | 37% | 42% | 4.35 | 7.78 | 25.11 | 49.26 | 33.19 | 37.95 |
| SQ38 | 2 | 74782096 | 74782223 | 0% | 1% | 1% | 10% | 15% | 22% | 12% | 2.00 | 2.91 | 35.72 | 55.09 | 79.79 | 42.48 |
| SQ39 | 17 | 75370492 | 75370581 | 0% | 1% | 2% | 8% | 2% | 10% | 12% | 1.80 | 4.40 | 17.44 | 3.81 | 22.86 | 26.56 |
| SQ40 | 17 | 27940477 | 27940568 | 0% | 1% | 5% | 9% | 59% | 22% | 25% | 3.44 | 21.98 | 34.20 | 238.86 | 87.69 | 99.96 |
| SQ41 | 6 | 6004298 | 6004338 | 1% | 5% | 21% | 40% | 58% | 34% | 61% | 7.31 | 33.74 | 64.23 | 93.83 | 54.50 | 99.42 |
| SQ42 | 17 | 8054628 | 8054698 | 0% | 1% | 12% | 5% | 7% | 12% | 11% | 16.75 | 186.95 | 78.17 | 101.84 | 186.95 | 166.28 |
| SQ43 | 17 | 73073700 | 73073810 | 0% | 0% | 0% | 15% | 8% | 17% | 0% | 1.26 | 1.07 | 39.05 | 21.72 | 46.29 | 0.42 |

FIG. 5 (cont'd)

| Squamous Cell marker region ref. # | Chromosome | Gene | Transcript | Strand | In Exon | Tss Distance | In CpG Island | Entrez ID | Gene title |
|---|---|---|---|---|---|---|---|---|---|
| SQ24 | 19 | ZNF382 | NM_032825 | + | 0 | -391 | 1 | 84911 | zinc finger protein 382 |
| SQ25 | 8 | OPLAH | NM_017570 | - | 0 | 8842 | 1 | 26873 | 5-oxoprolinase (ATP-hydrolysing) |
| SQ26 | 5 | GDNF | NM_001190469;NM_001190468;NM_199231 | - | 0 | 1213;1213;5066,877 | 1 | 2668 | glial cell derived neurotrophic factor |
| SQ27 | 2 | C2orf55 | NM_000514;NM_207362 | - | 1 | 113414 | 1 | 343990 | chromosome 2 open reading frame 55 |
| SQ28 | 1 | TRIM58 | NM_015431 | + | 1 | 171 | 1 | 25893 | tripartite motif-containing 58 |
| SQ29 | 17 | RAPGEFL1 | NM_016339 | + | 0 | 13783 | 0 | 51195 | Rap guanine nucleotide exchange factor (GEF)-like 1 |
| SQ30 | 20 | DIDO1 | NM_033081;NM_001193369;NM_022105;NM_080797;NM_001193370;NM_080796 | - | 0 | 8612;-2789;8612;8612;-2789;-2789 | 1 | 11083 | death inducer-obliterator 1 |
| SQ31 | 3 | PARP15 | NM_001113523 | + | 0 | 261 | 1 | 165631 | poly (ADP-ribose) polymerase family, member 15 |
| SQ32 | 2 | FAM59B | NM_001191033;NM_001168241 | + | 1 | 4137;11762 | 1 | 150946 | family with sequence similarity 59, member B |
| SQ33 | 10 | MAX.chr10.225441891-225541996 | - | - | 0 | - | 1 | - | - |
| SQ34 | 8 | MAX.chr8.145105570-145105675 | - | - | 0 | - | 1 | - | - |
| SQ35 | 15 | PIF1 | NM_025049 | - | 1 | 1442 | 1 | 80119 | PIF1 5'-to-3' DNA helicase homolog (S. cerevisiae) |
| SQ36 | 2 | DOK1 | NM_001197260;NM_001381 | + | 1 | 6179;814 | 1 | 1796 | docking protein 1, 62kDa (downstream of tyrosine kinase 1) |
| SQ37 | 5 | GDNF | NM_001190469;NM_001190468;NM_199231 | - | 1 | 1013;1013;4866;677 | 1 | 2668 | glial cell derived neurotrophic factor |
| SQ38 | 2 | DOK1 | NM_001197260;NM_001381 | + | 0 | 5950;585 | 1 | 1796 | docking protein 1, 62kDa (downstream of tyrosine kinase 1) |
| SQ39 | 17 | SEPT9 | NM_006640;NM_001113494;NM_001113492;NM_001113493;NM_001113491 | + | 0 | 54896;-1672;86520;1221;9300 | 1 | 10801 | septin 9 |
| SQ40 | 17 | ANKRD13B | NM_152345 | + | 1 | 19951 | 1 | 124930 | ankyrin repeat domain 13B |
| SQ41 | 6 | NRN1 | NM_016588 | - | 0 | 3335 | 1 | 51299 | neuritin 1 |
| SQ42 | 17 | PER1 | NM_002616 | - | 0 | 1125 | 1 | 5187 | period homolog 1 (Drosophila) |
| SQ43 | 17 | MAX.chr17.73073700-73073810 | - | - | 0 | - | 1 | - | - |

FIG. 5 (cont'd)

| Squamous Cell marker region ref. # | Chromosome | Start position | Stop position | mean BC.island | mean normal.lung.island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SQ44 | 5 | 125930731 | 125930884 | 1% | 1% | 2% | 2% | 4% | 16% | 1% | 1.35 | 2.90 | 2.71 | 5.70 | 25.34 | 2.38 |
| SQ45 | 15 | 65116474 | 65116558 | 1% | 1% | 9% | 15% | 9% | 18% | 1% | 1.58 | 12.74 | 21.62 | 13.62 | 26.30 | 1.26 |
| SQ46 | 17 | 58499109 | 58499183 | 0% | 1% | 1% | 5% | 35% | 18% | 8% | 4.22 | 4.26 | 17.93 | 124.48 | 63.79 | 28.58 |
| SQ47 | 2 | 97193166 | 97193253 | 0% | 1% | 13% | 8% | 18% | 12% | 21% | 1.71 | 42.20 | 25.79 | 55.43 | 37.48 | 67.24 |
| SQ48 | 2 | 118981859 | 118981945 | 1% | 3% | 14% | 33% | 42% | 28% | 29% | 4.14 | 18.40 | 42.45 | 53.71 | 35.86 | 36.89 |
| SQ49 | 7 | 44349487 | 44349591 | 1% | 2% | 5% | 12% | 28% | 22% | 8% | 2.50 | 6.77 | 18.13 | 42.68 | 32.86 | 12.23 |
| SQ50 | 17 | 17627469 | 17627534 | 1% | 1% | 17% | 7% | 0% | 19% | 11% | 0.77 | 21.31 | 8.72 | 0.57 | 23.63 | 14.12 |
| SQ51 | 3 | 194208259 | 194208403 | 0% | 1% | 2% | 5% | 17% | 19% | 0% | 13.82 | 28.44 | 67.56 | 241.94 | 276.52 | 0.90 |
| SQ52 | 1 | 223936868 | 223936997 | 0% | 1% | 7% | 18% | 45% | 16% | 28% | 2.13 | 26.29 | 63.20 | 158.81 | 57.13 | 99.50 |
| SQ53 | 19 | 58238816 | 58238942 | 0% | 1% | 8% | 15% | 24% | 17% | 33% | 8.09 | 94.63 | 175.66 | 277.57 | 203.93 | 390.90 |
| SQ54 | 12 | 25055873 | 25055997 | 0% | 1% | 10% | 22% | 29% | 12% | 40% | 4.32 | 36.00 | 77.51 | 103.02 | 44.17 | 140.87 |
| SQ55 | 11 | 68622903 | 68622965 | 0% | 1% | 2% | 9% | 3% | 18% | 9% | 3.04 | 8.34 | 32.82 | 11.85 | 69.07 | 34.24 |
| SQ56 | 5 | 32710286 | 32710370 | 0% | 1% | 2% | 7% | 3% | 12% | 8% | 1.27 | 5.55 | 15.98 | 7.31 | 29.70 | 18.40 |
| SQ57 | 1 | 46632701 | 46632852 | 1% | 1% | 5% | 11% | 11% | 13% | 1% | 2.20 | 7.44 | 18.33 | 18.34 | 20.29 | 1.03 |
| SQ58 | 3 | 32443052 | 32443156 | 0% | 0% | 1% | 8% | 2% | 10% | 1% | 1.22 | 1.50 | 20.54 | 5.05 | 26.69 | 2.69 |
| SQ59 | 15 | 90319850 | 90319863 | 0% | 0% | 0% | 4% | 0% | 13% | 0% | 0.84 | 0.00 | 10.45 | 0.72 | 34.01 | 0.00 |
| SQ60 | 17 | 43339264 | 43339345 | 1% | 1% | 4% | 11% | 41% | 12% | 11% | 1.45 | 8.50 | 22.19 | 82.48 | 23.48 | 21.17 |
| SQ61 | 19 | 37288426 | 37288510 | 0% | 1% | 15% | 22% | 30% | 19% | 27% | 1.79 | 39.22 | 55.94 | 78.85 | 49.81 | 69.01 |
| SQ62 | 8 | 145104291 | 145104342 | 0% | 1% | 6% | 13% | 3% | 12% | 10% | 3.80 | 26.23 | 54.77 | 13.90 | 49.84 | 41.94 |

FIG. 5 (cont'd)

| Squamous Cell marker region ref. # | Chromosome | Gene | Transcript | Strand | In Exon | Tss Distance | In CpG Island | Entrez ID | Gene title |
|---|---|---|---|---|---|---|---|---|---|
| SQ44 | 5 | ALDH7A1 | NM_001182 | - | 1 | 351 | 1 | 501 | aldehyde dehydrogenase 7 family, member A1 |
| SQ45 | 15 | PIF1 | NM_025049 | - | 1 | 1364 | 1 | 80119 | PIF1 5'-to-3' DNA helicase homolog (S. cerevisiae) |
| SQ46 | 17 | C17orf64 | NM_181707 | + | 0 | -755 | 1 | 124773 | chromosome 17 open reading frame 64 |
| SQ47 | 2 | MAX.chr2.97193166-97193253 | - | - | 0 | - | 1 | - | - |
| SQ48 | 2 | MAX.chr2.118981859-118981945 | - | - | 0 | - | 1 | - | - |
| SQ49 | 7 | CAMK2B | NM_172078;NM_172084;NM_1720 83;NM_001220;NM_172080;NM_17 2079;NM_172082;NM_172081 | - | 0 | 15743;15743;15743;15743;15 743;15743;15743;1574 3;15743 | 1 | 816 | calcium/calmodulin-dependent protein kinase II beta |
| SQ50 | 17 | RAI1 | NM_030665 | + | 1 | 42683 | 1 | 10743 | retinoic acid induced 1 |
| SQ51 | 3 | FLJ34208 | NR_033929 | + | 1 | 391 | 1 | 401106 | hypothetical LOC401106 |
| SQ52 | 1 | CAPN2 | NM_001146068;NM_001748 | + | 0 | 47574;36750 | 1 | 824 | calpain 2, (m/II) large subunit |
| SQ53 | 19 | ZNF671 | NM_024833 | - | 1 | 179 | 1 | 79891 | zinc finger protein 671 |
| SQ54 | 12 | BCAT1 | NM_001178092;NM_005504;NM_0 01178094;NM_001178091;NM_001 178093 | - | 0 | 46520;46520;- 551;46520;136 | 1 | 586 | branched chain amino-acid transaminase 1, cytosolic |
| SQ55 | 11 | MAX.chr11.68622903-68622965 | - | - | 0 | - | 1 | - | - |
| SQ56 | 5 | NPR3 | NM_000908 | + | 0 | -1378 | 1 | 4883 | natriuretic peptide receptor C/guanylate cyclase C (atrionatriuretic peptide receptor C) |
| SQ57 | 1 | MAX.chr1.46632701-46632852 | - | - | 0 | - | 0 | - | - |
| SQ58 | 3 | CMTM7 | NM_138410;NM_181472 | + | 0 | 9890;9890 | 0 | 112616 | CKLF-like MARVEL transmembrane domain containing 7 |
| SQ59 | 15 | MESP2 | NM_001039958 | + | 1 | 262 | 1 | 145873 | mesoderm posterior 2 homolog (mouse) |
| SQ60 | 17 | C17orf46 | NM_152343 | - | 0 | 215 | 1 | 124783 | chromosome 17 open reading frame 46 |
| SQ61 | 19 | MAX.chr19.37288426-37288510 | - | - | 0 | - | 1 | - | - |
| SQ62 | 8 | MAX.chr8.145104291-145104342 | - | - | 0 | - | 1 | - | - |

FIG. 5 (cont'd)

| Squamous Cell marker region ref. # | Chromosome | Start position | Stop position | mean BC.island | mean lung.normal.island | mean Adenocarcinoma Lung.island | mean Large cell Lung.island | mean Small cell Lung.island | mean Squamous Lung.island | mean undefined cancer Lung.island | Norm/BC | Ad/BC | LC/BC | SC/BC | SQ/BC | UND/BC |
|---|---|---|---|---|---|---|---|---|---|---|---|---|---|---|---|---|
| SQ63 | 8 | 145104247 | 145104276 | 0% | 1% | 5% | 13% | 3% | 11% | 7% | 9.51 | 48.36 | 126.04 | 32.55 | 112.97 | 73.75 |
| SQ64 | 3 | 128212061 | 128212125 | 0% | 2% | 10% | 16% | 4% | 20% | 25% | 7.50 | 33.85 | 56.41 | 12.62 | 68.60 | 85.89 |
| SQ65 | 21 | 38119920 | 38119971 | 0% | 1% | 0% | 8% | 7% | 11% | 9% | 1.98 | 0.80 | 16.93 | 14.11 | 23.88 | 18.66 |
| SQ66 | 19 | 37288523 | 37288615 | 1% | 2% | 19% | 22% | 26% | 18% | 30% | 2.72 | 25.92 | 30.28 | 34.88 | 24.73 | 40.51 |
| SQ67 | 1 | 226925087 | 226925208 | 0% | 1% | 3% | 9% | 2% | 11% | 1% | 1.79 | 7.13 | 25.23 | 5.25 | 29.82 | 3.21 |
| SQ68 | 19 | 17346575 | 17346695 | 0% | 1% | 9% | 24% | 2% | 13% | 20% | 6.09 | 68.86 | 178.14 | 15.24 | 98.45 | 144.24 |

FIG. 5 (cont'd)

| Squamous Cell marker region ref. # | Chromosome | Gene | Transcript | Strand | In Exon | Tss Distance | In CpG Island | Entrez ID | Gene title |
|---|---|---|---|---|---|---|---|---|---|
| SQ63 | 8 | MAX.chr8.145104247-145104276 | - | - | 0 | - | 1 | - | - |
| SQ64 | 3 | GATA2 | NM_032638;NM_001145661 | - | 0 | -31;-4688 | 1 | 2624 | GATA binding protein 2 |
| SQ65 | 21 | SIM2 | NM_005069 | + | 0 | 47930 | 1 | 6493 | single-minded homolog 2 (Drosophila) |
| SQ66 | 19 | MAX.chr19.37288523-37288615 | - | - | 0 | - | 1 | - | - |
| SQ67 | 1 | ITPKB | NM_002221 | - | 1 | 1789 | 1 | 3707 | inositol 1,4,5-trisphosphate 3-kinase B |
| SQ68 | 19 | NR2F6 | NM_005234 | - | 1 | 9576 | 1 | 2063 | nuclear receptor subfamily 2, group F, member 6 |

FIG. 6

| SEQ ID NO | Description | Sequence (all are shown 5' to 3') |
|---|---|---|
| SEQ ID NO:1 | AGRN Target DNA | GTTCCCGGAACGGCCCTCTTGGGGGGCGGTTCCAGCCCACGGACCCCGCAGGGAGTCCCCGCCGCAATTTGCATGGGGGC TCATTTGCATGACGACCCCGCCCCGCCCCGCGGGGAGTCGGGGGCGC |
| SEQ ID NO:2 | AGRN Converted DNA | GTTTTCGGAACGGTTTTTGTTTGGGGGGCGTTTAGTTTTACGGATTCGTAGGGAGTTTTCGTCGTAATTGTATGGGGGTTT ATTTGTATGATTTCGTTTCGCGCGGGAGTCGGGGGCGT |
| SEQ ID NO:3 | AGRN Forward Primer | GGCGTTTTAGTTTTACGGATTCG |
| SEQ ID NO:4 | AGRN Reverse Primer | ACAAATAAACCCCATACAAATTACGAC |
| SEQ ID NO:5 | AGRN Flap oligonucleotide | CGCCGAGGCGAAAACTCCCT/3C6/ |
| SEQ ID NO:6 | ANGPT1 Target DNA | CGGATTCAACATGGCAATGTGCTCACACTTTCATTCTTCCAGAACACGATGGCAACTGTCGTGAGAGTACGACAGA CCAGTACAACACAAACGCTCTGCAGAGAGATGCTCCACACGTGGAACCG |
| SEQ ID NO:7 | ANGPT1 Converted DNA | CGGATTTAATATGGGTAATGTGTTTATATTTTTATTTTTTAGAATACGATGGTAATTGTCGTGAGAGTACGATAGAT TAGTATAATATAAACGTTTTGTAGAGAGATGTTTTATACGTGGAATCG |
| SEQ ID NO:8 | ANGPT1 Forward Primer | TTTTAGAATACGATGGTAATTGTCGT |
| SEQ ID NO:9 | ANGPT1 Reverse Primer | ACATCTCTCTACAAAACGTTTATATTATTATTACTAATC |
| SEQ ID NO:10 | ANGPT1 Flap oligonucleotide | CGCCGAGGCTATCGTACTCT/3C6/ |
| SEQ ID NO:11 | ANKRD13B Target DNA | GGAGCTACGACGAGCAGCTGCGGCTGGCGATGGAACTGTCGCGGCAGGAGCAGGAGGAGGAGGCGGCGGCGCGC GCGCCAGGAGGAGGAGGAGGAGCTGGAGCGCATCCTGAG |
| SEQ ID NO:12 | ANKRD13B Converted DNA | GGAGTTACGACGAGTAGTTGCGGTTGGCGATGGAATTGTCGCGGCAGGAGTAGGAGGAGGAGGCGGCGGCGCGCG CGTTAGGAGGAGGAGGAGTTGGAGCGTATTTTGAG |
| SEQ ID NO:13 | ANKRD13B Forward Primer | AGTTACGACGAGTAGTTGCG |
| SEQ ID NO:14 | ANKRD13B Reverse Primer | TCCTCCTACTCCTACGCC |
| SEQ ID NO:15 | ANKRD13B Flap oligonucleotide | CCACGGACGCGACAATTCCAT/3C6/ |
| SEQ ID NO:16 | ARHGEF4 Target DNA | GGTGGCAACGGCTGGAGTGCCGTCGCCGCCCACTCACCCGCGCGCGCCCTGCGCGCGGCCGCTCAGCGGAAG GCCAGCAGGAAGATCAGTACGACGTTGATGAACCAGGAGCGCCAGCACGCGGAGACCACCACGCG |
| SEQ ID NO:17 | ARHGEF4 Converted DNA | GGTGGTAACGGTTGGAGTGTCGTCGTTGCGGTTATTTATTTCGGCGCGCGTTTTGCGCGCGGCGTGTTTAGCGGAAGGT TAGTAGGAAGATTAGTACGACGTTGATGAAGAATTAGGAGCGTTAGTACGGCGGAGATTATTACGCG |
| SEQ ID NO:18 | ARHGEF4 Forward Primer | CGTTCGCGGTTATTTATTTCGGCG |
| SEQ ID NO:19 | ARHGEF4 Reverse Primer | GCTCCTAATTCTCATCAACGTCGT |
| SEQ ID NO:20 | ARHGEF4 Flap oligonucleotide | CGCCGAGGGCGGCGGCGTTTTTGC/3C6/ |
| SEQ ID NO:21 | BARX1 Target DNA | GGCCCGGGCGGCCGCCTGGGCCCTAGGGGGCTGGACGTCAACCTGTTAGATAGAGGGCGTGGGACCCCCCGCAGGCG GCTGCTCGGACGACGACCGCATCCGGAG |
| SEQ ID NO:22 | BARX1 Converted DNA | GGTTCGGGGTCGTTGGGTTTTTAGGGGTTGGACGTTAATTTGTTAGATAGAGGGCGTGGGATTTTTTCGTAGGCGG TTGTTCGGACGATCGTATTCGGAG |
| SEQ ID NO:23 | BARX1 Forward Primer | CGTTAATTTGTTAGATAGAGGGCG |
| SEQ ID NO:24 | BARX1 Reverse Primer | ACGATCGTCCGAACAACC |
| SEQ ID NO:25 | BARX1 Flap oligonucleotide | CCACGGACGCGCCTACGAAAA/3C6/ |
| SEQ ID NO:26 | BARX1 Reverse Primer Universal | TCCGAACAACCGCCTAC |

FIG. 6 (cont'd)

| | Description | Sequence (all are shown 5' to 3') |
|---|---|---|
| SEQ ID NO:27 | BARX1 Flap oligonucleotide Universal | CCACGGACGCGAAAAATCCCA/3C6/ |
| SEQ ID NO:28 | BCAT1 Target DNA | GCTTCCAGCCGCGCGGCTCCGTCCGTGCCACTGCCGGCTCTCTGCAGCCCGGCTCCCGAGCCTCCCATGGCCAGCCCGC TTCGCTTCCGCTGCGGCGCCCTTGCCCGCCAGGTACCTCGAACCC |
| SEQ ID NO:29 | BCAT1 Converted DNA | GTTTTAGTCGCGGCGGTTTCGTGTTATTGTGTTTTGTTAGTTCGCGTTTCGTAGTTTTTTATGGTTAGTTCGTTTC GTTCGTTGCGGTTTTTGTTCGTTAGGTATTTCGAATTT |
| SEQ ID NO:30 | BCAT1 Forward Primer | GTGTTATTGTCGTTTTTGTAGTTTCG |
| SEQ ID NO:31 | BCAT1 Reverse Primer | CGCAACGAAACGAAACGA |
| SEQ ID NO:32 | BCAT1 Flap oligonucleotide | CGCCGAGGGCGTTTTCGTAG/3C6/ |
| SEQ ID NO:33 | BCL2L11 Target DNA | GCCCGCCGCACGCGCAATGCTCCGCGCTCCCCGCGGGGTCGGGCGACTCAGACAGGACCGGAAAAGAACCACG CAGAAGAAAGCCCTATTTCTTGTCGTCGTTGTCGTCGTTCCTGTGCAGCCTGCAGCCTCGCCGCCCCGCGT |
| SEQ ID NO:34 | BCL2L11 Converted DNA | GTTCGTCGTACGTCGTAATGTTTCGCGTTTTCGCGGTTTTTGTTTGTTTTTTGTGTAGTTTTGTCGTTTTCGCGT GAAGAAAGTTTATTTTGTCGTTGTTTGTTGTGTAGTTTTGTCGTTTTCGCGT |
| SEQ ID NO:35 | BCL2L11 Forward Primer | CGTAATGTTTCGCGTTTTCG |
| SEQ ID NO:36 | BCL2L11 Reverse Primer | ACTTTCTTCTACGTAATTCTTTTCCGA |
| SEQ ID NO:37 | BCL2L11 Flap oligonucleotide | CGCCGAGGGCGGGGGTCGGGGC/3C6/ |
| SEQ ID NO:38 | BHLHE23 Target DNA | GCCGGGGAGTCGAGAAGCAAGTACTAGCGCTCCAGGACCGCGCGCGCCCCGCGCCCCCGCGCGCCCCTC GGTCCAGAGC |
| SEQ ID NO:39 | BHLHE23 Converted DNA | GTCGGGGAGTCGAGAAGTAAGTATTAGCGTTTTAGGATCGCGCGTCGTTTCGCGTCGTGTTTTCGG TTTAGAGT |
| SEQ ID NO:40 | BHLHE23 Forward Primer | AGTATTAGCGTTTTAGGATCGCG |
| SEQ ID NO:41 | BHLHE23 Reverse Primer | ACTCTAAACCGAAAAACGACG |
| SEQ ID NO:42 | BHLHE23 Flap oligonucleotide | CCACGGACGGCGAAACGACGC/3C6/ |
| SEQ ID NO:43 | BIN2 Target DNA | GCCGGGAGCCCGCCGCACTTCCTCCTCGGGGGCCTCAGAAAACCACAGGGGCGCGGGGCCAGGGCGGCGGCCCC CAGG |
| SEQ ID NO:44 | BIN2 Converted DNA | GTCGGGGAGTTCGTATTTTTTTTTCGGGGGGTTTTAGAAAATTATAGGGCGCGGGGTTAGGGCGGCGGTTTT TAGG |
| SEQ ID NO:45 | BIN2 Forward Primer | TCGGGAGTTCGTATTTTTTTTCGG |
| SEQ ID NO:46 | BIN2 Reverse Primer | AAAACCGCCGCCTAAC |
| SEQ ID NO:47 | BIN2 Flap oligonucleotide | CGCCGAGGCCCCGCCCCTA/3C6/ |
| SEQ ID NO:48 | BIN2_Z Target DNA | CGGGGCCTACCCTCAGGCAGCGCTCGCTCGAGGCCAGCTTCCGAGCTCCAACCCTGCCGAAACCTCGGCCTCACT G |
| SEQ ID NO:49 | BIN2_Z Converted DNA | CGGGGGTTTATTTTTAGGTAGCGTTCGTTCGAGGTTAGTTTTCGAGGTTTAATTTTGTTGAAATTTCGGTTTTATTG |
| SEQ ID NO:50 | BIN2_Z Forward Primer | GGGTTTATTTTTAGGTAGCGTTCG |
| SEQ ID NO:51 | BIN2_Z Reverse Primer | CGAAATTTCGAACAAAATTAAAACTCGA |
| SEQ ID NO:52 | BIN2_Z Flap oligonucleotide | CCACGGACGGTTCGAGGTTAG/3C6/ |

FIG. 6 (cont'd)

| | Description | Sequence (all are shown 5' to 3') |
|---|---|---|
| SEQ ID NO:53 | CAPN2 Target DNA | TGTCCTGACACGATGGCCACAGGCACAGTTTGTGGTGATGCCCAGGGCCCCGCGGCCCCACGGTGGTCCAGTTT ACACTCGGGCCCCGCGACTCCTGAAGTTCCGCGCGGGAGGAGAAGGGCGTCCCTTTCGCAGCTCGG |
| SEQ ID NO:54 | CAPN2 Converted DNA | TGTTTTGATACGATGGTTATAGGTATAGTTTGTGGTGATGTTTAGGGGTTCGCGGTTTTACGGTGGTTTAGTTTAT ATTCGGGTTTCGTATTTTGAAGTTTCGCGCGGGAGGAGAAGGGCGTTTTTTCGTAGTTCGG |
| SEQ ID NO:55 | CAPN2 Forward Primer | TGATGTTTAGGGGTTCGCG |
| SEQ ID NO:56 | CAPN2 Reverse Primer | CGAAACTTCAAAAATACGAAACCCGA |
| SEQ ID NO:57 | CAPN2 Flap oligonucleotide | CGCCGAGG GCGGGTTTACGG/3C6/ |
| SEQ ID NO:58 | chr5_132 Target DNA | CCGGAGCACTCGCCGCTGCCGCCCTGAAGCCGCTGGCGTAGGCGGCCCTCGAGGCCGGCGGGCTGGGCGGCTC GGCAGCCTGCGCCGCGCCGGCCTCGCCTCGGCCGCCAGC |
| SEQ ID NO:59 | chr5_132 Converted DNA | TCGGAGTATTCGTCGTTGCGCGGTTTGAAGTCGTTGGCGGTAGGCGGTTTCGAGGTCGGCGGGTTGGGCGGGTTCG GTAGTTTGCGTCGGCGGTTTTCGTTTCGGTCGTTAGT |
| SEQ ID NO:60 | chr5_132 Forward Primer | GTATTCGTCGTTGCGCG |
| SEQ ID NO:61 | chr5_132 Reverse Primer | CCTCGAAAACCGGCTACC |
| SEQ ID NO:62 | chr5_132 Flap oligonucleotide | CCACGGACGCGCGCAACGACTT/3C6/ |
| SEQ ID NO:63 | chr7_636 Target DNA | CGCCGTGAGTGTTATAGTTCTTAAAGGCGGCGTGTCCGGAGTTCTTCCTTCGTGGGGTTCGTGGTCTCGCCGGC TCAGGAGTGAAGCTGCAGATCTTCGCGGTGAGTGTTACAGCTCCTAAGGCGGCGCAT |
| SEQ ID NO:64 | chr7_636 Converted DNA | CGTCGTGAGTGTTATAGTTTTTAAAGGCGGCGTGTCGGGAGTTTTTTTTTTGGTGGGGTTCGTGGTTTCGTGGTT TAGGAGTGAAGTTGTAGATTGTAGAATTTTCGCGGTGAGTGTTGAGTGTTATAGTTTTTAAGGCGGCGTAT |
| SEQ ID NO:65 | chr7_636 Forward Primer | TAAAGGCGGCGTGTTCG |
| SEQ ID NO:66 | chr7_636 Reverse Primer | CAACTTCACTCCTAAACCGAC |
| SEQ ID NO:67 | chr7_636 Flap oligonucleotide | CCACGGACGCGAAACCACGAA/3C6/ |
| SEQ ID NO:68 | CYP26C1 Target DNA | AACTGGCCTTCTGGCTACTCCGAATCGCCAAGCAGCAGATGAGGCCAGACCGCCGCTGATCACGCGCGCTCC CACAGGTCCTGGCCGCGGTGTTCAGCCGCGC |
| SEQ ID NO:69 | CYP26C1 Converted DNA | AATGGTTTTTTTGGTTATTTCGGAATCGTTAAGTAGATGAGGTTAGATCGTCGTTAGCGTTGATTACGCGCGTTTTA TAGGTTTTTGGCGCGGCGTGTTTTTAGTCGT |
| SEQ ID NO:70 | CYP26C1 Forward Primer | TGGTTTTTTGGTTATTTCGGAATCGT |
| SEQ ID NO:71 | CYP26C1 Reverse Primer | GCGCGTAATCAACGCTAAC |
| SEQ ID NO:72 | CYP26C1 Flap oligonucleotide | CGCCGAGGCGACGATCTAAC/3C6/ |
| SEQ ID NO:73 | DIDO1 Target DNA | GGAGCGGGCAGAGGAGGAGGCCCGAGGCCCAGGCGCGCCCCGCCCTCGCCCCGTGCCCCTCCCCC GCTGCTCCCC |
| SEQ ID NO:74 | DIDO1 Converted DNA | GGAGCGGGTAGAGGAGGAGGAGTTTAGCGTCGAGGTTTAGGCGCGTTTCGTTTTCGTTTTTTTCGTGTGTTTTTTTTCGTT GTTTTT |
| SEQ ID NO:75 | DIDO1 Forward Primer | GAGGAGGAGTTTAGCGTCG |
| SEQ ID NO:76 | DIDO1 Reverse Primer | CACGAAAAAAACGAAAACGAAAC |
| SEQ ID NO:77 | DIDO1 Flap oligonucleotide | CGCCGAGGCGCGCCTAAACC/3C6/ |
| SEQ ID NO:78 | DLX4 Target DNA | GCGGTCTATCACGGGCACCCTAACACTTGGTGAGTGCGCAGTGCTCTCGGCCAGTCTCTGGGCTCCATACGATGCCT ACCGCACGCCCTAGCAGAGGAGGTCTCTGT |

FIG. 6 (cont'd)

| | Description | Sequence (all are shown 5' to 3') |
|---|---|---|
| SEQ ID NO:79 | DLX4 Converted DNA | GCGGTTTATTACGGGTATTTTAAATATTTGGTGAGTGCGTAGTGTTTTCGGTAGTGTTTTGGGTTTTATACGATGTTTAT CGTACGTTTTAGTAGAGAGGAGGTTTTTGT |
| SEQ ID NO:80 | DLX4 Forward Primer | TGAGTGCGTAGTGTTTTCGG |
| SEQ ID NO:81 | DLX4 Reverse Primer | CTCCTCTACTAAAACGTACGATAAACA |
| SEQ ID NO:82 | DLX4 Flap oligonucleotide | CGCCGAGGATCGTATAAAAC/3C6/ |
| SEQ ID NO:83 | DLX4 Forward Primer Universal | ATATTTGGTGAGTGCGTAGTG |
| SEQ ID NO:84 | DLX4 Reverse Primer Universal | ACGTACGATAAACATCGTATAAAACC |
| SEQ ID NO:85 | DLX4 Flap oligonucleotide Universal | CGCCGAGGGTTTTCGGTAGT/3C6/ |
| SEQ ID NO:86 | DMRTA2 Target DNA | TACTCCACTGCCGGCTTGGTGCCCACGCTCGGCTTCCGCCCACCCATGGACTACGCCTTTAGCGATCTCATGCGTGAC CGCTCGGCGCCGCCGCTGCTGCGGCGGGTGCACAAGGAGCCGAACCT |
| SEQ ID NO:87 | DMRTA2 Converted DNA | TATTTTATTGTCGGTTTGTTGCGGCGGTGTTATTTATTTGGATTACGTTTTTAGCGGATTTTATGCGTGATCG TTCGGTCGTCGTTGTTGTTACGTTCGGTTTTCGT |
| SEQ ID NO:88 | DMRTA2 Forward Primer | TGGTGTTTACGTTCGGTTTTCGT |
| SEQ ID NO:89 | DMRTA2 Reverse Primer | CCGCAACAACGACGACC |
| SEQ ID NO:90 | DMRTA2 Flap oligonucleotide | CGCCGAGGCGAACGATCACG/3C6/ |
| SEQ ID NO:91 | DNMT3A Target DNA | AGGCCGGTCACGAACAAAGCGTTGGCGAGTGCGCGCCCGCCCACGCGCACCAGGTGCCCGGACAAGAGCGCCCGT CCCCGCCCACGCGGCCCCCCGCGGGCTGAGCC |
| SEQ ID NO:92 | DNMT3A Converted DNA | AGGTCGGTTACGAATAAAGCGTTGGCGAGTGCGCGTTCGTTTACGCGTATAGGTGTTCGCGATAAGACGTTTCGTTT TCGTTTACGCGGTTTTCGCGGGTTGAGTT |
| SEQ ID NO:93 | DNMT3A Forward Primer | GTTACGAATAAAGCGTTGGCG |
| SEQ ID NO:94 | DNMT3A Reverse Primer | AACGAAACGTCTTATCGCGA |
| SEQ ID NO:95 | DNMT3A Flap oligonucleotide | CCACGGACGGAGTGCGGTTC/3C6/ |
| SEQ ID NO:96 | DOCK2 Target DNA | GCCGGCCCCGCCAGCATCCTCGTCTGCGCGGCGTCTCCGCCCACCTGTCCCGCTCCCGCCGGCCCTGGGGCCGCAC CTACCCAC |
| SEQ ID NO:97 | DOCK2 Converted DNA | GTCGGTTTCGTAGTATTTTTTGTTCGCGGTTTTTCGTTTTGTTCGTTTGTGTCGGTTTTTGTTTTTGTCGCGGTTCGTATTTAT TTAT |
| SEQ ID NO:98 | DOCK2 Forward Primer | CGGTTTCGTAGTATTTTTTGTTCG |
| SEQ ID NO:99 | DOCK2 Reverse Primer | GAACCCCAAAACGCGAC |
| SEQ ID NO:100 | DOCK2 Flap oligonucleotide | CGCCGAGGGCGGTTTTTTCG/3C6/ |
| SEQ ID NO:101 | DTX1 Target DNA | CGCCTCCTCGGGCTCCCCCCGGAGTGGGAGGGAGCCGCGGTCCCGCGCTCCGCGCCGGTTCCCTCCCCAGGCCCTCGG CCGCCGCCGCCGAGCTTTCCGCGCGGTTGGACAGACTGCCCGCCGACGGACGCAGG |
| SEQ ID NO:102 | DTX1 Converted DNA | CGTTTTTGGGGTTTTTTCGCGCGGTTCGTTTCGCGTTCGTTTTTTTAGGTTTTTCGGTCG TCGGTCGCGAGTTTTTCGCGCGGTGGATAGATTGTTCGGTCGCGACGGACGTAGG |
| SEQ ID NO:103 | DTX1 Forward Primer | GAGTCGCGGTTTCGTTTTC |
| SEQ ID NO:104 | DTX1 Reverse Primer | GACGCGACGACCGAAAAAC |
| SEQ ID NO:105 | DTX1 Flap oligonucleotide | CGCCGAGGCGCGTTCGTTTT/3C6/ |

FIG. 6 (cont'd)

| | Description | Sequence (all are shown 5' to 3') |
|---|---|---|
| SEQ ID NO:106 | EMX1 Target DNA | TCCGGCGCCGCGTTTTCTAGAGAACCGGGTCTCAGCGATGCTCATTTCAGCCCGCGTCTTAATGCAACAAACGAAACC CCACACGAACGAAAAGGAACATGTCTGCGCT |
| SEQ ID NO:107 | EMX1 Converted DNA | TCGGCGTCGCGTTTTTAGAGAATCGGGTTTTAGCGATGTTTATTTTAGTTTCGTTTTAATGTAATAAACGAAATTTA TACGAACGAAAAGGAATATGTTTGCGTT |
| SEQ ID NO:108 | EMX1 Forward Primer | GGCGTCGCGTTTTTAGAGAA |
| SEQ ID NO:109 | EMX1 Reverse Primer | TTCCTTTTCGTTCGTATAAAATTTCGTT |
| SEQ ID NO:110 | EMX1 Flap oligonucleotide | CCACGGACGATCGGGTTTTAG/3C6/ |
| SEQ ID NO:111 | FAM59B Target DNA | GGGCCTGCTGCCGGGGACCCGCCGTCGAGCGCGTGGTGCGCGACAGCGCCTCCTACTGCCGCGAGCGCTTCGA CCCCGACGAGTACTCCACGGCCGTGCGCGGAGGCGCCAGCGGAGCTCGCCGAAG |
| SEQ ID NO:112 | FAM59B Converted DNA | GGGTTTGTTGGTCGGGGATTCGTCGGCGTTTGGTGCGCGATAGCGTTTTATTGTCGCGAGCGTTTCGATT TCGACGAGTATTTTACGGTCGTGTGCGGAGGCGTTAGCGGAGTTCGTCGAAG |
| SEQ ID NO:113 | FAM59B Forward Primer | CGATAGCGTTTTTTATTGTCGCG |
| SEQ ID NO:114 | FAM59B Reverse Primer | GCACGACCGTAAAATACTCGTC |
| SEQ ID NO:115 | FAM59B Flap oligonucleotide | CCACGGACGCGAAATCGAAAC/3C6/ |
| SEQ ID NO:116 | FERMT3 Target DNA | TAGCAGCAGCCCGCAGCCATGGCGGGGATGAAGACAGCCTCCGGGGACTACATCGACTCGTCATGGGAGCTGCGGG TGTTTGGGAGGAGGAGGACCCAGAGGCCGAGTCGGTCACCCTGCGGGTCACTGGGGAGTCGCAC |
| SEQ ID NO:117 | FERMT3 Converted DNA | TAGTAGTAGTCGTAGTTATGGCGGGGATGAAGATAGTTTCGGGGATTATATCGATTCGTTATGGGAGTTGCGGGT GTTTGTTGGGAGGAGGAGGATTTAGAGGTCGAGTCGGTTATTTGCGGGTTATTGGGGAGTCGTAT |
| SEQ ID NO:118 | FERMT3 Forward Primer | GTTTTCGGGGATTATATCGATTCG |
| SEQ ID NO:119 | FERMT3 Reverse Primer | CCCAATAACCCGCAAAATAACC |
| SEQ ID NO:120 | FERMT3 Flap oligonucleotide | CGCCGAGGCGACTCGACCTC/3C6/ |
| SEQ ID NO:121 | FGF14 Target DNA | GTCCCAGAGACGCCCTAGGGTCAGAGGTCATCTCCGTGGCAACGGAAACTTCCGCGCTACGGCGGCTCCAACGGG CCGCTTCCGCCGCCATTGCGTAGCGAAGC |
| SEQ ID NO:122 | FGF14 Converted DNA | GTTTTAGAGACGTTTAGGGTTAGAGGTTATTTTCGTGGTAACGGAAATTTTCGCGTTACGGCGGTTTTAACGGGT CGTTTTCGTCGTATTGCGTAGCGAAGT |
| SEQ ID NO:123 | FGF14 Forward Primer | TTTCGTTGGTAACGGAAATTTTCG |
| SEQ ID NO:124 | FGF14 Reverse Primer | CGACGAAAACGACCCGT |
| SEQ ID NO:125 | FGF14 Flap oligonucleotide | CGCCGAGGCGGTTACGGCGG/3C6/ |
| SEQ ID NO:126 | FLJ34208 Target DNA | GCGCCCCGGCGCGCAGGCGGAGGAGGACAGGGAGGAGGAGCGCACGAGAAAGCTCCCACGAGAGAAAGCTCCCATCCGCCCTCGCCTCCG ACGGGAAGGCGCCCTCTTCCGACCGTCCTGGATG |
| SEQ ID NO:127 | FLJ34208 Converted DNA | GCGTTTCGGTCGTGTAGGCGGAGGATAGGGAGGAGGAGCGTATACGAGAAAGTTTTACGCGGTTCGTCGTTTCGTTTTCGAC GGGAAGGCGTTTTTTTTCGATCGTTTTGGATG |
| SEQ ID NO:128 | FLJ34208 Forward Primer | GAGCGTATACGAGAAAGTTTTACG |
| SEQ ID NO:129 | FLJ34208 Reverse Primer | AACGCCTTCCCGTCGAA |
| SEQ ID NO:130 | FLJ34208 Flap oligonucleotide | CCACGGACG GCGTTCGCGTT/3C6/ |
| SEQ ID NO:131 | FLJ45983 Target DNA | CGAGAGGGCGGCGAGCACGAGCCATGGAGGTGACGGCGGACCAGCCGCGCTGGGGTGAGCCACCACCACCC CGCCGTGCTCAACGGGCCGCAGCACCCGGCACGCGCAC |

FIG. 6 (cont'd)

| Description | Sequence (all are shown 5' to 3') |
|---|---|
| SEQ ID NO:132 | FLJ45983 Converted DNA | CGAGAGGGGCGCGAGTAGTCGAGGTATAGTCGAGGTTATGGGAGGTGACGGCGGATTAGTCGCGTTGGGTGAGTTATTATTTTCG TCGTGTTTAACGGGTAGTATTCGGATACGTAT |
| SEQ ID NO:133 | FLJ45983 Forward Primer | GGGCGCGAGTATAGTCG |
| SEQ ID NO:134 | FLJ45983 Reverse Primer | CAACGCGACTAATCCGC |
| SEQ ID NO:135 | FLJ45983 Flap oligonucleotide | CGCCGAGGCCGTCACCTCCA/3C6/ |
| SEQ ID NO:136 | GRIN2D Target DNA | CGCCCCCTCCACCTCCCGATCATGCCGTTCCAGACGCCATCGATCTTCTTCCGTGCTTGCCATTGGTGACCAGGTAG AGGTCGTAGCTGAAGCCGATGGTATGCGCCAGCCGCTTCAGAATGTCGATGCAGAAACCCTTG |
| SEQ ID NO:137 | GRIN2D Converted DNA | CGTTTTTTATTTTTCGGATTATGTCGTTTAGACGTTATCGATTTTTTTCGTGTTTGTTATTGGTGATTAGGTAGAG GTCGTAGTTGAAGTCGGATGGTATGCGTTAGTCGTTAGTCGTTTTTAGAATGTCGATGTAGAAATTTTTG |
| SEQ ID NO:138 | GRIN2D Forward Primer | TCGATTATGTCGTTTAGACGTTATCG |
| SEQ ID NO:139 | GRIN2D Reverse Primer | TCTACATCGACATTCTAAAACGACTAAC |
| SEQ ID NO:140 | GRIN2D Flap oligonucleotide | CCACGGACGGCGCATACCATCG/3C6/ |
| SEQ ID NO:141 | HIST1H2BE Target DNA | CGGCGAGGCTTCCCGCCTGGCGCATTACAACAAGCGCTGGACCATCACCTCCAGGGAGATCCAGGGGAGATCCAGACGCGCCGTGCGC CTGCTGCTTCCCGGGGA |
| SEQ ID NO:142 | HIST1H2BE Converted DNA | CGGCGAGGTTTTTCGTTTGGCGTATTATAATAAAGCGTTCGATTATTATTTTTAGGGAGGATTTAGACGGTCGTGCGTTT GTTGTTTTTCGGGGA |
| SEQ ID NO:143 | HIST1H2BE Forward Primer | TGGCGTATTATAATAAAGCGTTCG |
| SEQ ID NO:144 | HIST1H2BE Reverse Primer | AACAACAAACGCACGACC |
| SEQ ID NO:145 | HIST1H2BE Flap oligonucleotide | CCACGGACGCGTCTAAATCTC/3C6/ |
| SEQ ID NO:146 | HOXA9 Target DNA | GGGGCGGGCCCAGGCGCTGGGCACGGTGATGGCCACCACTGGGCCCTGGCAACTACTACGTGGACTCGTTCCTGC TGGGCGCCGACGCCGCGGATGAGCTG |
| SEQ ID NO:147 | HOXA9 Converted DNA | GGGGCGGGTTAGGCGTTGGGTACGGTGATGGTTATTAITGGGGTTTTGGGTAATTATTAttACGTGGATTCGTTTTTGTTTTTGTTG GGCGTCGACGTGCGCGGATGAGTTG |
| SEQ ID NO:148 | HOXA9 Forward Primer | TTGGGTAATTATTACGTGGATTCG |
| SEQ ID NO:149 | HOXA9 Reverse Primer | ACTCATCGCGCGACGTC |
| SEQ ID NO:150 | HOXA9 Flap oligonucleotide | CCACGGACGCGACGCCCAACA/3C6/ |
| SEQ ID NO:151 | HOXB2 Target DNA | GGGCCATTGCCAGAAGAACGCTCTTCTCGGGGCGCGCCAGGATTCACCTTTCTTCCCGACCTCAACTTCTTCGCGGCCGA CTCCTGTCTCCAGCTATC |
| SEQ ID NO:152 | HOXB2 Converted DNA | GGGTTATTGTTAGAAGAACGTTTTTTCGGGGCGGCGTTAGGATTTAITTTTTTTTTCGATTTAATTTTTTCGCGGCGTCGATTT TTGTTTTTAGTTATT |
| SEQ ID NO:153 | HOXB2 Forward Primer | GTTAGAAGACGTTTTTTCGGGG |
| SEQ ID NO:154 | HOXB2 Reverse Primer | AAAACAAAAATCGACCGCGA |
| SEQ ID NO:155 | HOXB2 Flap oligonucleotide | CGCCGAGGGCGTTAGGATTT/3C6/ |
| SEQ ID NO:156 | KLHDC7B Target DNA | GGCCCCGGAAGCCCAGCTCCCGGGCGCCTGGAGCCCGCCAGCCCTGCGCGGCGGGGCTGGACCTGGGCA GTTGCCTGGACGTGCTGGCCTTTGCCCAGCA |
| SEQ ID NO:157 | KLHDC7B Converted DNA | GGTTTCGGAAGTTTTAGTTTTCGGGTTTTGGAGTTTCGTTTACGGCGGTAGTTTTGCGGCGGCGGCGGTTGGGATTTGGGTAGT TGTTTGGACGTGTTGTTTTTTGTTTAGTA |

FIG. 6 (cont'd)

| | Description | Sequence (all are shown 5' to 3') |
|---|---|---|
| SEQ ID NO:158 | KLHDC7B Forward Primer | AGTTTTCGGGTTTTGGAGTTCGTTA |
| SEQ ID NO:159 | KLHDC7B Reverse Primer | CCAAATCCAACCGCCGC |
| SEQ ID NO:160 | KLHDC7B Flap oligonucleotide | CGCCGAGGACGGCGGTAGTT/3C6/ |
| SEQ ID NO:161 | LOC100129726 Target DNA | GGCGGCCGCGGCGCGTGCGCGGGGGGCGCCAGGCCCTGCTGCTGCTGCTGACTGCGGTAGTAGGCGGC<br>GGCGGCCACGGCGGCAAAGTTGTGGGTCTGGA |
| SEQ ID NO:162 | LOC100129726 Converted DNA | GGCGGCGTCGGCGGTTGCGCGGGGGGCGTTAGGTTTTGTTGTTGTTGTTGATTGCGGTAGTAGGCGGCGG<br>CGGTTACGGCGGTAAAGTTGTGGGTTTGGA |
| SEQ ID NO:163 | LOC100129726 Forward Primer | TTGATTGCGGTAGTAGGCG |
| SEQ ID NO:164 | LOC100129726 Reverse Primer | AACCCACAACTTTACCGCC |
| SEQ ID NO:165 | LOC100129726 Flap oligonucleotide | CGCCGAGGCGTAACCGCCGC/3C6/ |
| SEQ ID NO:166 | MATK Target DNA | GGTTTCCCCCACCCCGGCCTCGGGGTCTCTCCACGTCTCCCCGCCGACGTGCTCACCTGCTCAGGGGGCGCCCCG<br>AGCCGCGCCCCGCGCCCCGCCCCCAGGAGGGCGCCTCCGCGAGCGGCCGGTCACCCCGAGGCGGTCCCGGCTGCACA<br>AC |
| SEQ ID NO:167 | MATK Converted DNA | GGTTTTTTTATTTCGGTTTCGGGGTTTTTTTCGTCGACGTGTTTATTTGTTTAGGGGGCGTTTCGAGT<br>CGCGTTTCGCGTTCGTTTTTTAGGAGGGTTTTCGCGAGTCGGTTGTATATTCGAGGCGGTTTCGGTTGTTATAAT |
| SEQ ID NO:168 | MATK Forward Primer | GTTTCGGGGTTTTTTTTACGTTTTTCG |
| SEQ ID NO:169 | MATK Reverse Primer | AAACGCGACTCGAAAACGC |
| SEQ ID NO:170 | MATK Flap oligonucleotide | CGCCGAGGGTCGACGTTGT/3C6/ |
| SEQ ID NO:171 | MAX_Chr10.225 Target DNA | CTCCGGTTTCGCGGTTCTCAGCGATATTAGGCGCGGCCAGTGTCTGAAAGCTCCTCGGGGTTACGTCCTCGGGGGCGA<br>CTGGAGGCGGCTCACGAC |
| SEQ ID NO:172 | MAX_Chr10.225 Converted DNA | TTTCGGTTTCGCGGTTTTAGCGATATTAGGCGCGGTTAGTGTTTGAAAGTTTTCGGGGTTACGTTTTTGGGGGCGAT<br>TGGAGGCGGTTTACGAT |
| SEQ ID NO:173 | MAX_Chr10.225 Forward Primer | CGGTTTTTAGCGATATTAGGCG |
| SEQ ID NO:174 | MAX_Chr10.225 Reverse Primer | CCCAAAACGTAACCCCGA |
| SEQ ID NO:175 | MAX_Chr10.225 Flap oligonucleotide | CGCCGAGGGCGGTTAGTGTT/3C6/ |
| SEQ ID NO:176 | MAX_Chr10.226 Target DNA | CGACGGGCCGCGGAGGAGGAAGGCCAGGGGGAAATTGCATTTCGTAAAACCGCGGTTAAGAAATGACGATGCCAC<br>GTAGACAAGCCAGTTGTGACGTTCAGCACAACGTTCACTGAACTACCGAGATCCGCACCAAATGGC |
| SEQ ID NO:177 | MAX_Chr10.226 Converted DNA | CGACGGTTCGCGGAGGAGGAAGGTTAGGGGGAAATTGTATTTCGTAAAATCGCGGTTAAGAAATGACGATGTTAC<br>GTAGATAAGTTAGTTGTGACGTTTAGTATAAACGTGTTATTGAATTATCGAGATTCGTTATTAAATGGT |
| SEQ ID NO:178 | MAX_Chr10.226 Forward Primer | GGGAAATTTGTATTTCGTAAAATCG |
| SEQ ID NO:179 | MAX_Chr10.226 Reverse Primer | ACAACTAACTTATCTACGTAACATCGT |
| SEQ ID NO:180 | MAX_Chr10.226 Flap oligonucleotide | CCACGGACGGCGGTTAAGAAA/3C6/ |
| SEQ ID NO:181 | MAX.chr12.52 Target DNA | GGCTTGGGGTCCAGCGCGCCCCGCCCCCTGCCGCCACCGCACCATGTCCTGCCTCACTCCCGCCTCACTCCCGCCCCCTGCG<br>GGGGTCCGCGCCTTCAGCGTGCATCTCGGCCTGCGGGCCCC |
| SEQ ID NO:182 | MAX.chr12.52 Converted DNA | GGTTTGGGGTTTAGTCGTTCGTTTTTGTCGTTATCGTATTGTTTTTATTTCGTTTTATGTTGTTTTTGCGGGTTTT<br>TTCGCGTTTTTAGTTGTATTTCGGTTTGCGGGTTTT |

FIG. 6 (cont'd)

| | Description | Sequence (all are shown 5' to 3') |
|---|---|---|
| SEQ ID NO:183 | MAX.chr12.52 Forward Primer | TCGTTCGTTTTTGTCGTTATCG |
| SEQ ID NO:184 | MAX.chr12.52 Reverse Primer | AACCGAAATACAACTAAAAACGC |
| SEQ ID NO:185 | MAX.chr12.52 Flap oligonucleotide | CCACGGACGCGAACCCCGCAA/3C6/ |
| SEQ ID NO:186 | MAX.chr16.50 Target DNA | GGAAGGCTGCAGCGAGAGAGATTTACATATTCATCCGAGCTTAAGGAAGCCGCGATAATGCAGGTACAGCCCGAAACC CACGCCCCCAGACCTTATCTGCGCGCCCCGCC |
| SEQ ID NO:187 | MAX.chr16.50 Converted DNA | GGAAGGTTGTAGCGAGAGAGATTTATATATTTATTCGAGTTTAAGGAAGTCGCGATAATGTAGGTATAGTTCGAAATTT ACGTTTTTAGATTTTATTTGCGCGTTTCGTT |
| SEQ ID NO:188 | MAX.chr16.50 Forward Primer | TTCGAGTTTAAGGAAGTCG |
| SEQ ID NO:189 | MAX.chr16.50 Reverse Primer | TCTAAAAACGTAAAATTCGAACT |
| SEQ ID NO:190 | MAX.chr16.50 Flap Oligonucleotide | CCACGGACGGCGATAAATGTAG/3C6/ |
| SEQ ID NO:191 | MAX.chr19.16 Target DNA | GGAGTTATTTTTAACCATCGCCTCCCAGAACATTACGGAGCTTCCTCTCTCCAACACGCAGGAAACCCTACTTGGCTG TGCTTCCTGCTAACACGAGCCCTGCGATTGTGAGAAACAACAGCCCGAGACTGCGCG |
| SEQ ID NO:192 | MAX.chr19.16 Converted DNA | GGAGTTATTTTTAATTATCGTTTTTAGAATATTACGGAGTTTTTTTTTAATACGTAGGAAATTTTATTGGTTGTG TTTTTGTTAATACGAGGTTTGCGATTGTTGAGAATAATAGTTTCGAGATTGCGCG |
| SEQ ID NO:193 | MAX.chr19.16 Forward Primer | TTTAATTATCGTTTTTAGAATATTACGGA |
| SEQ ID NO:194 | MAX.chr19.16 Reverse Primer | ACTATTATTCTCAACAATCGCAAAAC |
| SEQ ID NO:195 | MAX.chr19.16 Flap oligonucleotide | CCACGGACGCCTCGTATTAAC/3C6/ |
| SEQ ID NO:196 | MAX.chr19.37 Target DNA | GGCGGGGCGCTTGGCCAAACAGCCCAAGACTGCGGAATCACACTCGCCACTGTGTACCTGGACGCGCCATCTGCAGACC CAGCGCCTGCGCGGGGATTCCGGAAACGGGAGAGGCGGGCTTCC |
| SEQ ID NO:197 | MAX.chr19.37 Converted DNA | GGCGGGGCGTTTGGTTAAATAGTTTAAGATTGCGGAATTATATTCGTTATTGTGTATTTGGACGTTATTTGTAGATTTA GCGTTTGCGGGGATTTCGGAAACGGGAGAGGCGGGGTTTTT |
| SEQ ID NO:198 | MAX.chr19.37 Forward Primer | AGTTTAAGATTGCGGAATTATATTCGT |
| SEQ ID NO:199 | MAX.chr19.37 Reverse Primer | TTCCGAAATCCCCGCAA |
| SEQ ID NO:200 | MAX.chr19.37 Flap oligonucleotide | CGCCGAGGAAACGCTAAATCT/3C6/ |
| SEQ ID NO:201 | MAX_Chr8.124 Target DNA | CGCAGGCTGAGGCCCTCGGGTCCCCAGCGGGTCCTCGCCATCAGTCACTCTCTACGGGCCAGGCCTGGGGGTCACG GCCTGCGCAGGAGCCTCCCTGCGCGGCCCCACTCCCTCATCTGCGACCCCGTGGGGAGGCGACCCCTGACCACCCTCGTT CCG |
| SEQ ID NO:202 | MAX_Chr8.124 Converted DNA | CGTAGGTTGGAGGTTTTCGGGGTTTTTAGCGGGGTTTTCGTTATTGTTAGTTATTTTTACGGGTTGGGGGGTTACGGT TTGTAGGAGTTTTTTTGTCGCGGCGGTTTTATTTTTTATTTGCGGATTTCGTGGGGGAGGCGGATTTTGATTATTTCGTTTCG |
| SEQ ID NO:203 | MAX_Chr8.124 Forward Primer | GGTTGAGGTTTTCGGGGTTTTTAG |
| SEQ ID NO:204 | MAX_Chr8.124 Reverse Primer | CCTCCCCACGAAATCGC |
| SEQ ID NO:205 | MAX_Chr8.124 Flap oligonucleotide | CGCCGAGGGCGGGTTTTCGT/3C6/ |
| SEQ ID NO:206 | MAX_Chr8.124 Forward Primer v2 | AGGAGTTTTTTGCGCGG |
| SEQ ID NO:207 | MAX_Chr8.124 Reverse Primer v2 | ACGAAAAATAATCAAAATCGCCTCC |
| SEQ ID NO:208 | MAX_Chr8.124 Flap oligonucleotide v2 | CGCCGAGGCCCACGAAATCG/3C6/ |

FIG. 6 (cont'd)

| | Description | Sequence (all are shown 5' to 3') |
|---|---|---|
| SEQ ID NO:209 | MAX_Chr8.145 Target DNA | CGGGGGAGGGGCGGCATCAGCCAGAGAGCTCAGCCGACGGCGCTCCCGACGGGCGCTCCCGCTCCGACTCCACTTCCCGCTCCGATACCCTCCCC CTAAGCACGATACCCAGGGCCCAGGGCTGCTCTTGGCG |
| SEQ ID NO:210 | MAX_Chr8.145 Converted DNA | CGGGGGAGGGGCGGGTATTAGTTAGGGTTAGAGTTTAGTCGACGGCGGCGTTTTTTAGGTTATTTTCGTTTCGATATTTTTTTTTTA AGTACGATATTTAGGGTTTAGGGTTGTTTTGGCG |
| SEQ ID NO:211 | MAX_Chr8.145 Forward Primer | GCCGTATTAGTTAGAGTTTAGTCG |
| SEQ ID NO:212 | MAX_Chr8.145 Reverse Primer | ACAACCCTAAACCCTAAATATCGT |
| SEQ ID NO:213 | MAX_Chr8.145 Flap oligonucleotide | CCACGGACGGACGGCGTTTTT/3C6/ |
| SEQ ID NO:214 | MAX_Chr1.110 Target DNA | CTCCGCTCCCGCCAGGCCTGGCCGCGCGACGGGCACCCAGCGGGGTTGTTATCAATTATTCAGGCCCCAAGTTCACG GGCACTGCATCCCATTTCCCTCGCGTGCGCCC |
| SEQ ID NO:215 | MAX_Chr1.110 Converted DNA | TTTCGTTTTTCGTAGGTTTGGTCGCGGACGGGGTATTTAGCGGGGTTGTTATTAATTATTTAGGTTTAAGTTTACGGG TATTGTATTTATTTTTTCGCGTGCGTTT |
| SEQ ID NO:216 | MAX_Chr1.110 Forward Primer | TTTCGTAGGTTTGGTCGCG |
| SEQ ID NO:217 | MAX_Chr1.110 Reverse Primer | AACCTAAATAATTAATAACAACCGC |
| SEQ ID NO:218 | MAX_Chr1.110 Flap oligonucleotide | CCACGGACGGCGACGGGTATT/3C6/ |
| SEQ ID NO:219 | NFIX Target DNA | GTGGGCCGGGCGTGACGCGCGGGTCAAAGTGCAATGATTTTTCAGTTCGGTTGGCTAAACAGGGTCAGAGCTGAGA GCGAAGCAGAAGG |
| SEQ ID NO:220 | NFIX Converted DNA | GTGGGTCGGGCGTGACGCGCGGGTTAAAGTGTAATGATTTTTTAGTTCGGTTGGTTAAATAGGGTTAGAGTTGAGAG CGAAGTAGAAGG |
| SEQ ID NO:221 | NFIX Forward Primer | TGGTTCGGGCGGTGACGCG |
| SEQ ID NO:222 | NFIX Reverse Primer | TCTAACCCTATTTAACCAACCGA |
| SEQ ID NO:223 | NFIX Flap oligonucleotide | CGCCGAGGCGGGTTAAAGTG/3C6/ |
| SEQ ID NO:224 | NKX2-6 Target DNA | GGACCTCCCTGCCCGCCCCATCCGCCTTCGGGATGCTGCTGAGCCCGTCACCTCCACCCCCTTCTCGGTCAAGG ACATCCTGCGACTGGAG |
| SEQ ID NO:225 | NKX2-6 Converted DNA | GGATTTTTTCGGTTTCGTTTTATTCGTTTTCGTTGTTGTGAGTTTCGTTTATTTTTTTATTTTTTTCGGTTAAGGATAT TTTGCGATTGGAG |
| SEQ ID NO:226 | NKX2-6 Forward Primer | GATTTTTTCGGTTTCGTTTTATTCG |
| SEQ ID NO:227 | NKX2-6 Reverse Primer | CAATCGCAAAATATCCTTAACCGA |
| SEQ ID NO:228 | NKX2-6 Flap oligonucleotide | CCACGGACGGTTTTCGGGATG/3C6/ |
| SEQ ID NO:229 | OPLAH Target DNA | CTGTCAGTGCTGACCGAGCGCCGCCTTCCGGCCATACGGGCTCCGGCGGTTCCCCAGCCCTCGCGGCC CTCCCCGCCCCCG |
| SEQ ID NO:230 | OPLAH Converted DNA | TTGTTAGTGTTGATCGAGCGTCGCCGTTTTCGGTTATACGGGTTTACGGTGCGCGGGTTTTTTCGCGGTTTTT TTCGTTTTCG |
| SEQ ID NO:231 | OPLAH Forward Primer | CGTCGCGTTTTTCGGTTATACG |
| SEQ ID NO:232 | OPLAH Reverse Primer | CGCGAAAACTAAAAAACCGCG |
| SEQ ID NO:233 | OPLAH Flap oligonucleotide | CCACGGACGGCACCGTAAAAC/3C6/ |
| SEQ ID NO:234 | PARP15 Target DNA | CGGAGTATGGTGAGGAGCGCGGGGACGGGTGCGGGAAGGGGACAGCAGGGCTGAGCCTGGGCCCGCAAGAC CCAGCAGCCCGAGCGGGCGCAGAGACCCCACGCCACGCACA |

FIG. 6 (cont'd)

| | Description | Sequence (all are shown 5' to 3') |
|---|---|---|
| SEQ ID NO:235 | PARP15 Converted DNA | CGGAGTATGGTGAGGAGCGCGGGGGACGGGTGCGGGAAGGGGATAGTAGGGTTGAGTTTGGGGTTCGTAAGATT TAGTAGTTCGAGCGGCGGCGTAGAGATTTTACGTTACGTATA |
| SEQ ID NO:236 | PARP15 Forward Primer | GGTTGAGTTTGGGGTTCG |
| SEQ ID NO:237 | PARP15 Reverse Primer | CGTAACGTAAAATCTCTACGCCC |
| SEQ ID NO:238 | PARP15 Flap oligonucleotide | CCACGGACGCGCTCGAACTAC/3C6/ |
| SEQ ID NO:239 | PRDM14 Target DNA | GGAGAGCAGCCGCAGAACCTGGCCGCCGTACTACACGCCCTTTCCCGTCCTATGGACACTACAGAAAACAGCCTGGCC ACCGTGAGGAGAAGACTTCC |
| SEQ ID NO:240 | PRDM14 Converted DNA | GGAGAGTAGTTCGTAGAAATTTGGTCGCGTATTATACGTTTTTTTCGTTTTATGGATATTATAGAAATAGTTTGGTTATC GTGGAGGAAGATTTTT |
| SEQ ID NO:241 | PRDM14 Forward Primer | GAGTAGTTCGTAGAATTTGGTCG |
| SEQ ID NO:242 | PRDM14 Reverse Primer | CCACGATAACCAAACTATTTCTATAATATCC |
| SEQ ID NO:243 | PRDM14 Flap oligonucleotide | CCACGGACGGCGTATTATACG/3C6/ |
| SEQ ID NO:244 | PRDM14 Forward Primer v3 | GGAGAGTAGTTCGTAGAATTTGG |
| SEQ ID NO:245 | PRDM14 Reverse Primer v3 | CTATTTCTATATATCCATAAAACGAAAAAAACGT |
| SEQ ID NO:246 | PRDM14 Flap oligonucleotide v3 | CCACGGACGGTCGCGTATTAT/3C6/ |
| SEQ ID NO:247 | PRKCB_28 Target DNA | GGGAAGGTAGTGCCCTGCGCGCGCGCGCTCACCAGATGAAGTCGGTGCAGTGGCTGCAGAAGGTGGGCTGCTTGAAGA AGCGGCGGTGAATTTG |
| SEQ ID NO:248 | PRKCB_28 Converted DNA | GGGAAGGTGTTTTGCGCGCGCGCGTTTATTAGATGAAGTCGGTGTAGTGGTTGTAGAAGGTGGGTTGTTTGAAGAA GCGGGCGGTGAATTTG |
| SEQ ID NO:249 | PRKCB_28 Forward Primer | GGAAGGTGTTTTGCGCG |
| SEQ ID NO:250 | PRKCB_28 Reverse Primer | CTTCTACAACCACTACACCGA |
| SEQ ID NO:251 | PRKCB_28 Flap oligonucleotide | CCACGGACGCGCGCGTTTAT/3C6/ |
| SEQ ID NO:252 | PTGDR_9 Target DNA | GCCTCGGGGCGCCCGGGGACTCACAATTACGGGCAGAGAACACATAGTGAAGAGCACGGTCATCAGCGCCAGCAGCA GGAGGTGATCCAGCTCCTCCAGGGGCTGAGGG |
| SEQ ID NO:253 | PTGDR Converted DNA | GTTTCGGGGGTTCGGGGGATTTATAATTACGGGTAGAGAATTATATAGTGAAGAGTACGGTTATTAGCGTTAGTAGTAG GAGGTGATTTAGTTTTTTTAGGGGTTGAGGG |
| SEQ ID NO:254 | PTGDR Forward Primer | GGGTTCGGGGGATTTATAATTACGG |
| SEQ ID NO:255 | PTGDR Reverse Primer | CCTCCTACTACTAACGCTAATAACC |
| SEQ ID NO:256 | PTGDR Flap oligonucleotide | CCACGGACGCGTACTCTTCAC/3C6/ |
| SEQ ID NO:257 | PTGDR_9 Target DNA | GGCGGGCTGCAGCGGCCACCCGCGCTCCTGCACCAGGGACTGTGCCGAGCCGCGCGCGGACGGGAGGGAAGCGTCC CCTCAG |
| SEQ ID NO:258 | PTGDR_9 Converted DNA | GGCGGGTTGTAGCGGTTATTCGCGTTTTTGTATTAGGGATTGTGTCGAGTCGCGCGCGGACGGGAGGGAAGCGTTTTT TTAG |
| SEQ ID NO:259 | PTGDR_9 Forward Primer | GTTGTAGCGGTATTCGCG |
| SEQ ID NO:260 | PTGDR_9 Reverse Primer | CTTCTCTCCCGTCCGCGC |
| SEQ ID NO:261 | PTGDR_9 Flap oligonucleotide | CGCCGAGGCGGCGACTCGACA/3C6/ |

FIG. 6 (cont'd)

| SEQ ID NO | Description | Sequence (all are shown 5' to 3') |
|---|---|---|
| SEQ ID NO:262 | RASSF1 (Human) Target DNA | TCCAGAAACACGGGTATCTCCGCGTGGTGCTTTGCGGTCGCCGCGTCGTTGTTGGCGGTCCGGGGTGGGGTGTGAGGA GGGGGACGAAGGAGGAGGGAAGGAAGGGAAGGGGGGCTCGCGAGAGCGCGCCCAGCCCGCCTTC |
| SEQ ID NO:263 | RASSF1 (Human) Converted DNA | TTTAGAAATACGGGTATTTTCGCGTGGTGTTTTGCGGTCGTCGTTTGTTGGCGGTTCGGGGTGGGGTGTGAGGAG GGGGACGAAGGAGGAGGGAAGGAAGGGTAAGGCGGGGAGGGGGTTTTGCGAGAGCGCGTTTAGTTTCGTTTT |
| SEQ ID NO:264 | RASSF1 (Human) Forward Primer | AGAAATACGGGTATTTTCGCG |
| SEQ ID NO:265 | RASSF1 (Human) Reverse Primer | CCACAACGACGACGACC |
| SEQ ID NO:266 | RASSF1 (Human) Flap oligonucleotide | CCACGGACGGCAAAACACCA/3C6/ |
| SEQ ID NO:267 | SHOX2 Target DNA | CGGTCGGGCAGGCGGCGACGGAGATTACCTGGCTGTCCAGGGGACCTTATGCAGGGTTTGGCCCGAGCCCAGGGGGC AGCGAGGGGCGTCTGCGGACGGCGGCTCCCTGCGGCACAACACC |
| SEQ ID NO:268 | SHOX2 convereted DNA | CGGTCGGGTAGGCGGCGACGGAGATTATTTGGTTGTTTAGGGGATTTATGTAGGGTTTGGTTCGAGTTTAGGGGTA GCGAGGGGCGTTTGCGGATGCGGGTTTTTTGTGCGGTATAATATT |
| SEQ ID NO:269 | SHOX2 Forward Primer | GTTCGAGTTTAGGGGTAGCG |
| SEQ ID NO:270 | SHOX2 Reverse Primer | CCGCACAAAAAAACCGCA |
| SEQ ID NO:271 | SHOX2 Flap oligonucleotide | CCACGGACGATCCGCAAAACGC/3C6/ |
| SEQ ID NO:272 | SHROOM1 Target DNA | CCGGAGCCACTCGCCGCTCGCGCCCTGAAAGCCGCTGGCGGTAGGCGGCCCTCGAG |
| SEQ ID NO:273 | SHROOM1 Converted DNA | TCGGAGTATTCGTCGTTGCGGTTTGAAGTCGTTGGCGGTAGGCGGTTTTCGAG |
| SEQ ID NO:274 | SHROOM1 Forward Primer | GGAGTATTCGTCGTTGCG |
| SEQ ID NO:275 | SHROOM1 Reverse Primer | CGAAAACCGCCTACCGC |
| SEQ ID NO:276 | SHROOM1 Flap oligonucleotide | CGCCGAGGGCGTTTGAAGT/3C6/ |
| SEQ ID NO:277 | SKI Target DNA | CCCGGCCTACGGTCCTCCGCCACCTCCACGCGGCGGCGGCTGTTGGGGCCCCACCAGGCAGAGCCGTGTTCTCAGGC GTTGGCTCTCATGGAGGTGG |
| SEQ ID NO:278 | SKI Converted DNA | TTCGGGTTTACGGTTTTTCGTTATTTTTACGGGTGGTTTATTTGGGGTTTTATTAGGTAGAGTCGTGTTTTTAGGCGT TGGTTTTTATGGAGGTGG |
| SEQ ID NO:279 | SKI Forward Primer | ACGGTTTTTCGTTATTTTTACGGGG |
| SEQ ID NO:280 | SKI Reverse Primer | CAACGCCTAAAAACACGACTC |
| SEQ ID NO:281 | SKI Flap oligonucleotide | CGCCGAGGGGCGGTTGTTGG/3C6/ |
| SEQ ID NO:282 | S1PR4 Target DNA | GGGCCTGTCCCGTTCCCGTGCTCCCCATACAGGCGAGGCTGCGTGCACACAGCTTCCTGTACCCAGGAGGGGCCTGCC TGGCACGCACCCGGTGGCTGCACCATCCACACGCAAGACTGCAACTTCAGATGCTCCGCACGCTGGAGATG |
| SEQ ID NO:283 | S1PR4 Converted DNA | GGGGTTTGTTTCGTTTTGTTTTTTATATAGGCGAGGTTGCGTGTATATAGTTTTTGTATTTAGGAGGGGTTTGTTTG GTACGTATTCGGTTGGTTGTTATTATTTATACGTAAGATTGTAATTTTAGATGTTTCGTACGTTGGAGATG |
| SEQ ID NO:284 | S1PR4 Forward Primer | TTATATAGGCGAGGTTGCGT |
| SEQ ID NO:285 | S1PR4 Reverse Primer | CTTACGTATAAATAATAATACAACCACCGAATA |
| SEQ ID NO:286 | S1PR4 Flap oligonucleotide | CCACGGACGACGTACCAAACA/3C6/ |
| SEQ ID NO:287 | SLC12A8 Target DNA | CGGAGCTAGGAGGGGTGGGGCTCGGAGGAAGGAGAGAGCGGCTCTGCGAGGAAAGGGAAAGGGAGAGGAGGCCGCT TCTGGGAAGGGACCC |

FIG. 6 (cont'd)

| | Description | Sequence (all are shown 5' to 3') |
|---|---|---|
| SEQ ID NO:288 | SLC12A8 Converted DNA | CGGAGTTAGGAGGAGGTGGGGTTCGGAGGGGCGTAGGAAGAGAGCCGGTTTTGCGAGGAAAGGGAAAGGAGAGGAGGGTCGTTTTTTGGGAAGGGATTT |
| SEQ ID NO:289 | SLC12A8 Forward Primer | TTAGGAGGGTGGGGTTCG |
| SEQ ID NO:290 | SLC12A8 Reverse Primer | CTTTCCTCGCAAAACCGC |
| SEQ ID NO:291 | SLC12A8 Flap oligonucleotide | CCACGGACGGGAGGGCGTAGG/3C6/ |
| SEQ ID NO:292 | SOBP Target DNA | GCCCCGCGCGGGCCCCGAGCGCGCCGCCGGCCTGCAACGTCATCGTGAACGGCACGCGCGG |
| SEQ ID NO:293 | SOBP Converted DNA | GTTTCGGCGCGGTTTCGAGGCGGTCGCGGTTTGTAACGTATCGTGAACGGTACGCGCGG |
| SEQ ID NO:294 | SOBP Forward Primer | TTTCGGCGGCGGTTTCGAG |
| SEQ ID NO:295 | SOBP Reverse Primer | CGTACCGTTCACGATAACGT |
| SEQ ID NO:296 | SOBP Flap oligonucleotide | CGCCGAGGGGCGGTCGCGGT/3C6/ |
| SEQ ID NO:297 | SOBP Flap oligonucleotide v2 | CGCCGAGGTTACAAACCGCG/3C6/ |
| SEQ ID NO:298 | SPOCK2 Target DNA | CTAGGCGAGATGGTGGAAGGCGTGTCCGTACGGGGGTGGGCTGGGGTCCCGTGCAGAAGGGCGCGCGAGGACCCAGGCTGGTTTTCCC |
| SEQ ID NO:299 | SPOCK2 Converted DNA | TTAGGCGAGATGGTGGAAGGCGTGTTCGTACGGGGGTGGGTTGGGGTTTTCGTGTAGAAGGGCGCGCGAGGATTTAGGTTGGTTTTTTT |
| SEQ ID NO:300 | SPOCK2 Forward Primer | CGAGATGGTGGAAGGCG |
| SEQ ID NO:301 | SPOCK2 Reverse Primer | GCGCCCTTCTACACGAA |
| SEQ ID NO:302 | SPOCK2 Flap oligonucleotide | CCACGGACGGTGTTCGTACGG/3C6/ |
| SEQ ID NO:303 | ST8SIA1 Target DNA | GCGCTGCTGCGCGCCAGGCAAGGGCAAGGGAGAGGGTCCGGCTCCGCTCCCTCCTAAACATGTGGCCCGTGGCGTCCCCTTGTCCCCTCCGAGCGATGCTCCTGCCCCTTGCGCGCCGGCGATGGTTGTCGGCCAGGCAA |
| SEQ ID NO:304 | ST8SIA1 Converted DNA | GGCGAGGGTTCGGGAGAGAAGGTTCGGTTTTTTTTAAATATGGTTCGTGGCGTTTTTTGTTTTTTCGAGCGATGTTTTGCGTTTTTCGTCGTTTTTTCGCGGTTTTCGTGTTTGTTTGCGCGTCGTTAGGTAA |
| SEQ ID NO:305 | ST8SIA1 Forward Primer | AAATATGTTGGTTCGTGGCGTT |
| SEQ ID NO:306 | ST8SIA1 Reverse Primer | ACGCAACAACGCGAAAAAC |
| SEQ ID NO:307 | ST8SIA1 Flap oligonucleotide | CGCCGAGGCGACGAAAAACG/3C6/ |
| SEQ ID NO:308 | ST8SIA1_22 Target DNA | ACGAGAAAGAGATCGTGCAGGGGGTGCTGCAACAGGCACGCGGTGGAGGAGGAACCAGACCGCGGCCGCCAGAGCGTTCAGGTACTCCTGCCCTCGCGGGCTCCTCCTTTCCTCCCCGAGTGCAGAGG |
| SEQ ID NO:309 | ST8SIA1_22 Converted DNA | ACGAGAAAGAGATCGTGTAGGGGGTGTTGTAATAGGTACGCGGTGGAGGAGGAATTAGATCGCGGTTAGAGCGTTTAGGTATTTTGTTTTCGCGGTTTTTTTTTTTTAGCGTTTTTTTTCGAGTGTAGAGG |
| SEQ ID NO:310 | ST8SIA1_22 Forward Primer | GGGGTGTTGTAATAGGGTACG |
| SEQ ID NO:311 | ST8SIA1_22 Reverse Primer | CTAAACGCTCTAACCGCGA |
| SEQ ID NO:312 | ST8SIA1_22 Flap oligonucleotide | CCACGGACGGGGGTACAGCCGTGGAGGAG/3C6/ |
| SEQ ID NO:313 | SP9 Target DNA | CGCGCCGTTGGTCACCTCGCCGGCCGCCAGCGTCGAATGGAAGCCCGACTTGTACCAGGACTCGTACGGGTGCGCCATGCCCACGCGCGGGTACAGCCCGTCGGCTCGGCGTGCCGTCGTG |
| SEQ ID NO:314 | SP9 Converted DNA | CGCGTCGTTGGTTATTTCGTCGGTCGTTAGCGTCGAATGGAAGTTCGATTTGTATTTAGGATTCGTACGGGTGCGTTATGTTTACGCGCGGGTATAGTTTCGTCGGTTGTCGGTGTCGTTA |

FIG. 6 (cont'd)

| | Description | Sequence (all are shown 5' to 3') |
|---|---|---|
| SEQ ID NO:315 | SP9 Forward Primer | TAGCGTCGAATGGAAGTTCGA |
| SEQ ID NO:316 | SP9 Forward Primer Universal | GGTCGTTAGCGTCGAATG |
| SEQ ID NO:317 | SP9 Reverse Primer | GCGCGTAAACATAACGCACC |
| SEQ ID NO:318 | SP9 Flap oligonucleotide | CCACGGACGCGTACGAATCC/3C6/ |
| SEQ ID NO:319 | SUCLG2 Target DNA | GGTTCCTTCCCGTGGGGTTCTTAATCGTCTCGCTGACTTCCAGAATGAAACTCGACACCCTCGCGGTAAAGATGGCGT GACCAGAA |
| SEQ ID NO:320 | SUCLG2 Converted DNA | GGTTTTTTTCGTGGGGTTTTAATCGTTTCGTTGATTTTTAGAATGAAATGTAGAATTTCGCGGTAAAGATGGCGTGA TTAGAA |
| SEQ ID NO:321 | SUCLG2 Forward Primer | TCGTGGGGTTTTTAATCGTTTCG |
| SEQ ID NO:322 | SUCLG2 Reverse Primer | TCACGCCATCTTTACCGC |
| SEQ ID NO:323 | SUCLG2 Flap oligonucleotide | CCACGGACGCGAAAATCTACA/3C6/ |
| SEQ ID NO:324 | SUCLG2 Forward Primer Universal | GGTTTTTTTCGTGGGGTTTTTAATCG |
| SEQ ID NO:325 | SUCLG2 Reverse Primer Universal | CTAATCACGCCATCTTTACCG |
| SEQ ID NO:326 | SUCLG2 Flap oligonucleotide Universal | CCACGGACGGTTTCGTTGATT/3C6/ |
| SEQ ID NO:327 | TBX15 Target DNA | GGAGTGAGTGCCTACAACGCGGACGGCCAGGCCGATGATCCCCGTTGCTGCGTGGTGCCCCAAGCTGCGGGTGCTC GGGGCGCCAACTAAAGCCAGCTCGTCTCCAGACGCGGAAAG |
| SEQ ID NO:328 | TBX15 Converted DNA | GGAGTGAGTGTTTATAACGCGTAGGTCGGATTGATTTTCGTTGTTGTAGGTGGTGTTTAAGTTGCGGGTGTTCG GGCGTTAATTAAAGTTAGTTTGTTTAGACGCGGAAAG |
| SEQ ID NO:329 | TBX15 Reg. 1 Forward Primer | CGTAGGTCGGATTGATTTTCGT |
| SEQ ID NO:330 | TBX15 Reg. 1 Reverse Primer | TCTAAACAAAACTAACTTTAATTAACGCCC |
| SEQ ID NO:331 | TBX15 Reg. 1 Flap oligonucleotide | CCACGGACGCGAACACCCGCA/3C6/ |
| SEQ ID NO:403 | TBX15 Reg. 2 Target DNA | GGAAGGAAATTGCGGGTTCCCGTCCGTCGCCTTGTCTCGCTGAAGCCCGGTAGCAGTGAATGCGCGCTGA CTTTCAGCGACGACTCCTGGAAGCAACGCCA |
| SEQ ID NO:404 | TBX15 Reg. 2 Converted DNA | GGAAGGAAATTGCGGGTTTCGTTTGTTTGTTTTTTTAGTTTTTTGTTGAAGTTCGGTAGTAGTGAATGCGCGTTGAT TTTTAGCGACGATTTTTGGAAGTAACGTTA |
| SEQ ID NO:332 | TBX15 Reg. 2 Forward Primer | AGGAAATTGCGGGTTTTCG |
| SEQ ID NO:333 | TBX15 Reg. 2 Forward Primer Univ. | GGAAGGAAATTGCGGGTTTC |
| SEQ ID NO:334 | TBX15 Reg. 2 Reverse Primer | CCAAAAATCGTCGCTAAAAATCAAC |
| SEQ ID NO:335 | TBX15 Reg. 2 Flap oligonucleotide | CCACGGACGCGCGCATTCACT/3C6/ |
| SEQ ID NO:336 | TRH Target DNA | GGCGGCCGCGACCCCTCCCCGCTGACCTCACTCGAGCCGCGCCTCGGCGCAGATATAAGCGGCGCCCATCTGAAG AGGGCTCGGCGCAGGCGCCCGGGGTC |
| SEQ ID NO:337 | TRH Converted DNA | GGCGGTCGCGATTTTTTTCGTTGATTTTATTCGAGTCGTCGTTGGCGTAGATATAAGCGGCGGTTTATTTGAAGAG GGTTCGGTAGGCGTTCGGGGTT |
| SEQ ID NO:338 | TRH Forward Primer | TTTCGTTGATTTTATTCGAGTCG |
| SEQ ID NO:339 | TRH Reverse Primer | TCTTCAAATAAAACCGCCGC |
| SEQ ID NO:340 | TRH Flap oligonucleotide | CGCCGAGGGTCGTTTGGCGT/3C6/ |

FIG. 6 (cont'd)

| | Description | Sequence (all are shown 5' to 3') |
|---|---|---|
| SEQ ID NO:341 | TSC22D4 Target DNA | CGGGTGGTGAAGCTGCCCCACGGCCTGGGAGAGAGCCTTATCGCCGCGGTCGCTGGACGTGTGTGGATGTTTATGAGC GAGACCTGGAGCCCCACAGCTTCGGCGGACTCCTGGAGGGAA |
| SEQ ID NO:342 | TSC22D4 Converted DNA | CGGGTGGTGAAGTGTTTACGGTTTGGGAGAGTTTATCGTCGCGGTCGTTGGACGTGTGTGGATGTTTATGAGC GAGATTTGGAGTTTATAGTTTCGGCGGATTTTTGGAGGGAA |
| SEQ ID NO:343 | TSC22D4 Forward Primer | GTTTGGGAGAGTTTATCGTCG |
| SEQ ID NO:344 | TSC22D4 Reverse Primer | CCTCCAAAAATCCGCCGA |
| SEQ ID NO:345 | TSC22D4 Flap oligonucleotide | CGCCGAGGGCGGTCGTTGGA/3C6/ |
| SEQ ID NO:346 | ZDHHC1 Target DNA | GGGGCCGGGGCCGACAGCCCACGCTGGCGCGGCAGGCGCGTGCGCCGCCGTTTCGTGAGCCGAGCAG |
| SEQ ID NO:347 | ZDHHC1 Converted DNA | GGGGTCGGGGTCGATAGTTTACGTTGGCGCGGTAGGCGCGTGCGTTTCGTGTTTCGTGAGTTCGAGTAG |
| SEQ ID NO:348 | ZDHHC1 Forward Primer | GTCGGGGTCGATAGTTTACG |
| SEQ ID NO:349 | ZDHHC1 Reverse Primer | ACTCGAACTCACGAAAACG |
| SEQ ID NO:350 | ZDHHC1 Flap oligonucleotide | CGCCGAGGGACGAAACGCACG/3C6/ |
| SEQ ID NO:351 | ZMIZ1 Target DNA | GGAGCCCCAGCCCACGCGGGCACACGCAGGGTGGGTGGTCACGCCCGCAGGGTCCGCGAGGGCGGCGGCGCGAGAG CGCGGGCCGTGGGAAGTTTCTC |
| SEQ ID NO:352 | ZMIZ1 Converted DNA | GGAGTTTTAGTTTACGCGGGTATACGTAGGGTTCGTTGGTTACGTTCGCGAGGCGGCGGCGTAGAGCG CGGGTCGTGGGAAGTTTTT |
| SEQ ID NO:353 | ZMIZ1 Forward Primer | GTAGGGTGGGTGGTTACG |
| SEQ ID NO:354 | ZMIZ1 Reverse Primer | AACTTCCCACGACCCGC |
| SEQ ID NO:355 | ZMIZ1 Flap oligonucleotide | CGCCGAGGGTTCGTAGGGTT/3C6/ |
| SEQ ID NO:356 | ZNF132 Target DNA | GGCGCGCCCATTGCGGTCCTCATTTTGCTGCTGGTGGGCTACAGCAGGCCTCGAGCCACACCAGGGCAC GGGAGTGGGTGCAGGGACCGTCACCGCGCCTTCACACGCACCACCATAGTGCCC |
| SEQ ID NO:357 | ZNF132 Converted DNA | GGCGTCGTTATTGCGGTTTTATTTTGTTGTTGGTTAGGTTTTGGAGTTATATTAGGGTACGG GAGTGGGTGTAGGGATCGTTATCGCGTTTTATACGTATTATAGTGTTT |
| SEQ ID NO:358 | ZNF132 Forward Primer | TGGAGTTATATTAGGGTACGGGA |
| SEQ ID NO:359 | ZNF132 Reverse Primer | ACACTATAATACGTATAAAAACGCGATA |
| SEQ ID NO:360 | ZNF132 Flap oligonucleotide | CCACGGACGAAACGATCCCTAC/3C6/ |
| SEQ ID NO:361 | ZNF329 Target DNA | GGCGGCGAGGGGCGCGGTCCGCGGGTGGGTTTCACCTGGGTGGTGGGCATGTCGGGCCCGCTAGGGCGAGGGTCT GGCCAGGGGGGCGTAGTTCTCCTGGTGGGGTGGTGGGTGGTGGGTGGTGGGACGCTCCGTGGGCGATTGGGGTCACTCCTCTGAGG |
| SEQ ID NO:362 | ZNF329 Converted DNA | GGCGGCGAGGGGCGCGGTTTCGCGGGTGGGTTTTATTTGGGTGGTGGGTATGTCGGGTTCGTTAGGGCGAGGGTTTG GTTAGGGGGGCGTAGTTTTTTTTGGTGGGGTGGTGGGTGGTGGGACGTTTCGTGGGCGATTGGGGTTATTTTTTGAGG |
| SEQ ID NO:363 | ZNF329 Forward Primer | GGTGGTGGGTATGTCGG |
| SEQ ID NO:364 | ZNF329 Reverse Primer | CCAATCGCCACGAAACG |
| SEQ ID NO:365 | ZNF329 Flap oligonucleotide | CCACGGACGGGTTCGTTAGGG/3C6/ |
| SEQ ID NO:366 | ZNF671 Target DNA | CCGTGGGCGCGGACAGCTGCCGGAGCGGCAGGCGGTCTCGATCGGGACGGCAGGCACTTCCGTCCCTGCAGAGCA TCAGACGCGTCTCGGGACACTGGGGACAACATCTCCTCCGCG |
| SEQ ID NO:367 | ZNF671 Converted DNA | TCGTGGGCGCGGATAGTTGTCGGGAGCGGTAGGCGGTTTCGATCGGGACGGTAGGTATTTTCGTTTTTGTAGAGTAT TAGACGCGTTTCGGGATATTGGGGATAAATATTTTTTCGCG |

FIG. 6 (cont'd)

| | Description | Sequence (all are shown 5' to 3') |
|---|---|---|
| SEQ ID NO:368 | ZNF671 Forward Primer | GTTGTCGGGAGCGGTAGG |
| SEQ ID NO:369 | ZNF671 Reverse Primer | CCAATATCCCGAAACGCGTCT |
| SEQ ID NO:370 | ZNF671 Flap oligonucleotide | CCACGGACGGCGTTTCGATCG/3C6/ |
| SEQ ID NO:371 | ZNF781 Target DNA | AAGCTGCGCCCGGAGACGTGGGAGCGTTCTCTTGTTTCCGAGTGCGCGGACTCATCGGGTCACAGTTTATGCTTTT ATGACGGCGGTGAGTCCAGCCACTGATTCCTAACGGTTTAGAGT |
| SEQ ID NO:372 | ZNF781 Converted DNA | AAGTTGCGTTCGGAGACGTGGGAGCGTTTTTTGTTTTTCGAGTGCGCGGATTTATCGGGTTATAGTTTATGTTTTTA TGACGCGGTGAGTTTAGTTATTGATTTTTAACGGTTTAGAGT |
| SEQ ID NO:373 | ZNF781 Forward Primer | CGTTTTTTGTTTTCGAGTGCG |
| SEQ ID NO:374 | ZNF781 Reverse Primer | TCAATAACTAAACTCACCGGTC |
| SEQ ID NO:375 | ZNF781 Flap oligonucleotide | CCACGGACGGCGGATTTATCG/3C6/ |
| SEQ ID NO:376 | β-actin Target DNA (ACTB) | CTCTGACCTGAGTCTCCTTGGAACTCTGCAGGTTCATTGCTTTCCCAGATGAGCTCTTTTCTGGTGTTTGTCTC TCTGACTAGGTGTCTAAGACAGTTGTGTGGGTAGGTACTAACACTGGCTCGTGTGACAAGGCCATGAGGCTGGT GTAAAGCGGCCTTGGAGTTGTGTATTAAGTAGGTGCACAGTAGGTCTGAACAGACTCCCCATCCCAAGA |
| SEQ ID NO:377 | β-actin Converted (BTACT) | TTTTGATTTGAGTTTTTTTTTGGAATTTGTAGAGTTTATTTGTTTTTTTTTAGATGAGTTTTTTTTTGGTGTTTGTTTTT TGATTAGGTGTTTAAGATAGTGTTTGTGGGTAGGTATTAATATTGGTTTGTGTGATAAGGTTATGAGGTTGGTGTA AAGTGGTTTTGGAGTTGTGTATTAAGTAGGTGTATAGTAGGTTGAATAGATTTTTATTTTAAGA |
| SEQ ID NO:378 | β-actin UT Forward primer | CCATGAGGCTGGTGTAAAG |
| SEQ ID NO:379 | β-actin UT Reverse primer | CTACTGTGCACCTACTTAATACAC |
| SEQ ID NO:380 | β-actin UT Probe (Arm 1 ) | CGCCGAGGGCGGCCTTGGAG/3C6/ |
| SEQ ID NO:381 | β-actin BT Forward primer 65 | GTGTTTGTTTTTGATTAGGTGTTAAGA |
| SEQ ID NO:382 | β-actin BT Reverse primer 65 | CTTTACACCAACCTCATAACCTTATC |
| SEQ ID NO:383 | β-actin BT probe (Arm 3) | GACGCGGAGATAGTGTTGTGG/3C6/ |
| SEQ ID NO:384 | B3GALT6 Target DNA | GGCCACACAGGCCCACTCTGGCCCTCTGAGCCCCGGCGGACCCAGGGCATTCAAGGAGGGGCTGGGCTGCCA GCGGAGGCCTCCGCGCAAACACAGCAGGCTGGAAGTGGCGCTCATCACCGGCACGTCTTCCCAG |
| SEQ ID NO:385 | B3GALT6 Converted DNA | GGTTATATAGGTTATTTGGTTTTTGGAGTTTTCGGCGGATTTAAGGAGGCGGTTTTGGGTTGTTAGCG TAGGTTTTCGCGTAAATATAGTAGGTTGGAAGTGGCGTTTATTATCGGTACGTTTTTTAG |
| SEQ ID NO:386 | B3GALT6 Forward Primer | GGTTTTATTTTGGTTTTTGAGTTTTCGG |
| SEQ ID NO:387 | B3GALT6 Reverse Primer | TCCAACCTACTATATTTACGCGAA |
| SEQ ID NO:388 | B3GALT6 Flap oligonucleotide (Arm 5) | CCACGGACGGCGGATTTAGGG/3C6/ |
| SEQ ID NO:389 | Zebrafish (ZF) Synthetic Target DNA (RASSF1) | TCCAC/iMe-dC/GTGGTGCCCACTCTGACAGGTGGAGCAGAGGGGAAGGTGGTG/iMe-dC/GCATGGTGGG/iMe-dC/GAG/iMe-dC/G/iMe-dC/GTG/iMe-dC/GCCTGGAGGACCC/iMe-dC/iMe-dC/GATTGGCTGA/iMe-dC/GTGTAAACCAGGA/iMe-dC/GAGGACATGACTTTCAGCCCTGCAGCCCGACACAGCTGAGCTGGTGTGACCTGGTGTGGAGAGTTCATCTGG |

FIG. 6 (cont'd)

| | Description | Sequence (all are shown 5' to 3') |
|---|---|---|
| SEQ ID NO:390 | Zebrafish (ZF) Convert. Synthetic Target DNA | TTTATCGTGGGTGTTTATTTTGGATAGGTGGAGTAGAGGGAAGGTGGTGCGTATGGTGGGCGAGCGCGTGCGTTTGG AGGATTTCGATTGGTTGACGTGTAAATTAGGACGAGGATATGATTTTTAGTTTTGTAGTTTAGATATAGTTGAGTTGG TGTGATTTGTGTGGAGAGTTATTTGG |
| SEQ ID NO:391 | ZF_RASSF1 UT Forward primer | CGCATGGTGGGCGAG |
| SEQ ID NO:392 | ZF_RASSF1 UT Reverse primer | ACACGTCAGCCAATCGGG |
| SEQ ID NO:393 | ZF_RASSF1 UT Probe (Arm 3) | GACGCGGAGGCGCGTGCGCC/3C6/ |
| SEQ ID NO:394 | ZF_RASSF1 BT Forward primer | TGCGTATGGTGGGCGAG |
| SEQ ID NO:395 | ZF_RASSF1 BT Reverse primer | CCTAATTTACACGTCAACCAATCGAA |
| SEQ ID NO:396 | ZF_RASSF1 BT probe (Arm 3) | GACGCGGAGGCGCGTGCGTTT/3C6/ |
| SEQ ID NO:397 | ZF_RASSF1 BT probe (Arm 5) | CCACGGACACGGCGCGTGCGTTT/3C6/ |
| SEQ ID NO:398 | Arm 1 QUASAR-670 FRET cassette | Q670-TCT-BHQ-2-AGCCGGTTTTCCGGCTGAGACCTCGGCG/3C6/ |
| SEQ ID NO:399 | Arm 1 HEX FRET cassette | /HEX/ TCT/BHQ-1/AGCCGGTTTTCCGGCTGAGACCTCGGCG/3C6/ |
| SEQ ID NO:400 | Arm 3 QUASAR-670 FRET cassette | Q670-TCT-BHQ-2/AGCCGGTTTTCCGGCTGAGACTCCGGTC/3C6 |
| SEQ ID NO:401 | Arm 5 FAM FRET cassette | d-FAM-TCT-BHQ-1-AGCCGGTTTTCCGGCTGAGACGTCCGTGG/3C6/ |
| SEQ ID NO:402 | Arm 7 FAM FRET cassette | d-FAM-TCT-BHQ-1-AGCCGGTTTTCCGGCTGAGAGGACGCGC/3C6/ |

```
                            SEQUENCE LISTING

<160> NUMBER OF SEQ ID NOS: 404

<210> SEQ ID NO 1
<211> LENGTH: 116
<212> TYPE: DNA
<213> ORGANISM: Homo sapiens

<400> SEQUENCE: 1
gttcccggaa cggcctcttg ggggcgttcc agccccacgg acccgcaggg agtccccgcc       60
gcaatttgca tggggctcat ttgcatgacc ccgccccgcg cgggagtcgg gggcgc         116

<210> SEQ ID NO 2
<211> LENGTH: 116
<212> TYPE: DNA
<213> ORGANISM: Artificial sequence
<220> FEATURE:
<223> OTHER INFORMATION: Synthetic DNA

<400> SEQUENCE: 2
gttttcggaa cggttttttg ggggcgtttt agttttacgg attcgtaggg agttttcgtc       60
gtaatttgta tggggtttat ttgtatgatt tcgtttcgcg cgggagtcgg gggcgt         116

<210> SEQ ID NO 3
<211> LENGTH: 23
<212> TYPE: DNA
<213> ORGANISM: Artificial sequence
<220> FEATURE:
<223> OTHER INFORMATION: Synthetic DNA

<400> SEQUENCE: 3
ggcgttttag ttttacggat tcg                                              23

<210> SEQ ID NO 4
<211> LENGTH: 27
<212> TYPE: DNA
<213> ORGANISM: Artificial sequence
<220> FEATURE:
<223> OTHER INFORMATION: Synthetic DNA

<400> SEQUENCE: 4
acaaataaac cccatacaaa ttacgac                                          27

<210> SEQ ID NO 5
<211> LENGTH: 20
<212> TYPE: DNA
<213> ORGANISM: Artificial sequence
<220> FEATURE:
<223> OTHER INFORMATION: Synthetic DNA

<400> SEQUENCE: 5
cgccgaggcg aaaactccct                                                  20

<210> SEQ ID NO 6
<211> LENGTH: 126
<212> TYPE: DNA
<213> ORGANISM: Homo sapiens

<400> SEQUENCE: 6
```

-continued

```
cggattcaac atgggcaatg tgcctacact ttcattcttc cagaacacga tggcaactgt     60
cgtgagagta cgacagacca gtacaacaca aacgctctgc agagagatgc tccacacgtg    120
gaaccg                                                               126
```

```
<210> SEQ ID NO 7
<211> LENGTH: 126
<212> TYPE: DNA
<213> ORGANISM: Artificial sequence
<220> FEATURE:
<223> OTHER INFORMATION: Synthetic DNA

<400> SEQUENCE: 7
cggatttaat atgggtaatg tgtttatatt tttatttttt tagaatacga tggtaattgt     60
cgtgagagta cgatagatta gtataatata aacgttttgt agagagatgt tttatacgtg    120
gaatcg                                                               126
```

```
<210> SEQ ID NO 8
<211> LENGTH: 26
<212> TYPE: DNA
<213> ORGANISM: Artificial sequence
<220> FEATURE:
<223> OTHER INFORMATION: Synthetic DNA

<400> SEQUENCE: 8
ttttagaata cgatggtaat tgtcgt                                          26
```

```
<210> SEQ ID NO 9
<211> LENGTH: 35
<212> TYPE: DNA
<213> ORGANISM: Artificial sequence
<220> FEATURE:
<223> OTHER INFORMATION: Synthetic DNA

<400> SEQUENCE: 9
acatctctct acaaaacgtt tatattatac taatc                                35
```

```
<210> SEQ ID NO 10
<211> LENGTH: 20
<212> TYPE: DNA
<213> ORGANISM: Artificial sequence
<220> FEATURE:
<223> OTHER INFORMATION: Synthetic DNA

<400> SEQUENCE: 10
cgccgaggct atcgtactct                                                 20
```

```
<210> SEQ ID NO 11
<211> LENGTH: 109
<212> TYPE: DNA
<213> ORGANISM: Homo sapiens

<400> SEQUENCE: 11
ggagctacga cgagcagctg cggctggcga tggaactgtc ggcgcaggag caggaggaga     60
ggcggcggcg cgcgcgccag gaggaggagg agctggagcg catcctgag               109
```

```
<210> SEQ ID NO 12
<211> LENGTH: 109
<212> TYPE: DNA
<213> ORGANISM: Artificial sequence
<220> FEATURE:
<223> OTHER INFORMATION: Synthetic DNA
```

<400> SEQUENCE: 12
ggagttacga cgagtagttg cggttggcga tggaattgtc ggcgtaggag taggaggaga     60
ggcggcggcg cgcgcgttag gaggaggagg agttggagcg tattttgag               109

<210> SEQ ID NO 13
<211> LENGTH: 20
<212> TYPE: DNA
<213> ORGANISM: Artificial sequence
<220> FEATURE:
<223> OTHER INFORMATION: Synthetic DNA

<400> SEQUENCE: 13
agttacgacg agtagttgcg                                                20

<210> SEQ ID NO 14
<211> LENGTH: 18
<212> TYPE: DNA
<213> ORGANISM: Artificial sequence
<220> FEATURE:
<223> OTHER INFORMATION: Synthetic DNA

<400> SEQUENCE: 14
tcctcctact cctacgcc                                                  18

<210> SEQ ID NO 15
<211> LENGTH: 21
<212> TYPE: DNA
<213> ORGANISM: Artificial sequence
<220> FEATURE:
<223> OTHER INFORMATION: Synthetic DNA

<400> SEQUENCE: 15
ccacggacgc gacaattcca t                                              21

<210> SEQ ID NO 16
<211> LENGTH: 143
<212> TYPE: DNA
<213> ORGANISM: Homo sapiens

<400> SEQUENCE: 16
ggtggcaacg gctggagtgc cgtcgcccgc gccactcacc ccggcgcggc gccctgcgcg     60
gccgctcagc ggaaggccag caggaagatc agtacgacgt tgatgagaac caggagcgcc    120
agcacggcgg agaccaccac gcg                                           143

<210> SEQ ID NO 17
<211> LENGTH: 143
<212> TYPE: DNA
<213> ORGANISM: Artificial sequence
<220> FEATURE:
<223> OTHER INFORMATION: Synthetic DNA

<400> SEQUENCE: 17
ggtggtaacg gttggagtgt cgtcgttcgc gttatttatt tcggcgcggc gttttgcgcg     60
gtcgtttagc ggaaggttag taggaagatt agtacgacgt tgatgagaat taggagcgtt    120
agtacggcgg agattattac gcg                                           143

<210> SEQ ID NO 18
<211> LENGTH: 23
<212> TYPE: DNA
<213> ORGANISM: Artificial sequence
<220> FEATURE:
<223> OTHER INFORMATION: Synthetic DNA -continued

<400> SEQUENCE: 18
cgttcgcgtt atttatttcg gcg                                                 23

<210> SEQ ID NO 19
<211> LENGTH: 24
<212> TYPE: DNA
<213> ORGANISM: Artificial sequence
<220> FEATURE:
<223> OTHER INFORMATION: Synthetic DNA

<400> SEQUENCE: 19
gctcctaatt ctcatcaacg tcgt                                               24

<210> SEQ ID NO 20
<211> LENGTH: 20
<212> TYPE: DNA
<213> ORGANISM: Artificial sequence
<220> FEATURE:
<223> OTHER INFORMATION: Synthetic DNA

<400> SEQUENCE: 20
cgccgagggc ggcgttttgc                                                    20

<210> SEQ ID NO 21
<211> LENGTH: 100
<212> TYPE: DNA
<213> ORGANISM: Homo sapiens

<400> SEQUENCE: 21
ggcccggggc cgcctgggcc cctaggggct ggacgtcaac ctgttagata gagggcgtgg        60 gacccccgc aggcggctgc tcggacgacc gcatccggag                               100

<210> SEQ ID NO 22
<211> LENGTH: 100
<212> TYPE: DNA
<213> ORGANISM: Artificial sequence
<220> FEATURE:
<223> OTHER INFORMATION: Synthetic DNA

<400> SEQUENCE: 22
ggttcggggt cgtttgggtt tttaggggtt ggacgttaat ttgttagata gagggcgtgg        60
gatttttcgt aggcggttgt tcggacgatc gtattcggag                              100

<210> SEQ ID NO 23
<211> LENGTH: 24
<212> TYPE: DNA
<213> ORGANISM: Artificial sequence
<220> FEATURE:
<223> OTHER INFORMATION: Synthetic DNA

<400> SEQUENCE: 23
cgttaatttg ttagatagag ggcg                                               24

<210> SEQ ID NO 24
<211> LENGTH: 18
<212> TYPE: DNA
<213> ORGANISM: Artificial sequence
<220> FEATURE:
<223> OTHER INFORMATION: Synthetic DNA

<400> SEQUENCE: 24
acgatcgtcc gaacaacc                                                      18

-continued

```
<210> SEQ ID NO 25
<211> LENGTH: 21
<212> TYPE: DNA
<213> ORGANISM: Artificial sequence
<220> FEATURE:
<223> OTHER INFORMATION: Synthetic DNA

<400> SEQUENCE: 25
ccacggacgc gcctacgaaa a                                                   21

<210> SEQ ID NO 26
<211> LENGTH: 17
<212> TYPE: DNA
<213> ORGANISM: Artificial sequence
<220> FEATURE:
<223> OTHER INFORMATION: Synthetic DNA

<400> SEQUENCE: 26
tccgaacaac cgcctac                                                       17

<210> SEQ ID NO 27
<211> LENGTH: 21
<212> TYPE: DNA
<213> ORGANISM: Artificial sequence
<220> FEATURE:
<223> OTHER INFORMATION: Synthetic DNA

<400> SEQUENCE: 27
ccacggacgc gaaaaatccc a                                                   21

<210> SEQ ID NO 28
<211> LENGTH: 119
<212> TYPE: DNA
<213> ORGANISM: Homo sapiens

<400> SEQUENCE: 28
gcttccagcc gcgcgctccg tgccactgcc gctctctgca gccccgcgtc cccgcagcct        60
ccccatggcc agcccgcttc gctccgctgc ggcccttgcc cgccaggtac ctcgaaccc        119

<210> SEQ ID NO 29
<211> LENGTH: 119
<212> TYPE: DNA
<213> ORGANISM: Artificial sequence
<220> FEATURE:
<223> OTHER INFORMATION: Synthetic DNA

<400> SEQUENCE: 29
gtttttagtc gcgcgtttcg tgttattgtc gtttttttgta gtttcgcgtt ttcgtagttt       60
ttttatggtt agttcgtttc gtttcgttgc ggttttttgtt cgttaggtat ttcgaattt       119

<210> SEQ ID NO 30
<211> LENGTH: 27
<212> TYPE: DNA
<213> ORGANISM: Artificial sequence
<220> FEATURE:
<223> OTHER INFORMATION: Synthetic DNA

<400> SEQUENCE: 30
gtgttattgt cgtttttttgt agtttcg                                           27

<210> SEQ ID NO 31
<211> LENGTH: 18
<212> TYPE: DNA
<213> ORGANISM: Artificial sequence
```

```
<220> FEATURE:
<223> OTHER INFORMATION: Synthetic DNA

<400> SEQUENCE: 31
cgcaacgaaa cgaaacga                                                       18

<210> SEQ ID NO 32
<211> LENGTH: 20
<212> TYPE: DNA
<213> ORGANISM: Artificial sequence
<220> FEATURE:
<223> OTHER INFORMATION: Synthetic DNA

<400> SEQUENCE: 32
cgccgagggc gttttcgtag                                                     20

<210> SEQ ID NO 33
<211> LENGTH: 140
<212> TYPE: DNA
<213> ORGANISM: Homo sapiens

<400> SEQUENCE: 33
gcccgccgca cgccgcaatg ctccgcgctc cccgcggggt cgggcgactc agacagggac        60
cggaaaagaa ccacgcagaa gaaagcccta tttcttgtcg tctgttcctg tgcagccttg       120
cagcctcgcc gcccccgcgt                                                    140

<210> SEQ ID NO 34
<211> LENGTH: 140
<212> TYPE: DNA
<213> ORGANISM: Artificial sequence
<220> FEATURE:
<223> OTHER INFORMATION: Synthetic DNA

<400> SEQUENCE: 34
gttcgtcgta cgtcgtaatg tttcgcgttt ttcgcggggt cgggcgattt agatagggat        60
cggaaaagaa ttacgtagaa gaaagtttta ttttttgtcg tttgtttttg tgtagttttg       120
tagtttcgtc gttttcgcgt                                                    140

<210> SEQ ID NO 35
<211> LENGTH: 21
<212> TYPE: DNA
<213> ORGANISM: Artificial sequence
<220> FEATURE:
<223> OTHER INFORMATION: Synthetic DNA

<400> SEQUENCE: 35
cgtaatgttt cgcgtttttc g                                                   21

<210> SEQ ID NO 36
<211> LENGTH: 27
<212> TYPE: DNA
<213> ORGANISM: Artificial sequence
<220> FEATURE:
<223> OTHER INFORMATION: Synthetic DNA

<400> SEQUENCE: 36
actttcttct acgtaattct tttccga                                             27

<210> SEQ ID NO 37
<211> LENGTH: 20
<212> TYPE: DNA
<213> ORGANISM: Artificial sequence
<220> FEATURE:
```

<223> OTHER INFORMATION: Synthetic DNA

<400> SEQUENCE: 37
cgccgagggc ggggtcgggc                                              20

<210> SEQ ID NO 38
<211> LENGTH: 85
<212> TYPE: DNA
<213> ORGANISM: Homo sapiens

<400> SEQUENCE: 38
gccggggagt cgagaagcaa gtactagcgc tccaggaccg cgcgcgccgc cccgcgccgc    60
cccgcgccgc ccctcggtcc agagc                                        85

<210> SEQ ID NO 39
<211> LENGTH: 85
<212> TYPE: DNA
<213> ORGANISM: Artificial sequence
<220> FEATURE:
<223> OTHER INFORMATION: Synthetic DNA

<400> SEQUENCE: 39
gtcggggagt cgagaagtaa gtattagcgt tttaggatcg cgcgcgtcgt ttcgcgtcgt    60
ttcgcgtcgt ttttcggttt agagt                                        85

<210> SEQ ID NO 40
<211> LENGTH: 23
<212> TYPE: DNA
<213> ORGANISM: Artificial sequence
<220> FEATURE:
<223> OTHER INFORMATION: Synthetic DNA

<400> SEQUENCE: 40
agtattagcg ttttaggatc gcg                                          23

<210> SEQ ID NO 41
<211> LENGTH: 21
<212> TYPE: DNA
<213> ORGANISM: Artificial sequence
<220> FEATURE:
<223> OTHER INFORMATION: Synthetic DNA

<400> SEQUENCE: 41
actctaaacc gaaaaacgac g                                            21

<210> SEQ ID NO 42
<211> LENGTH: 21
<212> TYPE: DNA
<213> ORGANISM: Artificial sequence
<220> FEATURE:
<223> OTHER INFORMATION: Synthetic DNA

<400> SEQUENCE: 42
ccacggacgg cgaaacgacg c                                            21

<210> SEQ ID NO 43
<211> LENGTH: 74
<212> TYPE: DNA
<213> ORGANISM: Homo sapiens

<400> SEQUENCE: 43
gccgggagcc cgcacttcct cctcgggggc ctcagaaaac cacagggcgc ggggccaggg    60
cggcggcccc cagg                                                    74

-continued

```
<210> SEQ ID NO 44
<211> LENGTH: 74
<212> TYPE: DNA
<213> ORGANISM: Artificial sequence
<220> FEATURE:
<223> OTHER INFORMATION: Synthetic DNA

<400> SEQUENCE: 44
gtcgggagtt cgtatttttt tttcgggggt tttagaaaat tatagggcgc ggggttaggg     60
cggcggtttt tagg                                                      74

<210> SEQ ID NO 45
<211> LENGTH: 25
<212> TYPE: DNA
<213> ORGANISM: Artificial sequence
<220> FEATURE:
<223> OTHER INFORMATION: Synthetic DNA

<400> SEQUENCE: 45
tcgggagttc gtattttttt ttcgg                                          25

<210> SEQ ID NO 46
<211> LENGTH: 17
<212> TYPE: DNA
<213> ORGANISM: Artificial sequence
<220> FEATURE:
<223> OTHER INFORMATION: Synthetic DNA

<400> SEQUENCE: 46
aaaaccgccg ccctaac                                                   17

<210> SEQ ID NO 47
<211> LENGTH: 20
<212> TYPE: DNA
<213> ORGANISM: Artificial sequence
<220> FEATURE:
<223> OTHER INFORMATION: Synthetic DNA

<400> SEQUENCE: 47
cgccgaggcc ccgcgcccta                                                20

<210> SEQ ID NO 48
<211> LENGTH: 78
<212> TYPE: DNA
<213> ORGANISM: Homo sapiens

<400> SEQUENCE: 48
cggggcctac cctcaggcag cgctcgctcg aggccagctt ccgagctcca acccctgccc     60
gaaacctcgg cctcactg                                                  78

<210> SEQ ID NO 49
<211> LENGTH: 78
<212> TYPE: DNA
<213> ORGANISM: Artificial sequence
<220> FEATURE:
<223> OTHER INFORMATION: Synthetic DNA

<400> SEQUENCE: 49
cggggtttat ttttaggtag cgttcgttcg aggttagttt tcgagtttta atttttgttc     60
gaaatttcgg ttttattg                                                  78

<210> SEQ ID NO 50
```

```
<211> LENGTH: 24
<212> TYPE: DNA
<213> ORGANISM: Artificial sequence
<220> FEATURE:
<223> OTHER INFORMATION: Synthetic DNA

<400> SEQUENCE: 50
gggtttattt ttaggtagcg ttcg                                               24

<210> SEQ ID NO 51
<211> LENGTH: 29
<212> TYPE: DNA
<213> ORGANISM: Artificial sequence
<220> FEATURE:
<223> OTHER INFORMATION: Synthetic DNA

<400> SEQUENCE: 51
cgaaatttcg aacaaaaatt aaaactcga                                          29

<210> SEQ ID NO 52
<211> LENGTH: 21
<212> TYPE: DNA
<213> ORGANISM: Artificial sequence
<220> FEATURE:
<223> OTHER INFORMATION: Synthetic DNA

<400> SEQUENCE: 52
ccacggacgg ttcgaggtta g                                                  21

<210> SEQ ID NO 53
<211> LENGTH: 141
<212> TYPE: DNA
<213> ORGANISM: Homo sapiens

<400> SEQUENCE: 53
tgtcctgaca cgatggccac aggcacagtt tgtggtgatg cccaggggcc cgcgcggccc       60
cacggtggtc cagtttacac tcgggccccg cactcctgaa gttccgcgcg ggaggagaag      120
ggcgtccctt tcgcagctcg g                                                 141

<210> SEQ ID NO 54
<211> LENGTH: 141
<212> TYPE: DNA
<213> ORGANISM: Artificial sequence
<220> FEATURE:
<223> OTHER INFORMATION: Synthetic DNA

<400> SEQUENCE: 54
tgttttgata cgatggttat aggtatagtt tgtggtgatg tttaggggtt cgcgcggttt       60
tacggtggtt tagtttatat tcgggtttcg tatttttgaa gtttcgcgcg ggaggagaag      120
ggcgtttttt tcgtagttcg g                                                 141

<210> SEQ ID NO 55
<211> LENGTH: 19
<212> TYPE: DNA
<213> ORGANISM: Artificial sequence
<220> FEATURE:
<223> OTHER INFORMATION: Synthetic DNA

<400> SEQUENCE: 55
tgatgtttag gggttcgcg                                                     19

<210> SEQ ID NO 56
<211> LENGTH: 26
```

-continued

```
<212> TYPE: DNA
<213> ORGANISM: Artificial sequence
<220> FEATURE:
<223> OTHER INFORMATION: Synthetic DNA

<400> SEQUENCE: 56
cgaaacttca aaaatacgaa acccga                                          26

<210> SEQ ID NO 57
<211> LENGTH: 20
<212> TYPE: DNA
<213> ORGANISM: Artificial sequence
<220> FEATURE:
<223> OTHER INFORMATION: Synthetic DNA

<400> SEQUENCE: 57
cgccgagggc ggttttacgg                                                 20

<210> SEQ ID NO 58
<211> LENGTH: 112
<212> TYPE: DNA
<213> ORGANISM: Homo sapiens

<400> SEQUENCE: 58
ccggagcact cgccgctgcg cgccctgaag ccgctggcgg taggcggccc tcgaggccgg    60
cgggctgggc ggctcggcag cctgcgccgc ggcctccgcc tcggccgcca gc           112

<210> SEQ ID NO 59
<211> LENGTH: 112
<212> TYPE: DNA
<213> ORGANISM: Artificial sequence
<220> FEATURE:
<223> OTHER INFORMATION: Synthetic DNA

<400> SEQUENCE: 59
tcggagtatt cgtcgttgcg cgttttgaag tcgttggcgg taggcggttt tcgaggtcgg    60
cgggttgggc ggttcggtag tttgcgtcgc ggttttcgtt tcggtcgtta gt           112

<210> SEQ ID NO 60
<211> LENGTH: 17
<212> TYPE: DNA
<213> ORGANISM: Artificial sequence
<220> FEATURE:
<223> OTHER INFORMATION: Synthetic DNA

<400> SEQUENCE: 60
gtattcgtcg ttgcgcg                                                    17

<210> SEQ ID NO 61
<211> LENGTH: 18
<212> TYPE: DNA
<213> ORGANISM: Artificial sequence
<220> FEATURE:
<223> OTHER INFORMATION: Synthetic DNA

<400> SEQUENCE: 61
cctcgaaaac cgcctacc                                                   18

<210> SEQ ID NO 62
<211> LENGTH: 21
<212> TYPE: DNA
<213> ORGANISM: Artificial sequence
<220> FEATURE:
<223> OTHER INFORMATION: Synthetic DNA
```

```
<400> SEQUENCE: 62
ccacggacgc gccaacgact t                                              21

<210> SEQ ID NO 63
<211> LENGTH: 134
<212> TYPE: DNA
<213> ORGANISM: Homo sapiens

<400> SEQUENCE: 63
cgccgtgagt gttatagttc ttaaaggcgg cgtgtccgga gtttcttcct tctggtgggg    60
ttcgtggtct cgccggctca ggagtgaagc tgcagatctt cgcggtgagt gttacagctc   120
ctaaggcggc gcat                                                     134

<210> SEQ ID NO 64
<211> LENGTH: 134
<212> TYPE: DNA
<213> ORGANISM: Artificial sequence
<220> FEATURE:
<223> OTHER INFORMATION: Synthetic DNA

<400> SEQUENCE: 64
cgtcgtgagt gttatagttt ttaaaggcgg cgtgttcgga gttttttttt tttggtgggg    60
ttcgtggttt cgtcggttta ggagtgaagt tgtagatttt cgcggtgagt gttatagttt   120
ttaaggcggc gtat                                                     134

<210> SEQ ID NO 65
<211> LENGTH: 17
<212> TYPE: DNA
<213> ORGANISM: Artificial sequence
<220> FEATURE:
<223> OTHER INFORMATION: Synthetic DNA

<400> SEQUENCE: 65
taaaggcggc gtgttcg                                                   17

<210> SEQ ID NO 66
<211> LENGTH: 21
<212> TYPE: DNA
<213> ORGANISM: Artificial sequence
<220> FEATURE:
<223> OTHER INFORMATION: Synthetic DNA

<400> SEQUENCE: 66
caacttcact cctaaaccga c                                              21

<210> SEQ ID NO 67
<211> LENGTH: 21
<212> TYPE: DNA
<213> ORGANISM: Artificial sequence
<220> FEATURE:
<223> OTHER INFORMATION: Synthetic DNA

<400> SEQUENCE: 67
ccacggacgc gaaaccacga a                                              21

<210> SEQ ID NO 68
<211> LENGTH: 107
<212> TYPE: DNA
<213> ORGANISM: Homo sapiens

<400> SEQUENCE: 68
aactggcctt ctggctactc cggaatcgcc aagcagatga ggccagaccg ccgccagcgc    60
```

-continued tgatcacgcg cgctcccaca ggtcctggcg cgcgtgttca gccgcgc                          107

<210> SEQ ID NO 69
<211> LENGTH: 107
<212> TYPE: DNA
<213> ORGANISM: Artificial sequence
<220> FEATURE:
<223> OTHER INFORMATION: Synthetic DNA

<400> SEQUENCE: 69
aattggtttt ttggttattt cggaatcgtt aagtagatga ggttagatcg tcgttagcgt          60
tgattacgcg cgtttttata ggttttggcg cgcgtgttta gtcgcgt                         107

<210> SEQ ID NO 70
<211> LENGTH: 26
<212> TYPE: DNA
<213> ORGANISM: Artificial sequence
<220> FEATURE:
<223> OTHER INFORMATION: Synthetic DNA

<400> SEQUENCE: 70
tggttttttg gttatttcgg aatcgt                                                26

<210> SEQ ID NO 71
<211> LENGTH: 19
<212> TYPE: DNA
<213> ORGANISM: Artificial sequence
<220> FEATURE:
<223> OTHER INFORMATION: Synthetic DNA

<400> SEQUENCE: 71
gcgcgtaatc aacgctaac                                                        19

<210> SEQ ID NO 72
<211> LENGTH: 20
<212> TYPE: DNA
<213> ORGANISM: Artificial sequence
<220> FEATURE:
<223> OTHER INFORMATION: Synthetic DNA

<400> SEQUENCE: 72
cgccgaggcg acgatctaac                                                       20

<210> SEQ ID NO 73
<211> LENGTH: 85
<212> TYPE: DNA
<213> ORGANISM: Homo sapiens

<400> SEQUENCE: 73
ggagcgggca gaggaggagc ccagcgccga ggcccaggcg cgcccgccc tcgccctcc            60 ccgtgcccct cccccgctgc tcccc                                                 85

<210> SEQ ID NO 74
<211> LENGTH: 85
<212> TYPE: DNA
<213> ORGANISM: Artificial sequence
<220> FEATURE:
<223> OTHER INFORMATION: Synthetic DNA

<400> SEQUENCE: 74
ggagcgggta gaggaggagt ttagcgtcga ggtttaggcg cgtttcgttt tcgttttttt          60
tcgtgttttt ttttcgttgt ttttt                                                 85

-continued

```
<210> SEQ ID NO 75
<211> LENGTH: 19
<212> TYPE: DNA
<213> ORGANISM: Artificial sequence
<220> FEATURE:
<223> OTHER INFORMATION: Synthetic DNA

<400> SEQUENCE: 75
gaggaggagt ttagcgtcg                                                19

<210> SEQ ID NO 76
<211> LENGTH: 24
<212> TYPE: DNA
<213> ORGANISM: Artificial sequence
<220> FEATURE:
<223> OTHER INFORMATION: Synthetic DNA

<400> SEQUENCE: 76
cacgaaaaaa aacgaaaacg aaac                                          24

<210> SEQ ID NO 77
<211> LENGTH: 20
<212> TYPE: DNA
<213> ORGANISM: Artificial sequence
<220> FEATURE:
<223> OTHER INFORMATION: Synthetic DNA

<400> SEQUENCE: 77
cgccgaggcg cgcctaaacc                                               20

<210> SEQ ID NO 78
<211> LENGTH: 107
<212> TYPE: DNA
<213> ORGANISM: Homo sapiens

<400> SEQUENCE: 78
gcggtctatc acgggcaccc ctaacacttg gtgagtgcgc agtgctctcg gcagtctctg   60
ggctccatac gatgcctacc gcacgcccta gcagaggagg tctctgt                107

<210> SEQ ID NO 79
<211> LENGTH: 107
<212> TYPE: DNA
<213> ORGANISM: Artificial sequence
<220> FEATURE:
<223> OTHER INFORMATION: Synthetic DNA

<400> SEQUENCE: 79
gcggtttatt acgggtattt ttaatatttg gtgagtgcgt agtgttttcg gtagtttttg   60
ggttttatac gatgtttatc gtacgtttta gtagaggagg tttttgt                107

<210> SEQ ID NO 80
<211> LENGTH: 20
<212> TYPE: DNA
<213> ORGANISM: Artificial sequence
<220> FEATURE:
<223> OTHER INFORMATION: Synthetic DNA

<400> SEQUENCE: 80
tgagtgcgta gtgttttcgg                                               20

<210> SEQ ID NO 81
<211> LENGTH: 27
<212> TYPE: DNA
<213> ORGANISM: Artificial sequence
```

-continued

<220> FEATURE:
<223> OTHER INFORMATION: Synthetic DNA

<400> SEQUENCE: 81
ctcctctact aaaacgtacg ataaaca                                          27

<210> SEQ ID NO 82
<211> LENGTH: 20
<212> TYPE: DNA
<213> ORGANISM: Artificial sequence
<220> FEATURE:
<223> OTHER INFORMATION: Synthetic DNA

<400> SEQUENCE: 82
cgccgaggat cgtataaaac                                                  20

<210> SEQ ID NO 83
<211> LENGTH: 21
<212> TYPE: DNA
<213> ORGANISM: Artificial sequence
<220> FEATURE:
<223> OTHER INFORMATION: Synthetic DNA

<400> SEQUENCE: 83
atatttggtg agtgcgtagt g                                                21

<210> SEQ ID NO 84
<211> LENGTH: 26
<212> TYPE: DNA
<213> ORGANISM: Artificial sequence
<220> FEATURE:
<223> OTHER INFORMATION: Synthetic DNA

<400> SEQUENCE: 84
acgtacgata aacatcgtat aaaacc                                           26

<210> SEQ ID NO 85
<211> LENGTH: 20
<212> TYPE: DNA
<213> ORGANISM: Artificial sequence
<220> FEATURE:
<223> OTHER INFORMATION: Synthetic DNA

<400> SEQUENCE: 85
cgccgagggt tttcggtagt                                                  20

<210> SEQ ID NO 86
<211> LENGTH: 121
<212> TYPE: DNA
<213> ORGANISM: Homo sapiens

<400> SEQUENCE: 86
tactccactg ccggcttggt gcccacgctc ggcttccgcc cacccatgga ctacgccttt      60
agcgatctca tgcgtgaccg ctcggccgcc gctgctgcgg cggtgcacaa ggagccgacc     120
t                                                                    121

<210> SEQ ID NO 87
<211> LENGTH: 121
<212> TYPE: DNA
<213> ORGANISM: Artificial sequence
<220> FEATURE:
<223> OTHER INFORMATION: Synthetic DNA

<400> SEQUENCE: 87

-continued

```
tattttattg tcggtttggt gtttacgttc ggttttcgtt tatttatgga ttacgttttt        60
agcgatttta tgcgtgatcg ttcggtcgtc gttgttgcgg cggtgtataa ggagtcgatt       120
t                                                                       121

<210> SEQ ID NO 88
<211> LENGTH: 23
<212> TYPE: DNA
<213> ORGANISM: Artificial sequence
<220> FEATURE:
<223> OTHER INFORMATION: Synthetic DNA

<400> SEQUENCE: 88
tggtgtttac gttcggtttt cgt                                                 23

<210> SEQ ID NO 89
<211> LENGTH: 17
<212> TYPE: DNA
<213> ORGANISM: Artificial sequence
<220> FEATURE:
<223> OTHER INFORMATION: Synthetic DNA

<400> SEQUENCE: 89
ccgcaacaac gacgacc                                                        17

<210> SEQ ID NO 90
<211> LENGTH: 20
<212> TYPE: DNA
<213> ORGANISM: Artificial sequence
<220> FEATURE:
<223> OTHER INFORMATION: Synthetic DNA

<400> SEQUENCE: 90
cgccgaggcg aacgatcacg                                                     20

<210> SEQ ID NO 91
<211> LENGTH: 106
<212> TYPE: DNA
<213> ORGANISM: Homo sapiens

<400> SEQUENCE: 91
aggccggtca cgaacaaagc gctggcgagt gcgcgcccgc ccacgcgcac aggtgcccgc        60
gacaagacgc cccgtccccg cccacgcggc ccccgcgggc tgagcc                      106

<210> SEQ ID NO 92
<211> LENGTH: 106
<212> TYPE: DNA
<213> ORGANISM: Artificial sequence
<220> FEATURE:
<223> OTHER INFORMATION: Synthetic DNA

<400> SEQUENCE: 92
aggtcggtta cgaataaagc gttggcgagt gcgcgttcgt ttacgcgtat aggtgttcgc        60
gataagacgt ttcgttttcg tttacgcggt tttcgcgggt tgagtt                      106

<210> SEQ ID NO 93
<211> LENGTH: 21
<212> TYPE: DNA
<213> ORGANISM: Artificial sequence
<220> FEATURE:
<223> OTHER INFORMATION: Synthetic DNA

<400> SEQUENCE: 93
gttacgaata aagcgttggc g                                                   21
```

-continued

```
<210> SEQ ID NO 94
<211> LENGTH: 20
<212> TYPE: DNA
<213> ORGANISM: Artificial sequence
<220> FEATURE:
<223> OTHER INFORMATION: Synthetic DNA

<400> SEQUENCE: 94
aacgaaacgt cttatcgcga                                                      20

<210> SEQ ID NO 95
<211> LENGTH: 21
<212> TYPE: DNA
<213> ORGANISM: Artificial sequence
<220> FEATURE:
<223> OTHER INFORMATION: Synthetic DNA

<400> SEQUENCE: 95
ccacggacgg agtgcgcgtt c                                                    21

<210> SEQ ID NO 96
<211> LENGTH: 85
<212> TYPE: DNA
<213> ORGANISM: Homo sapiens

<400> SEQUENCE: 96
gccggccccg cagcatcctc ctgctcgcgg ctctcccgcc acctgtcccg ctccctgccg         60
cgccctgggg cccgcaccta cccac                                               85

<210> SEQ ID NO 97
<211> LENGTH: 85
<212> TYPE: DNA
<213> ORGANISM: Artificial sequence
<220> FEATURE:
<223> OTHER INFORMATION: Synthetic DNA

<400> SEQUENCE: 97
gtcggtttcg tagtattttt ttgttcgcgg ttttttcgtt atttgtttcg tttttgtcg          60 cgttttgggg ttcgtattta tttat                                               85

<210> SEQ ID NO 98
<211> LENGTH: 25
<212> TYPE: DNA
<213> ORGANISM: Artificial sequence
<220> FEATURE:
<223> OTHER INFORMATION: Synthetic DNA

<400> SEQUENCE: 98
cggtttcgta gtattttttt gttcg                                               25

<210> SEQ ID NO 99
<211> LENGTH: 17
<212> TYPE: DNA
<213> ORGANISM: Artificial sequence
<220> FEATURE:
<223> OTHER INFORMATION: Synthetic DNA

<400> SEQUENCE: 99
gaaccccaaa acgcgac                                                        17

<210> SEQ ID NO 100
<211> LENGTH: 20
<212> TYPE: DNA
```

```
<213> ORGANISM: Artificial sequence
<220> FEATURE:
<223> OTHER INFORMATION: Synthetic DNA

<400> SEQUENCE: 100
cgccgagggc ggttttttcg                                              20

<210> SEQ ID NO 101
<211> LENGTH: 134
<212> TYPE: DNA
<213> ORGANISM: Homo sapiens

<400> SEQUENCE: 101
cgcctcctgg gctcccccg gagtgggagg gagccgcggt cccgcctccg cgcccgttcc      60
ctcccaggcc cctcggccgc cgcgccgagc tttccgcgcg tggacagact gcccggccga     120
cggacggacg cagg                                                     134

<210> SEQ ID NO 102
<211> LENGTH: 134
<212> TYPE: DNA
<213> ORGANISM: Artificial sequence
<220> FEATURE:
<223> OTHER INFORMATION: Synthetic DNA

<400> SEQUENCE: 102
cgttttttgg gttttttcg gagtgggagg gagtcgcggt ttcgttttcg cgttcgtttt      60
tttttaggtt tttcggtcgt cgcgtcgagt ttttcgcgcg tggatagatt gttcggtcga     120
cggacggacg tagg                                                     134

<210> SEQ ID NO 103
<211> LENGTH: 19
<212> TYPE: DNA
<213> ORGANISM: Artificial sequence
<220> FEATURE:
<223> OTHER INFORMATION: Synthetic DNA

<400> SEQUENCE: 103
gagtcgcggt ttcgttttc                                               19

<210> SEQ ID NO 104
<211> LENGTH: 19
<212> TYPE: DNA
<213> ORGANISM: Artificial sequence
<220> FEATURE:
<223> OTHER INFORMATION: Synthetic DNA

<400> SEQUENCE: 104
gacgcgacga ccgaaaaac                                               19

<210> SEQ ID NO 105
<211> LENGTH: 20
<212> TYPE: DNA
<213> ORGANISM: Artificial sequence
<220> FEATURE:
<223> OTHER INFORMATION: Synthetic DNA

<400> SEQUENCE: 105
cgccgaggcg cgttcgtttt                                              20

<210> SEQ ID NO 106
<211> LENGTH: 108
<212> TYPE: DNA
<213> ORGANISM: Homo sapiens
```

<400> SEQUENCE: 106
tccggcgccg cgttttctag agaaccgggt ctcagcgatg ctcatttcag ccccgtctta     60
atgcaacaaa cgaaaccccca cacgaacgaa aaggaacatg tctgcgct               108

<210> SEQ ID NO 107
<211> LENGTH: 107
<212> TYPE: DNA
<213> ORGANISM: Artificial sequence
<220> FEATURE:
<223> OTHER INFORMATION: Synthetic DNA

<400> SEQUENCE: 107
tcggcgtcgc gttttttaga gaatcgggtt ttagcgatgt ttattttagt ttcgttttaa     60
tgtaataaac gaaattttat acgaacgaaa aggaatatgt ttgcgtt                107

<210> SEQ ID NO 108
<211> LENGTH: 21
<212> TYPE: DNA
<213> ORGANISM: Artificial sequence
<220> FEATURE:
<223> OTHER INFORMATION: Synthetic DNA

<400> SEQUENCE: 108
ggcgtcgcgt tttttagaga a                                             21

<210> SEQ ID NO 109
<211> LENGTH: 28
<212> TYPE: DNA
<213> ORGANISM: Artificial sequence
<220> FEATURE:
<223> OTHER INFORMATION: Synthetic DNA

<400> SEQUENCE: 109
ttccttttcg ttcgtataaa atttcgtt                                      28

<210> SEQ ID NO 110
<211> LENGTH: 21
<212> TYPE: DNA
<213> ORGANISM: Artificial sequence
<220> FEATURE:
<223> OTHER INFORMATION: Synthetic DNA

<400> SEQUENCE: 110
ccacggacga tcgggtttta g                                             21

<210> SEQ ID NO 111
<211> LENGTH: 128
<212> TYPE: DNA
<213> ORGANISM: Homo sapiens

<400> SEQUENCE: 111
gggcctgctg gccggggacc cgcgcgtcga gcgcctggtg cgcgacagcg cctcctactg     60
ccgcgagcgc ttcgacccccg acgagtactc cacggccgtg cgcgaggcgc cagcggagct    120
cgccgaag                                                           128

<210> SEQ ID NO 112
<211> LENGTH: 128
<212> TYPE: DNA
<213> ORGANISM: Artificial sequence
<220> FEATURE:
<223> OTHER INFORMATION: Synthetic DNA -continued

```
<400> SEQUENCE: 112
gggtttgttg gtcggggatt cgcgcgtcga gcgtttggtg cgcgatagcg ttttttattg      60
tcgcgagcgt ttcgatttcg acgagtattt tacggtcgtg cgcgaggcgt tagcggagtt     120
cgtcgaag                                                             128

<210> SEQ ID NO 113
<211> LENGTH: 23
<212> TYPE: DNA
<213> ORGANISM: Artificial sequence
<220> FEATURE:
<223> OTHER INFORMATION: Synthetic DNA

<400> SEQUENCE: 113
cgatagcgtt ttttattgtc gcg                                              23

<210> SEQ ID NO 114
<211> LENGTH: 22
<212> TYPE: DNA
<213> ORGANISM: Artificial sequence
<220> FEATURE:
<223> OTHER INFORMATION: Synthetic DNA

<400> SEQUENCE: 114
gcacgaccgt aaaatactcg tc                                               22

<210> SEQ ID NO 115
<211> LENGTH: 21
<212> TYPE: DNA
<213> ORGANISM: Artificial sequence
<220> FEATURE:
<223> OTHER INFORMATION: Synthetic DNA

<400> SEQUENCE: 115
ccacggacgc gaaatcgaaa c                                                21

<210> SEQ ID NO 116
<211> LENGTH: 140
<212> TYPE: DNA
<213> ORGANISM: Homo sapiens

<400> SEQUENCE: 116
tagcagcagc cgcagccatg gcggggatga agacagcctc cggggactac atcgactcgt      60
catgggagct gcgggtgttt gtgggagagg aggacccaga ggccgagtcg gtcaccctgc     120
gggtcactgg ggagtcgcac                                                 140

<210> SEQ ID NO 117
<211> LENGTH: 140
<212> TYPE: DNA
<213> ORGANISM: Artificial sequence
<220> FEATURE:
<223> OTHER INFORMATION: Synthetic DNA

<400> SEQUENCE: 117
tagtagtagt cgtagttatg gcggggatga agatagtttt cggggattat atcgattcgt      60
tatgggagtt gcgggtgttt gtgggagagg aggatttaga ggtcgagtcg gttattttgc     120
gggttattgg ggagtcgtat                                                 140

<210> SEQ ID NO 118
<211> LENGTH: 24
<212> TYPE: DNA
<213> ORGANISM: Artificial sequence
```

-continued

```
<220> FEATURE:
<223> OTHER INFORMATION: Synthetic DNA

<400> SEQUENCE: 118
gttttcgggg attatatcga ttcg                                                  24

<210> SEQ ID NO 119
<211> LENGTH: 22
<212> TYPE: DNA
<213> ORGANISM: Artificial sequence
<220> FEATURE:
<223> OTHER INFORMATION: Synthetic DNA

<400> SEQUENCE: 119
cccaataacc cgcaaaataa cc                                                     22

<210> SEQ ID NO 120
<211> LENGTH: 20
<212> TYPE: DNA
<213> ORGANISM: Artificial sequence
<220> FEATURE:
<223> OTHER INFORMATION: Synthetic DNA

<400> SEQUENCE: 120
cgccgaggcg actcgacctc                                                        20

<210> SEQ ID NO 121
<211> LENGTH: 104
<212> TYPE: DNA
<213> ORGANISM: Homo sapiens

<400> SEQUENCE: 121
gtcccagaga cgccctaggg tcagaggtca tctccgtggc aacggaaact tcccgcgcta      60
cggcggctcc aacgggccgc ttccgccgca ttgcgtagcg aagc                    104

<210> SEQ ID NO 122
<211> LENGTH: 104
<212> TYPE: DNA
<213> ORGANISM: Artificial sequence
<220> FEATURE:
<223> OTHER INFORMATION: Synthetic DNA

<400> SEQUENCE: 122
gttttagaga cgttttaggg ttagaggtta ttttcgtggt aacggaaatt tttcgcgtta      60
cggcggtttt aacgggtcgt tttcgtcgta ttgcgtagcg aagt                    104

<210> SEQ ID NO 123
<211> LENGTH: 24
<212> TYPE: DNA
<213> ORGANISM: Artificial sequence
<220> FEATURE:
<223> OTHER INFORMATION: Synthetic DNA

<400> SEQUENCE: 123
tttcgtggta acggaaattt ttcg                                                  24

<210> SEQ ID NO 124
<211> LENGTH: 17
<212> TYPE: DNA
<213> ORGANISM: Artificial sequence
<220> FEATURE:
<223> OTHER INFORMATION: Synthetic DNA

<400> SEQUENCE: 124
```
cgacgaaaac gacccgt                                                    17

<210> SEQ ID NO 125
<211> LENGTH: 20
<212> TYPE: DNA
<213> ORGANISM: Artificial sequence
<220> FEATURE:
<223> OTHER INFORMATION: Synthetic DNA

<400> SEQUENCE: 125
cgccgagggc gttacggcgg                                                 20

<210> SEQ ID NO 126
<211> LENGTH: 107
<212> TYPE: DNA
<213> ORGANISM: Homo sapiens

<400> SEQUENCE: 126
gcgccccggc cgcaggcgga ggacagggag gagcgcacac gagaaagctc ccacgcgccc     60
gcgcctcgcc tccgacggga aggcgcctct tccgaccgtc ctggatg                  107

<210> SEQ ID NO 127
<211> LENGTH: 107
<212> TYPE: DNA
<213> ORGANISM: Artificial sequence
<220> FEATURE:
<223> OTHER INFORMATION: Synthetic DNA

<400> SEQUENCE: 127
gcgtttcggt cgtaggcgga ggatagggag gagcgtatac gagaaagttt ttacgcgttc     60
gcgtttcgtt ttcgacggga aggcgttttt ttcgatcgtt ttggatg                  107

<210> SEQ ID NO 128
<211> LENGTH: 25
<212> TYPE: DNA
<213> ORGANISM: Artificial sequence
<220> FEATURE:
<223> OTHER INFORMATION: Synthetic DNA

<400> SEQUENCE: 128
gagcgtatac gagaaagttt ttacg                                           25

<210> SEQ ID NO 129
<211> LENGTH: 17
<212> TYPE: DNA
<213> ORGANISM: Artificial sequence
<220> FEATURE:
<223> OTHER INFORMATION: Synthetic DNA

<400> SEQUENCE: 129
aacgccttcc cgtcgaa                                                    17

<210> SEQ ID NO 130
<211> LENGTH: 21
<212> TYPE: DNA
<213> ORGANISM: Artificial sequence
<220> FEATURE:
<223> OTHER INFORMATION: Synthetic DNA

<400> SEQUENCE: 130
ccacggacgg cgttcgcgtt t                                               21

<210> SEQ ID NO 131
<211> LENGTH: 108

-continued

```
<212> TYPE: DNA
<213> ORGANISM: Homo sapiens

<400> SEQUENCE: 131
cgagagggcg cgagcacagc cgaggccatg gaggtgacgg cggaccagcc gcgctgggtg      60
agccaccacc accccgccgt gctcaacggg cagcacccgg acacgcac               108

<210> SEQ ID NO 132
<211> LENGTH: 108
<212> TYPE: DNA
<213> ORGANISM: Artificial sequence
<220> FEATURE:
<223> OTHER INFORMATION: Synthetic DNA

<400> SEQUENCE: 132
cgagagggcg cgagtatagt cgaggttatg gaggtgacgg cggattagtc gcgttgggtg      60
agttattatt atttcgtcgt gtttaacggg tagtattcgg atacgtat              108

<210> SEQ ID NO 133
<211> LENGTH: 17
<212> TYPE: DNA
<213> ORGANISM: Artificial sequence
<220> FEATURE:
<223> OTHER INFORMATION: Synthetic DNA

<400> SEQUENCE: 133
gggcgcgagt atagtcg                                               17

<210> SEQ ID NO 134
<211> LENGTH: 17
<212> TYPE: DNA
<213> ORGANISM: Artificial sequence
<220> FEATURE:
<223> OTHER INFORMATION: Synthetic DNA

<400> SEQUENCE: 134
caacgcgact aatccgc                                               17

<210> SEQ ID NO 135
<211> LENGTH: 20
<212> TYPE: DNA
<213> ORGANISM: Artificial sequence
<220> FEATURE:
<223> OTHER INFORMATION: Synthetic DNA

<400> SEQUENCE: 135
cgccgaggcc gtcacctcca                                            20

<210> SEQ ID NO 136
<211> LENGTH: 141
<212> TYPE: DNA
<213> ORGANISM: Homo sapiens

<400> SEQUENCE: 136 cgcccctca cctccccgat catgccgttc cagacgccat cgatcttctt tccgtgcttg      60
ccattggtga ccaggtagag gtcgtagctg aagccgatgg tatgcgccag ccgcttcaga    120
atgtcgatgc agaaaccctt g                                          141

<210> SEQ ID NO 137
<211> LENGTH: 141
<212> TYPE: DNA
<213> ORGANISM: Artificial sequence
<220> FEATURE:
```

<223> OTHER INFORMATION: Synthetic DNA

<400> SEQUENCE: 137
cgttttttta tttttttcgat tatgtcgttt tagacgttat cgattttttt ttcgtgtttg     60
ttattggtga ttaggtagag gtcgtagttg aagtcgatgg tatgcgttag tcgttttaga    120
atgtcgatgt agaaattttt g                                               141

<210> SEQ ID NO 138
<211> LENGTH: 27
<212> TYPE: DNA
<213> ORGANISM: Artificial sequence
<220> FEATURE:
<223> OTHER INFORMATION: Synthetic DNA

<400> SEQUENCE: 138
tcgattatgt cgttttagac gttatcg                                          27

<210> SEQ ID NO 139
<211> LENGTH: 28
<212> TYPE: DNA
<213> ORGANISM: Artificial sequence
<220> FEATURE:
<223> OTHER INFORMATION: Synthetic DNA

<400> SEQUENCE: 139
tctacatcga cattctaaaa cgactaac                                         28

<210> SEQ ID NO 140
<211> LENGTH: 21
<212> TYPE: DNA
<213> ORGANISM: Artificial sequence
<220> FEATURE:
<223> OTHER INFORMATION: Synthetic DNA

<400> SEQUENCE: 140
ccacggacgc gcataccatc g                                                21

<210> SEQ ID NO 141
<211> LENGTH: 93
<212> TYPE: DNA
<213> ORGANISM: Homo sapiens

<400> SEQUENCE: 141
cggcgaggct tcccgcctgg cgcattacaa caagcgctcg accatcacct ccagggagat     60
ccagacggcc gtgcgcctgc tgcttcccgg gga                                   93

<210> SEQ ID NO 142
<211> LENGTH: 93
<212> TYPE: DNA
<213> ORGANISM: Artificial sequence
<220> FEATURE:
<223> OTHER INFORMATION: Synthetic DNA

<400> SEQUENCE: 142
cggcgaggtt tttcgtttgg cgtattataa taagcgttcg attattattt ttagggagat     60
ttagacggtc gtgcgtttgt tgtttttcgg gga                                   93

<210> SEQ ID NO 143
<211> LENGTH: 23
<212> TYPE: DNA
<213> ORGANISM: Artificial sequence
<220> FEATURE:
<223> OTHER INFORMATION: Synthetic DNA -continued

<400> SEQUENCE: 143
tggcgtatta taataagcgt tcg                                                                23

<210> SEQ ID NO 144
<211> LENGTH: 18
<212> TYPE: DNA
<213> ORGANISM: Artificial sequence
<220> FEATURE:
<223> OTHER INFORMATION: Synthetic DNA

<400> SEQUENCE: 144
aacaacaaac gcacgacc                                                                      18

<210> SEQ ID NO 145
<211> LENGTH: 21
<212> TYPE: DNA
<213> ORGANISM: Artificial sequence
<220> FEATURE:
<223> OTHER INFORMATION: Synthetic DNA

<400> SEQUENCE: 145
ccacggacgc gtctaaatct c                                                                  21

<210> SEQ ID NO 146
<211> LENGTH: 101
<212> TYPE: DNA
<213> ORGANISM: Homo sapiens

<400> SEQUENCE: 146
gggcgggcca ggcgctgggc acggtgatgg ccaccactgg ggccctgggc aactactacg        60
tggactcgtt cctgctgggc gccgacgccg cggatgagct g                           101

<210> SEQ ID NO 147
<211> LENGTH: 101
<212> TYPE: DNA
<213> ORGANISM: Artificial sequence
<220> FEATURE:
<223> OTHER INFORMATION: Synthetic DNA

<400> SEQUENCE: 147
gggcgggtta ggcgttgggt acggtgatgg ttattattgg ggttttgggt aattattacg        60
tggattcgtt tttgttgggc gtcgacgtcg cggatgagtt g                           101

<210> SEQ ID NO 148
<211> LENGTH: 24
<212> TYPE: DNA
<213> ORGANISM: Artificial sequence
<220> FEATURE:
<223> OTHER INFORMATION: Synthetic DNA

<400> SEQUENCE: 148
ttgggtaatt attacgtgga ttcg                                                               24

<210> SEQ ID NO 149
<211> LENGTH: 16
<212> TYPE: DNA
<213> ORGANISM: Artificial sequence
<220> FEATURE:
<223> OTHER INFORMATION: Synthetic DNA

<400> SEQUENCE: 149
actcatccgc gacgtc                                                                        16

-continued

```
<210> SEQ ID NO 150
<211> LENGTH: 21
<212> TYPE: DNA
<213> ORGANISM: Artificial sequence
<220> FEATURE:
<223> OTHER INFORMATION: Synthetic DNA

<400> SEQUENCE: 150
ccacggacgc gacgcccaac a                                          21

<210> SEQ ID NO 151
<211> LENGTH: 95
<212> TYPE: DNA
<213> ORGANISM: Homo sapiens

<400> SEQUENCE: 151
gggccattgc cagaagacgt cttctcgggg cgccaggatt cacctttcct tcccgacctc    60
aacttcttcg cggccgactc ctgtctccag ctatc                              95

<210> SEQ ID NO 152
<211> LENGTH: 95
<212> TYPE: DNA
<213> ORGANISM: Artificial sequence
<220> FEATURE:
<223> OTHER INFORMATION: Synthetic DNA

<400> SEQUENCE: 152
gggttattgt tagaagacgt tttttcgggg cgttaggatt tatttttttt tttcgatttt    60
aattttttcg cggtcgattt ttgtttttag ttatt                              95

<210> SEQ ID NO 153
<211> LENGTH: 22
<212> TYPE: DNA
<213> ORGANISM: Artificial sequence
<220> FEATURE:
<223> OTHER INFORMATION: Synthetic DNA

<400> SEQUENCE: 153
gttagaagac gttttttcgg gg                                          22

<210> SEQ ID NO 154
<211> LENGTH: 20
<212> TYPE: DNA
<213> ORGANISM: Artificial sequence
<220> FEATURE:
<223> OTHER INFORMATION: Synthetic DNA

<400> SEQUENCE: 154
aaaacaaaaa tcgaccgcga                                            20

<210> SEQ ID NO 155
<211> LENGTH: 20
<212> TYPE: DNA
<213> ORGANISM: Artificial sequence
<220> FEATURE:
<223> OTHER INFORMATION: Synthetic DNA

<400> SEQUENCE: 155
cgccgagggc gttaggattt                                            20

<210> SEQ ID NO 156
<211> LENGTH: 106
<212> TYPE: DNA
<213> ORGANISM: Homo sapiens
```

-continued

<400> SEQUENCE: 156
ggccccggaa gcccagctcc cgggccctgg agcccgccac ggcggcagcc ctgcggcggc      60
ggctggacct gggcagttgc ctggacgtgc tggcctttgc ccagca      106

<210> SEQ ID NO 157
<211> LENGTH: 106
<212> TYPE: DNA
<213> ORGANISM: Artificial sequence
<220> FEATURE:
<223> OTHER INFORMATION: Synthetic DNA

<400> SEQUENCE: 157
ggtttcggaa gtttagtttt cgggttttgg agttcgttac ggcggtagtt ttgcggcggc      60
ggttggattt gggtagttgt ttggacgtgt tggttttgt ttagta      106

<210> SEQ ID NO 158
<211> LENGTH: 25
<212> TYPE: DNA
<213> ORGANISM: Artificial sequence
<220> FEATURE:
<223> OTHER INFORMATION: Synthetic DNA

<400> SEQUENCE: 158
agttttcggg ttttggagtt cgtta      25

<210> SEQ ID NO 159
<211> LENGTH: 17
<212> TYPE: DNA
<213> ORGANISM: Artificial sequence
<220> FEATURE:
<223> OTHER INFORMATION: Synthetic DNA

<400> SEQUENCE: 159
ccaaatccaa ccgccgc      17

<210> SEQ ID NO 160
<211> LENGTH: 20
<212> TYPE: DNA
<213> ORGANISM: Artificial sequence
<220> FEATURE:
<223> OTHER INFORMATION: Synthetic DNA

<400> SEQUENCE: 160
cgccgaggac ggcggtagtt      20

<210> SEQ ID NO 161
<211> LENGTH: 106
<212> TYPE: DNA
<213> ORGANISM: Homo sapiens

<400> SEQUENCE: 161
ggcggcgccg gcggctgcgc ggggggcgcc aggccctgct gctgctgctg ctgctgactg      60
cggtagtagg cggcggcggc cacggcggca aagttgtggg tctgga      106

<210> SEQ ID NO 162
<211> LENGTH: 106
<212> TYPE: DNA
<213> ORGANISM: Artificial sequence
<220> FEATURE:
<223> OTHER INFORMATION: Synthetic DNA

<400> SEQUENCE: 162

-continued

```
ggcggcgtcg gcggttgcgc ggggggcgtt aggttttgtt gttgttgttg ttgttgattg      60
cggtagtagg cggcggcggt tacggcggta aagttgtggg tttgga                     106

<210> SEQ ID NO 163
<211> LENGTH: 19
<212> TYPE: DNA
<213> ORGANISM: Artificial sequence
<220> FEATURE:
<223> OTHER INFORMATION: Synthetic DNA

<400> SEQUENCE: 163
ttgattgcgg tagtaggcg                                                   19

<210> SEQ ID NO 164
<211> LENGTH: 19
<212> TYPE: DNA
<213> ORGANISM: Artificial sequence
<220> FEATURE:
<223> OTHER INFORMATION: Synthetic DNA

<400> SEQUENCE: 164
aacccacaac tttaccgcc                                                   19

<210> SEQ ID NO 165
<211> LENGTH: 20
<212> TYPE: DNA
<213> ORGANISM: Artificial sequence
<220> FEATURE:
<223> OTHER INFORMATION: Synthetic DNA

<400> SEQUENCE: 165
cgccgaggcg taaccgccgc                                                  20

<210> SEQ ID NO 166
<211> LENGTH: 154
<212> TYPE: DNA
<213> ORGANISM: Homo sapiens

<400> SEQUENCE: 166
ggtttccccc cacccggcc tcggggtctc tccacgtctc cccgccgacg tgctcacctg       60 ctcaggggc gccccgagc cgcgccccgc gcccgccccc aggagggcct ccgcgagccg        120
gctgcacacc ccgaggcggt cccggctgca caac                                  154

<210> SEQ ID NO 167
<211> LENGTH: 154
<212> TYPE: DNA
<213> ORGANISM: Artificial sequence
<220> FEATURE:
<223> OTHER INFORMATION: Synthetic DNA

<400> SEQUENCE: 167
ggtttttttt tatttcggtt tcggggtttt tttacgtttt ttcgtcgacg tgtttatttg      60 tttaggggc gttttcgagt cgcgtttcgc gttcgttttt aggagggttt tcgcgagtcg       120
gttgtatatt tcgaggcggt ttcggttgta taat                                  154

<210> SEQ ID NO 168
<211> LENGTH: 27
<212> TYPE: DNA
<213> ORGANISM: Artificial sequence
<220> FEATURE:
<223> OTHER INFORMATION: Synthetic DNA

<400> SEQUENCE: 168
```
gtttcggggt tttttttacgt tttttcg                                                27

<210> SEQ ID NO 169
<211> LENGTH: 19
<212> TYPE: DNA
<213> ORGANISM: Artificial sequence
<220> FEATURE:
<223> OTHER INFORMATION: Synthetic DNA

<400> SEQUENCE: 169
aaacgcgact cgaaaacgc                                                          19

<210> SEQ ID NO 170
<211> LENGTH: 20
<212> TYPE: DNA
<213> ORGANISM: Artificial sequence
<220> FEATURE:
<223> OTHER INFORMATION: Synthetic DNA

<400> SEQUENCE: 170
cgccgagggt cgacgtgttt                                                         20

<210> SEQ ID NO 171
<211> LENGTH: 95
<212> TYPE: DNA
<213> ORGANISM: Homo sapiens

<400> SEQUENCE: 171
ctccggtttt cgcggttctc agcgatatta ggcgcggcca gtgtctgaaa gctcctcggg       60
gttacgtcct ggggcgactg gaggcggctc acgac                                  95

<210> SEQ ID NO 172
<211> LENGTH: 95
<212> TYPE: DNA
<213> ORGANISM: Artificial sequence
<220> FEATURE:
<223> OTHER INFORMATION: Synthetic DNA

<400> SEQUENCE: 172
tttcggtttt cgcggttttt agcgatatta ggcgcggtta gtgtttgaaa gtttttcggg       60
gttacgtttt ggggcgattg gaggcggttt acgat                                  95

<210> SEQ ID NO 173
<211> LENGTH: 22
<212> TYPE: DNA
<213> ORGANISM: Artificial sequence
<220> FEATURE:
<223> OTHER INFORMATION: Synthetic DNA

<400> SEQUENCE: 173
cggtttttag cgatattagg cg                                                      22

<210> SEQ ID NO 174
<211> LENGTH: 18
<212> TYPE: DNA
<213> ORGANISM: Artificial sequence
<220> FEATURE:
<223> OTHER INFORMATION: Synthetic DNA

<400> SEQUENCE: 174
cccaaaacgt aaccccga                                                           18

<210> SEQ ID NO 175

-continued

```
<211> LENGTH: 20
<212> TYPE: DNA
<213> ORGANISM: Artificial sequence
<220> FEATURE:
<223> OTHER INFORMATION: Synthetic DNA

<400> SEQUENCE: 175
cgccgagggc ggttagtgtt                                                   20

<210> SEQ ID NO 176
<211> LENGTH: 143
<212> TYPE: DNA
<213> ORGANISM: Homo sapiens

<400> SEQUENCE: 176
cgacggccgc ggaggaggaa ggccaggggg aaatttgcat ttcgtaaaac cgcggttaag      60
aaatgacgat gccacgtaga caagccagtt gtgacgttca gcacaacgtg ctactgaact     120
accgagatcc gccaccaaat ggc                                             143

<210> SEQ ID NO 177
<211> LENGTH: 143
<212> TYPE: DNA
<213> ORGANISM: Artificial sequence
<220> FEATURE:
<223> OTHER INFORMATION: Synthetic DNA

<400> SEQUENCE: 177
cgacggtcgc ggaggaggaa ggttaggggg aaatttgtat ttcgtaaaat cgcggttaag      60
aaatgacgat gttacgtaga taagttagtt gtgacgttta gtataacgtg ttattgaatt     120
atcgagattc gttattaaat ggt                                             143

<210> SEQ ID NO 178
<211> LENGTH: 25
<212> TYPE: DNA
<213> ORGANISM: Artificial sequence
<220> FEATURE:
<223> OTHER INFORMATION: Synthetic DNA

<400> SEQUENCE: 178
gggaaatttg tatttcgtaa aatcg                                             25

<210> SEQ ID NO 179
<211> LENGTH: 27
<212> TYPE: DNA
<213> ORGANISM: Artificial sequence
<220> FEATURE:
<223> OTHER INFORMATION: Synthetic DNA

<400> SEQUENCE: 179
acaactaact tatctacgta acatcgt                                           27

<210> SEQ ID NO 180
<211> LENGTH: 21
<212> TYPE: DNA
<213> ORGANISM: Artificial sequence
<220> FEATURE:
<223> OTHER INFORMATION: Synthetic DNA

<400> SEQUENCE: 180
ccacggacgg cggttaagaa a                                                 21

<210> SEQ ID NO 181
<211> LENGTH: 116
```

<212> TYPE: DNA
<213> ORGANISM: Homo sapiens

<400> SEQUENCE: 181
ggcttggggt ccagccgccc gcccctgccg ccaccgcacc atgtcctgcc tctactcccg    60
cctcagcgcc ccctgcgggg tccgcgcctt cagctgcatc tcggcctgcg ggcccc       116

<210> SEQ ID NO 182
<211> LENGTH: 116
<212> TYPE: DNA
<213> ORGANISM: Artificial sequence
<220> FEATURE:
<223> OTHER INFORMATION: Synthetic DNA

<400> SEQUENCE: 182
ggtttggggt ttagtcgttc gtttttgtcg ttatcgtatt atgttttgtt tttattttcg    60
ttttagcgtt ttttgcgggg ttcgcgtttt tagttgtatt tcggtttgcg ggtttt       116

<210> SEQ ID NO 183
<211> LENGTH: 22
<212> TYPE: DNA
<213> ORGANISM: Artificial sequence
<220> FEATURE:
<223> OTHER INFORMATION: Synthetic DNA

<400> SEQUENCE: 183
tcgttcgttt ttgtcgttat cg                                             22

<210> SEQ ID NO 184
<211> LENGTH: 23
<212> TYPE: DNA
<213> ORGANISM: Artificial sequence
<220> FEATURE:
<223> OTHER INFORMATION: Synthetic DNA

<400> SEQUENCE: 184
aaccgaaata caactaaaaa cgc                                            23

<210> SEQ ID NO 185
<211> LENGTH: 21
<212> TYPE: DNA
<213> ORGANISM: Artificial sequence
<220> FEATURE:
<223> OTHER INFORMATION: Synthetic DNA

<400> SEQUENCE: 185
ccacggacgc gaaccccgca a                                              21

<210> SEQ ID NO 186
<211> LENGTH: 108
<212> TYPE: DNA
<213> ORGANISM: Homo sapiens

<400> SEQUENCE: 186
ggaaggctgc agcgagagat ttacatattc atccgagctt aaggaagccg cgataatgca    60
ggtacagccc gaaacccacg cccccagacc ttatctgcgc gccccgcc                108

<210> SEQ ID NO 187
<211> LENGTH: 108
<212> TYPE: DNA
<213> ORGANISM: Artificial sequence
<220> FEATURE:
<223> OTHER INFORMATION: Synthetic DNA -continued

<400> SEQUENCE: 187
ggaaggttgt agcgagagat ttatatattt attcgagttt aaggaagtcg cgataatgta      60
ggtatagttc gaaatttacg tttttagatt ttatttgcgc gtttcgtt      108

<210> SEQ ID NO 188
<211> LENGTH: 19
<212> TYPE: DNA
<213> ORGANISM: Artificial sequence
<220> FEATURE:
<223> OTHER INFORMATION: Synthetic DNA

<400> SEQUENCE: 188
ttcgagttta aggaagtcg      19

<210> SEQ ID NO 189
<211> LENGTH: 23
<212> TYPE: DNA
<213> ORGANISM: Artificial sequence
<220> FEATURE:
<223> OTHER INFORMATION: Synthetic DNA

<400> SEQUENCE: 189
tctaaaaacg taaatttcga act      23

<210> SEQ ID NO 190
<211> LENGTH: 21
<212> TYPE: DNA
<213> ORGANISM: Artificial sequence
<220> FEATURE:
<223> OTHER INFORMATION: Synthetic DNA

<400> SEQUENCE: 190
ccacggacgg cgataatgta g      21

<210> SEQ ID NO 191
<211> LENGTH: 137
<212> TYPE: DNA
<213> ORGANISM: Homo sapiens

<400> SEQUENCE: 191
ggagttattt ttaaccatcg cctcccagaa cattacggag cttcctctct ccaacacgca      60
ggaaacccta cttggctgtg cttcctgcta acacgaggcc ctgcgattgc tgagaacaac      120
agccccgaga ctgcgcg      137

<210> SEQ ID NO 192
<211> LENGTH: 137
<212> TYPE: DNA
<213> ORGANISM: Artificial sequence
<220> FEATURE:
<223> OTHER INFORMATION: Synthetic DNA

<400> SEQUENCE: 192
ggagttattt ttaattatcg ttttttagaa tattacggag ttttttttttt ttaatacgta      60 ggaaatttta tttggttgtg tttttttgtta atacgaggtt ttgcgattgt tgagaataat      120
agtttcgaga ttgcgcg      137

<210> SEQ ID NO 193
<211> LENGTH: 30
<212> TYPE: DNA
<213> ORGANISM: Artificial sequence
<220> FEATURE:
<223> OTHER INFORMATION: Synthetic DNA -continued

<400> SEQUENCE: 193
tttaattatc gttttttaga atattacgga                                              30

<210> SEQ ID NO 194
<211> LENGTH: 26
<212> TYPE: DNA
<213> ORGANISM: Artificial sequence
<220> FEATURE:
<223> OTHER INFORMATION: Synthetic DNA

<400> SEQUENCE: 194
actattattc tcaacaatcg caaaac                                                  26

<210> SEQ ID NO 195
<211> LENGTH: 21
<212> TYPE: DNA
<213> ORGANISM: Artificial sequence
<220> FEATURE:
<223> OTHER INFORMATION: Synthetic DNA

<400> SEQUENCE: 195
ccacggacgc ctcgtattaa c                                                       21

<210> SEQ ID NO 196
<211> LENGTH: 117
<212> TYPE: DNA
<213> ORGANISM: Homo sapiens

<400> SEQUENCE: 196
ggcgggcgct tggccaaaca gcccaagact gcggaatcac actcgccact gtgtacctgg            60
acgccatctg cagacccagc gcctgcgggg attccggaaa cgggagagcg ggcttcc              117

<210> SEQ ID NO 197
<211> LENGTH: 117
<212> TYPE: DNA
<213> ORGANISM: Artificial sequence
<220> FEATURE:
<223> OTHER INFORMATION: Synthetic DNA

<400> SEQUENCE: 197
ggcgggcgtt tggttaaata gtttaagatt gcggaattat attcgttatt gtgtatttgg            60
acgttatttg tagatttagc gtttgcgggg atttcggaaa cgggagagcg ggttttt              117

<210> SEQ ID NO 198
<211> LENGTH: 27
<212> TYPE: DNA
<213> ORGANISM: Artificial sequence
<220> FEATURE:
<223> OTHER INFORMATION: Synthetic DNA

<400> SEQUENCE: 198
agtttaagat tgcggaatta tattcgt                                                 27

<210> SEQ ID NO 199
<211> LENGTH: 17
<212> TYPE: DNA
<213> ORGANISM: Artificial sequence
<220> FEATURE:
<223> OTHER INFORMATION: Synthetic DNA

<400> SEQUENCE: 199
ttccgaaatc cccgcaa                                                            17

-continued

```
<210> SEQ ID NO 200
<211> LENGTH: 20
<212> TYPE: DNA
<213> ORGANISM: Artificial sequence
<220> FEATURE:
<223> OTHER INFORMATION: Synthetic DNA

<400> SEQUENCE: 200
cgccgaggaa cgctaaatct                                                           20

<210> SEQ ID NO 201
<211> LENGTH: 156
<212> TYPE: DNA
<213> ORGANISM: Homo sapiens

<400> SEQUENCE: 201
cgcaggctga ggccctcggg tccccagcgg gtcctcgcca tcagtcactc tctacgggcc       60
aggcctgggg gtcacggcct gcaggagcct ccctgcgcgg ccccactccc tcatctgcga      120
ccccgtgggg aggcgaccct gaccaccctc gttccg                                    156

<210> SEQ ID NO 202
<211> LENGTH: 156
<212> TYPE: DNA
<213> ORGANISM: Artificial sequence
<220> FEATURE:
<223> OTHER INFORMATION: Synthetic DNA

<400> SEQUENCE: 202
cgtaggttga ggttttcggg tttttagcgg gttttcgtta ttagttattt tttacgggtt       60
aggtttgggg gttacggttt gtaggagttt ttttgcgcgg ttttattttt ttatttgcga      120
tttcgtgggg aggcgatttt gattattttc gtttcg                                    156

<210> SEQ ID NO 203
<211> LENGTH: 23
<212> TYPE: DNA
<213> ORGANISM: Artificial sequence
<220> FEATURE:
<223> OTHER INFORMATION: Synthetic DNA

<400> SEQUENCE: 203
ggttgaggtt ttcgggtttt tag                                                   23

<210> SEQ ID NO 204
<211> LENGTH: 17
<212> TYPE: DNA
<213> ORGANISM: Artificial sequence
<220> FEATURE:
<223> OTHER INFORMATION: Synthetic DNA

<400> SEQUENCE: 204
cctccccacg aaatcgc                                                          17

<210> SEQ ID NO 205
<211> LENGTH: 20
<212> TYPE: DNA
<213> ORGANISM: Artificial sequence
<220> FEATURE:
<223> OTHER INFORMATION: Synthetic DNA

<400> SEQUENCE: 205
cgccgagggc gggttttcgt                                                       20
```

-continued

```
<210> SEQ ID NO 206
<211> LENGTH: 18
<212> TYPE: DNA
<213> ORGANISM: Artificial sequence
<220> FEATURE:
<223> OTHER INFORMATION: Synthetic DNA

<400> SEQUENCE: 206
aggagttttt ttgcgcgg                                                          18

<210> SEQ ID NO 207
<211> LENGTH: 24
<212> TYPE: DNA
<213> ORGANISM: Artificial sequence
<220> FEATURE:
<223> OTHER INFORMATION: Synthetic DNA

<400> SEQUENCE: 207
acgaaaataa tcaaaatcgc ctcc                                                   24

<210> SEQ ID NO 208
<211> LENGTH: 20
<212> TYPE: DNA
<213> ORGANISM: Artificial sequence
<220> FEATURE:
<223> OTHER INFORMATION: Synthetic DNA

<400> SEQUENCE: 208
cgccgaggcc cacgaaatcg                                                        20

<210> SEQ ID NO 209
<211> LENGTH: 114
<212> TYPE: DNA
<213> ORGANISM: Homo sapiens

<400> SEQUENCE: 209
cgggggaggg cggcatcagc cagagcctca gccgacggcg ctccccaggt ccacttcccg           60
ctccgatacc ctcccctaa gcacgatacc cagggcccag ggctgctctt ggcg                 114

<210> SEQ ID NO 210
<211> LENGTH: 114
<212> TYPE: DNA
<213> ORGANISM: Artificial sequence
<220> FEATURE:
<223> OTHER INFORMATION: Synthetic DNA

<400> SEQUENCE: 210
cgggggaggg cggtattagt tagagtttta gtcgacggcg ttttttaggt ttatttttcg           60
tttcgatatt ttttttttaa gtacgatatt tagggtttag ggttgttttt ggcg               114

<210> SEQ ID NO 211
<211> LENGTH: 25
<212> TYPE: DNA
<213> ORGANISM: Artificial sequence
<220> FEATURE:
<223> OTHER INFORMATION: Synthetic DNA

<400> SEQUENCE: 211
gcggtattag ttagagtttt agtcg                                                  25

<210> SEQ ID NO 212
<211> LENGTH: 24
<212> TYPE: DNA
<213> ORGANISM: Artificial sequence
<220> FEATURE:
```

-continued

<223> OTHER INFORMATION: Synthetic DNA

<400> SEQUENCE: 212
acaaccctaa accctaaata tcgt                                                                    24

<210> SEQ ID NO 213
<211> LENGTH: 21
<212> TYPE: DNA
<213> ORGANISM: Artificial sequence
<220> FEATURE:
<223> OTHER INFORMATION: Synthetic DNA

<400> SEQUENCE: 213
ccacggacgg acggcgtttt t                                                                       21

<210> SEQ ID NO 214
<211> LENGTH: 107
<212> TYPE: DNA
<213> ORGANISM: Homo sapiens

<400> SEQUENCE: 214
ctccgctccc cgcaggcctg gccgcgcgac gggcacccag cgggttgtta tcaattattc      60
aggccccaag ttcacgggca ctgcatccat ttccctcgcg tgcgccc                   107

<210> SEQ ID NO 215
<211> LENGTH: 107
<212> TYPE: DNA
<213> ORGANISM: Artificial sequence
<220> FEATURE:
<223> OTHER INFORMATION: Synthetic DNA

<400> SEQUENCE: 215
tttcgttttt cgtaggtttg gtcgcgcgac gggtatttag cgggttgtta ttaattattt      60
aggttttaag tttacgggta ttgtatttat tttttcgcg tgcgttt                    107

<210> SEQ ID NO 216
<211> LENGTH: 19
<212> TYPE: DNA
<213> ORGANISM: Artificial sequence
<220> FEATURE:
<223> OTHER INFORMATION: Synthetic DNA

<400> SEQUENCE: 216
tttcgtaggt ttggtcgcg                                                                          19

<210> SEQ ID NO 217
<211> LENGTH: 26
<212> TYPE: DNA
<213> ORGANISM: Artificial sequence
<220> FEATURE:
<223> OTHER INFORMATION: Synthetic DNA

<400> SEQUENCE: 217
aacctaaata attaataaca acccgc                                                                  26

<210> SEQ ID NO 218
<211> LENGTH: 21
<212> TYPE: DNA
<213> ORGANISM: Artificial sequence
<220> FEATURE:
<223> OTHER INFORMATION: Synthetic DNA

<400> SEQUENCE: 218
ccacggacgg cgacgggtat t                                                                       21

<210> SEQ ID NO 219
<211> LENGTH: 88
<212> TYPE: DNA
<213> ORGANISM: Homo sapiens

<400> SEQUENCE: 219
gtgggccggg cgtgacgcgc ggtcaaagtg caatgatttt tcagttcggt tggctaaaca    60
gggtcagagc tgagagcgaa gcagaagg                                       88

<210> SEQ ID NO 220
<211> LENGTH: 88
<212> TYPE: DNA
<213> ORGANISM: Artificial sequence
<220> FEATURE:
<223> OTHER INFORMATION: Synthetic DNA

<400> SEQUENCE: 220
gtgggtcggg cgtgacgcgc ggttaaagtg taatgatttt ttagttcggt tggttaaata    60
gggttagagt tgagagcgaa gtagaagg                                       88

<210> SEQ ID NO 221
<211> LENGTH: 18
<212> TYPE: DNA
<213> ORGANISM: Artificial sequence
<220> FEATURE:
<223> OTHER INFORMATION: Synthetic DNA

<400> SEQUENCE: 221
tggttcgggc gtgacgcg                                                  18

<210> SEQ ID NO 222
<211> LENGTH: 23
<212> TYPE: DNA
<213> ORGANISM: Artificial sequence
<220> FEATURE:
<223> OTHER INFORMATION: Synthetic DNA

<400> SEQUENCE: 222 tctaaccta tttaaccaac cga                                             23

<210> SEQ ID NO 223
<211> LENGTH: 20
<212> TYPE: DNA
<213> ORGANISM: Artificial sequence
<220> FEATURE:
<223> OTHER INFORMATION: Synthetic DNA

<400> SEQUENCE: 223
cgccgagggc ggttaaagtg                                                20

<210> SEQ ID NO 224
<211> LENGTH: 94
<212> TYPE: DNA
<213> ORGANISM: Homo sapiens

<400> SEQUENCE: 224
ggacctcctc ggccccgccc catccgcctt cgggatgctg ctgagccccg tcacctccac    60
ccccttctcg gtcaaggaca tcctgcgact ggag                                94

<210> SEQ ID NO 225
<211> LENGTH: 94
<212> TYPE: DNA

<213> ORGANISM: Artificial sequence
<220> FEATURE:
<223> OTHER INFORMATION: Synthetic DNA

<400> SEQUENCE: 225
ggattttttc ggtttcgttt tattcgtttt cgggatgttg ttgagtttcg ttatttttat        60
ttttttttcg gttaaggata ttttgcgatt ggag                                     94

<210> SEQ ID NO 226
<211> LENGTH: 25
<212> TYPE: DNA
<213> ORGANISM: Artificial sequence
<220> FEATURE:
<223> OTHER INFORMATION: Synthetic DNA

<400> SEQUENCE: 226
gattttttcg gtttcgtttt attcg                                                25

<210> SEQ ID NO 227
<211> LENGTH: 24
<212> TYPE: DNA
<213> ORGANISM: Artificial sequence
<220> FEATURE:
<223> OTHER INFORMATION: Synthetic DNA

<400> SEQUENCE: 227
caatcgcaaa atatccttaa ccga                                                 24

<210> SEQ ID NO 228
<211> LENGTH: 21
<212> TYPE: DNA
<213> ORGANISM: Artificial sequence
<220> FEATURE:
<223> OTHER INFORMATION: Synthetic DNA

<400> SEQUENCE: 228
ccacggacgg ttttcgggat g                                                    21

<210> SEQ ID NO 229
<211> LENGTH: 89
<212> TYPE: DNA
<213> ORGANISM: Homo sapiens

<400> SEQUENCE: 229
ctgtcagtgc tgaccgagcg ccgcgccttc cggccatacg ggctccacgg tgcgcggttc        60
cccagccctc gcggccctcc ccgcccccg                                           89

<210> SEQ ID NO 230
<211> LENGTH: 89
<212> TYPE: DNA
<213> ORGANISM: Artificial sequence
<220> FEATURE:
<223> OTHER INFORMATION: Synthetic DNA

<400> SEQUENCE: 230
ttgttagtgt tgatcgagcg tcgcgttttt cggttatacg ggtttttacgg tgcgcggttt        60 tttagttttc gcggtttttt tcgtttttcg                                          89

<210> SEQ ID NO 231
<211> LENGTH: 22
<212> TYPE: DNA
<213> ORGANISM: Artificial sequence
<220> FEATURE:
<223> OTHER INFORMATION: Synthetic DNA -continued

<400> SEQUENCE: 231
cgtcgcgttt ttcggttata cg                                          22

<210> SEQ ID NO 232
<211> LENGTH: 21
<212> TYPE: DNA
<213> ORGANISM: Artificial sequence
<220> FEATURE:
<223> OTHER INFORMATION: Synthetic DNA

<400> SEQUENCE: 232
cgcgaaaact aaaaaaccgc g                                           21

<210> SEQ ID NO 233
<211> LENGTH: 21
<212> TYPE: DNA
<213> ORGANISM: Artificial sequence
<220> FEATURE:
<223> OTHER INFORMATION: Synthetic DNA

<400> SEQUENCE: 233
ccacggacgg caccgtaaaa c                                           21

<210> SEQ ID NO 234
<211> LENGTH: 114
<212> TYPE: DNA
<213> ORGANISM: Homo sapiens

<400> SEQUENCE: 234
cggagtatgg tgaggagcgc gggggacggg tgcgggaagg ggacagcagg gctgagcctg    60
gggcccgcaa gacccagcag cccgagcggg cgcagagacc ccacgccacg caca          114

<210> SEQ ID NO 235
<211> LENGTH: 114
<212> TYPE: DNA
<213> ORGANISM: Artificial sequence
<220> FEATURE:
<223> OTHER INFORMATION: Synthetic DNA

<400> SEQUENCE: 235
cggagtatgg tgaggagcgc gggggacggg tgcgggaagg ggatagtagg gttgagtttg    60
gggttcgtaa gatttagtag ttcgagcggg cgtagagatt ttacgttacg tata          114

<210> SEQ ID NO 236
<211> LENGTH: 18
<212> TYPE: DNA
<213> ORGANISM: Artificial sequence
<220> FEATURE:
<223> OTHER INFORMATION: Synthetic DNA

<400> SEQUENCE: 236
ggttgagttt ggggttcg                                              18

<210> SEQ ID NO 237
<211> LENGTH: 23
<212> TYPE: DNA
<213> ORGANISM: Artificial sequence
<220> FEATURE:
<223> OTHER INFORMATION: Synthetic DNA

<400> SEQUENCE: 237
cgtaacgtaa aatctctacg ccc                                         23

-continued

```
<210> SEQ ID NO 238
<211> LENGTH: 21
<212> TYPE: DNA
<213> ORGANISM: Artificial sequence
<220> FEATURE:
<223> OTHER INFORMATION: Synthetic DNA

<400> SEQUENCE: 238
ccacggacgc gctcgaacta c                                                21

<210> SEQ ID NO 239
<211> LENGTH: 95
<212> TYPE: DNA
<213> ORGANISM: Homo sapiens

<400> SEQUENCE: 239
ggagagcagc ccgcagaacc tggccgcgta ctacacgcct ttcccgtcct atggacacta      60
cagaaacagc ctggccaccg tggaggaaga cttcc                                 95

<210> SEQ ID NO 240
<211> LENGTH: 95
<212> TYPE: DNA
<213> ORGANISM: Artificial sequence
<220> FEATURE:
<223> OTHER INFORMATION: Synthetic DNA

<400> SEQUENCE: 240
ggagagtagt tcgtagaatt tggtcgcgta ttatacgttt ttttcgtttt atggatatta      60
tagaaatagt ttggttatcg tggaggaaga ttttt                                 95

<210> SEQ ID NO 241
<211> LENGTH: 23
<212> TYPE: DNA
<213> ORGANISM: Artificial sequence
<220> FEATURE:
<223> OTHER INFORMATION: Synthetic DNA

<400> SEQUENCE: 241
gagtagttcg tagaatttgg tcg                                              23

<210> SEQ ID NO 242
<211> LENGTH: 31
<212> TYPE: DNA
<213> ORGANISM: Artificial sequence
<220> FEATURE:
<223> OTHER INFORMATION: Synthetic DNA

<400> SEQUENCE: 242
ccacgataac caaactattt ctataatatc c                                     31

<210> SEQ ID NO 243
<211> LENGTH: 21
<212> TYPE: DNA
<213> ORGANISM: Artificial sequence
<220> FEATURE:
<223> OTHER INFORMATION: Synthetic DNA

<400> SEQUENCE: 243
ccacggacgg cgtattatac g                                                21

<210> SEQ ID NO 244
<211> LENGTH: 23
<212> TYPE: DNA
<213> ORGANISM: Artificial sequence
```

-continued

<220> FEATURE:
<223> OTHER INFORMATION: Synthetic DNA

<400> SEQUENCE: 244
ggagagtagt tcgtagaatt tgg                                                              23

<210> SEQ ID NO 245
<211> LENGTH: 35
<212> TYPE: DNA
<213> ORGANISM: Artificial sequence
<220> FEATURE:
<223> OTHER INFORMATION: Synthetic DNA

<400> SEQUENCE: 245
ctatttctat aatatccata aaacgaaaaa aacgt                                                 35

<210> SEQ ID NO 246
<211> LENGTH: 21
<212> TYPE: DNA
<213> ORGANISM: Artificial sequence
<220> FEATURE:
<223> OTHER INFORMATION: Synthetic DNA

<400> SEQUENCE: 246
ccacggacgg tcgcgtatta t                                                                21

<210> SEQ ID NO 247
<211> LENGTH: 92
<212> TYPE: DNA
<213> ORGANISM: Homo sapiens

<400> SEQUENCE: 247
gggaaggtgc cctgcgcgcg cgcgctcacc agatgaagtc ggtgcagtgg ctgcagaagg                     60
tgggctgctt gaagaagcgg gcggtgaatt tg                                                    92

<210> SEQ ID NO 248
<211> LENGTH: 92
<212> TYPE: DNA
<213> ORGANISM: Artificial sequence
<220> FEATURE:
<223> OTHER INFORMATION: Synthetic DNA

<400> SEQUENCE: 248
gggaaggtgt tttgcgcgcg cgcgtttatt agatgaagtc ggtgtagtgg ttgtagaagg                     60
tgggttgttt gaagaagcgg gcggtgaatt tg                                                    92

<210> SEQ ID NO 249
<211> LENGTH: 17
<212> TYPE: DNA
<213> ORGANISM: Artificial sequence
<220> FEATURE:
<223> OTHER INFORMATION: Synthetic DNA

<400> SEQUENCE: 249
ggaaggtgtt ttgcgcg                                                                     17

<210> SEQ ID NO 250
<211> LENGTH: 21
<212> TYPE: DNA
<213> ORGANISM: Artificial sequence
<220> FEATURE:
<223> OTHER INFORMATION: Synthetic DNA

<400> SEQUENCE: 250
cttctacaac cactacaccg a                                              21

<210> SEQ ID NO 251
<211> LENGTH: 21
<212> TYPE: DNA
<213> ORGANISM: Artificial sequence
<220> FEATURE:
<223> OTHER INFORMATION: Synthetic DNA

<400> SEQUENCE: 251
ccacggacgg cgcgcgttta t                                              21

<210> SEQ ID NO 252
<211> LENGTH: 107
<212> TYPE: DNA
<213> ORGANISM: Homo sapiens

<400> SEQUENCE: 252
gcctcggggc ccggggactc acaattacgg gcagagaaca catagtgaag agcacggtca    60
tcagcgccag cagcaggagg tgatccagct cctccagggg ctgaggg                 107

<210> SEQ ID NO 253
<211> LENGTH: 107
<212> TYPE: DNA
<213> ORGANISM: Artificial sequence
<220> FEATURE:
<223> OTHER INFORMATION: Synthetic DNA

<400> SEQUENCE: 253
gtttcggggt tcggggattt ataattacgg gtagagaata tatagtgaag agtacggtta    60
ttagcgttag tagtaggagg tgatttagtt tttttagggg ttgaggg                 107

<210> SEQ ID NO 254
<211> LENGTH: 24
<212> TYPE: DNA
<213> ORGANISM: Artificial sequence
<220> FEATURE:
<223> OTHER INFORMATION: Synthetic DNA

<400> SEQUENCE: 254
gggttcgggg atttataatt acgg                                          24

<210> SEQ ID NO 255
<211> LENGTH: 25
<212> TYPE: DNA
<213> ORGANISM: Artificial sequence
<220> FEATURE:
<223> OTHER INFORMATION: Synthetic DNA

<400> SEQUENCE: 255
cctcctacta ctaacgctaa taacc                                         25

<210> SEQ ID NO 256
<211> LENGTH: 21
<212> TYPE: DNA
<213> ORGANISM: Artificial sequence
<220> FEATURE:
<223> OTHER INFORMATION: Synthetic DNA

<400> SEQUENCE: 256
ccacggacgc gtactcttca c                                              21

<210> SEQ ID NO 257
<211> LENGTH: 80

```
<212> TYPE: DNA
<213> ORGANISM: Homo sapiens

<400> SEQUENCE: 257
ggcggctgca gcggcacccg cgctcctgca ccagggactg tgccgagccg cgcgcggacg      60
ggagggaagc gtcccctcag                                                  80

<210> SEQ ID NO 258
<211> LENGTH: 80
<212> TYPE: DNA
<213> ORGANISM: Artificial sequence
<220> FEATURE:
<223> OTHER INFORMATION: Synthetic DNA

<400> SEQUENCE: 258
ggcggttgta gcggtattcg cgtttttgta ttagggattg tgtcgagtcg cgcgcggacg      60
ggagggaagc gttttttttag                                                 80

<210> SEQ ID NO 259
<211> LENGTH: 18
<212> TYPE: DNA
<213> ORGANISM: Artificial sequence
<220> FEATURE:
<223> OTHER INFORMATION: Synthetic DNA

<400> SEQUENCE: 259
gttgtagcgg tattcgcg                                                    18

<210> SEQ ID NO 260
<211> LENGTH: 18
<212> TYPE: DNA
<213> ORGANISM: Artificial sequence
<220> FEATURE:
<223> OTHER INFORMATION: Synthetic DNA

<400> SEQUENCE: 260
cttctctccc gtccgcgc                                                    18

<210> SEQ ID NO 261
<211> LENGTH: 20
<212> TYPE: DNA
<213> ORGANISM: Artificial sequence
<220> FEATURE:
<223> OTHER INFORMATION: Synthetic DNA

<400> SEQUENCE: 261
cgccgaggcg cgactcgaca                                                  20

<210> SEQ ID NO 262
<211> LENGTH: 143
<212> TYPE: DNA
<213> ORGANISM: Homo sapiens

<400> SEQUENCE: 262
tccagaaaca cgggtatctc cgcgtggtgc tttgcggtcg ccgtcgttgt ggccgtccgg      60
ggtggggtgt gaggagggga cgaaggaggg aaggaagggc aaggcggggg gggctctgcg     120
agagcgcgcc cagccccgcc ttc                                             143

<210> SEQ ID NO 263
<211> LENGTH: 143
<212> TYPE: DNA
<213> ORGANISM: Artificial sequence
<220> FEATURE:
```

-continued

<223> OTHER INFORMATION: Synthetic DNA

<400> SEQUENCE: 263
tttagaaata cgggtatttt cgcgtggtgt tttgcggtcg tcgtcgttgt ggtcgttcgg     60
ggtggggtgt gaggagggga cgaaggaggg aaggaagggt aaggcggggg gggttttgcg    120
agagcgcgtt tagtttcgtt ttt                                            143

<210> SEQ ID NO 264
<211> LENGTH: 21
<212> TYPE: DNA
<213> ORGANISM: Artificial sequence
<220> FEATURE:
<223> OTHER INFORMATION: Synthetic DNA

<400> SEQUENCE: 264
agaaatacgg gtattttcgc g                                               21

<210> SEQ ID NO 265
<211> LENGTH: 17
<212> TYPE: DNA
<213> ORGANISM: Artificial sequence
<220> FEATURE:
<223> OTHER INFORMATION: Synthetic DNA

<400> SEQUENCE: 265
ccacaacgac gacgacc                                                    17

<210> SEQ ID NO 266
<211> LENGTH: 21
<212> TYPE: DNA
<213> ORGANISM: Artificial sequence
<220> FEATURE:
<223> OTHER INFORMATION: Synthetic DNA

<400> SEQUENCE: 266
ccacggacgc gcaaaacacc a                                               21

<210> SEQ ID NO 267
<211> LENGTH: 120
<212> TYPE: DNA
<213> ORGANISM: Homo sapiens

<400> SEQUENCE: 267
cggtcgggca ggcgggacgg agattacctg gctgtccagg ggaccttatg cagggtttgg     60
cccgagccca ggggcagcga ggggcgtctg cggatgcggc tccctgtgcg gcacaacacc    120

<210> SEQ ID NO 268
<211> LENGTH: 120
<212> TYPE: DNA
<213> ORGANISM: Artificial sequence
<220> FEATURE:
<223> OTHER INFORMATION: Synthetic DNA

<400> SEQUENCE: 268
cggtcgggta ggcgggacgg agattatttg gttgtttagg ggattttatg tagggtttgg     60
ttcgagttta ggggtagcga ggggcgtttg cggatgcggt tttttgtgcg gtataatatt    120

<210> SEQ ID NO 269
<211> LENGTH: 20
<212> TYPE: DNA
<213> ORGANISM: Artificial sequence
<220> FEATURE:
<223> OTHER INFORMATION: Synthetic DNA -continued

<400> SEQUENCE: 269
gttcgagttt aggggtagcg                                                                                          20

<210> SEQ ID NO 270
<211> LENGTH: 17
<212> TYPE: DNA
<213> ORGANISM: Artificial sequence
<220> FEATURE:
<223> OTHER INFORMATION: Synthetic DNA

<400> SEQUENCE: 270
ccgcacaaaa aaccgca                                                                                             17

<210> SEQ ID NO 271
<211> LENGTH: 21
<212> TYPE: DNA
<213> ORGANISM: Artificial sequence
<220> FEATURE:
<223> OTHER INFORMATION: Synthetic DNA

<400> SEQUENCE: 271
ccacggacga tccgcaaacg c                                                                                        21

<210> SEQ ID NO 272
<211> LENGTH: 55
<212> TYPE: DNA
<213> ORGANISM: Homo sapiens

<400> SEQUENCE: 272
ccggagcact cgccgctgcg cgccctgaag ccgctggcgg taggcggccc tcgag                                                   55

<210> SEQ ID NO 273
<211> LENGTH: 55
<212> TYPE: DNA
<213> ORGANISM: Artificial sequence
<220> FEATURE:
<223> OTHER INFORMATION: Synthetic DNA

<400> SEQUENCE: 273
tcggagtatt cgtcgttgcg cgttttgaag tcgttggcgg taggcggttt tcgag                                                   55

<210> SEQ ID NO 274
<211> LENGTH: 18
<212> TYPE: DNA
<213> ORGANISM: Artificial sequence
<220> FEATURE:
<223> OTHER INFORMATION: Synthetic DNA

<400> SEQUENCE: 274
ggagtattcg tcgttgcg                                                                                            18

<210> SEQ ID NO 275
<211> LENGTH: 17
<212> TYPE: DNA
<213> ORGANISM: Artificial sequence
<220> FEATURE:
<223> OTHER INFORMATION: Synthetic DNA

<400> SEQUENCE: 275
cgaaaaccgc ctaccgc                                                                                             17

<210> SEQ ID NO 276
<211> LENGTH: 20
<212> TYPE: DNA

-continued

```
<213> ORGANISM: Artificial sequence
<220> FEATURE:
<223> OTHER INFORMATION: Synthetic DNA

<400> SEQUENCE: 276
cgccgagggc gttttgaagt                                                  20

<210> SEQ ID NO 277
<211> LENGTH: 96
<212> TYPE: DNA
<213> ORGANISM: Homo sapiens

<400> SEQUENCE: 277
cccgggccta cggtcctccc gccacctcca cggggcggct gttggggccc caccaggcag    60
agccgtgttc tcaggcgttg gctctcatgg aggtgg                              96

<210> SEQ ID NO 278
<211> LENGTH: 96
<212> TYPE: DNA
<213> ORGANISM: Artificial sequence
<220> FEATURE:
<223> OTHER INFORMATION: Synthetic DNA

<400> SEQUENCE: 278
ttcgggttta cggttttttc gttatttta cggggcggtt gttggggttt tattaggtag    60
agtcgtgttt ttaggcgttg gtttttatgg aggtgg                              96

<210> SEQ ID NO 279
<211> LENGTH: 25
<212> TYPE: DNA
<213> ORGANISM: Artificial sequence
<220> FEATURE:
<223> OTHER INFORMATION: Synthetic DNA

<400> SEQUENCE: 279
acggtttttt cgttattttt acggg                                          25

<210> SEQ ID NO 280
<211> LENGTH: 21
<212> TYPE: DNA
<213> ORGANISM: Artificial sequence
<220> FEATURE:
<223> OTHER INFORMATION: Synthetic DNA

<400> SEQUENCE: 280
caacgcctaa aaacacgact c                                              21

<210> SEQ ID NO 281
<211> LENGTH: 20
<212> TYPE: DNA
<213> ORGANISM: Artificial sequence
<220> FEATURE:
<223> OTHER INFORMATION: Synthetic DNA

<400> SEQUENCE: 281
cgccgagggg cggttgttgg                                                20

<210> SEQ ID NO 282
<211> LENGTH: 148
<212> TYPE: DNA
<213> ORGANISM: Homo sapiens

<400> SEQUENCE: 282
gggcctgtcc cgttccctgc tccccataca ggcgaggctg cgtgcacaca gcttcctgta    60
```

-continued

```
ccccaggagg gcctgcctgg cacgcacccg gtggctgcac catccacacg caagactgca      120
acttcagatg ctccgcacgc tggagatg                                         148

<210> SEQ ID NO 283
<211> LENGTH: 148
<212> TYPE: DNA
<213> ORGANISM: Artificial sequence
<220> FEATURE:
<223> OTHER INFORMATION: Synthetic DNA

<400> SEQUENCE: 283
gggtttgttt cgtttttttgt tttttatata ggcgaggttg cgtgtatata gtttttttgta     60 ttttaggagg gtttgtttgg tacgtattcg gtggttgtat tatttatacg taagattgta      120
attttagatg tttcgtacgt tggagatg                                         148

<210> SEQ ID NO 284
<211> LENGTH: 20
<212> TYPE: DNA
<213> ORGANISM: Artificial sequence
<220> FEATURE:
<223> OTHER INFORMATION: Synthetic DNA

<400> SEQUENCE: 284
ttatataggc gaggttgcgt                                                    20

<210> SEQ ID NO 285
<211> LENGTH: 30
<212> TYPE: DNA
<213> ORGANISM: Artificial sequence
<220> FEATURE:
<223> OTHER INFORMATION: Synthetic DNA

<400> SEQUENCE: 285
cttacgtata aataatacaa ccaccgaata                                         30

<210> SEQ ID NO 286
<211> LENGTH: 21
<212> TYPE: DNA
<213> ORGANISM: Artificial sequence
<220> FEATURE:
<223> OTHER INFORMATION: Synthetic DNA

<400> SEQUENCE: 286
ccacggacga cgtaccaaac a                                                  21

<210> SEQ ID NO 287
<211> LENGTH: 88
<212> TYPE: DNA
<213> ORGANISM: Homo sapiens

<400> SEQUENCE: 287
cggagctagg agggtggggc tcggagggcg caggaagagc ggctctgcga ggaaagggaa       60
aggagaggcc gcttctggga agggaccc                                          88

<210> SEQ ID NO 288
<211> LENGTH: 88
<212> TYPE: DNA
<213> ORGANISM: Artificial sequence
<220> FEATURE:
<223> OTHER INFORMATION: Synthetic DNA

<400> SEQUENCE: 288
```

-continued

```
cggagttagg agggtggggt tcggagggcg taggaagagc ggttttgcga ggaaagggaa        60
aggagaggtc gtttttggga agggattt                                           88

<210> SEQ ID NO 289
<211> LENGTH: 18
<212> TYPE: DNA
<213> ORGANISM: Artificial sequence
<220> FEATURE:
<223> OTHER INFORMATION: Synthetic DNA

<400> SEQUENCE: 289
ttaggagggt ggggttcg                                                      18

<210> SEQ ID NO 290
<211> LENGTH: 18
<212> TYPE: DNA
<213> ORGANISM: Artificial sequence
<220> FEATURE:
<223> OTHER INFORMATION: Synthetic DNA

<400> SEQUENCE: 290
ctttcctcgc aaaaccgc                                                      18

<210> SEQ ID NO 291
<211> LENGTH: 21
<212> TYPE: DNA
<213> ORGANISM: Artificial sequence
<220> FEATURE:
<223> OTHER INFORMATION: Synthetic DNA

<400> SEQUENCE: 291
ccacggacgg gagggcgtag g                                                  21

<210> SEQ ID NO 292
<211> LENGTH: 59
<212> TYPE: DNA
<213> ORGANISM: Homo sapiens

<400> SEQUENCE: 292
gccccggcgg gccccgaggc ggccgcggcc tgcaacgtca tcgtgaacgg cacgcgcgg         59

<210> SEQ ID NO 293
<211> LENGTH: 59
<212> TYPE: DNA
<213> ORGANISM: Artificial sequence
<220> FEATURE:
<223> OTHER INFORMATION: Synthetic DNA

<400> SEQUENCE: 293
gtttcggcgg gtttcgaggc ggtcgcggtt tgtaacgtta tcgtgaacgg tacgcgcgg         59

<210> SEQ ID NO 294
<211> LENGTH: 17
<212> TYPE: DNA
<213> ORGANISM: Artificial sequence
<220> FEATURE:
<223> OTHER INFORMATION: Synthetic DNA

<400> SEQUENCE: 294
tttcggcggg tttcgag                                                       17

<210> SEQ ID NO 295
<211> LENGTH: 20
<212> TYPE: DNA
<213> ORGANISM: Artificial sequence
```

-continued

```
<220> FEATURE:
<223> OTHER INFORMATION: Synthetic DNA

<400> SEQUENCE: 295
cgtaccgttc acgataacgt                                              20

<210> SEQ ID NO 296
<211> LENGTH: 20
<212> TYPE: DNA
<213> ORGANISM: Artificial sequence
<220> FEATURE:
<223> OTHER INFORMATION: Synthetic DNA

<400> SEQUENCE: 296
cgccgagggg cggtcgcggt                                              20

<210> SEQ ID NO 297
<211> LENGTH: 20
<212> TYPE: DNA
<213> ORGANISM: Artificial sequence
<220> FEATURE:
<223> OTHER INFORMATION: Synthetic DNA

<400> SEQUENCE: 297
cgccgaggtt acaaaccgcg                                              20

<210> SEQ ID NO 298
<211> LENGTH: 89
<212> TYPE: DNA
<213> ORGANISM: Homo sapiens

<400> SEQUENCE: 298
ctaggcgaga tggtggaagg cgtgtccgta cgggggtggg ctggggtccc cgtgcagaag    60
ggcgcgcgag gacccaggct ggttttccc                                    89

<210> SEQ ID NO 299
<211> LENGTH: 89
<212> TYPE: DNA
<213> ORGANISM: Artificial sequence
<220> FEATURE:
<223> OTHER INFORMATION: Synthetic DNA

<400> SEQUENCE: 299
ttaggcgaga tggtggaagg cgtgttcgta cgggggtggg ttggggtttt cgtgtagaag    60
ggcgcgcgag gatttaggtt ggttttttt                                    89

<210> SEQ ID NO 300
<211> LENGTH: 17
<212> TYPE: DNA
<213> ORGANISM: Artificial sequence
<220> FEATURE:
<223> OTHER INFORMATION: Synthetic DNA

<400> SEQUENCE: 300
cgagatggtg gaaggcg                                                 17

<210> SEQ ID NO 301
<211> LENGTH: 17
<212> TYPE: DNA
<213> ORGANISM: Artificial sequence
<220> FEATURE:
<223> OTHER INFORMATION: Synthetic DNA

<400> SEQUENCE: 301
```

-continued gcgcccttct acacgaa                                                        17

<210> SEQ ID NO 302
<211> LENGTH: 21
<212> TYPE: DNA
<213> ORGANISM: Artificial sequence
<220> FEATURE:
<223> OTHER INFORMATION: Synthetic DNA

<400> SEQUENCE: 302
ccacggacgg tgttcgtacg g                                                   21

<210> SEQ ID NO 303
<211> LENGTH: 145
<212> TYPE: DNA
<213> ORGANISM: Homo sapiens

<400> SEQUENCE: 303
gcgctgctgc gccgccaggc aaggcgaggg tccgggagaa ggctcggctc cctcctaaac   60
atgtggcccg tggcgtcccc ttgtcccctc cgagcgatgc tcctgcgccc ttcgccgcct   120
cccgcgctgc tgcgccgcca ggcaa                                            145

<210> SEQ ID NO 304
<211> LENGTH: 123
<212> TYPE: DNA
<213> ORGANISM: Artificial sequence
<220> FEATURE:
<223> OTHER INFORMATION: Synthetic DNA

<400> SEQUENCE: 304
ggcgagggtt cgggagaagg ttcggttttt ttttaaatat gtggttcgtg gcgttttttt   60
gtttttttcg agcgatgttt ttgcgttttt cgtcgttttt cgcgttgttg cgtcgttagg   120
taa                                                                    123

<210> SEQ ID NO 305
<211> LENGTH: 21
<212> TYPE: DNA
<213> ORGANISM: Artificial sequence
<220> FEATURE:
<223> OTHER INFORMATION: Synthetic DNA

<400> SEQUENCE: 305
aaatatgtgg ttcgtggcgt t                                                  21

<210> SEQ ID NO 306
<211> LENGTH: 19
<212> TYPE: DNA
<213> ORGANISM: Artificial sequence
<220> FEATURE:
<223> OTHER INFORMATION: Synthetic DNA

<400> SEQUENCE: 306
acgcaacaac gcgaaaaac                                                      19

<210> SEQ ID NO 307
<211> LENGTH: 20
<212> TYPE: DNA
<213> ORGANISM: Artificial sequence
<220> FEATURE:
<223> OTHER INFORMATION: Synthetic DNA

<400> SEQUENCE: 307
cgccgaggcg acgaaaaacg                                                     20

-continued

```
<210> SEQ ID NO 308
<211> LENGTH: 137
<212> TYPE: DNA
<213> ORGANISM: Homo sapiens

<400> SEQUENCE: 308
acgagaaaga gatcgtgcag ggggtgctgc aacagggcac ggcgtggagg aggaaccaga      60
ccgcggccag agcgttcagg tactcctgcc ctcgcggctc ctcccctcta gcgtcctttc     120
ctccccgagt gcagagg                                                    137

<210> SEQ ID NO 309
<211> LENGTH: 137
<212> TYPE: DNA
<213> ORGANISM: Artificial sequence
<220> FEATURE:
<223> OTHER INFORMATION: Synthetic DNA

<400> SEQUENCE: 309
acgagaaaga gatcgtgtag ggggtgttgt aatagggtac ggcgtggagg aggaattaga      60
tcgcggttag agcgtttagg tatttttgtt ttcgcggttt ttttttttta gcgttttttt     120
tttttcgagt gtagagg                                                    137

<210> SEQ ID NO 310
<211> LENGTH: 21
<212> TYPE: DNA
<213> ORGANISM: Artificial sequence
<220> FEATURE:
<223> OTHER INFORMATION: Synthetic DNA

<400> SEQUENCE: 310
ggggtgttgt aatagggtac g                                                21

<210> SEQ ID NO 311
<211> LENGTH: 19
<212> TYPE: DNA
<213> ORGANISM: Artificial sequence
<220> FEATURE:
<223> OTHER INFORMATION: Synthetic DNA

<400> SEQUENCE: 311
ctaaacgctc taaccgcga                                                   19

<210> SEQ ID NO 312
<211> LENGTH: 21
<212> TYPE: DNA
<213> ORGANISM: Artificial sequence
<220> FEATURE:
<223> OTHER INFORMATION: Synthetic DNA

<400> SEQUENCE: 312
ccacggacgg gcgtggagga g                                                21

<210> SEQ ID NO 313
<211> LENGTH: 117
<212> TYPE: DNA
<213> ORGANISM: Homo sapiens

<400> SEQUENCE: 313
cgcgccgttg gtcacctcgc cggccgccag cgtcgaatgg aagcccgact tgtaccagga      60
ctcgtacggg tgcgccatgc ccacgcgcgg gtacagcccg tcggctgccg tcgtgtg        117
```

-continued

<210> SEQ ID NO 314
<211> LENGTH: 117
<212> TYPE: DNA
<213> ORGANISM: Artificial sequence
<220> FEATURE:
<223> OTHER INFORMATION: Synthetic DNA

<400> SEQUENCE: 314
cgcgtcgttg gttatttcgt cggtcgttag cgtcgaatgg aagttcgatt tgtattagga      60
ttcgtacggg tgcgttatgt ttacgcgcgg gtatagttcg tcggttgtcg tcgtgtg      117

<210> SEQ ID NO 315
<211> LENGTH: 21
<212> TYPE: DNA
<213> ORGANISM: Artificial sequence
<220> FEATURE:
<223> OTHER INFORMATION: Synthetic DNA

<400> SEQUENCE: 315
tagcgtcgaa tggaagttcg a      21

<210> SEQ ID NO 316
<211> LENGTH: 18
<212> TYPE: DNA
<213> ORGANISM: Artificial sequence
<220> FEATURE:
<223> OTHER INFORMATION: Synthetic DNA

<400> SEQUENCE: 316
ggtcgttagc gtcgaatg      18

<210> SEQ ID NO 317
<211> LENGTH: 20
<212> TYPE: DNA
<213> ORGANISM: Artificial sequence
<220> FEATURE:
<223> OTHER INFORMATION: Synthetic DNA

<400> SEQUENCE: 317
gcgcgtaaac ataacgcacc      20

<210> SEQ ID NO 318
<211> LENGTH: 21
<212> TYPE: DNA
<213> ORGANISM: Artificial sequence
<220> FEATURE:
<223> OTHER INFORMATION: Synthetic DNA

<400> SEQUENCE: 318
ccacggacgc cgtacgaatc c      21

<210> SEQ ID NO 319
<211> LENGTH: 85
<212> TYPE: DNA
<213> ORGANISM: Homo sapiens

<400> SEQUENCE: 319
ggttccttcc cgtgggttct taatcgtctc gctgacttcc agaatgaaac tgcagaccct      60
cgcggtaaag atggcgtgac cagaa      85

<210> SEQ ID NO 320
<211> LENGTH: 85
<212> TYPE: DNA
<213> ORGANISM: Artificial sequence -continued

```
<220> FEATURE:
<223> OTHER INFORMATION: Synthetic DNA

<400> SEQUENCE: 320 ggttttttt cgtgggtttt taatcgtttc gttgattttt agaatgaaat tgtagatttt      60
cgcggtaaag atggcgtgat tagaa                                            85

<210> SEQ ID NO 321
<211> LENGTH: 22
<212> TYPE: DNA
<213> ORGANISM: Artificial sequence
<220> FEATURE:
<223> OTHER INFORMATION: Synthetic DNA

<400> SEQUENCE: 321
tcgtgggttt ttaatcgttt cg                                               22

<210> SEQ ID NO 322
<211> LENGTH: 18
<212> TYPE: DNA
<213> ORGANISM: Artificial sequence
<220> FEATURE:
<223> OTHER INFORMATION: Synthetic DNA

<400> SEQUENCE: 322
tcacgccatc tttaccgc                                                    18

<210> SEQ ID NO 323
<211> LENGTH: 21
<212> TYPE: DNA
<213> ORGANISM: Artificial sequence
<220> FEATURE:
<223> OTHER INFORMATION: Synthetic DNA

<400> SEQUENCE: 323
ccacggacgc gaaaatctac a                                                21

<210> SEQ ID NO 324
<211> LENGTH: 26
<212> TYPE: DNA
<213> ORGANISM: Artificial sequence
<220> FEATURE:
<223> OTHER INFORMATION: Synthetic DNA

<400> SEQUENCE: 324 ggttttttt cgtgggtttt taatcg                                            26

<210> SEQ ID NO 325
<211> LENGTH: 21
<212> TYPE: DNA
<213> ORGANISM: Artificial sequence
<220> FEATURE:
<223> OTHER INFORMATION: Synthetic DNA

<400> SEQUENCE: 325
ctaatcacgc catctttacc g                                                21

<210> SEQ ID NO 326
<211> LENGTH: 21
<212> TYPE: DNA
<213> ORGANISM: Artificial sequence
<220> FEATURE:
<223> OTHER INFORMATION: Synthetic DNA

<400> SEQUENCE: 326
```

-continued

```
ccacggacgg tttcgttgat t                                              21

<210> SEQ ID NO 327
<211> LENGTH: 115
<212> TYPE: DNA
<213> ORGANISM: Homo sapiens

<400> SEQUENCE: 327
ggagtgagtg cctacaacgc gcaggccgga ctgatccccc gttgctgcag gttggtgccc      60
caagctgcgg gtgctcgggc gccaactaaa gccagctctg tccagacgcg gaaag          115

<210> SEQ ID NO 328
<211> LENGTH: 115
<212> TYPE: DNA
<213> ORGANISM: Artificial sequence
<220> FEATURE:
<223> OTHER INFORMATION: Synthetic DNA

<400> SEQUENCE: 328
ggagtgagtg tttataacgc gtaggtcgga ttgatttttc gttgttgtag gttggtgttt      60
taagttgcgg gtgttcgggc gttaattaaa gttagttttg tttagacgcg gaaag          115

<210> SEQ ID NO 329
<211> LENGTH: 23
<212> TYPE: DNA
<213> ORGANISM: Artificial sequence
<220> FEATURE:
<223> OTHER INFORMATION: Synthetic DNA

<400> SEQUENCE: 329
cgtaggtcgg attgattttt cgt                                            23

<210> SEQ ID NO 330
<211> LENGTH: 30
<212> TYPE: DNA
<213> ORGANISM: Artificial sequence
<220> FEATURE:
<223> OTHER INFORMATION: Synthetic DNA

<400> SEQUENCE: 330
tctaaacaaa actaacttta attaacgccc                                     30

<210> SEQ ID NO 331
<211> LENGTH: 21
<212> TYPE: DNA
<213> ORGANISM: Artificial sequence
<220> FEATURE:
<223> OTHER INFORMATION: Synthetic DNA

<400> SEQUENCE: 331
ccacggacgc gaacacccgc a                                              21

<210> SEQ ID NO 332
<211> LENGTH: 19
<212> TYPE: DNA
<213> ORGANISM: Artificial sequence
<220> FEATURE:
<223> OTHER INFORMATION: Synthetic DNA

<400> SEQUENCE: 332
aggaaattgc gggttttcg                                                 19

<210> SEQ ID NO 333
<211> LENGTH: 21
```

-continued

```
<212> TYPE: DNA
<213> ORGANISM: Artificial sequence
<220> FEATURE:
<223> OTHER INFORMATION: Synthetic DNA

<400> SEQUENCE: 333
ggaaggaaat tgcgggtttt c                                           21

<210> SEQ ID NO 334
<211> LENGTH: 25
<212> TYPE: DNA
<213> ORGANISM: Artificial sequence
<220> FEATURE:
<223> OTHER INFORMATION: Synthetic DNA

<400> SEQUENCE: 334
ccaaaaatcg tcgctaaaaa tcaac                                       25

<210> SEQ ID NO 335
<211> LENGTH: 21
<212> TYPE: DNA
<213> ORGANISM: Artificial sequence
<220> FEATURE:
<223> OTHER INFORMATION: Synthetic DNA

<400> SEQUENCE: 335
ccacggacgc gcgcattcac t                                           21

<210> SEQ ID NO 336
<211> LENGTH: 100
<212> TYPE: DNA
<213> ORGANISM: Homo sapiens

<400> SEQUENCE: 336
ggcggccgcg acccctcccc gctgacctca ctcgagccgc cgcctggcgc agatataagc   60
ggcggcccat ctgaagaggg ctcggcaggc gcccggggtc                         100

<210> SEQ ID NO 337
<211> LENGTH: 100
<212> TYPE: DNA
<213> ORGANISM: Artificial sequence
<220> FEATURE:
<223> OTHER INFORMATION: Synthetic DNA

<400> SEQUENCE: 337
ggcggtcgcg atttttttc gttgatttta ttcgagtcgt cgtttggcgt agatataagc    60
ggcggtttat ttgaagaggg ttcggtaggc gttcggggtt                         100

<210> SEQ ID NO 338
<211> LENGTH: 23
<212> TYPE: DNA
<213> ORGANISM: Artificial sequence
<220> FEATURE:
<223> OTHER INFORMATION: Synthetic DNA

<400> SEQUENCE: 338
tttcgttgat tttattcgag tcg                                         23

<210> SEQ ID NO 339
<211> LENGTH: 19
<212> TYPE: DNA
<213> ORGANISM: Artificial sequence
<220> FEATURE:
<223> OTHER INFORMATION: Synthetic DNA
```

-continued

<400> SEQUENCE: 339
tcttcaaata aaccgccgc                                                    19

<210> SEQ ID NO 340
<211> LENGTH: 20
<212> TYPE: DNA
<213> ORGANISM: Artificial sequence
<220> FEATURE:
<223> OTHER INFORMATION: Synthetic DNA

<400> SEQUENCE: 340
cgccgagggt cgtttggcgt                                                   20

<210> SEQ ID NO 341
<211> LENGTH: 118
<212> TYPE: DNA
<213> ORGANISM: Homo sapiens

<400> SEQUENCE: 341
cgggtggtga agctgcccca cggcctggga gagccttatc gccgcggtcg ctggacgtgt        60
gtggatgttt atgagcgaga cctggagccc cacagcttcg gcggactcct ggagggaa        118

<210> SEQ ID NO 342
<211> LENGTH: 118
<212> TYPE: DNA
<213> ORGANISM: Artificial sequence
<220> FEATURE:
<223> OTHER INFORMATION: Synthetic DNA

<400> SEQUENCE: 342
cgggtggtga agttgtttta cggtttggga gagtttttatc gtcgcggtcg ttggacgtgt       60
gtggatgttt atgagcgaga tttggagttt tatagtttcg gcggattttt ggagggaa        118

<210> SEQ ID NO 343
<211> LENGTH: 22
<212> TYPE: DNA
<213> ORGANISM: Artificial sequence
<220> FEATURE:
<223> OTHER INFORMATION: Synthetic DNA

<400> SEQUENCE: 343
gtttgggaga gttttatcgt cg                                                 22

<210> SEQ ID NO 344
<211> LENGTH: 18
<212> TYPE: DNA
<213> ORGANISM: Artificial sequence
<220> FEATURE:
<223> OTHER INFORMATION: Synthetic DNA

<400> SEQUENCE: 344
cctccaaaaa tccgccga                                                      18

<210> SEQ ID NO 345
<211> LENGTH: 20
<212> TYPE: DNA
<213> ORGANISM: Artificial sequence
<220> FEATURE:
<223> OTHER INFORMATION: Synthetic DNA

<400> SEQUENCE: 345
cgccgagggc ggtcgttgga                                                    20

-continued

```
<210> SEQ ID NO 346
<211> LENGTH: 70
<212> TYPE: DNA
<213> ORGANISM: Homo sapiens

<400> SEQUENCE: 346 ggggcgggggg ccgacagccc acgctggcgc ggcaggcgcg tgcgcccgcc gttttcgtga      60
gcccgagcag                                                               70

<210> SEQ ID NO 347
<211> LENGTH: 70
<212> TYPE: DNA
<213> ORGANISM: Artificial sequence
<220> FEATURE:
<223> OTHER INFORMATION: Synthetic DNA

<400> SEQUENCE: 347
ggggtcgggg tcgatagttt acgttggcgc ggtaggcgcg tgcgttcgtc gttttcgtga      60
gttcgagtag                                                               70

<210> SEQ ID NO 348
<211> LENGTH: 20
<212> TYPE: DNA
<213> ORGANISM: Artificial sequence
<220> FEATURE:
<223> OTHER INFORMATION: Synthetic DNA

<400> SEQUENCE: 348
gtcggggtcg atagtttacg                                                    20

<210> SEQ ID NO 349
<211> LENGTH: 19
<212> TYPE: DNA
<213> ORGANISM: Artificial sequence
<220> FEATURE:
<223> OTHER INFORMATION: Synthetic DNA

<400> SEQUENCE: 349
actcgaactc acgaaaacg                                                     19

<210> SEQ ID NO 350
<211> LENGTH: 20
<212> TYPE: DNA
<213> ORGANISM: Artificial sequence
<220> FEATURE:
<223> OTHER INFORMATION: Synthetic DNA

<400> SEQUENCE: 350
cgccgaggga cgaacgcacg                                                    20

<210> SEQ ID NO 351
<211> LENGTH: 96
<212> TYPE: DNA
<213> ORGANISM: Homo sapiens

<400> SEQUENCE: 351
ggagccccca gccccacgcg ggcacacgca gggtgggtgg tcacgcccgc agggtccgcg      60
agcgcggcgc agagcgcggg ccgtgggaag tttctc                                  96

<210> SEQ ID NO 352
<211> LENGTH: 96
<212> TYPE: DNA
<213> ORGANISM: Artificial sequence
<220> FEATURE:
```

-continued

<223> OTHER INFORMATION: Synthetic DNA

<400> SEQUENCE: 352
ggagttttta gttttacgcg ggtatacgta gggtgggtgg ttacgttcgt agggttcgcg      60
agcgcggcgt agagcgcggg tcgtgggaag tttttt      96

<210> SEQ ID NO 353
<211> LENGTH: 18
<212> TYPE: DNA
<213> ORGANISM: Artificial sequence
<220> FEATURE:
<223> OTHER INFORMATION: Synthetic DNA

<400> SEQUENCE: 353
gtagggtggg tggttacg      18

<210> SEQ ID NO 354
<211> LENGTH: 17
<212> TYPE: DNA
<213> ORGANISM: Artificial sequence
<220> FEATURE:
<223> OTHER INFORMATION: Synthetic DNA

<400> SEQUENCE: 354
aacttcccac gacccgc      17

<210> SEQ ID NO 355
<211> LENGTH: 20
<212> TYPE: DNA
<213> ORGANISM: Artificial sequence
<220> FEATURE:
<223> OTHER INFORMATION: Synthetic DNA

<400> SEQUENCE: 355
cgccgagggt tcgtagggtt      20

<210> SEQ ID NO 356
<211> LENGTH: 127
<212> TYPE: DNA
<213> ORGANISM: Homo sapiens

<400> SEQUENCE: 356
ggcgccgcca ttgcggtcct cattttgctg ctggtgggtt gggctacagc aggcctctgg      60
agccacacca gggcacggga gtgggtgcag ggaccgtcac cgcgccttca cacgcaccat     120
agtgccc     127

<210> SEQ ID NO 357
<211> LENGTH: 127
<212> TYPE: DNA
<213> ORGANISM: Artificial sequence
<220> FEATURE:
<223> OTHER INFORMATION: Synthetic DNA

<400> SEQUENCE: 357
ggcgtcgtta ttgcggtttt tattttgttg ttggtgggtt gggttatagt aggttttttgg     60 agttatatta gggtacggga gtgggtgtag ggatcgttat cgcgttttta tacgtattat     120
agtgttt     127

<210> SEQ ID NO 358
<211> LENGTH: 23
<212> TYPE: DNA
<213> ORGANISM: Artificial sequence -continued

```
<220> FEATURE:
<223> OTHER INFORMATION: Synthetic DNA

<400> SEQUENCE: 358
tggagttata ttagggtacg gga                                        23

<210> SEQ ID NO 359
<211> LENGTH: 28
<212> TYPE: DNA
<213> ORGANISM: Artificial sequence
<220> FEATURE:
<223> OTHER INFORMATION: Synthetic DNA

<400> SEQUENCE: 359
acactataat acgtataaaa acgcgata                                   28

<210> SEQ ID NO 360
<211> LENGTH: 21
<212> TYPE: DNA
<213> ORGANISM: Artificial sequence
<220> FEATURE:
<223> OTHER INFORMATION: Synthetic DNA

<400> SEQUENCE: 360
ccacggacga acgatcccta c                                          21

<210> SEQ ID NO 361
<211> LENGTH: 140
<212> TYPE: DNA
<213> ORGANISM: Homo sapiens

<400> SEQUENCE: 361
ggcggcgagg ggcgcgtccg cgggtgggtt tcacctgggt ggtgggcatg tcgggcccgc   60
tagggcgagg gtctggccag gggcgtagtt ctcctggtgg gtggggacgc tccgtggcga  120
ttggggtcac tcctctgagg                                            140

<210> SEQ ID NO 362
<211> LENGTH: 140
<212> TYPE: DNA
<213> ORGANISM: Artificial sequence
<220> FEATURE:
<223> OTHER INFORMATION: Synthetic DNA

<400> SEQUENCE: 362
ggcggcgagg ggcgcgttcg cgggtgggtt ttatttgggt ggtgggtatg tcgggttcgt   60
tagggcgagg gtttggttag gggcgtagtt tttttggtgg gtggggacgt ttcgtggcga  120
ttggggttat ttttttgagg                                            140

<210> SEQ ID NO 363
<211> LENGTH: 17
<212> TYPE: DNA
<213> ORGANISM: Artificial sequence
<220> FEATURE:
<223> OTHER INFORMATION: Synthetic DNA

<400> SEQUENCE: 363
ggtggtgggt atgtcgg                                               17

<210> SEQ ID NO 364
<211> LENGTH: 17
<212> TYPE: DNA
<213> ORGANISM: Artificial sequence
<220> FEATURE:
```

-continued

```
<223> OTHER INFORMATION: Synthetic DNA

<400> SEQUENCE: 364
ccaatcgcca cgaaacg                                                        17

<210> SEQ ID NO 365
<211> LENGTH: 21
<212> TYPE: DNA
<213> ORGANISM: Artificial sequence
<220> FEATURE:
<223> OTHER INFORMATION: Synthetic DNA

<400> SEQUENCE: 365
ccacggacgg gttcgttagg g                                                   21

<210> SEQ ID NO 366
<211> LENGTH: 117
<212> TYPE: DNA
<213> ORGANISM: Homo sapiens

<400> SEQUENCE: 366
ccgtgggcgc ggacagctgc cgggagcggc aggcgtctcg atcggggacg caggcacttc        60
cgtccctgca gagcatcaga cgcgtctcgg gacactgggg acaacatctc ctccgcg          117

<210> SEQ ID NO 367
<211> LENGTH: 117
<212> TYPE: DNA
<213> ORGANISM: Artificial sequence
<220> FEATURE:
<223> OTHER INFORMATION: Synthetic DNA

<400> SEQUENCE: 367
tcgtgggcgc ggatagttgt cgggagcggt aggcgtttcg atcggggacg taggtatttt        60
cgtttttgta gagtattaga cgcgtttcgg gatattgggg ataatatttt tttcgcg         117

<210> SEQ ID NO 368
<211> LENGTH: 18
<212> TYPE: DNA
<213> ORGANISM: Artificial sequence
<220> FEATURE:
<223> OTHER INFORMATION: Synthetic DNA

<400> SEQUENCE: 368
gttgtcggga gcggtagg                                                      18

<210> SEQ ID NO 369
<211> LENGTH: 21
<212> TYPE: DNA
<213> ORGANISM: Artificial sequence
<220> FEATURE:
<223> OTHER INFORMATION: Synthetic DNA

<400> SEQUENCE: 369
ccaatatccc gaaacgcgtc t                                                  21

<210> SEQ ID NO 370
<211> LENGTH: 21
<212> TYPE: DNA
<213> ORGANISM: Artificial sequence
<220> FEATURE:
<223> OTHER INFORMATION: Synthetic DNA

<400> SEQUENCE: 370
ccacggacgg cgtttcgatc g                                                  21
```

-continued

```
<210> SEQ ID NO 371
<211> LENGTH: 120
<212> TYPE: DNA
<213> ORGANISM: Homo sapiens

<400> SEQUENCE: 371
aagctgcgcc cggagacgtg ggagcgttct cttgttttcc gagtgcgcgg actcatcggg      60
tcacagttta tgcttttatg acgcggtgag tccagccact gattcctaac ggtttagagt     120

<210> SEQ ID NO 372
<211> LENGTH: 120
<212> TYPE: DNA
<213> ORGANISM: Artificial sequence
<220> FEATURE:
<223> OTHER INFORMATION: Synthetic DNA

<400> SEQUENCE: 372
aagttgcgtt cggagacgtg ggagcgtttt tttgtttttc gagtgcgcgg atttatcggg      60
ttatagttta tgtttttatg acgcggtgag tttagttatt gatttttaac ggtttagagt     120

<210> SEQ ID NO 373
<211> LENGTH: 23
<212> TYPE: DNA
<213> ORGANISM: Artificial sequence
<220> FEATURE:
<223> OTHER INFORMATION: Synthetic DNA

<400> SEQUENCE: 373
cgtttttttg tttttcgagt gcg                                              23

<210> SEQ ID NO 374
<211> LENGTH: 23
<212> TYPE: DNA
<213> ORGANISM: Artificial sequence
<220> FEATURE:
<223> OTHER INFORMATION: Synthetic DNA

<400> SEQUENCE: 374
tcaataacta aactcaccgc gtc                                              23

<210> SEQ ID NO 375
<211> LENGTH: 21
<212> TYPE: DNA
<213> ORGANISM: Artificial sequence
<220> FEATURE:
<223> OTHER INFORMATION: Synthetic DNA

<400> SEQUENCE: 375
ccacggacgg cggatttatc g                                                21

<210> SEQ ID NO 376
<211> LENGTH: 224
<212> TYPE: DNA
<213> ORGANISM: Homo sapiens

<400> SEQUENCE: 376
ctctgacctg agtctccttt ggaactctgc aggttctatt tgcttttttcc cagatgagct      60 cttttttctgg tgtttgtctc tctgactagg tgtctaagac agtgttgtgg gtgtaggtac     120
taacactggc tcgtgtgaca aggccatgag gctggtgtaa agcggccttg gagtgtgtat     180
taagtaggtg cacagtaggt ctgaacagac tccccatccc aaga                       224
```

<210> SEQ ID NO 377
<211> LENGTH: 224
<212> TYPE: DNA
<213> ORGANISM: Artificial sequence
<220> FEATURE:
<223> OTHER INFORMATION: Synthetic DNA

<400> SEQUENCE: 377
ttttgatttg agtttttttt ggaattttgt aggttttatt tgtttttttt tagatgagtt      60 tttttttgg tgtttgtttt tttgattagg tgtttaagat agtgttgtgg gtgtaggtat      120
taatattggt ttgtgtgata aggttatgag gttggtgtaa agtggttttg gagtgtgtat      180
taagtaggtg tatagtaggt ttgaatagat tttttatttt aaga                      224

<210> SEQ ID NO 378
<211> LENGTH: 19
<212> TYPE: DNA
<213> ORGANISM: Artificial sequence
<220> FEATURE:
<223> OTHER INFORMATION: Synthetic DNA

<400> SEQUENCE: 378
ccatgaggct ggtgtaaag                                                    19

<210> SEQ ID NO 379
<211> LENGTH: 24
<212> TYPE: DNA
<213> ORGANISM: Artificial sequence
<220> FEATURE:
<223> OTHER INFORMATION: Synthetic DNA

<400> SEQUENCE: 379
ctactgtgca cctacttaat acac                                             24

<210> SEQ ID NO 380
<211> LENGTH: 20
<212> TYPE: DNA
<213> ORGANISM: Artificial sequence
<220> FEATURE:
<223> OTHER INFORMATION: Synthetic DNA

<400> SEQUENCE: 380
cgccgagggc ggccttggag                                                  20

<210> SEQ ID NO 381
<211> LENGTH: 30
<212> TYPE: DNA
<213> ORGANISM: Artificial sequence
<220> FEATURE:
<223> OTHER INFORMATION: Synthetic DNA

<400> SEQUENCE: 381
gtgtttgttt ttttgattag gtgtttaaga                                       30

<210> SEQ ID NO 382
<211> LENGTH: 26
<212> TYPE: DNA
<213> ORGANISM: Artificial sequence
<220> FEATURE:
<223> OTHER INFORMATION: Synthetic DNA

<400> SEQUENCE: 382
ctttacacca acctcataac cttatc                                           26

```
<210> SEQ ID NO 383
<211> LENGTH: 21
<212> TYPE: DNA
<213> ORGANISM: Artificial sequence
<220> FEATURE:
<223> OTHER INFORMATION: Synthetic DNA

<400> SEQUENCE: 383
gacgcggaga tagtgttgtg g                                                      21

<210> SEQ ID NO 384
<211> LENGTH: 139
<212> TYPE: DNA
<213> ORGANISM: Homo sapiens

<400> SEQUENCE: 384
ggccacacag gcccactctg gccctctgag cccccggcgg acccagggca ttcaaggagc     60
ggctctgggc tgccagcgca ggcctccgcg caaacacagc aggctggaag tggcgctcat    120
caccggcacg tcttcccag                                                        139

<210> SEQ ID NO 385
<211> LENGTH: 139
<212> TYPE: DNA
<213> ORGANISM: Artificial sequence
<220> FEATURE:
<223> OTHER INFORMATION: Synthetic DNA

<400> SEQUENCE: 385
ggttatatag gtttattttg gttttttgag ttttcggcgg atttagggta tttaaggagc     60
ggttttgggt tgttagcgta ggttttcgcg taaatatagt aggttggaag tggcgtttat    120
tatcggtacg ttttttttag                                                       139

<210> SEQ ID NO 386
<211> LENGTH: 28
<212> TYPE: DNA
<213> ORGANISM: Artificial sequence
<220> FEATURE:
<223> OTHER INFORMATION: Synthetic DNA

<400> SEQUENCE: 386
ggtttatttt ggtttttttga gttttcgg                                             28

<210> SEQ ID NO 387
<211> LENGTH: 24
<212> TYPE: DNA
<213> ORGANISM: Artificial sequence
<220> FEATURE:
<223> OTHER INFORMATION: Synthetic DNA

<400> SEQUENCE: 387
tccaacctac tatatttacg cgaa                                                  24

<210> SEQ ID NO 388
<211> LENGTH: 21
<212> TYPE: DNA
<213> ORGANISM: Artificial sequence
<220> FEATURE:
<223> OTHER INFORMATION: Synthetic DNA

<400> SEQUENCE: 388
ccacggacgg cggatttagg g                                                     21

<210> SEQ ID NO 389
```

-continued

```
<211> LENGTH: 171
<212> TYPE: DNA
<213> ORGANISM: Artificial sequence
<220> FEATURE:
<223> OTHER INFORMATION: Synthetic DNA

<400> SEQUENCE: 389
tccacgtggt gcccactctg dacaggtgga gcagagggaa ggtggtggca tggtggggag      60
ggtggcctgg aggacccgat tggctgagtg taaaccagga gaggacatga ctttcagccc     120
tgcagccaga cacagctgag ctggtgtgac ctgtgtggag agttcatctg g             171

<210> SEQ ID NO 390
<211> LENGTH: 180
<212> TYPE: DNA
<213> ORGANISM: Artificial sequence
<220> FEATURE:
<223> OTHER INFORMATION: Synthetic DNA

<400> SEQUENCE: 390
tttatcgtgg tgtttatttt ggataggtgg agtagaggga aggtggtgcg tatggtgggc      60
gagcgcgtgc gtttggagga tttcgattgg ttgacgtgta aattaggacg aggatatgat     120
ttttagtttt gtagttagat atagttgagt tggtgtgatt tgtgtggaga gtttatttgg     180

<210> SEQ ID NO 391
<211> LENGTH: 15
<212> TYPE: DNA
<213> ORGANISM: Artificial sequence
<220> FEATURE:
<223> OTHER INFORMATION: Synthetic DNA

<400> SEQUENCE: 391
cgcatggtgg gcgag                                                        15

<210> SEQ ID NO 392
<211> LENGTH: 18
<212> TYPE: DNA
<213> ORGANISM: Artificial sequence
<220> FEATURE:
<223> OTHER INFORMATION: Synthetic DNA

<400> SEQUENCE: 392
acacgtcagc caatcggg                                                     18

<210> SEQ ID NO 393
<211> LENGTH: 20
<212> TYPE: DNA
<213> ORGANISM: Artificial sequence
<220> FEATURE:
<223> OTHER INFORMATION: Synthetic DNA

<400> SEQUENCE: 393
gacgcggagg cgcgtgcgcc                                                   20

<210> SEQ ID NO 394
<211> LENGTH: 17
<212> TYPE: DNA
<213> ORGANISM: Artificial sequence
<220> FEATURE:
<223> OTHER INFORMATION: Synthetic DNA

<400> SEQUENCE: 394
tgcgtatggt gggcgag                                                      17
```

-continued

```
<210> SEQ ID NO 395
<211> LENGTH: 26
<212> TYPE: DNA
<213> ORGANISM: Artificial sequence
<220> FEATURE:
<223> OTHER INFORMATION: Synthetic DNA

<400> SEQUENCE: 395
cctaatttac acgtcaacca atcgaa                                        26

<210> SEQ ID NO 396
<211> LENGTH: 21
<212> TYPE: DNA
<213> ORGANISM: Artificial sequence
<220> FEATURE:
<223> OTHER INFORMATION: Synthetic DNA

<400> SEQUENCE: 396
gacgcggagg cgcgtgcgtt t                                             21

<210> SEQ ID NO 397
<211> LENGTH: 21
<212> TYPE: DNA
<213> ORGANISM: Artificial sequence
<220> FEATURE:
<223> OTHER INFORMATION: Synthetic DNA

<400> SEQUENCE: 397
ccacggacgg cgcgtgcgtt t                                             21

<210> SEQ ID NO 398
<211> LENGTH: 28
<212> TYPE: DNA
<213> ORGANISM: Artificial sequence
<220> FEATURE:
<223> OTHER INFORMATION: Synthetic DNA

<400> SEQUENCE: 398
agccggtttt ccggctgaga cctcggcg                                      28

<210> SEQ ID NO 399
<211> LENGTH: 28
<212> TYPE: DNA
<213> ORGANISM: Artificial sequence
<220> FEATURE:
<223> OTHER INFORMATION: Synthetic DNA

<400> SEQUENCE: 399
agccggtttt ccggctgaga cctcggcg                                      28

<210> SEQ ID NO 400
<211> LENGTH: 29
<212> TYPE: DNA
<213> ORGANISM: Artificial sequence
<220> FEATURE:
<223> OTHER INFORMATION: Synthetic DNA

<400> SEQUENCE: 400
agccggtttt ccggctgaga ctccgcgtc                                     29

<210> SEQ ID NO 401
<211> LENGTH: 29
<212> TYPE: DNA
<213> ORGANISM: Artificial sequence
<220> FEATURE:
<223> OTHER INFORMATION: Synthetic DNA
```

-continued

```
<400> SEQUENCE: 401
agccggtttt ccggctgaga cgtccgtgg                                                    29

<210> SEQ ID NO 402
<211> LENGTH: 28
<212> TYPE: DNA
<213> ORGANISM: Artificial sequence
<220> FEATURE:
<223> OTHER INFORMATION: Synthetic DNA

<400> SEQUENCE: 402
agccggtttt ccggctgaga ggacgcgc                                                     28

<210> SEQ ID NO 403
<211> LENGTH: 108
<212> TYPE: DNA
<213> ORGANISM: Homo sapiens

<400> SEQUENCE: 403
ggaaggaaat tgcgggttcc cgtctgcctt gtctccagct tctctgctga agcccggtag        60
cagtgaatgc gcgctgactt tcagcgacga ctcctggaag caacgcca                    108

<210> SEQ ID NO 404
<211> LENGTH: 108
<212> TYPE: DNA
<213> ORGANISM: Artificial sequence
<220> FEATURE:
<223> OTHER INFORMATION: Synthetic DNA

<400> SEQUENCE: 404
ggaaggaaat tgcgggtttt cgtttgtttt gtttttagtt tttttgttga agttcggtag        60
tagtgaatgc gcgttgattt ttagcgacga tttttggaag taacgtta                    108
```

DETECTION AND ANALYSIS OF METHYLATED DNA

The present application is a divisional of U.S. patent application Ser. No. 16/460,647, filed Jul. 2, 2019, now allowed, which is a continuation of U.S. patent application Ser. No. 15/471,337, filed Mar. 28, 2017, now U.S. Pat. No. 10,385,406, which claims priority to U.S. Provisional Application Ser. No. 62/332,295, filed May 5, 2016 and 62/462, 677, filed Feb. 23, 2017, each of which is incorporated herein by reference.

SEQUENCE LISTING

The text of the computer readable sequence listing filed herewith, titled "34810-404_Sequence_Listing_ST25", created May 6, 2021, having a file size of 88,630 bytes, is hereby incorporated by reference in its entirety.

FIELD OF THE INVENTION

Provided herein is technology relating to detecting neoplasia and particularly, but not exclusively, to methods, compositions, and related uses for detecting neoplasms such as lung cancer.

BACKGROUND OF THE INVENTION

Lung cancer remains the number one cancer killer in the US, and effective screening approaches are desperately needed. Lung cancer alone accounts for 221,000 deaths annually. DNA methylation profiling has shown unique patterns in DNA promoter regions with cancer and has potential application for detection of lung malignancies. However, optimally discriminant markers and marker panels are needed.

SUMMARY OF THE INVENTION

Provided herein is a collection of methylated methylation markers assayed on tissue that achieves extremely high discrimination for all types of lung cancer while remaining negative in normal lung tissue and benign nodules. Markers selected from the collection can be used alone or in a panel, for example, to characterize blood or bodily fluid, with applications in lung cancer screening and discrimination of malignant from benign nodules. In some embodiments, markers from the panel are used to distinguish one form of lung cancer from another, e.g., for distinguishing the presence of a lung adenocarcinoma or large cell carcinoma from the presence of a lung small cell carcinoma, or for detecting mixed pathology carcinomas. Provided herein is technology for screening markers that provide a high signal-to-noise ratio and a low background level when detected from samples taken from a subject.

Methylation markers and/or panels of markers (e.g., chromosomal region(s)) having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329 were identified in studies by comparing the methylation state of methylation markers from lung cancer samples to the corresponding markers in normal (non-cancerous) samples.

As described herein, the technology provides a number of methylation markers and subsets thereof (e.g., sets of 2, 3, 4, 5, 6, 7, 8, 9, 10, 11, 12 or more markers) with high discrimination for lung cancer and, in some embodiments, with discrimination between lung cancer types. Experiments applied a selection filter to candidate markers to identify markers that provide a high signal to noise ratio and a low background level to provide high specificity and selectivity for purposes of characterizing biological samples, e.g., for cancer screening or diagnosis. For example, as described herein below, analysis of methylation of combination of 8 markers, SLC12A8, KLHDC7B, PARP15, OPLAH, BCL2L11, MAX.chr12.526, HOXB2, and EMX1, resulted in 98.5% sensitivity (134/136 cancers) for all of the cancer tissues tested, with 100% specificity. In another embodiment, a panel of 6 markers (SHOX2, SOBP, ZNF781, CYP26C1, SUCLG2, and SKI) resulted in a sensitivity of 92.2% at 93% specificity, and a panel of 4 markers (ZNF781, BARX1, EMX1, and HOXA9) resulted in an overall sensitivity of 96% and specificity of 94%.

Accordingly, provided herein is technology related to a method of processing a sample obtained from a subject, the method comprising assaying a methylation state of one or more marker genes in the sample. In preferred embodiments, the methylation state of the methylation marker is determined by measuring the amounts of a methylated marker and of a reference marker in the sample, and comparing the amount of the methylated marker to the amount of reference marker in the sample to determine a methylation state for the methylation marker in the sample. While not limiting the invention to any particular application or applications, the method finds use, e.g., in characterizing samples from a subject having or suspected of having lung cancer, when the methylation state of the methylation marker is different than a methylation state of that marker assayed in a subject that does not have a neoplasm. In preferred embodiments, the methylation marker comprises a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329.

In some embodiments, the technology comprises assaying a plurality of markers, e.g., comprising assaying the methylation states of 2 to 21 markers, preferably 2 to 8 markers, preferably 4 to 6 markers. For example, in some embodiments, the method comprises analysis of the methylation status of two or more markers selected from SLC12A8, KLHDC7B, PARP15, OPLAH, BCL2L11, MAX.chr12.526, HOXB2, EMX1, CYP26C1, SOBP, SUCLG2, SHOX2, ZDHHC1, NFIX, FLJ45983, HOXA9, B3GALT6, ZNF781, SP9, BARX1, and SKI. In some pre-
ferred embodiments, the method comprises analysis of the
methylation status of a set of markers comprising SLC12A8,
KLHDC7B, PARP15, OPLAH, BCL2L11,
MAX.chr12.526, HOXB2, and EMX1. In some embodi-
ments, the method comprises analysis of the methylation
status of a set of markers selected from: the group consisting
of ZNF781, BARX1, and EMX1; the group consisting of
SHOX2, SOBP, ZNF781, CYP26C1, SUCLG2, and SKI;
the group consisting of SLC12A8, KLHDC7B, PARP15,
OPLAH, BCL2L11, MAX.chr12.526, HOXB2, and EMX1;
the group consisting of SHOX2, SOBP, ZNF781, BTACT,
CYP26C1, and DLX4; and the group consisting of SHOX2,
SOBP, ZNF781, CYP26C1, SUCLG2, and SKI. In certain
embodiments, the at least one methylation marker comprises
the group selected from ZNF781, BARX1, and EMX1, and
further comprises SOBP and/or HOXA9.

The technology is not limited in the methylation state
assessed. In some embodiments assessing the methylation
state of the methylation marker in the sample comprises
determining the methylation state of one base. In some
embodiments, assaying the methylation state of the marker
in the sample comprises determining the extent of methyl-
ation at a plurality of bases. Moreover, in some embodi-
ments the methylation state of the marker comprises an
increased methylation of the marker relative to a normal
methylation state of the marker. In some embodiments, the
methylation state of the marker comprises a decreased
methylation of the marker relative to a normal methylation
state of the marker. In some embodiments the methylation
state of the marker comprises a different pattern of methyl-
ation of the marker relative to a normal methylation state of
the marker.

In some embodiments, the technology provides a method
of generating a record reporting a lung neoplasm in a
subject, the method comprising the steps of:

a) assaying a sample from a subject for an amount of at
least one methylated methylation marker gene selected
from the group consisting of BARX1, LOC100129726,
SPOCK2, TSC22D4, MAX.chr8.124, RASSF1,
ZNF671, ST8SIA1, NKX2-6, FAM59B, DIDO1,
MAX_Chr1.110, AGRN, SOBP, MAX_chr10.226,
ZMIZ1, MAX_chr8.145, MAX_chr10.225, PRDM14,
ANGPT1, MAX.chr16.50, PTGDR_9, ANKRD13B,
DOCK2, MAX_chr19.163, ZNF132, MAX chr19.372,
HOXA9, TRH, SP9, DMRTA2, ARHGEF4,
CYP26C1, ZNF781, PTGDR, GRIN2D, MATK,
BCAT1, PRKCB_28, ST8SIA_22, FLJ45983, DLX4,
SHOX2, EMX1, HOXB2, MAX.chr12.526, BCL2L11,
OPLAH, PARP15, KLHDC7B, SLC12A8, BHLHE23,
CAPN2, FGF14, FLJ34208, B3GALT6, BIN2_Z,
DNMT3A, FERMT3, NFIX, SIPR4, SKI, SUCLG2,
TBX15, ZDHHC1, and ZNF329 in a sample obtained
from a subject;

b) assaying said sample for an amount of reference
marker in said sample;

c) comparing the amount of said at least one methylated
methylation marker to the amount of reference marker
in said sample to determine a methylation state for said
at least one methylation marker in said sample; and d) generating a record reporting the methylation state for
said at least one marker gene in said sample, wherein
the methylation state of said methylation marker is
indicative of the presence or absence of a lung neo-
plasm in said subject.

In some embodiments, the sample is assayed for at least
two of the markers, and preferably the at least two methylated marker genes are selected from the group consisting of
SLC12A8, KLHDC7B, PARP15, OPLAH, BCL2L11,
MAX.chr12.526, HOXB2, EMX1 CYP26C1, SOBP,
SUCLG2, SHOX2, ZDHHC1, NFIX, FLJ45983, HOXA9,
B3GALT6, ZNF781, SP9, BARX1, and SKI. In certain
preferred embodiments, the method comprises analysis of
the methylation status of a set of markers selected from: the
group consisting of ZNF781, BARX1, and EMX1; the group
consisting of SHOX2, SOBP, ZNF781, CYP26C1,
SUCLG2, and SKI; the group consisting of SLC12A8,
KLHDC7B, PARP15, OPLAH, BCL2L11,
MAX.chr12.526, HOXB2, and EMX1; the group consisting
of SHOX2, SOBP, ZNF781, BTACT, CYP26C1, and DLX4;
and the group consisting of SHOX2, SOBP, ZNF781,
CYP26C1, SUCLG2, and SKI. In certain embodiments, the
at least one methylation marker comprises the group
selected from ZNF781, BARX1, and EMX1, and further
comprises SOBP and/or HOXA9. In some embodiments,
methylation markers are selected such that the methylation
status of said one or more markers is indicative of only one
of lung adenocarcinoma, large cell carcinoma, squamous
cell carcinoma, or small cell carcinoma. In other embodi-
ments, methylation markers are selected such that the meth-
ylation status of said one or more markers is indicative of
more than one of lung adenocarcinoma, large cell carci-
noma, squamous cell carcinoma, and small cell carcinoma.
In yet other embodiments, methylation markers are selected
such that the methylation status of said one or more markers
is indicative of any one of or combination of lung adeno-
carcinoma, large cell carcinoma, squamous cell carcinoma,
small cell carcinoma, generic non-small cell lung cancer,
and/or undefined lung carcinoma.

In some embodiments the method used for assaying
comprises obtaining a sample comprising DNA from a
subject, and treating DNA obtained from the sample with a
reagent that selectively modifies unmethylated cytosine resi-
dues in the obtained DNA to produce modified residues. In
preferred embodiments the reagent comprises a bisulfite
reagent.

In some embodiments assaying the methylation state of
the methylation marker in the sample comprises determining
the methylation state of one base, while in other embodi-
ments the assay comprises determining the extent of meth-
ylation at a plurality of bases. In some embodiments the
methylation state of the marker comprises an increased or
decreased methylation of the marker relative to a normal
methylation state of the marker, e.g., as the marker would
appear in a non-cancerous sample, while in some embodi-
ments the methylation state of the marker comprises a
different pattern of methylation of the marker relative to a
normal methylation state of the marker. In preferred embodi-
ments the reference marker is a methylated reference
marker.

The technology is not limited to particular sample types.
For example, in some embodiments the sample is a tissue
sample, a blood sample, a plasma sample, a serum sample,
or a sputum sample. In certain preferred embodiments a
tissue sample comprises lung tissue. In certain preferred
embodiments, the sample comprises DNA isolated from
plasma.

The technology is not limited to any particular method of
assaying DNA from samples. For example, in some embodi-
ments the assaying comprises using polymerase chain reac-
tion, nucleic acid sequencing, mass spectrometry, methyl-
ation specific nuclease, mass-based separation, and/or target
capture. In certain preferred embodiments the assaying
comprises using a flap endonuclease assay. In particularly preferred embodiments the sample DNA and/or reference marker DNA are bisulfite-converted and the assay for determining the methylation level of the DNA is achieved by a technique comprising the use of methylation-specific PCR, quantitative methylation-specific PCR, methylation-sensitive DNA restriction enzyme analysis, quantitative bisulfite pyrosequencing, flap endonuclease assay (e.g., a QUARTS flap endonuclease assay), and/or bisulfite genomic sequencing PCR.

The technology also provides kits. For example, in some embodiments the technology provides a kit, comprising a) at least one oligonucleotide, wherein at least a portion of the oligonucleotide specifically hybridizes to a marker selected from the group consisting of BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329. In preferred embodiments, the portion of the oligonucleotide that hybridizes to the marker specifically hybridizes to bisulfite-treated DNA comprising the methylation marker. In some embodiments, the kit comprises at least one additional oligonucleotide, wherein at least a portion of the additional oligonucleotide specifically hybridizes to a reference nucleic acid. In some embodiments the kit comprises at least two additional oligonucleotides and, in some embodiments, the kit further comprises a bisulfite reagent.

In certain embodiments at least a portion of the oligonucleotide specifically hybridizes to a least one the marker selected from the group consisting of SLC12A8, KLHDC7B, PARP15, OPLAH, BCL2L11, MAX.chr12.526, HOXB2, EMX1, CYP26C1, SOBP, SUCLG2, SHOX2, ZDHHC1, NFIX, FLJ45983, HOXA9, B3GALT6, ZNF781, SP9, BARX1, and SKI. In preferred embodiments, the kit comprises a set of oligonucleotides, each of which hybridizes to one marker in a set of markers, the set of markers selected from: the group consisting of ZNF781, BARX1, and EMX1; the group consisting of SHOX2, SOBP, ZNF781, CYP26C1, SUCLG2, and SKI; the group consisting of SLC12A8, KLHDC7B, PARP15, OPLAH, BCL2L11, MAX.chr12.526, HOXB2, and EMX1; the group consisting of SHOX2, SOBP, ZNF781, BTACT, CYP26C1, and DLX4; and the group consisting of SHOX2, SOBP, ZNF781, CYP26C1, SUCLG2, and SKI. In certain embodiments, the set of methylation markers comprises the group selected from ZNF781, BARX1, and EMX1, and further comprises SOBP and/or HOXA9.

In some embodiments, the at least one oligonucleotide in the kit is selected to hybridize to methylation marker(s) that are indicative of only one of type of lung carcinoma, e.g., lung adenocarcinoma, large cell carcinoma, squamous cell carcinoma, or small cell carcinoma. In other embodiments, the at least one oligonucleotide is selected to hybridize to methylation marker(s) that are indicative of more than one of lung adenocarcinoma, large cell carcinoma, squamous cell carcinoma, and small cell carcinoma. In yet other embodiments, the at least one oligonucleotide is selected to hybridize to methylation marker(s) that are indicative of any one of, or any combination of lung adenocarcinoma, large cell carcinoma, squamous cell carcinoma, small cell carcinoma, and/or undefined lung carcinoma.

In preferred embodiments, oligonucleotide(s) provided in the kit are selected from one or more of a capture oligonucleotide, a pair of nucleic acid primers, a nucleic acid probe, and an invasive oligonucleotide. In preferred embodiments, oligonucleotide(s) specifically hybridize to bisulfite-treated DNA comprising said methylation marker(s).

In some embodiments the kit further comprises a solid support, such a magnetic bead or particle. In preferred embodiments, a solid support comprises one or more capture reagents, e.g., oligonucleotides complementary said one or more markers genes.

The technology also provides compositions. For example, in some embodiments the technology provides a composition comprising a mixture, e.g., a reaction mixture, that comprises a complex of a target nucleic acid selected from the group consisting of BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12a, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329 and an oligonucleotide that specifically hybridizes to the target nucleic acid. In some embodiments, the target nucleic acid is bisulfite-converted target nucleic acid. In preferred embodiments, the mixture comprises a complex of a target nucleic acid selected from the group consisting of SLC12A8, KLHDC7B, PARP15, OPLAH, BCL2L11, MAX.chr12.526, HOXB2, EMX1, CYP26C1, SOBP, SUCLG2, SHOX2, ZDHHC1, NFIX, FLJ45983, HOXA9, B3GALT6, ZNF781, SP9, BARX1, and SKI, and an oligonucleotide that specifically hybridizes to the target nucleic acid (whether unconverted or bisulfite-converted). Oligonucleotides in the mixture include but are not limited to one or more of a capture oligonucleotide, a pair of nucleic acid primers, a hybridization probe, a hydrolysis probe, a flap assay probe, and an invasive oligonucleotide.

In some embodiments, the target nucleic acid in the mixture comprises a nucleic acid sequence selected from the group consisting of SEQ ID NOS: 1, 6, 11, 16, 21, 28, 33, 38, 43, 48, 53, 58, 63, 68, 73, 78, 86, 91, 96, 101, 106, 111, 116, 121, 126, 131, 136, 141, 146, 151, 156, 161, 166, 171, 176, 181, 186, 191, 196, 201, 214, 219, 224, 229, 234, 239, 247, 252, 257, 262, 267, 272, 277, 282, 287, 292, 298, 303, 308, 313, 319, 327, 336, 341, 346, 351, 356, 361, 366, 371, 384, and 403.

In some embodiments, the mixture comprises bisulfite-converted target nucleic acid that comprises a nucleic acid sequence selected from the group consisting of SEQ ID NOS: 2, 7, 12, 17, 22, 29, 34, 39, 44, 49, 54, 59, 64, 69, 74, 79, 87, 92, 97, 102, 107, 112, 117, 122, 127, 132, 137, 142, 147, 152, 157, 162, 167, 172, 177, 182, 187, 192, 197, 202, 210, 215, 220, 225, 230, 235, 240, 248, 253, 258, 263, 268, 273, 278, 283, 288, 293, 299, 304, 309, 314, 320, 328, 337, 342, 347, 352, 357, 362, 367, 372, 385, and 404.

In some embodiments, an oligonucleotide in said mixture comprises a reporter molecule, and in preferred embodiments, the reporter molecule comprises a fluorophore. In some embodiments the oligonucleotide comprises a flap sequence. In some embodiments the mixture further comprises one or more of a FRET cassette; a FEN-1 endonuclease and/or a thermostable DNA polymerase, preferably a bacterial DNA polymerase.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated. In some embodiments, a nucleic acid may be characterized as "unmethylated" if it is not methylated at a specific locus (e.g., the locus of a specific single CpG dinucleotide) or specific combination of loci, even if it is methylated at other loci in the same gene or molecule.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs. As used herein, the terms "marker gene" and "marker" are used interchangeably to refer to DNA that is associated with a condition, e.g., cancer, regardless of whether the marker region is in a coding region of DNA. Markers may include, e.g., regulatory regions, flanking regions, intergenic regions, etc.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides is the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g., Antequera, et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) *J Mol. Biol.* 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) *Proc. Natl. Acad. Sci. USA* 97: 5237-5242; Salmon and Kaye (1970) *Biochim. Biophys. Acta.* 204: 340-351; Grafstrom (1985) *Nucleic Acids Res.* 13: 2827-2842; Nyce (1986) *Nucleic Acids Res.* 14: 4353-4367; Woodcock (1987) *Biochem. Biophys. Res. Commun.* 145: 888-894).

As used herein, a "methylation-specific reagent" refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. An exemplary reagent is a bisulfite reagent.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxyben-zone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

A change in the nucleic acid nucleotide sequence by a methylation-specific reagent can also result in a nucleic acid molecule in which each methylated nucleotide is modified to a different nucleotide.

The term "methylation assay" refers to any assay for determining the methylation state of one or more CpG dinucleotide sequences within a sequence of a nucleic acid.

As used herein, the "sensitivity" of a given marker (or set of markers used together) refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a nucleotide that is typically methylated and an unmeth-ylated selected nucleotides refers specifically to a nucleotide that typically occurs in unmethylated form.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemi-methylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be suffi-ciently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are use-ful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and lumines-cent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleav-age assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

The term "marker", as used herein, refers to a substance (e.g., a nucleic acid, or a region of a nucleic acid, or a protein) that may be used to distinguish non-normal cells (e.g., cancer cells) from normal cells (non-cancerous cells), e.g., based on presence, absence, or status (e.g., methylation state) of the marker substance. As used herein "normal" methylation of a marker refers to a degree of methylation typically found in normal cells, e.g., in non-cancerous cells.

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the methylation state of a marker described herein.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985, 557, 5,994,069, 6,001,567, 6,090,543, and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288, 609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification plus invasive cleavage detection configurations, termed the QuARTS method, are described in, e.g., in U.S. Pat. Nos. 8,361,720; 8,715,937; 8,916,344; and 9,212,392, each of which is incorporated herein by reference for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

The term "probe oligonucleotide" or "flap oligonucleotide" when used in reference to flap assay, refers to an oligonucleotide that interacts with a target nucleic acid to form a cleavage structure in the presence of an invasive oligonucleotide.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archival thermophiles organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect.

As used herein, the term "FRET" refers to fluorescence resonance energy transfer, a process in which moieties (e.g., fluorophores) transfer energy e.g., among themselves, or, from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor fluorophore to a non-fluorescing molecule (e.g., a "dark" quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

In an exemplary flap detection assay, an invasive oligonucleotide and flap oligonucleotide are hybridized to a target nucleic acid to produce a first complex having an overlap as described above. An unpaired "flap" is included on the 5' end of the flap oligonucleotide. The first complex is a substrate for a flap endonuclease, e.g., a FEN-1 endonuclease, which cleaves the flap oligonucleotide to release the 5' flap portion. In a secondary reaction, the released 5' flap product serves as an invasive oligonucleotide on a FRET cassette to again create the structure recognized by the flap endonuclease, such that the FRET cassette is cleaved. When the fluorophore and the quencher are separated by cleavage of the FRET cassette, a detectable fluorescent signal above background fluorescence is produced.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QuARTS reactions is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein in reference to data collected during real time PCR and PCR+ INVADER assays refer to the cycle at which signal (e.g., fluorescent signal) crosses a predetermined threshold value indicative of positive signal. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the percentage of variant and/or non-variant constituents in an assay or sample.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides.

The term "system" as used herein refers to a collection of articles for use for a particular purpose. In some embodiments, the articles comprise instructions for use, as information supplied on e.g., an article, on paper, or on recordable media (e.g., DVD, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DESCRIPTION OF THE DRAWINGS

FIG. 1 shows schematic diagrams of marker target regions in unconverted form and bisulfite-converted form. Flap assay primers and probes for detection of bisulfite-converted target DNA are shown.

FIGS. 2-5 provide tables comparing Reduced Representation Bisulfite Sequencing (RRBS) results for selecting markers associated with lung carcinomas as described in Example 2, with each row showing the mean values for the indicated marker region (identified by chromosome and start and stop positions). The ratio of mean methylation for each tissue type (normal (Norm), adenocarcinoma (Ad), large cell carcinoma (LC), small cell carcinoma (SC), squamous cell carcinoma (SQ) and undefined cancer (UND)) is compared to the mean methylation of buffy coat samples from normal subjects (WBC or BC)) is shown for each region, and genes and transcripts identified with each region are indicated.

FIG. 2 provides a table comparing RRBS results for selecting markers associated with lung adenocarcinoma.

FIG. 3 provides a table comparing RRBS results for selecting markers associated with lung large cell carcinoma.

FIG. 4 provides a table comparing RRBS results for selecting markers associated with lung small cell carcinoma.

FIG. 5 provides a table comparing RRBS results for selecting markers associated with lung squamous cell carcinoma.

FIG. 6 provides a table of nucleic acid sequences of assay targets and detection oligonucleotides, with corresponding SEQ ID NOS.

DETAILED DESCRIPTION OF THE INVENTION

Figure 7:
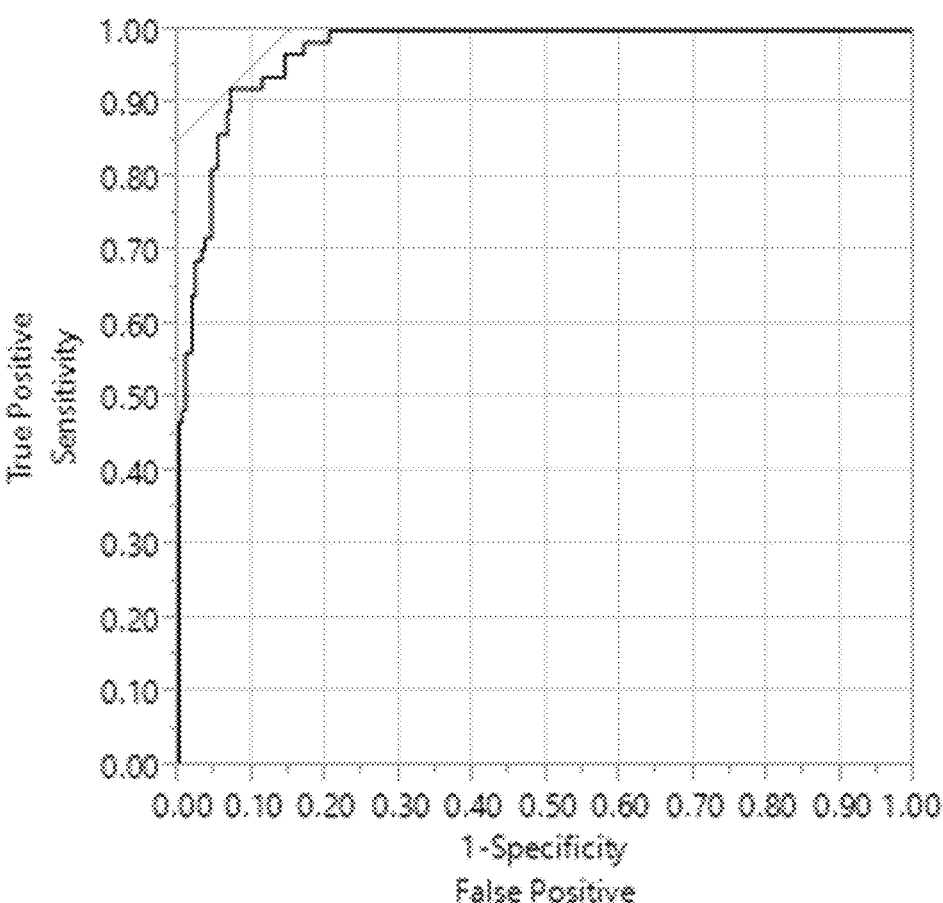
FIG. 7 provides a graph showing a 6-marker logistic fit of data from Example 3, using markers SHOX2, SOBP, ZNF781, BTACT, CYP26C1, and DLX4. The ROC curve analysis shows an area under the curve (AUC) of 0.973.

Provided herein is technology relating to selection of nucleic acid markers for use in assays for detection and quantification of DNA, e.g., methylated DNA, and use of the markers in nucleic acid detection assays. In particular, the technology relates to use of methylation assays to detect lung cancer.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

In some embodiments, a marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample, sputum, a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a differentially methylated region (DMR). In some embodiments, an oligonucleotide is provided, the oligonucleotide comprising a sequence complementary to a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329, preferably to a marker selected from the subset SLC12A8, KLHDC7B, PARP15, OPLAH, BCL2L11, MAX.chr12.526, HOXB2, EMX1, CYP26C1, SOBP, SUCLG2, SHOX2, ZDHHC1, NFIX, FLJ45983, HOXA9, B3GALT6, ZNF781, SP9, BARX1, and SKI; or a marker selected from any of the subsets of markers defining the group consisting of ZNF781, BARX1, and EMX1; the group consisting of SHOX2, SOBP, ZNF781, CYP26C1, SUCLG2, and SKI; the group consisting of SLC12A8, KLHDC7B, PARP15, OPLAH, BCL2L11, MAX.chr12.526, HOXB2, and EMX1; the group consisting of SHOX2, SOBP, ZNF781, BTACT, CYP26C1, and DLX4; or the group consisting of SHOX2, SOBP, ZNF781, CYP26C1, SUCLG2, and SKI.

Kit embodiments are provided, e.g., a kit comprising a bisulfite reagent; and a control nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above, and having a methylation state associated with a subject who does not have a cancer (e.g., lung cancer). In some embodiments, kits comprise a bisulfite reagent and an oligonucleotide as described herein. In some embodiments, kits comprise a bisulfite reagent; and a control nucleic acid comprising a sequence from such a chromosomal region and having a methylation state associated with a subject who has lung cancer.

The technology is related to embodiments of compositions (e.g., reaction mixtures).

In some embodiments are provided a composition comprising a nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above, and a bisulfite reagent. Some embodiments provide a composition comprising a nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329, preferably from any of the subsets of markers as recited above, and an oligonucleotide as described herein. Some embodiments provide a composition comprising a nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above, and a methylation-sensitive restriction enzyme.

Some embodiments provide a composition comprising a nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above, and a polymerase.

Additional related method embodiments are provided for screening for a neoplasm (e.g., lung carcinoma) in a sample obtained from a subject, e.g., a method comprising determining a methylation state of a marker in the sample comprising a base in a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above; comparing the methylation state of the marker from the subject sample to a methylation state of the marker from a normal control sample from a subject who does not have lung cancer; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above, with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the chromosomal region from a subject who does not have lung cancer to identify differences in the two sequences; and identifying the subject as having a neoplasm when a difference is present.

Systems for screening for lung cancer in a sample obtained from a subject are provided by the technology. Exemplary embodiments of systems include, e.g., a system for screening for lung cancer in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a cancer-associated methylation state. An alert is determined in some embodiments by a software component that receives the results from multiple assays (e.g., determining the methylation states of multiple markers, e.g., a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329, preferably from any of the subsets of markers as recited above, and calculating a value or result to report based on the multiple results. Some embodiments provide a database of weighted parameters associated with each a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329, preferably from any of the subsets of markers as recited above, provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a lung cancer risk in a subject.

In some embodiments of systems, a sample comprises a nucleic acid comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above. In some embodiments the system further comprises a component for isolating a nucleic acid, a component for collecting a sample such as a component for collecting a stool sample. In some embodiments, the system comprises nucleic acid sequences comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above. In some embodiments the database comprises nucleic acid sequences from subjects who do not have lung cancer. Also provided are nucleic acids, e.g., a set of nucleic acids, each nucleic acid having a sequence comprising a chromosomal region having an annotation selected from BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX, SIPR4, SKI, SUCLG2, TBX15, ZDHHC1, and ZNF329, preferably from any of the subsets of markers as recited above.

Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

In certain embodiments, methods for characterizing a sample obtained from a human subject are provided, comprising a) obtaining a sample from a human subject; b)

assaying a methylation state of one or more markers in the sample, wherein the marker comprises a base in a chromosomal region having an annotation selected from the following groups of markers: BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329, preferably from any of the subsets of markers as recited above; and c) comparing the methylation state of the assayed marker to the methylation state of the marker assayed in a subject that does not have a neoplasm.

In some embodiments, the technology is related to assessing the presence of and methylation state of one or more of the markers identified herein in a biological sample. These markers comprise one or more differentially methylated regions (DMR) as discussed herein. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) *Mol. Cell. Biol.* 14: 7421-7427) and another example involves methylation-sensitive arbitrarily primed PCR (Gonzalgo et al. (1997) *Cancer Res.* 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) *Nucl. Acids Res.* 18: 687). In addition, other techniques have been reported that utilize bisulfite treatment of DNA as a starting point for methylation analysis. These include methylation-specific PCR (MSP) (Herman et al. (1992) *Proc. Natl. Acad. Sci. USA* 93: 9821-9826) and restriction enzyme digestion of PCR products amplified from bisulfite-converted DNA (Sadri and Hornsby (1996) *Nucl. Acids Res.* 24: 5058-5059; and Xiong and Laird (1997) *Nucl. Acids Res.* 25: 2532-2534). PCR techniques have been developed for detection of gene mutations (Kuppuswamy et al. (1991) *Proc. Natl. Acad. Sci. USA* 88: 1143-1147) and quantification of allelic-specific expression (Szabo and Mann (1995) *Genes Dev.* 9: 3097-3108; and Singer-Sam et al. (1992) *PCR Methods Appl.* 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. Nos. 8,361, 720; 8,715,937; 8,916,344; and 9,212,392).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

Genomic DNA may be isolated by any means, including the use of commercially available kits. Briefly, wherein the DNA of interest is encapsulated by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

The technology is not limited in the methods used to prepare the samples and provide a nucleic acid for testing.

For example, in some embodiments, a DNA is isolated from a stool sample or from blood or from a plasma sample using direct gene capture, e.g., as detailed in U.S. Pat. Appl. Ser. No. 61/485,386 or by a related method.

The technology relates to the analysis of any sample that may be associated with lung cancer, or that may be examined to establish the absence of lung cancer. For example, in some embodiments the sample comprises a tissue and/or biological fluid obtained from a patient. In some embodiments, the sample comprises a secretion. In some embodiments, the sample comprises sputum, blood, serum, plasma, gastric secretions, lung tissue samples, lung cells or lung DNA recovered from stool. In some embodiments, the subject is human. Such samples can be obtained by any number of means known in the art, such as will be apparent to the skilled person.

I. Methylation Assays to Detect Lung Cancer

Candidate methylated DNA markers were identified by unbiased whole methylome sequencing of selected lung cancer case and lung control tissues. The top marker candidates were further evaluated in 255 independent patients with 119 controls, of which 37 were from benign nodules, and 136 cases inclusive of all lung cancer subtypes. DNA extracted from patient tissue samples was bisulfite treated and then candidate markers and β-actin (ACTB) as a normalizing gene were assayed by Quantitative Allele-Specific Real-time Target and Signal amplification (QuARTS amplification). QuARTS assay chemistry yields high discrimination for methylated marker selection and screening.

On receiver operator characteristics analyses of individual marker candidates, areas under the curve (AUCs) ranged from 0.512 to 0.941. At 100% specificity, a combined panel of 8 methylation markers (SLC12A8, KLHDC7B, PARP15, OPLAH, BCL2L11, MAX. 12.526, HOXB2, and EMX1) yielded a sensitivity of 98.5% across all subtypes of lung cancer. Furthermore, using the 8 markers panel, benign lung nodules yielded no false positives.

II. Methylation Detection Assays and Kits

The markers described herein find use in a variety of methylation detection assays. The most frequently used method for analyzing a nucleic acid for the presence of 5-methylcytosine is based upon the bisulfite method described by Frommer, et al. for the detection of 5-methylcytosines in DNA (Frommer et al. (1992) *Proc. Natl. Acad. Sci. USA* 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" *Clin Chem* 56: A199; and in U.S. Pat. Nos. 8,361,720; 8,715,937; 8,916,344; and 9,212,392.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) *Nucleic Acids Res.* 26: 2255.

The bisulfite technique typically involves amplifying short, specific fragments of a known nucleic acid subsequent to a bisulfite treatment, then either assaying the product by sequencing (Olek & Walter (1997) *Nat. Genet.* 17: 275-6) or a primer extension reaction (Gonzalgo & Jones (1997) *Nucleic Acids Res.* 25: 2529-31; WO 95/00669; U.S. Pat. No. 6,251,594) to analyze individual cytosine positions. Some methods use enzymatic digestion (Xiong & Laird (1997) *Nucleic Acids Res.* 25: 2532-4). Detection by hybridization has also been described in the art (Olek et al., WO 99/28498). Additionally, use of the bisulfite technique for methylation detection with respect to individual genes has been described (Grigg & Clark (1994) *Bioessays* 16: 431-6; Zeschnigk et al. (1997) *Hum Mol Genet.* 6: 387-95; Feil et al. (1994) *Nucleic Acids Res.* 22: 695; Martin et al. (1995) *Gene* 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) *Proc. Natl. Acad. Sci. USA* 89: 1827-1831). Additionally, restriction enzyme digestion of PCR products amplified from bisulfite-converted DNA finds use in assessing methylation state, e.g., as described by Sadri & Hornsby (1997) *Nucl. Acids Res.* 24: 5058-5059 or as embodied in the method known as COBRA (Combined Bisulfite Restriction Analysis) (Xiong & Laird (1997) *Nucleic Acids Res.* 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucle-otides. Alternatively, a qualitative test for genomic methyl-ation is achieved by probing the biased PCR pool with either control oligonucleotides that do not cover known methyl-ation sites (a fluorescence-based version of the HeavyM-ethyl™ and MSP techniques) or with oligonucleotides cov-ering potential methylation sites.

The QM™ process can be used with any suitable probe, e.g., "TaqMan®" probes, Lightcycler® probes, in the ampli-fication process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/exten-sion step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleo-tide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplifi-cation of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restric-tion enzyme digestion contains DNA methylation informa-tion for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clini-cal samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QuARTS) assay is used to evaluate methylation state. Three reactions sequentially occur in each QuARTS assay, including amplification (reac-tion 1) and target probe cleavage (reaction 2) in the primary reaction; and FRET cleavage and fluorescent signal genera-tion (reaction 3) in the secondary reaction. When target nucleic acid is amplified with specific primers, a specific detection probe with a flap sequence loosely binds to the amplicon. The presence of the specific invasive oligonucle-otide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199), and U.S. Pat. Nos. 8,361,720; 8,715,937; 8,916,344; and 9,212,392, each of which is incorporated herein by reference for all purposes.

In some embodiments, the bisulfite-treated DNA is puri-fied prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715, which is incorporated by refer-ence in its entirety). In some embodiments, the bisulfite treated DNA is bound to a solid support, e.g., a magnetic bead, and desulfonation and washing occurs while the DNA is bound to the support. Examples of such embodiments are provided, e.g., in WO 2013/116375 and U.S. Pat. No. 9,315,853. In certain preferred embodiments, support-bound DNA is ready for a methylation assay immediately after desulfonation and washing on the support. In some embodi-ments, the desulfonated DNA is eluted from the support prior to assay.

In some embodiments, fragments of the treated DNA are amplified using sets of primer oligonucleotides according to the present invention (e.g., see FIG. 1) and an amplification enzyme. The amplification of several DNA segments can be carried out simultaneously in one and the same reaction vessel. Typically, the amplification is carried out using a polymerase chain reaction (PCR).

Methods for isolating DNA suitable for these assay technologies are known in the art. In particular, some embodiments comprise isolation of nucleic acids as described in U.S. Pat. Nos. 9,000,146 and 9,163,278, each incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

In some embodiments, the sample comprises blood, serum, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

III. Applications

In some embodiments, diagnostic assays identify the presence of a disease or condition in an individual. In some embodiments, the disease is cancer (e.g., lung cancer). In some embodiments, markers whose aberrant methylation is associated with a lung cancer (e.g., one or more markers selected from the markers listed in Table 1, or preferably one or more of BARX1, LOC100129726, SPOCK2, TSC22D4, MAX.chr8.124, RASSF1, ZNF671, ST8SIA1, NKX2-6, FAM59B, DIDO1, MAX_Chr1.110, AGRN, SOBP, MAX_chr10.226, ZMIZ1, MAX_chr8.145, MAX_chr10.225, PRDM14, ANGPT1, MAX.chr16.50, PTGDR_9, ANKRD13B, DOCK2, MAX_chr19.163, ZNF132, MAX chr19.372, HOXA9, TRH, SP9, DMRTA2, ARHGEF4, CYP26C1, ZNF781, PTGDR, GRIN2D, MATK, BCAT1, PRKCB_28, ST8SIA_22, FLJ45983, DLX4, SHOX2, EMX1, HOXB2, MAX.chr12.526, BCL2L11, OPLAH, PARP15, KLHDC7B, SLC12A8, BHLHE23, CAPN2, FGF14, FLJ34208, B3GALT6, BIN2_Z, DNMT3A, FERMT3, NFIX SIPR4, SKI, SUCLG2, TBX15, ZDHHC1, and ZNF329) are used. In some embodiments, an assay further comprises detection of a reference gene (e.g., β-actin, ZDHHC1, B3GALT6. See, e.g., U.S. patent application Ser. No. 14/966,617, filed Dec. 11, 2015, and U.S. Pat. Appl. No. 62/364,082, filed Jul. 19, 2016, each of which is incorporated herein by reference for all purposes).

In some embodiments, the technology finds application in treating a patient (e.g., a patient with lung cancer, with early stage lung cancer, or who may develop lung cancer), the method comprising determining the methylation state of one or more markers as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments, the technology finds application in methods for diagnosing lung cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker, the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers disclosed herein.

Further, in some embodiments of the technology, multiple determinations of the biomarkers over time can be made to facilitate diagnosis and/or prognosis. A temporal change in the biomarker can be used to predict a clinical outcome, monitor the progression of lung cancer, and/or monitor the efficacy of appropriate therapies directed against the cancer. In such an embodiment for example, one might expect to see a change in the methylation state of one or more biomarkers disclosed herein (and potentially one or more additional biomarker(s), if monitored) in a biological sample over time during the course of an effective therapy.

The technology further finds application in methods for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with risk for developing lung, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted above, in some embodiments multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition, the chance of a given outcome (e.g., suffering from lung cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or ap value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with lung cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having lung cancer if, when compared to a control methylation state, there is a measurable difference in the methylation state of at least one biomarker in the sample. Conversely, when no change in methylation state is identified in the biological sample, the subject can be identified as not having lung cancer, not being at risk for the cancer, or as having a low risk of the cancer. In this regard, subjects having lung cancer or risk thereof can be differentiated from subjects having low to substantially no cancer or risk thereof. Those subjects having a risk of developing lung cancer can be placed on a more intensive and/or regular screening schedule. On the other hand, those subjects having low to substantially no risk may avoid being subjected to screening procedures, until such time as a future screening, for example, a screening conducted in accordance with the present technology, indicates that a risk of lung cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, lung cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

In some embodiments, a sample from a subject having or suspected of having lung cancer is screened using one or more methylation markers and suitable assay methods that provide data that differentiate between different types of lung cancer, e.g., non-small cell (adenocarcinoma, large cell carcinoma, squamous cell carcinoma) and small cell carcinomas. See, e.g., marker ref. #AC27 (FIG. 2; PLEC), which is highly methylated (shown as mean methylation compared to mean methylation at that locus in normal buffy coat) in adenocarcinoma and small cell carcinomas, but not in large cell or squamous cell carcinoma; marker ref. #AC23 (FIG. 2; ITPRIPL1), which is more highly methylated in adenocarcinoma than in any other sample type; marker ref. #LC2 (FIG. 3; DOCK2)), which is more highly methylated in large cell carcinomas than in any other sample type; marker ref #SC221 (FIG. 4; ST8SIA4), which is more highly methylated in small cell carcinomas than in any other sample type;

and marker ref #SQ36 (FIG. 5, DOK1), which is more highly methylated in squamous cell carcinoma than in than in any other sample type.

Methylation markers selected as described herein may be used alone or in combination (e.g., in panels) such that analysis of a sample from a subject reveals the presence of a lung neoplasm and also provides sufficient information to distinguish between lung cancer type, e.g., small cell carcinoma vs. non-small cell carcinoma. In preferred embodiments, a marker or combination of markers further provide data sufficient to distinguish between adenocarcinomas, large cell carcinomas, and squamous cell carcinomas; and/or to characterize carcinomas of undetermined or mixed pathologies. In other embodiments, methylation markers or combinations thereof are selected to provide a positive result (i.e., a result indicating the presence of lung neoplasm) regardless of the type of lung carcinoma present, without differentiating data.

Over recent years, it has become apparent that circulating epithelial cells, representing metastatic tumor cells, can be detected in the blood of many patients with cancer. Molecular profiling of rare cells is important in biological and clinical studies. Applications range from characterization of circulating epithelial cells (CEpCs) in the peripheral blood of cancer patients for disease prognosis and personalized treatment (See e.g., Cristofanilli M, et al. (2004) N Engl J Med 351:781-791; Hayes D F, et al. (2006) Clin Cancer Res 12:4218-4224; Budd G T, et al., (2006) Clin Cancer Res 12:6403-6409; Moreno J G, et al. (2005) Urology 65:713-718; Pantel et al., (2008) Nat Rev 8:329-340; and Cohen S J, et al. (2008) J Clin Oncol 26:3213-3221). Accordingly, embodiments of the present disclosure provide compositions and methods for detecting the presence of metastatic cancer in a subject by identifying the presence of methylated markers in plasma or whole blood.

EXPERIMENTAL EXAMPLES

Example 1

Sample Preparation Methods

Methods for DNA Isolation and QUARTS Assay

The following provides exemplary method for DNA isolation prior to analysis, and an exemplary QUARTS assay, such as may be used in accordance with embodiments of the technology. Application of QuARTS technology to DNA from blood and various tissue samples is described in this example, but the technology is readily applied to other nucleic acid samples, as shown in other examples.

DNA Isolation from Cells and Plasma

For cell lines, genomic DNA may be isolated from cell conditioned media using, for example, the "Maxwell® RSC ccfDNA Plasma Kit (Promega Corp., Madison, WI). Following the kit protocol, 1 mL of cell conditioned media (CCM) is used in place of plasma, and processed according to the kit procedure. The elution volume is 100 μL, of which 70 μL are generally used for bisulfite conversion.

An exemplary procedure for isolating DNA from a 4 mL sample of plasma is as follows:

To a 4 mL sample of plasma, 300 μL of Proteinase K (20 mg/mL) is added and mixed.

Add 3 μL of 1 μg/μL of Fish DNA to the plasma-proteinase K mixture.

Add 2 mL of plasma lysis buffer to plasma.
Plasma lysis buffer is:
4.3M guanidine thiocyanate
10% IGEPAL CA-630 (Octylphenoxy poly(ethyleneoxy)ethanol, branched)
(5.3 g of IGEPAL CA-630 combined with 45 mL of 4.8 M guanidine thiocyanate)
Incubate mixtures at 55° C. for 1 hour with shaking at 500 rpm.
Add 3 mL of plasma lysis buffer and mix.
Add 200 μL magnetic silica binding beads (16 g of beads/μL} and mix again.
Add 2 mL of 100% isopropanol and mix.
Incubate at 30° C. for 30 minutes with shaking at 500 rpm.
Place tube(s) on magnet and let the beads collect. Aspirate and discard the supernatant.
Add 750 μL GuHCl-EtOH to vessel containing the binding beads and mix.
GuHCl-EtOH wash buffer is:
3M GuHCl (guanidine hydrochloride)
57% EtOH (ethyl alcohol)
Shake at 400 rpm for 1 minute.
Transfer samples to a deep well plate or 2 mL microcentrifuge tubes.
Place tubes on magnet and let the beads collect for 10 minutes. Aspirate and discard the supernatant.
Add 1000 μL wash buffer (10 mM Tris HCl, 80% EtOH) to the beads, and incubate at 30° C. for 3 minutes with shaking.
Place tubes on magnet and let the beads collect. Aspirate and discard the supernatant.
Add 500 μL wash buffer to the beads and incubate at 30° C. for 3 minutes with shaking.
Place tubes on magnet and let the beads collect. Aspirate and discard the supernatant.
Add 250 μL wash buffer and incubate at 30° C. for 3 minutes with shaking.
Place tubes on magnet and let the beads collect. Aspirate and discard the remaining buffer.
Add 250 μL wash buffer and incubate at 30° C. for 3 minutes with shaking.
Place tubes on magnet and let the beads collect. Aspirate and discard the remaining buffer.
Dry the beads at 70° C. for 15 minutes, with shaking.
Add 125 μL elution buffer (10 mM Tris HCl, pH 8.0, 0.1 mM EDTA) to the beads and incubate at 65° C. for 25 minutes with shaking.
Place tubes on magnet and let the beads collect for 10 minutes.
Aspirate and transfer the supernatant containing the DNA to a new vessel or tube.

Bisulfite Conversion

I. Sulfonation of DNA Using Ammonium Hydrogen Sulfite
1. In each tube, combine 64 μL DNA, 7 μL 1 N NaOH, and 9 μL of carrier solution containing 0.2 mg/mL BSA and 0.25 mg/mL of fish DNA.
2. Incubate at 42° C. for 20 minutes.
3. Add 120 μL of 45% ammonium hydrogen sulfite and incubate at 66° for 75 minutes.
4. Incubate at 4° C. for 10 minutes.

II. Desulfonation Using Magnetic Beads

Materials
Magnetic beads (Promega MagneSil Paramagnetic Particles, Promega catalogue number AS1050, 16 μg/μL).
Binding buffer: 6.5-7 M guanidine hydrochoride.
Post-conversion Wash buffer: 80% ethanol with 10 mM Tris HCl (pH 8.0).
Desulfonation buffer: 70% isopropyl alcohol, 0.1 N NaOH was selected for the desulfonation buffer.

Samples are mixed using any appropriate device or technology to mix or incubate samples at the temperatures and mixing speeds essentially as described below. For example, a Thermomixer (Eppendorf) can be used for the mixing or incubation of samples. An exemplary desulfonation is as follows:

1. Mix bead stock thoroughly by vortexing bottle for 1 minute.
2. Aliquot 50 μL of beads into a 2.0 mL tube (e.g., from USA Scientific).
3. Add 750 μL of binding buffer to the beads.
4. Add 150 μL of sulfonated DNA from step I.
5. Mix (e.g., 1000 RPM at 30° C. for 30 minutes).
6. Place tube on the magnet stand and leave in place for 5 minutes. With the tubes on the stand, remove and discard the supernatant.
7. Add 1,000 μL of wash buffer. Mix (e.g., 1000 RPM at 30° C. for 3 minutes).
8. Place tube on the magnet stand and leave in place for 5 minutes. With the tubes on the stand, remove and discard the supernatant.
9. Add 250 μL of wash buffer. Mix (e.g., 1000 RPM at 30° C. for 3 minutes).
10. Place tube on magnetic rack; remove and discard supernatant after 1 minute.
11. Add 200 μL of desulfonation buffer. Mix (e.g., 1000 RPM at 30° C. for 5 minutes).
12. Place tube on magnetic rack; remove and discard supernatant after 1 minute.
13. Add 250 μL of wash buffer. Mix (e.g., 1000 RPM at 30° C. for 3 minutes).
14. Place tube on magnetic rack; remove and discard supernatant after 1 minute.
15. Add 250 μL of wash buffer to the tube. Mix (e.g., 1000 RPM at 30° C. for 3 minutes).
16. Place tube on magnetic rack; remove and discard supernatant after 1 minute.
17. Incubate all tubes at 30° C. with the lid open for 15 minutes.
18. Remove tube from magnetic rack and add 70 μL of elution buffer directly to the beads.
19. Incubate the beads with elution-buffer (e.g., 1000 RPM at 40° C. for 45 minutes).
20. Place tubes on magnetic rack for about one minute; remove and save the supernatant.

The converted DNA is then used in a detection assay, e.g., a pre-amplification and/or flap endonuclease assays, as described below.

See also U.S. Patent Appl. Ser. No. 62/249,097, filed Oct. 30, 2015; Ser. Nos. 15/335,111 and 15/335,096, both filed Oct. 26, 2016; and International Appl. Ser. No. PCT/US16/58875, filed Oct. 26, 2016, each of which is incorporated herein by reference in its entirety, for all purposes.

QuARTS Assay

The QuARTS technology combines a polymerase-based target DNA amplification process with an invasive cleavage-based signal amplification process. The technology is described, e.g., in U.S. Pat. Nos. 8,361,720; 8,715,937; 8,916,344; and 9,212,392, each of which is incorporated herein by reference. Fluorescence signal generated by the QuARTS reaction is monitored in a fashion similar to real-time PCR and permits quantitation of the amount of a target nucleic acid in a sample.

An exemplary QuARTS reaction typically comprises approximately 400-600 nmol/L (e.g., 500 nmol/L) of each primer and detection probe, approximately 100 nmol/L of the invasive oligonucleotide, approximately 600-700 nmol/L of each FRET cassette (FAM, e.g., as supplied commercially by Hologic, Inc.; HEX, e.g., as supplied commercially by BioSearch Technologies; and Quasar 670, e.g., as supplied commercially by BioSearch Technologies), 6.675 ng/μL FEN-1 endonuclease (e.g., Cleavase® 2.0, Hologic, Inc.), 1 unit Taq DNA polymerase in a 30 μL reaction volume (e.g., GoTaq® DNA polymerase, Promega Corp., Madison, WI), 10 mmol/L 3-(n-morpholino) propanesulfonic acid (MOPS), 7.5 mmol/L $MgCl_2$, and 250 μmol/L of each dNTP. Exemplary QuARTS cycling conditions are as shown in the table below. In some applications, analysis of the quantification cycle ($C_q$) provides a measure of the initial number of target DNA strands (e.g., copy number) in the sample.

| Stage | Temp/Time | # of Cycles |
|---|---|---|
| Denaturation | 95° C./3' | 1 |
| Amplification 1 | 95° C./20" | 10 |
| | 67° C./30" | |
| | 70° C./30" | |
| Amplification 2 | 95° C./20" | 37 |
| | 53° C./1' | |
| | 70° C./30" | |
| Cooling | 40° C./30" | 1 |

Multiplex Targeted Pre-Amplification of Large-Volume Bisulfite-Converted DNA

To pre-amplify most or all of the bisulfite-treated DNA from an input sample, a large volume of the treated DNA may be used in a single, large-volume multiplex amplification reaction. For example, DNA is extracted from a cell lines (e.g., DFCI032 cell line (adenocarcinoma); H1755 cell line (neuroendocrine), using, for example, the Maxwell Promega blood kit #AS1400, as described above. The DNA is bisulfite converted, e.g., as described above.

A pre-amplification is conducted, for example, in a reaction mixture containing 7.5 mM $MgCl_2$, 10 mM MOPS, 0.3 mM Tris-HCl, pH 8.0, 0.8 mM KCl, 0.1 μg/μL BSA, 0.0001% Tween-20, 0.0001% IGEPAL CA-630, 250 M each dNTP, oligonucleotide primers, (e.g., for 12 targets, 12 primer pairs/24 primers, in equimolar amounts (including but not limited to the ranges of, e.g., 200-500 nM each primer), or with individual primer concentrations adjusted to balance amplification efficiencies of the different target regions), 0.025 units/μL HotStart GoTaq concentration, and 20 to 50% by volume of bisulfite-treated target DNA (e.g., 10 μL of target DNA into a 50 μL reaction mixture, or 50 μL of target DNA into a 125 μL reaction mixture). Thermal cycling times and temperatures are selected to be appropriate for the volume of the reaction and the amplification vessel. For example, the reactions may be cycled as follows

| Stage | Temp/Time | #of Cycles |
|---|---|---|
| Pre-incubation | 95° C./5' | 1 |
| Amplification 1 | 95° C./30" | 10 |
| | 64° C./30" | |
| | 72° C./30" | |
| Cooling | 4° C./Hold | 1 |

After thermal cycling, aliquots of the pre-amplification reaction (e.g., 10 μL) are diluted to 500 μL in 10 mM Tris, 0.1 mM EDTA, with or without fish DNA. Aliquots of the diluted pre-amplified DNA (e.g., 10 μL) are used in a QuARTS PCR-flap assay, e.g., as described above. See also U.S. Patent Appl. Ser. No. 62/249,097, filed Oct. 30, 2015;

application Ser. No. 15/335,096, filed Oct. 26, 2016, and PCT/US16/58875, filed Oct. 26, 2016, each of which is incorporated herein by reference in its entirety for all purposes.

Example 2

Selection and Testing of Methylation Markers
Marker Selection Process:

Reduced Representation Bisulfite Sequencing (RRBS) data was obtained on tissues from 16 adenocarcinoma lung cancer, 11 large cell lung cancer, 14 small cell lung cancer, 24 squamous cell lung cancer, and 18 non-cancer lung as well as RRBS results of buffy coat samples obtained from 26 healthy patients.

After alignment to a bisulfite-converted form of the human genome sequence, average methylation at each CpG island was computed for each sample type (i.e., tissue or buffy coat) and marker regions were selected based on the following criteria:

Regions were selected to be 50 base pairs or longer.

For QuARTS flap assay designs, regions were selected to have a minimum of 1 methylated CpG under each of: a) the probe region, b) the forward primer binding region, and c) the reverse primer binding region. For the forward and reverse primers, it is preferred that the methylated CpGs are close to the 3'-ends of the primers, but not at the 3'terminal nucleotide. Exemplary flap endonuclease assay oligonucleotides are shown in FIG. 1.

Preferably, buffy coat methylation at any CpG in a region of interest is no more than >0.5%.

Preferably, cancer tissue methylation in a region of interest is >10%.

For assays designed for tissue analysis, normal tissue methylation in a region of interest is preferably <0.5%.

RRBS data for different lung cancer tissue types is shown in FIGS. 2-5. Based on the criteria above, the markers shown in the table below were selected and QuARTS flap assays were designed for them, as shown in FIG. 1.

TABLE 1

| Marker Name | Genomic coordinates |
| --- | --- |
| AGRN | chr1: 968467-968582, strand=+ |
| ANGPT1 | chr8: 108509559-108509684, strand=- |
| ANKRD13B | chr17: 27940470-27940578, strand=+ |
| ARHGEF4 | chr2: 131792758-131792900, strand=- |
| B3GALT6 | chr1: 1163595-1163733, strand=+ |
| BARX1 | chr9: 96721498-96721597, strand =- |
| BCAT1 | chr12: 25055868-25055986, strand=- |
| BCL2L11 | chr2: 111876620-111876759, strand=- |
| BHLHE23 | chr20: 61638462-61638546, strand=- |
| BIN2 | chr12: 51717898-51717971, strand=- |
| BIN2_Z | chr12: 51718088-51718165, strand=+ |
| CAPN2 | chr1: 223936858-223936998, strand=+ |
| chr17_737 | chr17: 73749814-73749919, strand=- |
| chr5_132 | chr5: 132161371-132161482,Strand=+ |
| chr7_636 | chr7: 104581684-104581817, Strand=- |
| CYP26C1 | chr10: 94822396-94822502, strand=+ |
| DIDO1 | chr20: 61560669-61560753, strand=- |
| DLX4 | chr17: 48042426-48042820, strand=- |
| DMRTA2 | chr1: 50884390-50884519, strand=- |
| DNMT3A | chr2: 25499967-25500072, strand=- |
| DOCK2 | chr5: 169064370- 169064454, strand=- |
| EMX1 | chr2: 73147685-73147792, strand=+ |
| FAM59B | chr2: 26407701-26407828, strand=+ |
| FERMT3 | chr11: 63974820-63974959, strand=+ |
| FGF14 | chr13: 103046888-103046991, strand=+ |
| FLJ34208 | chr3: 194208249-194208355, strand=+ |
| FLJ45983 | chr10: 8097592-8097699, strand=+ |

TABLE 1-continued

| Marker Name | Genomic coordinates |
| --- | --- |
| GRIN2D | chr19: 48918160-48918300, strand=- |
| HIST1H2BE | chr6: 26184248-26184340, strand=+ |
| HOXA9 | chr7: 27205002-27205102, strand=- |
| HOXB2 | chr17: 46620545-46620639, strand=- |
| KLHDC7B | chr22: 50987199-50987256, strand=+ |
| LOC100129726 | chr2: 43451705-43451810, strand=+ |
| MATK | chr19: 3786127-3786197, strand=+ |
| MAX.chr10.22541891-22541946 | chr10: 22541881-22541975, strand=+ |
| MAX.chr10.22624430-22624544 | chr10: 22624411-22624553, strand=- |
| MAX.chr12.52652268-52652362 | chr12: 52652262-52652377, strand=- |
| MAX.chr16.50875223-50875241 | chr16: 50875167-50875274, strand=- |
| MAX.chr19.16394489-16394575 | chr19: 16394457-16394593, strand=- |
| MAX.chr19.37288426-37288480 | range=chr19: 37288396-37288512, strand=- |
| MAX.chr8.124173236-124173370 | chr8: 124173231-124173386, strand=- |
| MAX.chr8.145105646-145105653 | chr8: 145105572-145105685, strand=- |
| MAX_Chr1.110 | chr1: 110627118-110627224 strand=- |
| NFIX | chr19: 13207426-13207513, strand=+ |
| NKX2-6 | chr8: 23564052-23564145, strand=- |
| OPLAH | chr8: 145106777-145106865, strand=- |
| PARP15 | chr3: 122296692-122296805, strand=+ |
| PRDM14 | chr8: 70981945-70982039, strand=- |
| PRKAR1B | chr7: 644172-644237, strand=+ |
| PRKCB_28 | chr16: 23847607-23847698, strand=- |
| PTGDR | chr14: 52735270-52735400, strand=- |
| PTGDR_9 | chr14: 52735221-52735300, strand=+ |
| RASSF1 | chr3: 50378408-50378550, strand=- |
| SHOX2 | chr3: 157821263-157821382, strand=- |
| SHROOM1 | chr5: 132161371-132161425, strand=+ |
| SIPR4 | chr19: 3179921-3180068 strand=- |
| SKI | chr1: 2232328-2232423, strand=+ |
| SLC12A8 | chr3: 124860704-124860791, strand=+ |
| SOBP | chr6: 107956176-107956234, strand=+ |
| SP9 | chr2: 175201210-175201341, strand=- |
| SPOCK2 | chr10: 73847236-73847324, strand=- |
| ST8SIA1 | chr12: 22487518-22487630, strand=+ |
| ST8SIA1_22 | chr12: 22486873-22487009, strand=- |
| SUCLG2 | chr3: 67706477-677065610, strand=- |
| TBX15 Region 1 | chr1: 119527066-119527655, strand=+ |
| TBX15 Region 2 | chr1: 119532813-119532920 strand=- |
| TRH | chr3: 129693481-129693580, strand=+ |
| TSC22D4 | chr7: 100075328-100075445, strand=- |
| ZDHHC1 | chr16: 67428559-67428628, strand=- |
| ZMIZ1 | chr10: 81002910-81003005, strand=+ |
| ZNF132 | chr19: 58951403-58951529, strand=- |
| ZNF329 | chr19: 58661889- 58662028, strand=- |
| ZNF671 | chr19: 58238790-58238906, strand=+ |
| ZNF781 | ch19: 38183018-38183137, strand=- |

Analyzing Selected Markers for Cross-Reactivity with Buffy Coat.

1) Fluffy Coat Screening

Markers from the list above were screened on DNA extracted from buffy coat obtained from 10 mL blood of a healthy patient. DNA was extracted using Promega Maxwell RSC system (Promega Corp., Fitchburg, WI) and converted using Zymo EZ DNA Methylation™ Kit (Zymo Research, Irvine, CA). Using biplexed reaction with bisulfite-converted β-actin DNA ("BTACT"), and using approximately 40,000 strands of target genomic DNA, the samples were tested using a QuARTS flap endonuclease assay as described above, to test for cross reactivity. Doing so, the assays for 3 markers showed significant cross reactivity:

| Marker | % Cross reactivity |
| --- | --- |
| HIST1H2B | 72.93% |
| chr7_636 | 3495.47% |
| chr5_132 | 0.20% |

2) Tissue Screening 264 tissue samples were obtained from various commercial and non-commercial sources (Asuragen, BioServe, ConversantBio, Cureline, Mayo Clinic, M D Anderson, and PrecisionMed), as shown below in Table 2.

| No. of cases | Pathology | Subtype | Details |
|---|---|---|---|
| 82 | Normal | NA | 68 smokers, 34 never smokers, 17 smoking unknown |
| 37 | Normal | benign nodule | |
| 7 | NSCLC | bronchioalveolar | |
| 13 | NSCLC | large cell | |
| 2 | NSCLC | neuroendocrine | |
| 42 | NSCLC | squamous cell | |
| 68 | NSCLC | adenocarcinomas | |
| 4 | SCLC | small cell | |
| 9 | NSCLC | carcinoid | |

Tissue sections were examined by a pathologist, who circled histologically distinct lesions to direct the microdissection. Total nucleic acid extraction was performed using the Promega Maxwell RSC system. Formalin-fixed, paraffin-embedded (FFPE) slides were scraped and the DNA was extracted using the Maxwell® RSC DNA FFPE Kit (#AS1450) using the manufacturer's procedure but skipping the RNase treatment step. The same procedure was used for FFPE curls. For frozen punch biopsy samples, a modified procedure using the lysis buffer from the RSC DNA FFPE kit with the Maxwell® RSC Blood DNA kit (#AS1400) was utilized omitting the RNase step. Samples were eluted in 10 mM Tris, 0.1 mM EDTA, pH 8.5 and 10 uL were used to setup 6 multiplex PCR reactions.

The following multiplex PCR primer mixes were made at 10× concentration (10×=2 M each primer):

Multiplex PCR reaction 1 consisted of each of the following markers: BARX1, LOC100129726, SPOCK2, TSC22D4, PARP15, MAX.chr8.145105646-145105653, ST8SIA1_22, ZDHHC1, BIN2_Z, SKI, DNMT3A, BCL2L11, RASSF1, FERMT3, and BTACT.

Multiplex PCR reaction 2 consisted of each of the following markers: ZNF671, ST8SIA1, NKX2-6, SLC12A8, FAM59B, DIDO1, MAX_Chr1.110, AGRN, PRKCB_28, SOBP, and BTACT.

Multiplex PCR reaction 3 consisted of each of the following markers: MAX.chr10.22624430-22624544, ZMIZ1, MAX.chr8.145105646-145105653, MAX.chr10.22541891-22541946, PRDM14, ANGPT1, MAX.chr16.50875223-50875241, PTGDR_9, ANKRD13B, DOCK2, and BTACT.

Multiplex PCR reaction 4 consisted of each of the following markers: MAX.chr19.16394489-16394575, HOXB2, ZNF132, MAX.chr19.37288426-37288480, MAX.chr12.52652268-52652362, FLJ45983, HOXA9, TRH, SP9, DMRTA2, and BTACT.

Multiplex PCR reaction 5 consisted of each of the following markers: EMX1, ARHGEF4, OPLAH, CYP26C1, ZNF781, DLX4, PTGDR, KLHDC7B, GRIN2D, chr17_737, and BTACT.

Multiplex PCR reaction 6 consisted of each of the following markers: TBX15, MATK, SHOX2, BCAT1, SUCLG2, BIN2, PRKAR1B, SHROOM1, S1PR4, NFIX, and BTACT.

Each multiplex PCR reaction was setup to a final concentration of 0.2 μM reaction buffer, 0.2 μM each primer, 0.05 μM Hotstart Go Taq (5 U/μL), resulting in 40 μL of master mix that was combined with 10 μL of DNA template for a final reaction volume of 50 μL. The thermal profile for the multiplex PCR entailed a pre-incubation stage of 95° for 5 minutes, 10 cycles of amplification at 95° for 30 seconds, 64° for 30 seconds, 72° for 30 seconds, and a cooling stage of 4° that was held until further processing. Once the multiplex PCR was complete, the PCR product was diluted 1:10 using a diluent of 20 ng/μL of fish DNA (e.g., in water or buffer, see U.S. Pat. No. 9,212,392, incorporated herein by reference) and 10 μL of diluted amplified sample were used for each QuARTS assay reaction.

Each QuARTS assay was configured in triplex form, consisting of 2 methylation markers and BTACT as the reference gene.

From multiplex PCR product 1, the following 7 triplex QuARTS assays were run: (1) BARX1, LOC100129726, BTACT; (2) SPOCK2, TSC22D4, BTACT; (3) PARP15, MAXchr8145105646-145105653, BTACT; (4) ST8SIA1_22, ZDHHC1, BTACT; (5) BIN2_Z, SKI, BTACT; (6) DNMT3A, BCL2L11, BTACT; (7) RASSF1, FERMT3, and BTACT.

From multiplex PCR product 2, the following 5 triplex QuARTS assays were run: (1) ZNF671, ST8SIA1, BTACT; (2) NKX2-6, SLC12A8, BTACT; (3) FAM59B, DIDO1, BTACT; (4) MAX_Chr1110, AGRN, BTACT; (5) PRKCB_28, SOBP, and BTACT.

From multiplex PCR product 3, the following 5 triplex QuARTS assays were run: (1) MAXchr1022624430-22624544, ZMIZ1, BTACT; (2) MAXchr8145105646-145105653, MAXchr1022541891-22541946, BTACT; (3) PRDM14, ANGPT1, BTACT; (4) MAXchr1650875223-50875241, PTGDR_9, BTACT; (5) ANKRD13B, DOCK2, and BTACT.

From multiplex PCR product 4, the following 5 triplex QuARTS assays were run: (1) MAXchr1916394489-16394575, HOXB2, BTACT; (2) ZNF132, MAXchr1937288426-37288480, BTACT; (3) MAXchr1252652268-52652362, FLJ45983, BTACT; (4) HOXA9, TRH, BTACT; (5) SP9, DMRTA2, and BTACT.

From multiplex PCR product 5, the following 5 triplex QuARTS assays were run: (1) EMX1, ARHGEF4, BTACT; (2) OPLAH, CYP26C1, BTACT; (3) ZNF781, DLX4, BTACT; (4) PTGDR, KLHDC7B, BTACT; (5) GRIN2D, chr17_737, and BTACT.

From multiplex PCR product 6, the following 5 triplex QuARTS assays were run: (1) TBX15, MATK, BTACT; (2) SHOX2, BCAT1, BTACT; (3) SUCLG2, BIN2, BTACT; (4) PRKAR1B, SHROOM1, BTACT; (5) S1PR4, NFIX, and BTACT.

3) Data Analysis:

For tissue data analysis, markers that were selected based on RRBS criteria with <0.5% methylation in normal tissue and >10% methylation in cancer tissue were included. This resulted in 51 markers for further analysis.

To determine marker sensitivities, the following was performed:

1. % methylation for each marker was computed by dividing strand values obtained for that specific marker by the strand values of ACTB (β-actin).

2. The maximum % methylation for each marker was determined on normal tissue. This is defined as 100% specificity.

3. The cancer tissue positivity for each marker was determined as the number of cancer tissues that had greater than the maximum normal tissue % methylation for that marker.

The sensitivities for the 51 markers are shown below.

TABLE 2

| Marker | Maximum % methylation for normal | Cancer (N = 136) # Negative | # Positive | sensitivity |
|---|---|---|---|---|
| BARX1 | 1.665 | 66 | 70 | 51% |
| LOC100129726 | 1.847 | 109 | 27 | 20% |
| SPOCK2 | 0.261 | 86 | 50 | 37% |
| TSC22D4 | 0.618 | 70 | 66 | 49% |
| MAX.chr8.124 | 0.293 | 45 | 91 | 67% |
| RASSF1 | 1.605 | 79 | 57 | 42% |
| ZNF671 | 0.441 | 73 | 63 | 46% |
| ST8SIA1 | 1.56 | 119 | 17 | 13% |
| NKX2-6 | 15.58 | 102 | 34 | 25% |
| FAM59B | 0.433 | 85 | 51 | 38% |
| DIDO1 | 2.29 | 93 | 43 | 32% |
| MAX_Chr1.110 | 0.076 | 85 | 51 | 38% |
| AGRN | 2.16 | 66 | 70 | 51% |
| SOBP | 38.5 | 110 | 26 | 19% |
| MAX_chr10.226 | 0.7 | 52 | 84 | 62% |
| ZMIZ1 | 0.025 | 72 | 64 | 47% |
| MAX_chr8.145 | 5.56 | 57 | 79 | 58% |
| MAX_chr 10.225 | 0.77 | 72 | 64 | 47% |
| PRDM14 | 0.22 | 35 | 101 | 74% |
| ANGPT1 | 1.6 | 99 | 37 | 27% |
| MAX.chr 16.50 | 0.27 | 92 | 44 | 32% |
| PTGDR_9 | 4.62 | 82 | 54 | 40% |
| ANKRD13B | 7.03 | 93 | 43 | 32% |
| DOCK2 | 0.001 | 71 | 65 | 48% |
| MAX_chr19.163 | 0.61 | 56 | 80 | 59% |
| ZNF132 | 1.3 | 83 | 53 | 39% |
| MAX chr19.372 | 0.676 | 79 | 57 | 42% |
| HOXA9 | 16.7 | 53 | 83 | 61% |
| TRH | 2.64 | 61 | 75 | 55% |
| SP9 | 14.99 | 75 | 61 | 45% |
| DMRTA2 | 7.9 | 55 | 81 | 60% |
| ARHGEF4 | 7.41 | 113 | 23 | 17% |
| CYP26C1 | 39.2 | 101 | 35 | 26% |
| ZNF781 | 5.28 | 44 | 92 | 68% |
| PTGDR | 6.13 | 76 | 60 | 44% |
| GRIN2D | 16.1 | 113 | 23 | 17% |
| MATK | 0.04 | 93 | 43 | 32% |
| BCAT1 | 0.64 | 75 | 61 | 45% |
| PRKCB_28 | 1.68 | 57 | 79 | 58% |
| ST8SIA_22 | 1.934 | 55 | 81 | 60% |
| FLJ45983 | 8.34 | 39 | 97 | 71% |
| DLX4 | 15.1 | 41 | 95 | 70% |
| SHOX2 | 7.48 | 32 | 104 | 76% |
| EMX1 | 11.34 | 34 | 102 | 75% |
| HOXB2 | 0.114 | 61 | 75 | 55% |
| MAX.chr12.526 | 5.58 | 34 | 102 | 75% |
| BCL2L11 | 10.7 | 44 | 92 | 68% |
| OPLAH | 5.11 | 29 | 107 | 79% |
| PARP15 | 3.077 | 42 | 94 | 69% |
| KLHDC7B | 8.86 | 38 | 98 | 72% |
| SLC12A8 | 0.883 | 34 | 102 | 75% |

Combinations of markers may be used to increase specificity and sensitivity. For example, a combination of the 8 markers SLC12A8, KLHDC7B, PARP15, OPLAH, BCL2L11, MAX.chr12.526, HOXB2, and EMX1 resulted in 98.5% sensitivity (134/136 cancers) for all of the cancer tissues tested, with 100% specificity.

In some embodiments, markers are selected for sensitive and specific detection associated with a particular type of lung cancer tissue, e.g., adenocarcinoma, large cell carcinoma, squamous cell carcinoma, or small cell carcinoma, e.g., by use of markers that show sensitivity and specificity for particular cancer types or combinations of types.

This panel of methylated DNA markers assayed on tissue achieves extremely high discrimination for all types of lung cancer while remaining negative in normal lung tissue and benign nodules. Assays for this panel of markers can be also be applied to blood or bodily fluid-based testing, and finds applications in, e.g., lung cancer screening and discrimination of malignant from benign nodules.

Example 3

Testing a 30-Marker Set on Plasma Samples

From the list of markers in Example 2, 30 markers were selected for use in testing DNA from plasma samples from 295 subjects (64 with lung cancer, 231 normal controls. DNA was extracted from 2 mL of plasma from each subject and treated with bisulfite as described in Example 1. Aliquots of the bisulfite-converted DNA were used in two multiplex QuARTS assays, as described in Example 1. The markers selected for analysis are:

1. BARX1
2. BCL2L11
3. BIN2_Z
4. CYP26C1
5. DLX4
6. DMRTA2
7. DNMT3A
8. EMX1
9. FERMT3
10. FLJ45983
11. HOXA9
12. KLHDC7B
13. MAX.chr10.22624430-22624544
14. MAX.chr12.52652268-52652362
15. MAX.chr8.124173236-124173370
16. MAX.chr8.145105646-145105653
17. NFIX
18. OPLAH
19. PARP15
20. PRKCB_28
21. S1PR4
22. SHOX2
23. SKI
24. SLC12A8
25. SOBP
26. SP9
27. SUCLG2
28. TBX15
29. ZDHHC1
30. ZNF781

The target sequences, bisulfite converted target sequences, and the assay oligonucleotides for these markers were as shown in FIG. 1. The primers and flap oligonucleotides (probes) used for each converted target were as follows:

TABLE 3

| Marker | Oligonucleotide Name | Component | Sequence (5'-3') | SEQ ID NO: |
|---|---|---|---|---|
| BARX1 | BARX1_FP | Forward Primer | CGTTAATTTGTTAGATAGAGGGCG | 23 |
| | BARX1_RP | Reverse Primer | ACGATCGTCCGAACAACC | 24 |
| | BARX1_PB_A5 | Flap Oligo. | CCACGGACGCGCCTACGAAAA/3C6/ | 25 |

TABLE 3-continued

| SLC12A8 | SLC12A8_FP | Forward Primer | TTAGGAGGGTGGGGTTCG | 289 |
| | SLC12A8_RP | Reverse Primer | CTTTCCTCGCAAAACCGC | 290 |
| | SLC12A8_Pb_A1 | Flap Oligo. | CCACGGACGGGAGGGCGTAGG/3C6/ | 291 |
| PARP15 | PARP15_FP | Forward Primer | GGTTGAGTTTGGGGTTCG | 236 |
| | PARP15_RP | Reverse Primer | CGTAACGTAAAATCTCTACGCCC | 237 |
| | PARP15_Pb_A5 | Flap Oligo. | CCACGGACGCGCTCGAACTAC/3C6/ | 238 |
| MAX.Chr8.124 | MAX.Chr8.124_FP | Forward Primer | GGTTGAGGTTTTCGGGTTTTTAG | 203 |
| | MAX.Chr8.124_RP | Reverse Primer | CCTCCCCACGAAATCGC | 204 |
| | MAX.Chr8.124_Pb_A1 | Flap Oligo. | CGCCGAGGGCGGGTTTTCGT/3C6/ | 205 |
| SHOX2 | SHOX2_FP | Forward Primer | GTTCGAGTTTAGGGGTAGCG | 269 |
| | SHOX2_RP | Reverse Primer | CCGCACAAAAAACCGCA | 270 |
| | SHOX2_Pb_A5 | Flap Oligo. | CCACGGACGATCCGCAAACGC/3C6/ | 271 |
| ZDHHC1 | ZDHHC1FP | Forward Primer | GTCGGGGTCGATAGTTTACG | 348 |
| | ZDHHC1RP_V3 | Reverse Primer | ACTCGAACTCACGAAACG | 349 |
| | ZDHHC1Probe_v3_A1 | Flap Oligo. | CGCCGAGGGACGAACGCACG/3C6/ | 350 |
| BIN2_Z | BIN2_FP_Z | Forward Primer | GGGTTTATTTTTAGGTAGCGTTCG | 50 |
| | BIN2_RP_Z | Reverse Primer | CGAAATTTCGAACAAAAATTAAAACTCGA | 51 |
| | BIN2_Pb_A5_Z | Flap Oligo. | CCACGGACGGTTCGAGGTTAG/3C6/ | 52 |
| SKI | SKI_FP | Forward Primer | ACGGTTTTTTCGTTATTTTTACGGG | 279 |
| | SKI_RP | Reverse Primer | CAACGCCTAAAAACACGACTC | 280 |
| | SKI_Pb_A1 | Flap Oligo. | CGCCGAGGGGCGGTTGTTGG/3C6/ | 281 |
| DNMT3A | DNMT3A_FP | Forward Primer | GTTACGAATAAAGCGTTGGCG | 93 |
| | DNMT3A_RP | Reverse Primer | AACGAAACGTCTTATCGCGA | 94 |
| | DNMT3A_Pb_A5 | Flap Oligo. | CCACGGACGGAGTGCGCGTTC/3C6/ | 95 |
| BC2L11 | BCL2L11_FP | Forward Primer | CGTAATGTTTCGCGTTTTTCG | 35 |
| | BCL2L11_RP | Reverse Primer | ACTTTCTTCTACGTAATTCTTTTCCGA | 36 |
| | BCL2L11_Pb_A1 | Flap Oligo. | CGCCGAGGGCGGGGTCGGGC/3C6/ | 37 |
| TBX15 | TBX15_Reg2_FP | Forward Primer | AGGAAATTGCGGGTTTTCG | 332 |
| | TBX15_Reg2_RP | Reverse Primer | CCAAAAATCGTCGCTAAAAATCAAC | 334 |
| | TBX15_Reg2_Pb_A5 | Flap Oligo. | CCACGGACGCGCGCATTCACT/3C6/ | 335 |
| FERMT3 | FERMT3_FP | Forward Primer | GTTTTCGGGGATTATATCGATTCG | 118 |
| | FERMT3_RP | Reverse Primer | CCCAATAACCCGCAAAATAACC | 119 |
| | FERMT3_Pb_A1 | Flap Oligo. | CGCCGAGGCGACTCGACCTC/3C6/ | 120 |
| PRKCB_28 | PRKCB_28_FP | Forward Primer | GGAAGGTGTTTTGCGCG | 249 |
| | PRKCB_28_RP | Reverse Primer | CTTCTACAACCACTACACCGA | 250 |
| | PRKCB_28_Pb_A5 | Flap Oligo. | CCACGGACGGCGCGCGTTTAT/3C6/ | 251 |
| SOBP_HM | SOBP_HM_FP | Forward Primer | TTTCGGCGGGTTTCGAG | 294 |
| | SOBP_HM_RP | Reverse Primer | CGTACCGTTCACGATAACGT | 295 |
| | SOBP_HM_Pb_A1 | Flap Oligo. | CGCCGAGGGGCGGTCGCGGT/3C6/ | 296 |

TABLE 3-continued

| | | | | |
|---|---|---|---|---|
| MAX.chr8.145 | MAX.Chr8.145_FP | Forward Primer | GCGGTATTAGTTAGAGTTTTAGTCG | 211 |
| | MAX.Chr8.145_RP | Reverse Primer | ACAACCCTAAACCCTAAATATCGT | 212 |
| | MAX.Chr8.145_Pb_A5 | Flap Oligo. | CCACGGACGGACGGCGTTTTT/3C6/ | 213 |
| MAX.chr10.226 | MAX.Chr10.226_FP | Forward Primer | GGGAAATTTGTATTTCGTAAAATCG | 178 |
| | MAX.Chr10.226_RP | Reverse Primer | ACAACTAACTTATCTACGTAACATC GT | 179 |
| | MAX.Chr10.226_Pb_A1 | Flap Oligo. | CGCCGAGGGCGGTTAAGAAA/3C6/ | 180 |
| MAX.chr12.52 | MAX.Chr12.52_FP | Forward Primer | TCGTTCGTTTTTGTCGTTATCG | 183 |
| | MAX.Chr12.52_RP | Reverse Primer | AACCGAAATACAACTAAAAACGC | 184 |
| | MAX.Chr12.52PbA1 | Flap Oligo. | CCACGGACGCGAACCCCGCAA/3C6/ | 185 |
| FLJ45983 | FLJ45983_FP | Forward Primer | GGGCGCGAGTATAGTCG | 133 |
| | FLJ45983_RP | Reverse Primer | CAACGCGACTAATCCGC | 134 |
| | FLJ45983_Pb_A1 | Flap Oligo. | CGCCGAGGCCGTCACCTCCA/3C6/ | 135 |
| HOXA9 | HOXA9_FP | Forward Primer | TTGGGTAATTATTACGTGGATTCG | 148 |
| | HOXA9_RP | Reverse Primer | ACTCATCCGCGACGTC | 149 |
| | HOXA9_Pb_A5 | Flap Oligo. | CCACGGACGCGACGCCCAACA/3C6/ | 150 |
| EMX1 | EMX1_FP | Forward Primer | GGCGTCGCGTTTTTTAGAGAA | 108 |
| | EMX1_RP | Reverse Primer | TTCCTTTTCGTTCGTATAAAATTTCG TT | 109 |
| | EMX1PbA1 | Flap Oligo. | CGCCGAGGATCGGGTTTTAG/3C6/ | 110 |
| SP9 | SP9_FP | Forward Primer | TAGCGTCGAATGGAAGTTCGA | 315 |
| | SP9_RP | Reverse Primer | GCGCGTAAACATAACGCACC | 317 |
| | SP9_Pb_A5 | Flap Oligo. | CCACGGACGCCGTACGAATCC/3C6/ | 318 |
| DMRTA2 | DMRTA2_FP | Forward Primer | TGGTGTTTACGTTCGGTTTTCGT | 88 |
| | DMRTA2_RP | Reverse Primer | CCGCAACAACGACGACC | 89 |
| | DMRTA2_Pb_A1 | Flap Oligo. | CGCCGAGGCGAACGATCACG/3C6/ | 90 |
| OPLAH | FPrimerOPLAH | Forward Primer | cGTcGcGTTTTTcGGTTATACG | 231 |
| | RPrimerOPLAH | Reverse Primer | CGCGAAAACTAAAAAACCGCG | 232 |
| | ProbeA5OPLAH | Flap Oligo. | CCACGGACG-GCACCGTAAAAC/3C6/ | 233 |
| CYP26C1 | CYP26C1_FP | Forward Primer | TGGTTTTTTGGTTATTTCGGAATCGT | 70 |
| | CYP26C1_RP | Reverse Primer | GCGCGTAATCAACGCTAAC | 71 |
| | CYP26C1_Pb_A1 | Flap Oligo. | CGCCGAGGCGACGATCTAAC/3C6/ | 72 |
| ZNF781 | ZNF781F.primer | Forward Primer | CGTTTTTTTGTTTTTCGAGTGCG | 373 |
| | ZNF781R.primer | Reverse Primer | TCAATAACTAAACTCACCGCGTC | 374 |
| | ZNF781probe.A5 | Flap Oligo. | CCACGGACGGCGGATTTATCG/3C6/ | 375 |
| DLX4 | DLX4_FP | Forward Primer | TGAGTGCGTAGTGTTTTCGG | 80 |
| | DLX4_RP | Reverse Primer | CTCCTCTACTAAAACGTACGATAAA CA | 81 |
| | DLX4_Pb_A1 | Flap Oligo. | CGCCGAGGATCGTATAAAAC/3C6/ | 82 |
| SUCLG2 | SUCLG2_HM_FP | Forward Primer | TCGTGGGTTTTTAATCGTTTCG | 321 |
| | SUCLG2_HM_RP | Reverse Primer | TCACGCCATCTTTACCGC | 322 |
| | SUCLG2_HM_Pb_A5 | Flap Oligo. | CCACGGACGCGAAAATCTACA/3C6/ | 323 |
| KLHDC7B | KLHDC7B_FP | Forward Primer | AGTTTTCGGGTTTTGGAGTTCGTTA | 158 |

TABLE 3-continued

| | KLHDC7B_RP | Reverse Primer | CCAAATCCAACCGCCGC | 159 |
| | KLHDC7B_Pb_A1 | Flap Oligo. | CGCCGAGGACGGCGGTAGTT/3C6/ | 160 |
| S1PR4_HM | S1PR4_HM_FP | Forward Primer | TTATATAGGCGAGGTTGCGT | 284 |
| | S1PR4_HM_RP | Reverse Primer | CTTACGTATAAATAATACAACCACC GAATA | 285 |
| | S1PR4_HM_Pb_A5 | Flap Oligo. | CCACGGACGACGTACCAAACA/3C6/ | 286 |
| NFIX_HM | NFIX_HM_FP | Forward Primer | TGGTTCGGGCGTGACGCG | 221 |
| | NFIX_HM_RP | Reverse Primer | TCTAACCCTATTTAACCAACCGA | 222 |
| | NFIX_HM_Pb_A1 | Flap Oligo. | CGCCGAGGGCGGTTAAAGTG/3C6/ | 223 |

| Reference DNAS | Oligonucleotide Name | Component | Sequence (5'-3') | |
|---|---|---|---|---|
| Zebrafish Synthetic (RASSF1) BT converted)[†] | ZF_RASSF1_FP | BT Forward Primer | TGCGTATGGTGGGCGAG | 394 |
| | ZF_RASSF1_RP | BT Reverse Primer | CCTAATTTACACGTCAACCAATCGA A | 395 |
| | ZF_RASSF1_Pb_A5 | BT Flap Oligo. | CCACGGACGGCGCGTGCGTTT/3C6/ | 397 |
| B3GALT6* | B3GALT6_FP_V2 | Forward Primer | GGTTTATTTTGGTTTTTTGAGTTTTC GG | 386 |
| | B3GALT6_RP | Reverse Primer | TCCAACCTACTATATTTACGCGAA | 387 |
| | B3GALT6_Pb_A1 | Flap Oligo. | CCACGGACGGCGGATTTAGGG/3C6/ | 388 |
| BTACT | ACTB_BT_FP65 | Forward Primer | GTGTTTGTTTTTTTGATTAGGTGTTT AAGA | 381 |
| | ACTB_BT_RP65 | Reverse Primer | CTTTACACCAACCTCATAACCTTATC | 382 |
| | ACTBBTPbA3 | Flap Oligo. | GACGCGGAGATAGTGTTGTGG/3C6/ | 383 |

*The B3GALT6 marker is used as both a cancer methylation marker and as a reference target. See U.S. patent application Ser. No. 62/364,082, filed Jul. 19, 2016, which is incorporated herein by reference in its entirety.
[†]For zebrafish reference DNA see U.S. patent application Ser. No. 62/364,049, filed Jul. 19, 2016, which is incorporated herein by reference in its entirety.
The DNA prepared from plasma as described above was amplified in two multiplexed pre-amplification reactions, as described in Example 1. The multiplex pre-amplification reactions comprised reagents to amplify the following marker combinations.

TABLE 4

| Multiplex Mix 1 | Multiplex Mix 2 |
|---|---|
| B3GALT6 (reference) | B3GALT6 (reference) |
| ZF_RASSF1 (reference) | ZF_RASSF1 (reference) |
| BARX1 | CYP26C1 |
| BCL2L11 | DLX4 |
| BCL2L11 | DMRTA2 |
| BIN2_Z | EMX1 |
| DNMT3A | HOXA9 |
| FERMT3 | KLHDC7B |
| PARP15 | MAX.chr8.125 |
| PRKCB_28 | MAX_chr10.226 |
| SHOX2 | NFIX |
| SLC12A8 | OPLAH |
| SOBP | S1PR4 |
| TBX15_Reg2 | SP9 |
| ZDHHC1 | SUCLG2 |
| | ZNF781 |

Following pre-amplification, aliquots of the pre-amplified mixtures were diluted 1:10 in 10 mM Tri s HCl, 0.1 mM EDTA, then were assayed in triplex QuARTS PCR-flap assays, as described in Example 1. The Group 1 triplex reactions used pre-amplified material from Multiplex Mix 1, and the Group 2 reactions used the pre-amplified material from Multiplex Mix 2. The triplex combinations were as follows:

| Group 1: | |
|---|---|
| ZF_RASSF1-B3GALT6-BTACT | (ZBA Triplex) |
| BARX1-SLC12A8-BTACT | (BSA2 Triplex) |
| PARP15-MAX.chr8.124-BTACT | (PMA Triplex) |
| SHOX2-ZDHHC1-BTACT | (SZA2 Triplex) |
| BIN2_Z-SKI-BTACT | (BSA Triplex) |
| DNMT3A-BCL2L11-BTACT | (DBA Triplex) |
| TBX15-FERMT3-BTACT | (TFA Triplex) |
| PRKCB_28-SOBP-BTACT | (PSA2 Triplex) |

| Group 2: | |
|---|---|
| ZF_RASSF1-B3GALT6-BTACT | (ZBA Triplex) |
| MAX.chr8.145-MAX_chr10.226-BTACT | (MMA2 Triplex) |
| MAX.chr12.526-FLJ45983-BTACT | (MFA Triplex) |
| HOXA9-EMX1-BTACT | (HEA Triplex) |
| SP9-DMRTA2-BTACT | (SDA Triplex) |
| OPLAH-CYP26C1-BTACT | (OCA Triplex) |
| ZNF781-DLX4-BTACT | (ZDA Triplex) |
| SUCLG2-KLHDC7B-BTACT | (SKA Triplex) |
| S1PR4-NFIX-BTACT | (SNA Triplex) |

Each triplex acronym uses the first letter of each gene name (for example, the combination of HOXA9-EMX1-BTACT="HEA"). If an acronym is repeated for a different combination of markers or from another experiment, the second grouping having that acronym includes the number 2. The dye reporters used on the FRET cassettes for each member of the triplexes listed above is FAM-HEX-Quasar670, respectively.

Plasmids containing target DNA sequences were used to calibrate the quantitative reactions. For each calibrator plasmid, a series of 10× calibrator dilution stocks, having from 10 to $10^6$ copies of the target strand per $\mu$l in fish DNA diluent (20 ng/mL fish DNA in 10 mM Tris-HCl, 0.1 mM EDTA) were prepared. For triplex reactions, a combined stock having plasmids that contain each of the targets of the triplex were used. A mixture having each plasmid at $1 \times 10^5$ copies per $\mu$L was prepared and used to create a 1:10 dilution series. Strands in unknown samples were back calculated using standard curves generated by plotting Cp vs Log (strands of plasmid).

Using receiver operating characteristic (ROC) curve analysis, the area under the curve (AUC) for each marker was calculated and is shown in the table below, sorted by Upper 95 Pct Coverage Interval.

TABLE 5

| Marker Name | AUC | Sensitivity at 90% specificity |
|---|---|---|
| CYP26C1 | 0.940 | 80% |
| SOBP | 0.929 | 80% |
| SHOX2 | 0.905 | 73% |
| SUCLG2 | 0.905 | 64% |
| NFIX | 0.895 | 63% |
| ZDHHC1 | 0.890 | 69% |
| BIN2_Z | 0.872 | 59% |
| DLX4 | 0.856 | 56% |
| FLJ45983 | 0.834 | 67% |
| HOXA9 | 0.824 | 53% |
| TBX15 | 0.813 | 53% |
| ACTB | 0.803 | 50% |
| S1PR4 | 0.802 | 55% |
| SP9 | 0.782 | 38% |
| FERMT3 | 0.773 | 36% |
| ZNF781 | 0.769 | 55% |
| B3GALT6 | 0.746 | 39% |
| BTACT | 0.742 | 44% |
| BCL2L11 | 0.732 | 39% |
| PARP15 | 0.673 | 31% |
| DNMT3A | 0.689 | 20% |
| MAX.chr12.526 | 0.668 | 33% |
| MAX.chr10.226 | 0.671 | 30% |
| SLC12A8 | 0.655 | 19% |
| BARX1 | 0.663 | 25% |
| KLHDC7B | 0.604 | 10% |
| OPLAH | 0.571 | 14% |
| MAX.chr8.145 | 0.572 | 16% |
| SKI | 0.521 | 14% |

The markers worked very well in distinguishing samples from cancer patients from samples from normal subjects (see ROC table, above). Use of the markers in combination improved sensitivity. For example, using a logistic fit of the data and a six-marker fit, ROC curve analysis shows an AUC=0.973.

Figure 8:
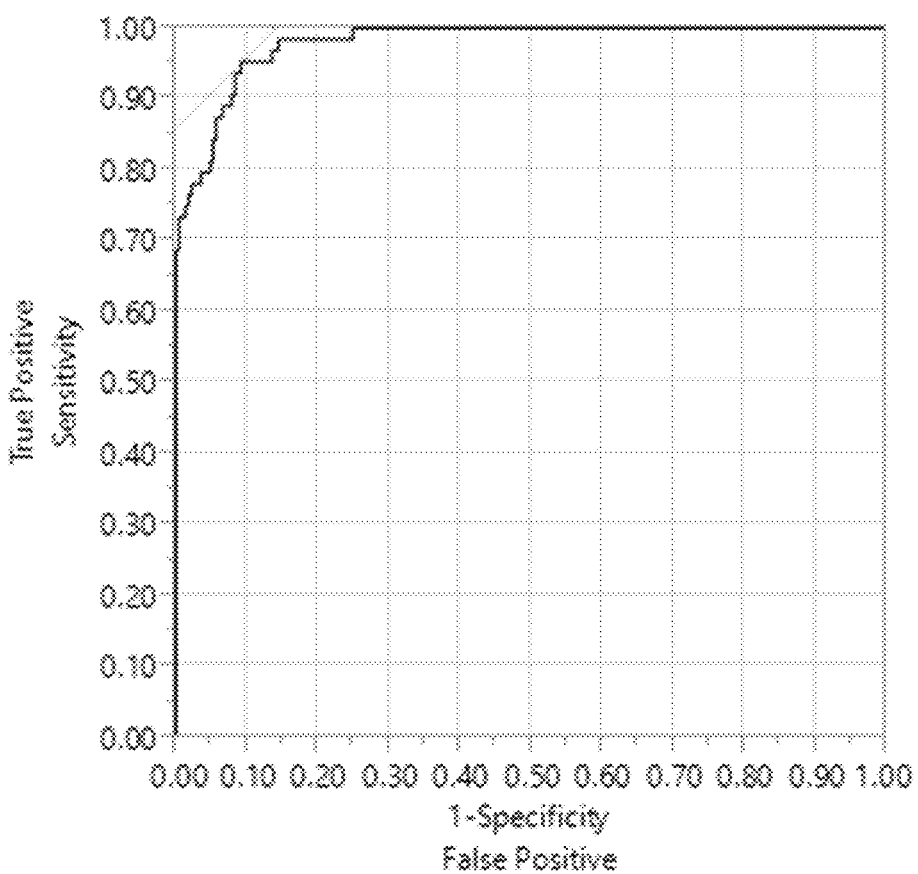
FIG. 8 provides a graph showing a 6-marker logistic fit of data from Example 3, using markers SHOX2, SOBP, ZNF781, CYP26C1, SUCLG2, and SKI. The ROC curve analysis shows an area under the curve (AUC) of 0.97982.

Using a 6-marker fit, sensitivity of 92.2% is obtained at 93% specificity. The group of 6 markers that together resulted in the best fit was SHOX2, SOBP, ZNF781, BTACT, CYP26C1, and DLX4 (see FIG. 7). Using SHOX2, SOBP, ZNF781, CYP26C1, SUCLG2, and SKI gave an ROC curve with AUC of 0.97982 (see FIG. 8).

Example 4

Archival plasmas from a second independent study group were tested in blinded fashion. Lung cancer cases and controls (apparently healthy smokers) for each group were balanced on age and sex (23 cases, 80 controls). Using multiplex PCR followed by QuARTS (Quantitative Allele-Specific Real-time Target and Signal amplification) assay as described in Example 1, a post-bisulfite quantification of methylated DNA markers on DNA extracted from plasma was performed. Top individual methylated markers from Example 3 were tested in this experiment to identify optimal marker panels for lung cancer detection (2 ml/patient).

Results: 13 high performance methylated DNA markers were tested (CYP26C1, SOBP, SUCLG2, SHOX2, ZDHHC1, NFIX, FLJ45983, HOXA9, B3GALT6, ZNF781, SP9, BARX1, and EMX1). Data were analyzed using two methods: a logistic regression fit and a regression partition tree approach. The logistic fit model identified a 4-marker panel (ZNF781, BARX1, EMX1, and SOBP) with an AUC of 0.96 and an overall sensitivity of 91% and 90% specificity. Analysis of the data using a regression partition tree approach identified 4 markers (ZNF781, BARX1, EMX1, and HOXA9) with AUC of 0.96 and an overall sensitivity of 96% and specificity of 94%. For both approaches, B3GALT6 was used as a standardizing marker of total DNA input. These panels of methylated DNA markers assayed in plasma achieved high sensitivity and specificity for all types of lung cancer.

Example 5

Differentiating Lung Cancers

Using the methods described above, methylation markers are selected that exhibit high performance in detecting methylation associated with specific types of lung cancer.

For a subject suspected of having lung cancer, a sample is collected, e.g., a plasma sample, and DNA is isolated from the sample and treated with bisulfite reagent, e.g., as described in Example 1. The converted DNA is analyzed using a multiplex PCR followed by QuARTS flap endonuclease assay as described in Example 1, configured to provide different identifiable signals for different methylation markers or combinations of methylation markers, thereby providing data sets configured to specifically identify the presence of one or more different types of lung carcinoma in the subject (e.g., adenocarcinoma, large cell carcinoma, squamous cell carcinoma, and/or small cell carcinoma). In preferred embodiments, a report is generated indicating the presence or absence of an assay result indicative of the presence of lung carcinoma and, if present, further indicative of the presence of one or more identified types of lung carcinoma. In some embodiments, samples from a subject are collected over the course of a period of time or a course of treatment, and assay results are compared to monitor changes in the cancer pathology.

Marker and marker panels sensitive to different types of lung cancer find use, e.g., in classifying type(s) of cancer present, identifying mixed pathologies, and/or in monitoring cancer progression over time and/or in response to treatment.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

What is claimed is:

1. A composition comprising a reaction mixture comprising:
   i) nucleic acid from a human sample;
   ii) for each of at least three methylation marker genes selected from the group consisting of SHOX2, HOXA9, ZNF781, BARX1, and EMX1, a pair of primers that specifically hybridize to and are extendible by a DNA polymerase from a region within a methylation marker gene in a target DNA when the target DNA is present in the nucleic acid from the human sample, wherein the target DNA comprises a differentially methylated region of the methylation marker gene that is differently methylated between DNA from a human subject having a lung neoplasm and DNA from a human subject who does not have a lung neoplasm;
   iii) amplicon DNA amplified from at least one target DNA by extension of a pair of primers of ii) and comprising a differentially methylated region of the methylation marker gene;
   iv) a pair of B3GALT6 primers that specifically hybridize to and are extendible by a DNA polymerase from a region within a B3GALT6 DNA;
   v) B3GALT6 amplicon DNA amplified from the B3GALT6 DNA by extension of a pair of primers of iv); and
   vi) one or more of a FRET cassette, a FEN-1 endonuclease, and a thermostable DNA polymerase.

2. The composition of claim 1, wherein the nucleic acid from a human sample comprises DNA treated with a methylation-sensitive restriction enzyme or with a reagent that selectively modifies unmethylated cytosine nucleotides in DNA.

3. The composition of claim 1, wherein the at least three methylation marker genes comprises the group consisting of ZNF781, BARX1, and EMX1.

4. The composition of claim 1, wherein the at least three methylation marker genes comprises the group consisting of ZNF781, BARX1, EMX1, and HOXA9.

5. The composition of claim 1, further comprising one or more oligonucleotides that each specifically hybridize to a differentially methylated region of methylation marker gene in one or more amplicon DNAs amplified from the at least one target DNA.

6. The composition of claim 5, wherein the one or more oligonucleotides comprise reporter molecules.

7. The composition of claim 6, where the reporter molecules comprise fluorophores.

8. The composition of claim 5, wherein at least one of the one or more oligonucleotides comprises a flap sequence.

9. The composition of claim 1, wherein the at least three methylation marker genes comprise a nucleic acid sequence selected from the group consisting of SEQ ID NOS: 21, 106, 146, 267, and 371.

10. The composition of claim 2, wherein the at least three methylation marker genes treated with a reagent that selectively modifies unmethylated cytosine residues in DNA comprise a nucleic acid sequence selected from the group consisting of SEQ ID NOS:22, 107, 147, 268, and 372.

11. The composition of claim 1, wherein the reaction mixture comprises:

i) thermostable DNA polymerase;

ii) dNTPs;

iii) a buffer comprising Mg$^{++}$;

iv) a flap endonuclease;

v) a flap oligonucleotide; and vi) a hairpin oligonucleotide comprising a region that is complementary to a portion of said flap oligonucleotide.

12. The composition of claim 1, wherein nucleic acid from a human sample comprises DNA prepared from a plasma sample.

13. A composition comprising a reaction mixture comprising:

i) nucleic acid from a human sample comprising DNA treated with a methylation-sensitive restriction enzyme or with a reagent that selectively modifies unmethylated cytosine nucleotides in DNA;

ii) for each of at least three methylation marker genes selected from the group consisting of SHOX2, HOXA9, ZNF781, BARX1, and EMX1, a pair of primers that specifically hybridize to and are extendible by a DNA polymerase from a region within the methylation marker gene in a target DNA when the target DNA is present in the nucleic acid from the human sample, wherein the target DNA comprises a differentially methylated region of the methylation marker gene that is differently methylated between DNA from a human subject having a lung neoplasm and DNA from a human subject who does not have a lung neoplasm;

iii) amplicon DNA amplified from at least one target DNA by extension of a pair of primers of ii) and comprising a differentially methylated region of the methylation marker gene;

iv) a pair of B3GALT6 primers that specifically hybridize to and are extendible by a DNA polymerase from a region within a B3GALT6 DNA; and v) B3GALT6 amplicon DNA amplified from the B3GALT6 DNA by extension of a pair of primers of iv).

14. The composition of claim 13, wherein the at least three methylation marker genes comprises the group consisting of ZNF781, BARX1, and EMX1.

15. The composition of claim 13, wherein the at least three methylation marker genes comprises the group consisting of ZNF781, BARX1, EMX1, and HOXA9.

* * * * *